US006958361B2

(12) United States Patent
Houghton et al.

(10) Patent No.: US 6,958,361 B2
(45) Date of Patent: Oct. 25, 2005

(54) COMPOSITIONS AND METHODS FOR THE THERAPY AND DIAGNOSIS OF BREAST CANCER

(75) Inventors: Raymond L. Houghton, Bothell, WA (US); Paul R. Sleath, Seattle, WA (US); David H. Persing, Redmond, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 10/076,622

(22) Filed: Feb. 13, 2002

(65) Prior Publication Data

US 2003/0023036 A1 Jan. 30, 2003

Related U.S. Application Data

(63) Continuation-in-part of application No. 10/007,805, filed on Dec. 7, 2001, which is a continuation-in-part of application No. 09/834,759, filed on Apr. 13, 2001, now Pat. No. 6,680,197, which is a continuation-in-part of application No. 09/620,405, filed on Jul. 20, 2000, now Pat. No. 6,528,054, which is a continuation-in-part of application No. 09/604,287, filed on Jun. 22, 2000, now Pat. No. 6,586,572, which is a continuation-in-part of application No. 09/590,751, filed on Jun. 8, 2000, now Pat. No. 6,756,477, which is a continuation-in-part of application No. 09/551,621, filed on Apr. 17, 2000, now Pat. No. 6,844,325, which is a continuation-in-part of application No. 09/433,826, filed on Nov. 3, 1999, now Pat. No. 6,579,973, which is a continuation-in-part of application No. 09/389,681, filed on Sep. 2, 1999, now Pat. No. 6,518,237, which is a continuation-in-part of application No. 09/339,338, filed on Jun. 23, 1999, now Pat. No. 6,573,368, which is a continuation-in-part of application No. 09/285,480, filed on Apr. 2, 1999, now Pat. No. 6,590,076, which is a continuation-in-part of application No. 09/222,575, filed on Dec. 28, 1998, now Pat. No. 6,387,697.

(51) Int. Cl.$^7$ .................. A01N 25/00; A01N 37/18; A61K 39/00
(52) U.S. Cl. .................. 514/885; 514/2; 424/184.1
(58) Field of Search .................. 514/885, 2; 530/828; 424/184.1

(56) References Cited

U.S. PATENT DOCUMENTS

| | | | | |
|---|---|---|---|---|
| 5,215,926 | A | 6/1993 | Etchells, III et al. | 436/501 |
| 5,240,856 | A | 8/1993 | Goffe et al. | 435/299 |
| 5,668,267 | A | 9/1997 | Watson et al. | 536/23.5 |
| 5,855,889 | A | 1/1999 | Watson et al. | 424/185.1 |
| 5,891,857 | A | 4/1999 | Holt et al. | 514/44 |
| 5,922,836 | A | 7/1999 | Watson et al. | 530/300 |
| 5,968,754 | A | 10/1999 | Watson et al. | 435/7.23 |
| 5,986,170 | A | 11/1999 | Subjeck | 800/2 |
| 6,004,756 | A | 12/1999 | Watson et al. | 435/6 |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

Doerks et al. (1998, Trends in Genetics 14:248–250).*
Anderson et al. Electrophoresis 1997, vol. 18, pp. 533–537.*
* A copy of this reference was previously forwarded to Applicants in U.S. Appl. No. 09/604,287.*
Skolnick et al. (2000, Trends in Biotech. 18:34–39).*
Bork (2000, Genome Research 10:398–400).*
Thompson (2001), Medicinal Research Reviews. vol. 21, No. 5, pp. 412–449.*
Gura (Science, 1997, vol. 278, pp. 1041–1042).*
Hartwell et al. (Science, 1997, vol. 278, pp. 1064–1068).*
GenBank Database, Accession No. AA219147, Feb. 7, 1997.
GenBank Database, Accession No. AI272025, Nov. 17, 1998.
GenBank Database, Accession No. AI687645, May 27, 1999.
GenBank Database, Accession No. AL049911, Oct. 22, 1999.
GenBank Database, Accession No. AQ280806, Nov. 22, 1998.
Geneseq (Derwent) Database, Accession No. AAV41453, Oct. 12, 1998.
Geneseq (Derwent) Database, Accession No. AAV90291, Feb. 15, 1999.
Chang and Shu, "Current status of adoptive immunotherapy of cancer," *Critical Reviews in Oncology/Hematology* 22(3):213–228, Apr. 1996.
Cheever and Chen, "Therapy with cultured T cells: principles revisited," *Immunological Reviews, 157:* 177–194, 1997.
Cheever et al., "Potential uses of interleukin 2 in cancer therapy," *Immunobiol, 172:*365–382, 1986.
Chen et al., "T–cells for tumor therapy can be obtained from antigen–loaded sponge implants," *Cancer Research* 54(4):1065–1070, Feb. 15, 1994.
Cole et al., "Characterization of the functional specificity of a cloned T–cell receptor heterodimer recognizing the MART–1 melanoma antigen," *Cancer Research,* 55:748–752, Feb. 15, 1995.

(Continued)

Primary Examiner—Andrew Wang
Assistant Examiner—Janet L. Epps-Ford
(74) Attorney, Agent, or Firm—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

2 Claims, 2 Drawing Sheets

OTHER PUBLICATIONS

Durrant L., "Cancer vaccines," *Anti–Cancer Drugs*, 8:727–733, 1997.

Eshhar Z., "Tumor–specific T–bodies: toward clinical application," *Cancer Immunol Immnother*, 45:131–136, 1997.

GenBank Accession No. AC069200, May 24, 2000.

GenBank Accession No. AF269087, Mar. 28, 2001.

GenBank Accession No. AAK27325, Mar. 28, 2001.

GenBank Accession No. AA864891, Feb. 20, 1998.

GenBank Accession No. AA398925, Apr. 25, 1997.

GenBank Accession No. AL359312, Dec. 7, 2001.

Geneseq Accession No. V84525 (Dec. 10, 1998).

Hwu et al., "In vivo antitumor activity of T cells redirected with chimeric antibody/T–cell receptor genes," *Cancer Research*, 55:3369–3373, Aug. 1, 1995.

Jäger et al., "Identification of a tissue–specific putative transcription factor in breast tissue by serological screening of a breast cancer library," *Cancer Research* 61(5):2055–2061, Mar. 1, 2001.

Porter–Jordan and Lippman, "Overview of the biologic markers of breast cancer," *Breast Cancer 8:*(1):73–100, Feb. 1994.

Prilliman et al., "HLA–B15 peptide ligands are preferentially anchored at their c termini," *The Journal of Immunology* 162(12):7277–7284, Jun. 15, 1999.

Sulston et al., "Toward a complete human genome sequence," *Genome Research* 8(11):1097–1108, 1998.

Stratagene 1991 product catalog, Prime–It™ Random Labeling Kit, catalog No. 300387, p. 66.

Wei et al., "Protection against mammary tumor growth by vaccination with full–length, modified human *ErbB–2* DNA," *Int. J. Cancer, 81:*748–754, 1999.

GenBank Accession No. AL157387, Feb. 18, 2000.

GenBank Accession No. AC036170, Apr. 9, 2000.

* cited by examiner

SYN18C6 Northern Blot

SEQUENCE LISTING

<160> NUMBER OF SEQ ID NOS: 627

<210> SEQ ID NO 1
<211> LENGTH: 281
<212> TYPE: DNA
<213> ORGANISM: Homo sapien

<400> SEQUENCE: 1

```
caatgacagt caatctctat cgacagcctg cttcatattt agctattgtt cgtattgcct      60
tctgtcctag gaacagtcat atctcaagtt caaatgccac aacctgagaa gcggtgggct     120
aagataggtc ctactgcaaa ccaccectcc atatttccgt acgcaattac aattcagttt     180
ctgtgacatc tctttacacc actggaggaa aaatgagata ttctctgatt tattctacta     240
taacactcta catagagcta tggtgagtgc taaccacatc g                         281
```

<210> SEQ ID NO 2
<211> LENGTH: 300
<212> TYPE: DNA
<213> ORGANISM: Homo sapien

<400> SEQUENCE: 2

```
gaggtcctgg gctaacctaa tggtttatta ttggtggaga gaaagatctg gaaatacttg      60
aggttattac atactagatt agcttctaat gtgaaccatt tttcttttaa cagtgataaa     120
ttattatttc cgaagttaac tgttcccttg gtcgtgatac acactcgatt aacaaacata     180
ctgttgtatt ttttccagtt ttgtttggct atgccaccac agtcatcccc agggtctata     240
catactatgt ctcaactgta ttatttgcca ttttttggcat tagaatgctt cgggaaggct    300
```

<210> SEQ ID NO 3
<211> LENGTH: 302
<212> TYPE: DNA
<213> ORGANISM: Homo sapien

<400> SEQUENCE: 3

```
ggccgaggta attggttaag tctaaagaga ttattattcc ttgatgtttg ctttgtattg      60
gctacaaatg tgcagaggta atacatatgt gatgtcgatg tctctgtctt tttttttgtc     120
tttaaaaaat aattggcagc aactgtattt gaataaaatg atttcttagt atgattgtac     180
agtaatgaat gaaagtggaa catgtttctt tttgaaaggg agagaattga ccatttattg     240
ttgtgatgtt taagttataa cttatcgagc acttttagta gtgataactg ttttaaact     300
tg                                                                    302
```

<210> SEQ ID NO 4
<211> LENGTH: 293
<212> TYPE: DNA
<213> ORGANISM: Homo sapien

<400> SEQUENCE: 4

```
tgtaccaatc ctttggcaca agaatatgta agaactatag ttgttttat tggtttttgt       60
tcttgagatt gtttttcattc tgtttttgac tgtatctctt taggaggctg aggatggcat    120
tattgcttat gatgactgtg gggtgaaact gactattgct tttcaagcca aggatgtgga    180
aggatctact tctccctcaaa tacgagataa ggcaagataa ttctgctcat tcgagagagg   240
gttaagagtt gtcatcttaa tcataaatcc tgcaggatgg gttcttcaaa ttt            293
```

<210> SEQ ID NO 5
<211> LENGTH: 275
<212> TYPE: DNA
<213> ORGANISM: Homo sapien

<400> SEQUENCE: 5

```
cgaggtttgg aatcagactt ctgtgtccag taaaaaactc ctgcactgaa gtcattgtga      60
cttgagtagt tacagactga ttccagtcag cttgatctaa tttctttga tctaatgaat    120
gtgtctgctt accttgtctc cttttaattg ataagctcca agtagttgct aattttttga   180
caactttaaa tgagtttcat tcacttcttt tacttaatgt tttaagtata gtaccaataa   240
tttcattaac ctgttctcaa gtggtttagc tacca                              275
```

<210> SEQ ID NO 6
<211> LENGTH: 301
<212> TYPE: DNA

<213> ORGANISM: Homo sapien

<400> SEQUENCE: 6

| | | | | | |
|---|---|---|---|---|---|
| gaggtctggt | ttcctgggta | tgcctggact | gttgcccagt | gtaagatctg | tgcaagccat | 60 |
| attggatgga | agtttacggc | caccaaaaaa | gacatgtcac | ctcaaaaatt | ttggggctta | 120 |
| acgcgatctg | ctctgttgcc | cacgatccca | gacactgaag | atgaaataag | tccagacaaa | 180 |
| gtaatactt | gcttgtaaac | agatgtgata | gagataaagt | tatctaacaa | attggttata | 240 |
| ttctaagatc | tgctttggaa | attattgcct | ctgatacata | cctaagtaaa | cataacatta | 300 |
| a | | | | | | 301 |

<210> SEQ ID NO 7
<211> LENGTH: 301
<212> TYPE: DNA
<213> ORGANISM: Homo sapien

<400> SEQUENCE: 7

| | | | | | |
|---|---|---|---|---|---|
| gtccagtttg | tacacagtga | ttccttatgc | acgccgaaag | ggtttccgta | aaaatgacat | 60 |
| tatatacaaa | tctgtacacc | catccaccag | agcgattctc | cagctcccag | agggagttat | 120 |
| caacttaaag | caggatacct | gaggtttcat | gtctttagtt | gccttatcat | aatcccaaat | 180 |
| atacatttca | gggtttgttt | ttgttttttaa | agacactttg | ctggaatatg | tgcactatgg | 240 |
| ttaaaattaa | aaacaaaagt | aataaaataa | aatgatcgct | ggaaggactg | acctccccac | 300 |
| c | | | | | | 301 |

<210> SEQ ID NO 8
<211> LENGTH: 301
<212> TYPE: DNA
<213> ORGANISM: Homo sapien

<400> SEQUENCE: 8

| | | | | | |
|---|---|---|---|---|---|
| ctgtcctcat | ctctgcaaag | ttcagcttcc | ttccccaggt | ctctgtgcac | tctgtcttgg | 60 |
| atgctctggg | gagctcatgg | gtggaggagt | ctccaccaga | gggaggctca | gggactggt | 120 |
| tgggccaggg | atgaatattc | gagggataaa | aattgtgtaa | gagccaaaga | attggtagta | 180 |
| ggggagaac | agagaggagc | tgggctatgg | gaaatgattt | gaataatgga | gctgggaata | 240 |
| tggctggata | tctggtacta | aaaaagggtc | tttaagaacc | tacttcctaa | tctcttcccc | 300 |
| a | | | | | | 301 |

<210> SEQ ID NO 9
<211> LENGTH: 301
<212> TYPE: DNA
<213> ORGANISM: Homo sapien

<400> SEQUENCE: 9

| | | | | | |
|---|---|---|---|---|---|
| gaggtctgcc | taagtagagg | acaaagactt | cctcctttca | aaggagaact | gagcccagga | 60 |
| ttggtaagtt | taaggcactt | aaccttgacc | agctctgtag | gtctggagca | ttctggtccc | 120 |
| tggccgcttt | caccaccagg | cccttctcac | ttatccacct | cacatactgc | cccagcattc | 180 |
| ctttggcatt | gcgagctgtg | acttgacaca | ttttaatgac | aagattgaag | tagctacctt | 240 |
| gcaggataga | ttttctgggg | tataggggac | aaaccaacag | tgccatcagg | tgtcttaaca | 300 |
| c | | | | | | 301 |

<210> SEQ ID NO 10
<211> LENGTH: 301
<212> TYPE: DNA
<213> ORGANISM: Homo sapien

<400> SEQUENCE: 10

| | | | | | |
|---|---|---|---|---|---|
| ggcaggtcca | acagttcttc | cagttctggt | cgagctttga | atcgtccctt | gaagtcttct | 60 |
| tcagtgtgct | ccttcactga | cagtctgact | ccttcaggaa | gactgctttg | gattatttcc | 120 |
| aagaaaattt | ctgcaaacgt | agcactcaaa | ccgctgatct | gaaccactcg | ctcatgggtg | 180 |
| gtaagcactg | agtccaggag | cattttgctg | ccttggtcct | gcaactgcaa | cacttctatg | 240 |
| gttttggttg | gcattgcata | actttcctcg | actttaatgg | agagagattg | cagaggttgt | 300 |
| g | | | | | | 301 |

<210> SEQ ID NO 11
<211> LENGTH: 301
<212> TYPE: DNA
<213> ORGANISM: Homo sapien

<400> SEQUENCE: 11

```
aggtctgtga ctttcaccca ggacccagga cgcagccctc cgtgggcact gccggcgcct       60
tgtctgcaca ctggaggtcc tccattacag aggcccagcg cacatcgctg gccccacaaa      120
cgttcagggg tacagccatg gcagctcctt cctctgccgt gagaaaagtg cttggagtac      180
ggtttgccac acacgtgact ggacagtgtc caattcaaat cttttcaggg agagtccgag      240
cagcgcttgg tgacagcctg tcctctcctg ctctccaaag gccctgctcc ctgtcctctc      300
t                                                                     301
```

<210> SEQ ID NO 12
<211> LENGTH: 301
<212> TYPE: DNA
<213> ORGANISM: Homo sapien

<400> SEQUENCE: 12

```
gaggtctggg attacaggca cgtgccacca cacctagcta attttttgagc atggggctca      60
aaggaactgc tctctgggc atgtcagatt tcggatttgg ggctgcacac tgatactctc      120
taagtggtgg aggaacttca tcccactgaa attcctttgg catttggggt tttgtttttc      180
ttttttttcct tcttcatcct cctccttttt taaaagtcaa cgagagcctt cgctgactcc      240
accgaagaag tgcaccactg ggagccaccc cagtgccagg cgcccgtcca gggacacaca      300
c                                                                     301
```

<210> SEQ ID NO 13
<211> LENGTH: 256
<212> TYPE: DNA
<213> ORGANISM: Homo sapien

<400> SEQUENCE: 13

```
tttttttggca taaaaaacac aatgatttaa tttctaaagc acttatatta ttatggcatg      60
gtttgggaaa caggttatta tattccacat aggtaattat gcagtgcttc tcatggaaaa     120
aatgcttagg tattggcctt ttctctggaa accatatttt tcctttttta ataatcaact     180
aaaatgtata tgttaaaaag cctcatcttt tgattttcaa tatacaaaat gctttctta      240
aaagaacaag attcaa                                                     256
```

<210> SEQ ID NO 14
<211> LENGTH: 301
<212> TYPE: DNA
<213> ORGANISM: Homo sapien

<400> SEQUENCE: 14

```
ggtccttgat agaggaagag gaatatccaa ggcaaagcca ccaccacgtc caacctcctc      60
atcctctacc tttcctgtcc ccagaggtat gagatagacc ccctggcctg gttcctgcac     120
tgtgctaggc ccacagtgga cacttccacc ttaatggaga ataggcccca tggagtggag     180
gtccctcctc catggcctgc aacccaatga ctatgggggt gacacaagtg acctctgccc     240
tgtgatggct caacaccatc acacgcaact gtccagacaa gcccctcaa cgggctgctg      300
t                                                                     301
```

<210> SEQ ID NO 15
<211> LENGTH: 259
<212> TYPE: DNA
<213> ORGANISM: Homo sapien

<400> SEQUENCE: 15

```
gtcttgaaag tatttattgt ttaataattc tttctcccct cagccccatc cggccactct      60
ctctttctgc ttttctgatc atcctaaagg ctgaatacat cctcctcctg tgtggaggac     120
acgaagcaat actaaaatca atacactcga tcaggtcttc atcagatacc acgtcactgt     180
gggtagagtg ctaattttca acaaatgtgg tgttcttagg gccccacaag gtagtccttt     240
ctcaaggtcg ctgggccac                                                  259
```

<210> SEQ ID NO 16
<211> LENGTH: 301
<212> TYPE: DNA
<213> ORGANISM: Homo sapien

<400> SEQUENCE: 16

```
cgaggttgtt cacattttca aataaataat actcccgta agtaataact gcaaccaatc       60
agtgttattc agtgctatgc ctccttgtaa tgggtagtta ttaattattt tcagagcttt     120
ctggaaatac tgtcctaact ggctatgttt aggatctttg ttatctctga agacaaagaa     180
agaactagga ctcttaattt tggggtgctt cttgactctt agttgggaaa ctgaaaatat     240
ttccaacctt ttacccacgt caatggcata ttctgggaat caccaccacc accaccacta     300
c                                                                     301
```

<210> SEQ ID NO 17
<211> LENGTH: 301
<212> TYPE: DNA
<213> ORGANISM: Homo sapien

<400> SEQUENCE: 17

```
gcccgggcag gtctggggcc tagggtggct ctttgcaaag ctgagggca agctaaggaa      60
gccaggcagg tcagggccc tttcggcctt ctcaagcctc cacctgagtt ctcgtcaatg     120
ccagtctccc tggtatgatt ggggacatta tcagagaaac atctaatagc gcacatctgg   180
gcacccacac tctgcttcag ttgcatccat cctcccaccc caaattcaac tcctgaccca    240
atacaaaaga cttttttaac caggatttct tcttgcagga aagctgactt ggaaacacgg   300
g                                                                    301
```

<210> SEQ ID NO 18
<211> LENGTH: 301
<212> TYPE: DNA
<213> ORGANISM: Homo sapien

<400> SEQUENCE: 18

```
attacaggca cgtgccacca cacctagcta attttttgagc atggggctca aaggaactgc    60
tctctggggc atgtcagatt tcggatttgg ggctgcacac tgatactctc taagtggtgg   120
aggaacttca tcccactgaa attcctttgg catttgggggt tttgttttc ttttttcct    180
tcttcatcct cctcctttt taaaagtcaa cgagagcctt cgctgactcc accgaagaag   240
tgcaccactg gggaccaccc agtgccaggc gcccgtccag ggacacacac agtcttcact   300
g                                                                    301
```

<210> SEQ ID NO 19
<211> LENGTH: 301
<212> TYPE: DNA
<213> ORGANISM: Homo sapien

<400> SEQUENCE: 19

```
agaatctctg cactgtcatc aggtacaaca aaagatcaaa cccctgtccc gatgttaact    60
ttttaactta aaagaatgcc agaaaaccca gatcaacact ttccagctac gagccgtcca   120
caaaggccac ccaaaggcca gtcagactcg tgcagatctt atttttttaat agtagtaacc   180
acaatacaca gctctttaaa gctgttcata ttcttccccc attaaacacc tgccccgggc    240
ggccaagggc gaattctgca gatatccatc acactggcgg ccgctcgagc atgcatctag   300
a                                                                    301
```

<210> SEQ ID NO 20
<211> LENGTH: 290
<212> TYPE: DNA
<213> ORGANISM: Homo sapien

<400> SEQUENCE: 20

```
aggttttttt tttttttt tttttttttt tttttccctt tcaattcatt taatttcaac     60
aatctgtcaa aaaacagcca ataaacaaat actgaattac attctgctgg gtttttttaaa  120
ggctctaaac tataaaaaca tcttgtgtct cccaccctga ccaccctgct acttttccat    180
ataccacagg ccacccataa acacaaagcc aggggtgaa gctgacatgg tctatttgga    240
gccagtaaac aggaggggcga taagtcctga taagcactta tggacaatat                290
```

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag    60
actctttaaa aaaaaaaaat acccagggtt tgtcatcatt ttcagaggca gagtgccaaa   120
tatcacccaa agctcttgtg tcttttttt accccttat tttattttta tttattaatt     180
ttttgtgcaa acatcaaatg tcactggtgt tcacagaagg cttttttgac tagccttaaa   240
ttcctgagtc aaaagattaa tcagattttc aggcagtgtt taatcaggtg ctttgtcctg   300
t                                                                    301
```

<210> SEQ ID NO 22
<211> LENGTH: 301
<212> TYPE: DNA

<213> ORGANISM: Homo sapien

<400> SEQUENCE: 22

```
gacgccatgc accctccggt aaccagcagc cgcctgtcca tcccccaaga ccggaaaggc    60
agcagcagcc cccgggagcc cagggctgtc ctcggtgcat ctggctgcag agggaaattg   120
atgacccttac acagcaacta gcggccatgc agtccttcac tgacaagttc caggaccttt  180
gaagttggag ccagcgtccg gagctgcagc caagcgagtt cctccttat cctccttagc    240
cagggctttt tctcttccgc tgcatttgcc cccttcccaa cgcaattcaa agcagttgtg   300
a                                                                    301
```

<210> SEQ ID NO 23
<211> LENGTH: 381
<212> TYPE: DNA
<213> ORGANISM: Homo sapien

<400> SEQUENCE: 23

```
cgaggtccag acagtggacc aagagatacg ctacataaat tggggtttca caattcttac    60
attatttgtc tgtcacagaa gagagctgct tatgattttg aagggtcag ggagggtggg    120
agttggtaaa gagtagggta tttctataac agatattatt cagtctatt tcctaagatt    180
ttgttgtaac ttaaggtatc ttgctacagt agacagaatt ggtaatagca acttttaaaa   240
ttgtcattag ttctgcaata ttagctgaaa tgtagtacag aaaagaatgt acatttagac   300
atttgggttc agttgcttgt agtctgtaaa tttaaaacag cttaatttgg tacaggttac   360
acatatggac ctcccgggcg g                                              381
```

<210> SEQ ID NO 24
<211> LENGTH: 214
<212> TYPE: DNA
<213> ORGANISM: Homo sapien

<400> SEQUENCE: 24

```
aatgatgtaa aaattaatca acagggctgc cacttgcgaa tcccctccaa ggatgctgtg    60
caaagggtct cattggtcct gatgaataat cttgtgactg tacatattcc tgggtgcatg   120
tccacaaata ctgaggtata gcctgcatgc cactaaaaat aacaaaggtt tcaggggtgg   180
aaacattgtc caccacactg tcatgaccat cttt                                214
```

<210> SEQ ID NO 25
<211> LENGTH: 302
<212> TYPE: DNA
<213> ORGANISM: Homo sapien

<400> SEQUENCE: 25

```
gggggcactg agaactccct ctggaattct tggggggtgt tggggagaga ctgtgggcct    60
ggagataaaa cttgtctcct ctaccaccac cctgtaccct agcctgcacc tgtcctcatc   120
tctgcaaagt tcagcttcct tccccaggtc tctgtgcact ctgtcttgga tgctctgggg   180
agctcatggg tggaggagtc tccaccagag ggaggctcag gggactggtt gggccaggga   240
tgaatatttg agggataaaa attgtgtaag aagccaaaga aattggtagt aggggggaga   300
ac                                                                   302
```

<210> SEQ ID NO 26
<211> LENGTH: 301
<212> TYPE: DNA
<213> ORGANISM: Homo sapien

<400> SEQUENCE: 26

```
ttggagaacg cgctgacata ctgctcggcc acagtcagtg aagctgctgc atctccatta    60
tgttgtgtca gagctgcagc caggattcga atagcttcag ctttagcctt ggcttcgcc    120
agaactgcac tggcctctcc tgctgcctga tttatctgtg cagcctttc tgcttcggag    180
gccaggatct gggcctgttt cttcccttct gccacattga tggccgactc tcgggtcccc   240
tcagactcta gaactgtggc ccgtttccgc cgctctgcct ccacctgcat ctgcatagac   300
t                                                                    301
```

<210> SEQ ID NO 27
<211> LENGTH: 301
<212> TYPE: DNA
<213> ORGANISM: Homo sapien

<400> SEQUENCE: 27

```
aaatcagtca tcacatctgt gaaaagagtg ctagttataa caaatgagat cacaaatttg    60
```

```
        accatttat    tagacaccct    ctattagtgt    taacagacaa    agatgaaggt    taagttgaaa        120
        tcaaattgaa    atcatcttcc    ctctgtacag    attgcaatat    ctgataatac    cctcaacttt        180
        cttggtgcaa    attaattgcc    tggtactcac    agtccagtgt    taacaggcaa    taatggtgtg        240
        attccagagg    agaggactag    gtggcaggaa    aataaatgag    attagcagta    tttgacttgg        300
        a                                                                                     301
```

<210> SEQ ID NO 28
<211> LENGTH: 286
<212> TYPE: DNA
<213> ORGANISM: Homo sapien

<400> SEQUENCE: 28

```
        tttttttttg    cacaggatgc    acttattcta    ttcattctcc    cccacccttc    ccatatttac         60
        atccttagag    gaagagaggg    gtaaggtgat    aaagtaactg    aaggaccgca    agacgggtat        120
        gtcccttgtt    caccaaatgg    tcaaagggtc    aaagatcgga    ggaggtcagg    gggtaacgca        180
        ggaacaggtg    agggcgtttc    gccctctctc    cctctcccct    tttcaacctc    ttaatcactg        240
        gctaactcgc    gacctcatgg    gttaattcgt    aagcttacac    gcgttg                            286
```

<210> SEQ ID NO 29
<211> LENGTH: 301
<212> TYPE: DNA
<213> ORGANISM: Homo sapien

<400> SEQUENCE: 29

```
        gtcatgttct    tgctcttcct    tctttacaca    tttgagttgt    gccttctgtt    cttaaagaga         60
        ttttcctttg    ttcaaaggat    ttattcctac    catttcacaa    atccgaaaat    aattgaggaa        120
        acaggttaca    tcattccaat    tttgccttgg    gtttgaagag    tctctcatgg    tggcacagtc        180
        ctccaggta    gctatgttgt    tgggctcccc    tacatcccag    aagctcagag    actttgtcaa        240
        aggtgtgccg    tccacccatt    gccactgacc    ctcgacaacc    tggtctgaca    gtccaataaa        300
        a                                                                                     301
```

<210> SEQ ID NO 30
<211> LENGTH: 332
<212> TYPE: DNA
<213> ORGANISM: Homo sapien

<400> SEQUENCE: 30

```
        gagcagaatt    gatgcctatg    gctccaagtc    aaatactgct    aatctcattt    attttcctgc         60
        cacctagtcc    tctcctctgg    aatcacacca    ttattgcctg    ttaacactgg    actgtgagta        120
        ccaggcaatt    aatttgcacc    aagaaagttg    agggtattat    cagatattgc    aatctgtaca        180
        gagggaagat    gatttcaatt    tgatttcaac    ttaaccttca    tctttgtctg    ttaacactaa        240
        tagagggtgt    ctaataaaat    ggtcaaattt    gtgatctcat    ttgttataac    tagcactctt        300
        ttcacagatg    tgatgactga    tttccagcag    ac                                            332
```

<210> SEQ ID NO 31
<211> LENGTH: 141
<212> TYPE: DNA
<213> ORGANISM: Homo sapien

<400> SEQUENCE: 31

```
        aaaggctatc    aagtactttg    aaggacagga    aggaatgaac    acacccaggt    ggacgtttgg         60
        tttcatttgc    aggggttcag    ggagggttgc    agggguttcag    ggagggctct    tgtcccacaa        120
        ccgggggaag    ggagagggca    c                                                           141
```

<210> SEQ ID NO 32
<211> LENGTH: 201
<212> TYPE: DNA
<213> ORGANISM: Homo sapien

<400> SEQUENCE: 32

```
        gagctgatct    cacagcacat    acagaatgat    gctactatgt    agaccctcac    tcccttggga         60
        aatctgtcat    ctaccttaaa    gagagaaaaa    agatggaaca    taggcccacc    tagtttcatc        120
        catccaccta    cataaccaac    atagatgtga    ggtccactgc    actgatagcc    agactgcctg        180
        gggtaaacct    tttcagggag    g                                                           201
```

<210> SEQ ID NO 33
<211> LENGTH: 181
<212> TYPE: DNA

<213> ORGANISM: Homo sapien

<400> SEQUENCE: 33

```
tttcaaaaca ctcatatgtt gcaaaaaaca catagaaaaa taaagtttgg tgggggtgct      60
gactaaactt caagtcacag acttttatgt gacagattgg agcagggttt gttatgcatg     120
tagagaaccc aaactaattt attaaacagg atagaaacag gctgtctggg tgaaatggtt     180
c                                                                     181
```

<210> SEQ ID NO 34
<211> LENGTH: 151
<212> TYPE: DNA
<213> ORGANISM: Homo sapien

<400> SEQUENCE: 34

```
atgtcctgca cagtatagct tggacctctg ggcctgaacc agggtgagca tcaaggcccc      60
catttctcct caccacgggg tcgcttgtca gctccaagaa ccagtctggc cccactgaga     120
acttttcagt cgagggcctg atgaatcttg g                                    151
```

<210> SEQ ID NO 35
<211> LENGTH: 291
<212> TYPE: DNA
<213> ORGANISM: Homo sapien

<400> SEQUENCE: 35

```
tctttagggc aaaatcatgt ttctgtgtac ctagcaatgt gttcccattt tattaagaaa      60
agctttaaca cgtgtaatct gcagtcctta acagtggcgt aattgtacgt acctgttgtg     120
tttcagtttg tttttcacct ataatgaatt gtaaaaacaa acatacttgt ggggtctgat     180
agcaaacata gaaatgatgt atattgtttt tgttatcta tttattttca tcaatacagt      240
attttgatgt attgcaaaaa tagataataa tttatataac aggttttctg t              291
```

<210> SEQ ID NO 36
<211> LENGTH: 201
<212> TYPE: DNA
<213> ORGANISM: Homo sapien

<400> SEQUENCE: 36

```
ctgatacaat tataataacg gttccctgaa ccttttagag tgcaattaag aacaaaaact      60
aaattttgtt tacatgaata tggaataaat acaataatca aaatatgact ctccctaaaa     120
gtgaaacaca caagccaatc cggaactgct gtgcgaaaga taaaatcgag aaaggcaagg     180
tttcggtagg aggacgcgat g                                               201
```

<210> SEQ ID NO 37
<211> LENGTH: 121
<212> TYPE: DNA
<213> ORGANISM: Homo sapien

<400> SEQUENCE: 37

```
catcacactg gcggccgctc gagcatgcat ctagagggcc caattcgccc tataatgagt      60
cgtattacaa ttcactggcc gtcgttttac aacgtcgtga ctgggaaaac cctggcgtta     120
c                                                                     121
```

<210> SEQ ID NO 38
<211> LENGTH: 200
<212> TYPE: DNA
<213> ORGANISM: Homo sapien

<400> SEQUENCE: 38

```
aaacatgtat tactctatat ccccaagtcc tagagcatga cctgcatgtt ggagatgttg      60
tacagcaatg tatttatcca gacatacata tatgatattt agagacacag tgattctttt     120
gataacacca cacatagaac attataatta cacacaaatt tatggtaaaa gaattaatat     180
gctgtctggt gctgctgtta                                                 200
```

<210> SEQ ID NO 39
<211> LENGTH: 760
<212> TYPE: DNA
<213> ORGANISM: Homo sapien

<400> SEQUENCE: 39

```
gcgtggtcgt cggccgaggt cctgggctag acctaatggt ttattattgg tggagagaaa      60
gatctggaaa tacttgaggt tattacatac tagattagct tctaatgtga accattttc      120
ttttaacagt gatcaaatta ttatttcgaa gttaatcgtt cccttggtgg ctgcatacac      180
atcgcattaa caaacatact gttgtatttt ttcccagttt tgtttggcta tgccaccaca      240
gtcatcccca gggtctatac atactatgtt tcaactgtat tatttgccat ttttggcatt      300
agaatgcttc gggaaggctt aaagatgagc cctgatgagg gtcaagagga actggaagaa      360
gttcaagctg aattaaagaa gaaagatgaa gaagtaagcc atggcactgt tgatctggac      420
caaaaagca ctcaactagg aataaacact ctacagaggt ttctcagtgg ccccatctgt      480
gtgatatgcg ggctacaca aaaatagctt cttttgcttt gttctgttct tatacctgtc      540
tgtgatctga cttggggttg gtgtgaatgt agtagagaaa ggaagctgac agatgaatac      600
tgaacacagg taatcagttt ccttaattag gttgattata agctcctgaa aagcaggaac      660
tgtattttat aattttacct gtttctcccg tggtgtctag gatagtaagt gagcagagca      720
gtaaatactg tttggtttgt tcagacctgc ccgggcggcc                            760
```

<210> SEQ ID NO 40
<211> LENGTH: 452
<212> TYPE: DNA
<213> ORGANISM: Homo sapien

<400> SEQUENCE: 40

```
aatcactaaa gatattgact agagaatgct gtgtgctatt tcaattacat ttgttttct       60
tttattaaca ggaattttga ttcttcaagg aagtggctca atttcaattt caggtgacca     120
ggtttatcgt gactttcct tcttgtttac ttttcgctag gaaggggagt tgtaggggca      180
gattcaggta ttggaatagg aaaattacgt ctaaaccatg gaaatcttgg aaatggaatt    240
ggtggaagtg ggcgaaatgg atatgggtaa ggaaaacaa aaaacccgta agctaattca      300
tcgctgtcac tgatacttct tttttctcgt tcctggtctt gagagactgg gaaaccaaca     360
gccactgcca agatggctgt gatcaggagg agaacttttct tcatctcaaa cgtttcagtc    420
agttcttttct ctcacctcgg ccgcgaccac gc                                   452
```

<210> SEQ ID NO 41
<211> LENGTH: 676
<212> TYPE: DNA
<213> ORGANISM: Homo sapien

<400> SEQUENCE: 41

```
aatctttgaa tgccaagtct cttctgtact ttcttttatt aacatcatag tctttgcatc       60
aagatacata gcaatgatag caggtttctt tttaaagctt agtattaata ttaaatattt     120
ttccccattt aaattttaca ttacttgcca agaaaaaaaa aaaattaaaa ctcaagttac      180
ttgaagcctg gacacacttc catgattagc cgggctaggt aaaagttggt ggctttattc      240
ttcctgctct ataagcagat ccaggcccta gaaagatggg accagggtat ataattgttt      300
ttgaaaagtg tgctacaaaa atggatggcc tgttataagc caggatacaa agttaaggat      360
ggggggtaagg gagggacatt ttcttccaga agaaaagaca gaatttctga agagtcccag    420
tccataattt tcccaaaatg gttggaggag agggtaaaat ctcaacatga gtttcaaagt     480
actgtctctg tgaggggccg gtagatgcct tgctgaggag ggatggctaa tttggaccat    540
gccccatccc cagctaggag aatggaaatg gaaactttaa ttgcccagtg ggtgtgaaag    600
tgggctgaag cttggttggt actgaattct ctaagaggtt tcttctagaa acagacaact    660
cagacctgcc cgggcg                                                      676
```

<210> SEQ ID NO 42
<211> LENGTH: 468
<212> TYPE: DNA
<213> ORGANISM: Homo sapien

<400> SEQUENCE: 42

```
agcgtggtcg cggccgaggt ttggccggga gcctgatcac ctgccctgct gagtcccagg       60
ctgagcctca gtctccctcc cttggggcct atgcagaggt ccacaacaca cagatttgag     120
ctcagccctg gtgggcagag aggtagggat ggggctgtgg ggatagtgag gcatcgcaat      180
gtaagactcg ggattagtac acacttgttg attaatggaa atgtttacag atccccaagc     240
ctggcaaggg aattttcttca actccctgcc ccccagccct ccttatcaaa ggacaccatt    300
ttggcaagct ctatgaccaa ggagccaaac atcctacaag acacagtgac catactaatt    360
aaaaccccct gcaaagccca gcttgaaacc ttcattagg aacgtaatcg tgtcccctat     420
cctacttccc cttcctaatt ccacagacct gcccgggcgg ccgctcga                  468
```

<210> SEQ ID NO 43
<211> LENGTH: 408
<212> TYPE: DNA
<213> ORGANISM: Homo sapien

<400> SEQUENCE: 43

```
    atcatatcaa aacactatct tcccatctgt ttctcaatgc ctgctacttc ttgtagatat      60
    ttcatttcag gagagcagca gttaaacccg tggattttgt agttaggaac ctgggttcaa     120
    acctcttttcc actaattggc tatgtctctg gacagttttt tttttttttt tttttttttaa   180
    accctttctg aactttcact ttctatggct acctcaaaga attgttgtga ggcttgagat     240
    aatgcatttg taagggtct gccagatagg aagatgctag ttatggatttt acaaggttgt     300
    taaggctgta agagtctaaa acctacagtg aatcacaatg catttacccc cactgacttg     360
    gacataagtg aaaactagcc cgaagtctct ttttcaaatt acttacag                  408

<210> SEQ ID NO 44
<211> LENGTH: 160
<212> TYPE: DNA
<213> ORGANISM: Homo sapien

<400> SEQUENCE: 44
tggtcgcggc cgaggtcttg tgtgccctgt ggtccagggg accaagaaca acaagatcca      60
    ctctctgtgc tacaatgatt gcaccttctc acgcaacact ccaaccagga ctttcaacta     120
    caacttctcc gctttggcaa acaccgtcac tcttgctgga                            160

<210> SEQ ID NO 45
<211> LENGTH: 231
<212> TYPE: DNA
<213> ORGANISM: Homo sapien

<400> SEQUENCE: 45
cgagcggccg cccgggcagg tctggggagg tgattccatc cagagtcata tctgttgtca      60
    ccccaataag tcgatcagca aggctgacag gctgtgagga aaccccggcc ttgtagcctg     120
    tcacctctgg ggggatgatg actgcctggc agacgtaggc tgtgatagat ttgggagaaa     180
    acctgactca ccctcaggaa tccggaggtc ggtgacattg tcggtgcaca c               231

<210> SEQ ID NO 46
<211> LENGTH: 371
<212> TYPE: DNA
<213> ORGANISM: Homo sapien

<400> SEQUENCE: 46
cccgggcagg tctgtgtaac atgccaaggc tttgcactttt ctgcagagca gttttttatt     60
    ttccttatca ggtacaggtt tggttttttc ttgactatct ctgatgaatt tttcatgagt    120
    ctgtatatgc agaatctttt ccctaaatac tgcttcgtcc catgtctgaa ggcgtaaaat    180
    aaagtcattc atcattttt cttgtacat gtttatttgt tcttttttcaa ttacaccaag    240
    cattactagt cagaaggaag cacttgctac ctcttgctct tcctctgcct ctggtttgga    300
    tcattttgat gacattgccc acattactca tgaaggatga caagattgca ctgtgcaatg    360
    tcaattgcct t                                                          371

<210> SEQ ID NO 47
<211> LENGTH: 261
<212> TYPE: DNA
<213> ORGANISM: Homo sapien

<400> SEQUENCE: 47
gccctgtttt tatacacttc acatttgcag aaatataatg atgccctcat tatcagtgag      60
    catgcacgaa tgaaagatgc tctggattac ttgaaagact tcttcagcaa tgtccgagca    120
    gcaggattcg atgagattga gcaagatctt actcagagat ttgaagaaaa gctgcaggaa    180
    ctagaaagtg tttccaggga tcccagcaat gagaatccta aacttgaaga cctctgcttc    240
    atcttacaag aagagtacca c                                              261

<210> SEQ ID NO 48
<211> LENGTH: 701
<212> TYPE: DNA
<213> ORGANISM: Homo sapien

<400> SEQUENCE: 48
cgagcggccc ccgggcaggt ccaattagta caagtctcat gatataatca ctgcctgcat      60
    acatatgcac agatccagtt agtgagtttg tcaagcttaa tctaattggt taagtctcaa    120
    agagattatt attccttgatg tttgctttgt attggctaac aaatgtgcag aggtaataac    180
    tatgtgatgt ccgatgtctc tgtcttttt tttgtcttta aaaataatt ggcagcaact     240
    gtatttgaat aaaatgattt cttagtatga ttgtaccgta atgaatgaaa gtggaacatg    300
    tttcttttttg aagggagag aattgaccat ttattattgt gatgttaag ttataactta    360
    ttgagcactt ttagtagtga taactgtttt taaacttgcc taataccttt cttgggtatt    420
    gttttgtaatg tgacttattt aacccccttt tttgttttgtt taagttgctg ctttaggtta   480
```

```
acagcgtgtt ttagaagatt taaatttttt tcctgtctgc acaattagtt attcagagca    540
agagggcctg attttataga agcccttga aaagaggtcc agatgagagc agagatacag     600
tgagaaatta tgtgatctgt gtgttgtggg aagagaattt tcaatatgta actacggagc   660
tgtagtgcca ttagaaactg tgaatttcca aataaatttg a                        701
```

<210> SEQ ID NO 49
<211> LENGTH: 270
<212> TYPE: DNA
<213> ORGANISM: Homo sapien

<400> SEQUENCE: 49

```
agcggccgcc cgggcaggtc tgatattagt agctttgcaa ccctgataga gtaaataaat    60
tttatgggcg ggtgccaaat actgctgtga atctatttgt atagtatcca tgaatgaatt   120
tatggaaata gatatttgtg cagctcaatt tatgcagaga ttaaatgaca tcataatact    180
ggatgaaaac ttgcatagaa ttctgattaa atagtgggtc tgtttcacat gtgcagtttg    240
aagtatttaa attaaccact cctttcacag                                     270
```

<210> SEQ ID NO 50
<211> LENGTH: 271
<212> TYPE: DNA
<213> ORGANISM: Homo sapien

<400> SEQUENCE: 50

```
atgcatttat ccatatgaac ttgattattc tgaattactg actataaaaa ggctattgtg    60
aaagatatca cactttgaaa cagcaaatga attttcaatt ttacatttaa ttataagacc    120
acaataaaaa gttgaacatg cgcatatcta tgcatttcac agaagattag taaaactgat    180
ggcaacttca gaattatttc atgaagggta caaacagtct ttaccacaat tttcccatgg    240
tcttatcctt caaaatgaaa ttccacacac t                                   271
```

<210> SEQ ID NO 51
<211> LENGTH: 241
<212> TYPE: DNA
<213> ORGANISM: Homo sapien

<400> SEQUENCE: 51

```
tggtcgcggc cgaggtgtga ggagatgaac tttgtgttaa tgggggcac tttaaatcga     60
aatggcttat ccccaccgcc atgtaagtta ccatgcctgt ctcctccctc ctacacattt    120
ccagctcctg ctgcagttat tcctacagaa gctgccattt accagccctc tgtgattttg    180
aatccacgag cactgcaggc cctccacagc gttactaccc agcaggcact cagctcttca    240
t                                                                   241
```

<210> SEQ ID NO 52
<211> LENGTH: 271
<212> TYPE: DNA
<213> ORGANISM: Homo sapien

<400> SEQUENCE: 52

```
tccaagactt aaaacttagg aaacaccttat gatgccactt taactggaag taatggagac    60
atctgattcc aaattcacat tttaaatgcc tatttgcaat cagcaaagag ccaggtatgc    120
tgcatgctgc ttgctgtaag ttacgatttg gcttcactag ctcaaatttt ttcactccac   180
caaaagataa ggcacaggcc cgtttgtcca atcaagtttg ctgaaaatac tgcagcctga   240
gtgtagacaa acttcccctg aatttgctag a                                  271
```

<210> SEQ ID NO 53
<211> LENGTH: 493
<212> TYPE: DNA
<213> ORGANISM: Homo sapien

<400> SEQUENCE: 53

```
ttagcgtggt cgcggtccga ggtctggcct gactagctca ctctgaagag tgtcttttcac    60
atggattaac caaaaaatgc attactgcct ttggcacact gtcttgaata ttctttctga   120
caatgagaaa atatgattta atggagtcgt tcaataacct cacaatctcg ctgttccgag   180
cagatagttt tcgtgccaac aggaactggc acatctagca ggttcacggc atgacctttt   240
tgtggactgg ctggcataat tggaatgggt tttgatttt cttctgctaa taactcttca    300
agcttttgaa gttttcaagc attcctctcc agttgcctgt ggttggttct tgaacaccat   360
ctccaacccc accacctcca gatgcaacct tgtctcgtga tacagacctg cccggcggc    420
cctcaagggc gaattctgca gatatccatc acactggcgg ccgctcgagc atgcatctag   480
agggcccaat tcg                                                      493
```

<210> SEQ ID NO 54
<211> LENGTH: 321
<212> TYPE: DNA
<213> ORGANISM: Homo sapien

<400> SEQUENCE: 54

```
cgtggtcgcg gccgaggtct gtttgcttgt tggtgtgagt ttttcttctg gagactttgt      60
actgaatgtc aataaactct gtgattttgt taggaagtaa aactgggatc tatttagcca     120
ctggtaagct tctgaggtga aggattcagg gacatctcgt ggaacaaaca ctccccactg     180
gactttctct ctggagatac ccttttgaat atacaatggc cttggctcac taggtttaaa     240
tacaaacaag tctgaaaccc actgaagact gagagattgc agcaatattc tctgaattag     300
gatcgggttc ataactcta a                                                321
```

<210> SEQ ID NO 55
<211> LENGTH: 281
<212> TYPE: DNA
<213> ORGANISM: Homo sapien

<400> SEQUENCE: 55

```
ttgcaaatga aactgtggat gtataataag aaaacacaag ggtttattct taacactaaa      60
attaacatgc cacacgaaga ctgcattaca gctctctgtt tctgtaatgc agaaaaatct     120
gaacagccca ccttggttac agctagcaaa gatggttact tcaaagtatg gatattaaca     180
gatgactctg acatatacaa aaaagctgtt ggctggacct gtgactttgt tggtagttat     240
cacaagtatc aagcaactaa ctgttgtttc tccgaagatg g                         281
```

<210> SEQ ID NO 56
<211> LENGTH: 612
<212> TYPE: DNA
<213> ORGANISM: Homo sapien

<400> SEQUENCE: 56

```
gcgtggtcgc ggccgaggtc ctgtccgggg gcactgagaa ctccctctgg aattcttggg      60
gggtgttggg gagagactgt gggcctggag ataaaacttg tctcctctac cacccaccctg    120
taccctagcc tgcacctgtc ctcatctctg caaagttcag cttccttccc caggtctctg     180
tgccactctg tcttggatgc tctggggagc tcatggtgtgg aggagtctcc accagaggga    240
ggctcagggg actggttggg ccagggatga atatttgagg gataaaaatt gtgtaagagc     300
caaagaattg gtagtagggg gagaacagag aggagctggg ctatgggaaa tgatttgaat     360
aatggagctg ggaatatggc tggatatctg gtactaaaaa agggtctta agaacctact     420
tcctaatctc ttccccaatc caaaccatag ctgtctgtcc agtgctctct tcctgcctcc     480
agctctgccc caggctcctc ctagactctg tccctgggct agggcagggg aggagggaga    540
gcagggttgg gggagaggct gaggagagtg tgacatgtgg ggagaggacc agacctgccc     600
gggcggccgt cg                                                         612
```

<210> SEQ ID NO 57
<211> LENGTH: 363
<212> TYPE: DNA
<213> ORGANISM: Homo sapien

<400> SEQUENCE: 57

```
gtcgcggccg aggtcctgag cgtcacccta gttctgcccc tttttagctg tgtagacttg      60
gacaagacat ttgacttccc tttctccttg tctataaaat gtggacagtg gacgtctgtc     120
acccaagaga gttgtgggag acaagatcac agctatgagc acctcgcacg gtgtccagga     180
tgcacagcac aatccatgat gcgttttctc cccttacgca ctttgaaacc catgctagaa     240
aagtgaatac atctgactgt gctccactcc aacctccagc gtggatgtcc ctgtctgggc     300
ccttttctg tttttttattc tatgttcagc accactggca ccaaatacat tttaattcac     360
cga                                                                   363
```

<210> SEQ ID NO 58
<211> LENGTH: 750
<212> TYPE: DNA
<213> ORGANISM: Homo sapien

<400> SEQUENCE: 58

```
cgtggtcgcg gccgaggtct aattccacct gactggcaga acctgcgccc ctcgcctaac      60
ctgcgccctt ctcccaactc gcgtgcctca cagaacccag gtgctgcaca gccccgagat     120
gtggcccttc ttcaggaaag agcaaataag ttggtccaag tacttgatgc ttaaggaata     180
cacaaaggtg cccatcaagc gctcagaaat gctgagagat atcatccgtg aatacactga     240
tgtttatcca gaaatcattg aacgtgcatg ctttgtccta gagaagaaat ttgggattca     300
actgaaagaa attgacaaag aagaacacct gtatattctc atcagtaccc ccgagtccct     360
```

```
      ggctggcata ctgggaacga ccaaagacac acccaagctc ggtctcttct tggtgattct    420
      gggtgtcatc ttcatgaatg caaccgtgc cagtgaggct gtcttttggg aggcactacg     480
      caagatggga ctgcgtcctg gggtgagaca tcccctccct ggagatcta aggaaacttc     540
      tcacctatga gtttgtaaag cagaaatacc tggactacag acgagtgccc aacagcaacc    600
      ccccggagta tgagttcctc tggggcctcc gtccctacca tgagactagc aagatgaaaa    660
      tgctgagatt cattgcagag gttcagaaaa gagaccctcg tgactggact gcacagttca    720
      tggaggctgc agatgaggac ctgcccgggc                                     750
```

<210> SEQ ID NO 59
<211> LENGTH: 505
<212> TYPE: DNA
<213> ORGANISM: Homo sapien

<400> SEQUENCE: 59

```
      tggccgcccg ggcaggtcca gtctacaagc agagcactct catggggagc accagatgag    60
      ttccagccgc agttcttta taagcttaa gtgcctcatg aagacgcgag gatctcttcc     120
      aagtgcaacc tggtcacatc agggcacatt cagcagcaga agtctgtttc cagtatagtc    180
      cttggtatgg ctaaattcca ctgtcccttt ctcagcagtc aataatccat gataaattct    240
      gtacaacact gtagtcaata acagcagcac cagacagcat attaattctt ttaccataaa    300
      tttgtgtgta attataatgt tctatgtgtg gtgttatcaa aagaatcact gtgtctctaa    360
      atatcatata tgtatgtctg gataaataca ttgctgtaca acatctccaa catgcaggtc    420
      atgctctaag acttggggat atagagtaat acatgtttcg tggacctcgg ccgcgaccac    480
      gctaagggcg aattctgcag atatc                                          505
```

<210> SEQ ID NO 60
<211> LENGTH: 520
<212> TYPE: DNA
<213> ORGANISM: Homo sapien

<400> SEQUENCE: 60

```
      cgtggtcgcg gccgaggtcc tcaggacaag gaaacaggta tcagcatgat ggtagcagaa    60
      accttatcac caaggtgcag gagctgactt cttccaaaga gttgtggttc cgggcagcgg    120
      tcattgcctc cccttgctgg agggctgatt ttagtgttgc ttattatgtt ggccctgagg    180
      atgcttcgaa gtgaaaataa gaggctgcag gatcagcggc aacagatgct ctcccgtttg    240
      cactacagct tcacggaca ccattccaaa aaggggcagg ttgcaaagtt agacttggaa      300
      tgcatggtgc cggtcagtgg gcacgagaac tgctgtctga cctgtgataa aatgagacaa    360
      gcagacctca gcaacgataa gatcctctcg cttgttcact ggggcatgta cagtgggcac    420
      gggaagctgg aattcgtatg acggagtctt atctgaacta cacttactga acagcttgaa    480
      ggacctgccc gggcggccgc tcgaaagggg cgaattctgc                          520
```

<210> SEQ ID NO 61
<211> LENGTH: 447
<212> TYPE: DNA
<213> ORGANISM: Homo sapien

<400> SEQUENCE: 61

```
      agagaggtgt tttattctt tggggacaaa gccgggttct gtgggtgtag gattctccag      60
      gttctccagg ctgtagggcc cagaggctta atcagaattt tcagacaaaa ctgaacctt     120
      tcttttttcc cgttggttta tttgtagtcc ttgggcaaac caatgtcttt gttcgaaaga    180
      gggaaaataa tccaaacgtt tttctttaa cttttttttt aggttcaggg gcacatgtgt      240
      aggcttgcta tataggtaaa ttgcatgtca ccaggggtttg ttgtacagat tatttcatca    300
      tccagataaa aagcatagta ccagataggt agtttttga tcctcaccct ccttccatgc      360
      tccgacctca ggtaggcccc agtgtctgac ctgcccggcg gcccgctcga aagggccaat    420
      tctgcagata tccatcacac tggccgg                                         447
```

<210> SEQ ID NO 62
<211> LENGTH: 83
<212> TYPE: PRT
<213> ORGANISM: Homo sapien

<400> SEQUENCE: 62

```
      Lys Lys Val Leu Leu Leu Ile Thr Ala Ile Leu Ala Val Ala Val Gly
      1               5                   10                  15
      Phe Pro Val Ser Gln Asp Gln Glu Arg Glu Lys Arg Ser Ile Ser Asp
                      20                  25                  30
      Ser Asp Glu Leu Ala Ser Gly Phe Phe Val Phe Pro Tyr Pro Tyr Pro
                      35                  40                  45
      Phe Arg Pro Leu Pro Pro Ile Pro Phe Pro Arg Phe Pro Trp Phe Arg
              50                  55                  60
      Arg Asn Phe Pro Ile Pro Ile Pro Ser Ala Pro Thr Thr Pro Leu Pro
      65                  70                  75                  80
```

<210> SEQ ID NO 63
<211> LENGTH: 683
<212> TYPE: DNA
<213> ORGANISM: Homo sapien

<400> SEQUENCE: 63

```
acaaagattg gtagctttta tattttttta aaaatgctat actaagagaa aaacaaaag      60
accacaacaa tattccaaat tataggttga gagaatgtga ctatgaagaa agtattctaa    120
ccaactaaaa aaaatattga aaccacttttt gattgaagca aaatgaataa tgctagattt    180
aaaaacagtg tgaaatcaca ctttggtctg taaacatatt tagctttgct tttcattcag    240
atgtatacat aaacttatttt aaaatgtcat ttaagtgaac cattccaagg cataataaaa    300
aaagwggtag caaatgaaaa ttaaagcatt tattttggta gttcttcaat aatgatrcga    360
gaaactgaat tccatccagt agaagcatct ccttttgggt aatctgaaca agtrccaacc    420
cagatagcaa catccactaa tccagcacca attccttcac aaagtccttc cacagaagaa    480
gtgcgatgaa tattaattgt tgaattcatt tcagggcttc cttggtccaa ataaattata    540
gcttcaatgg gaagaggtcc tgaacattca gctccattga atgtgaaata ccaacgctga    600
cagcatgcat ttctgcattt tagccgaagt gagccactga acaaaactct tagagcacta    660
tttgaacgca tctttgtaaa tgt                                             683
```

<210> SEQ ID NO 64
<211> LENGTH: 749
<212> TYPE: DNA
<213> ORGANISM: Homo sapiens
<220> FEATURE:
<221> NAME/KEY: misc_feature
<222> LOCATION: 534
<223> OTHER INFORMATION: n = A,T,C or G

<400> SEQUENCE: 64

```
ctgttcattt gtccgccagc tcctggactg gatgtgtgaa aggcatcaca tttccatttt     60
cctccgtgta aatgttttat gtgttcgcct actgatccca ttcgttgctt ctattgtaaa    120
tatttgtcat ttgtatttat tatctctgtg ttttccccct aaggcataaa atggtttact    180
gtgttcattt gaacccattt actgatctct gttgtatatt tttcatgcca ctgctttgtt    240
ttctcctcag aagtcgggta gatagcattt ctatcccatc cctcacgtta ttggaagcat    300
gcaacagtat ttattgctca gggtcttctg cttaaaactg aggaaggtcc acattcctgc    360
aagcattgat tgagacattt gcacaatcta aaatgtaagc aaagtaagtc attaaaaata    420
caccctctac ttgggcttta tactgcatac aaatttactc atgagccttc ctttgaggaa    480
ggatgtggat ctccaaataa agatttagtg tttattttga gctctgcatc ttancaagat    540
gatctgaaca cctctccttt gtatcaataa atagccctgt tattctgaag tgagaggacc    600
aagtatagta aaatgctgac atctaaaact aaataaatag aaaacaccag gccagaacta    660
tagtcatact cacacaaagg gagaaattta aactcgaacc aagcaaaagg cttcacgaaa    720
atagcatgga aaaacaatgc ttccagtgg                                       749
```

<210> SEQ ID NO 65
<211> LENGTH: 612
<212> TYPE: DNA
<213> ORGANISM: Homo sapiens

<400> SEQUENCE: 65

```
acagcagcag tagatggctg caacaacctt cctcctaccc cagcccagaa atatttctg      60
ccccacccca ggatccggga ccaaaataaa gagcaagcag gccccctcca ctgaggtgct    120
gggtagggct cagtgccaca ttactgtgct ttgagaaaga ggaagggat ttgtttggca    180
ctttaaaaat agaggagtaa gcaggactgg agaggccaga gaagatacca aaattggcag    240
ggagagacca tttggcgcca gtccctagg agatgggagg agggagatag tgatgagggt    300
aggcgctaag aagagtagga gggtccact ccaagtggca gggtgctgaa atgggctagg    360
accaacagga cactgactct aggtttatga cctgtccata cccgttccac agcagctggg    420
tgggagaaat caccattttg tgacttctaa taaataatg ggtctaggca acagtttca     480
atggatgcta aaacgattag gtgaaaagtt gatggagaat ttaattcag gggaattagg    540
ctgataccat ctgaaaccat ttggcatcat taaaaatgtg acaacctggt ggctgccagg    600
gaggaagggg ag                                                        612
```

<210> SEQ ID NO 66
<211> LENGTH: 703
<212> TYPE: DNA
<213> ORGANISM: Homo sapiens

<400> SEQUENCE: 66

```
tagcgtggtc gcggccgagg tacattgatg ggctggagag caggggttggc agcctgttct     60
gcacagaacc aagaattaca gaaaaaagtc caggagctgg agaggcacaa catctccttg    120
```

```
gtagctcagc tccgccagct gcagacgcta attgctcaaa cttccaacaa agctgcccag  180
accagcactt gtgttttgat tcttcttttt tccctggctc tcatcatcct gcccagcttc  240
agtccattcc agagtcgacc agaagctggg tctgaggatt accagcctca cggagtgact  300
tccagaaata tcctgaccca caaggacgta acagaaaatc tggagaccca agtggtagag  360
tccagactga gggagccacc tggagccaag gatgcaaatg gctcaacaag gacactgctt  420
gagaagatgg gagggaagcc aagacccagt gggcgcatcc ggtccgtgct gcatgcagat  480
gagatgtgag ctggaacaga ccttcctggc ccacttcctg atcacaagga atcctgggct  540
tccttatggc tttgcttccc actgggattc ctacttaggt gtctgccctc agggtccaa  600
atcacttcag gacaccccaa gagatgtcct ttagtctctg cctgaggcct agtctgcatt  660
tgtttgcata tatgagaggg tacctgcccg ggcggccgct cga                    703
```

<210> SEQ ID NO 67
<211> LENGTH: 1022
<212> TYPE: DNA
<213> ORGANISM: Homo sapiens

<400> SEQUENCE: 67

```
cttgagaaag caggattgtt ttaagttcca agatttaaca aacttactgt tcagcatcat    60
attcaagcct aaaaggaaga taggattttc aagatatatt tccaacttct ttaacatggc   120
accatggatg aactgttttct cagcactgtg ctgcttcact tggaattaag gatgaattgg   180
gaggagacag tatgacatag gtgggtaggt tgggtggtga ggggaaccag ttctaatagt   240
cctcaactcc actccagctg ttcctgttcc acacggtcca ctgagctggc ccagtccctt   300
tcactcagtg tgtcaccaaa ggcagcttca aggctcagtg caagagacc acctataacc   360
tcttcacctt ctgctgcctc tttctgctgc cactgactgc catgccatc tgctatagcc   420
gcattgtcct cagtgtgtcc aggcccagga caaggaaggg gagccatggt gagactccaa   480
ttcccaggcc ttaatcctta acccctagacc tgttgcctct agcatcattt atttatctac   540
ctacctaata gctatctacc agtcattaaa ccatggtag attctaacca tgtctagcac   600
ctgatgctag agataatttt gttgaatccc ttcaattata aacagctgag ttagctggac   660
aaggactagg gaggcaatca gtattattta ttcttgaaca ccatcaagtc tagacttggt   720
ggcttcatat ttctatcata atccctgggg gtaagaaatc atatagcccc aggttgggaa   780
ggggaaaacg gtttgcaaca ttctcctcct tgtaggaggc gagctctgtc tcactagcta   840
tgcccctcca tcaattcacc ctatactcag atcagaagct gagtgtctga attacagtat   900
atttttctaaa ttcctagccc ctgctggtga atttgccctc ccccgctcct tgacaattg   960
tccccgtgtt cgtctccggg ccctgagact ggccctgctt atcttgctga ccttcatcct  1020
ct                                                                1022
```

<210> SEQ ID NO 68
<211> LENGTH: 449
<212> TYPE: DNA
<213> ORGANISM: Homo sapiens

<400> SEQUENCE: 68

```
ccagatccat tttcagtggt ctggatttct tttattttc ttttcaactt gaaagaaact    60
ggacattagg ccactatgtg ttgttactgc cactagtgtt caagtgcctc ttgttttccc   120
agagatttcc tgggtctgcc agaggcccag acaggctcac tcaagctctt taactgaaaa   180
gcaacaagcc actccaggac aaggttcaaa atggttacaa cagcctctac ctgtcgcccc   240
agggagaaag gggtagtgat acaagtctca tagccagaga tggttttcca ctccttctag   300
atattcccaa aaagaggctg agacaggagg ttatttttcaa ttttattttg gaattaaata   360
cttttttttccc tttattactg ttgtagtccc tcacttggat atacctctgt tttcacgata   420
gaaataaggg aggtctagag cttctattc                                     449
```

<210> SEQ ID NO 69
<211> LENGTH: 387
<212> TYPE: DNA
<213> ORGANISM: Homo sapiens
<220> FEATURE:
<221> NAME/KEY: misc_feature
<222> LOCATION: 22, 26, 36, 45, 54, 56, 62, 63, 73, 92, 98, 105, 155, 174,
      194, 302, 312, 358, 375, 378, 381
<223> OTHER INFORMATION: n = A,T,C or G

<400> SEQUENCE: 69

```
gcccttagcg tgggtcgcgg cncgangtct ggagcntatg tgatnccta ggtncncagg    60
cnnatactgc tantctcatt tattctcctg cnacctantc ctctnctctg gaatcacacc   120
attattgcct gttaacactg gactgtgagt accangcaat taatttgcac caanaaagtt   180
gagggtatta tcanatattg caatctgtac agaggaaga tgatttcaat ttgatttcaa   240
cttaaccttc atctttgtct gttaacacta atagagggtg tctaataaaa tggcaaattt   300
gngatctcat tnggtataac tacactcttt tcacagatg tgatgactga atttccanca   360
acctgcccgg gcggncgntc naagggc                                       387
```

<210> SEQ ID NO 70
<211> LENGTH: 836

<212> TYPE: DNA
<213> ORGANISM: Homo sapiens

<400> SEQUENCE: 70

```
tattccattt acaaaataaa ttcagccctg cactttcttt agatgccttg atttccagaa   60
tggagcttag tgctactgaa taccctggcc acagagccac ctcaggatat tcttttctcc  120
accctagttt atttatttat agatatctgt ttacaaagtc tgtagtaaat cctgatgctg  180
accatctgaa atgtactttt tttctgaatg ctgtttcaat ctaaaatagc agcttttgag  240
aaaacaatga tgtaaattcc ttatgataaa aggatgattc tatatattct ttaatgatat  300
taaatatgcc gaagccaagc acacagtctt tctaaagtgt gtgtatgttt gtgtgaatgt  360
gaatgatact gatcttatat ctgttaaaag ttgttttaaa aagctgtggc atcccattgt  420
tcatatttgc caagtcttct gtaaagatgt ctaggacgaa atattttatg tgctaatgca  480
tgtatttgta aaccagattt gtttaccact caaaattaac ttgttttctt catccaaaaa  540
agtttatttc ttccacgtac ttaaattttc tgtgtgggta taatatagct ttctaatttt  600
tttctttcac aaaggcaggt tcaaaattct gttgaaagaa aaatgctttc tgaaactgag  660
gtataacacc agagcttgct gtttaaagga ttatatgatg tacatcagtt ctaaaatgt   720
gctcagcagt taacatgtg aatcctgttt taaagtgctc agatttcaac tgtgtaagcc  780
attgatataa cgctgtaatt aaaaatgttt atatgaaaaa aaaaaaaaaa aaaaaa      836
```

<210> SEQ ID NO 71
<211> LENGTH: 618
<212> TYPE: DNA
<213> ORGANISM: Homo sapiens

<400> SEQUENCE: 71

```
gttgcagtga gctcaagtgt tgggtgtatc agctcaaaac accatgtgat gccaatcatc   60
tccacaggag caatttgttt acctttttt tctgatgctt tactaacttc atcttttaga  120
tttaaatcat tagtagatcc tagaggagcc agtttcagaa aatatagatt ctagttcagc  180
accacccgta gttgtgcatt gaaataatta tcattatgat tatgtatcag agcttctggt  240
tttctcattc tttattcatt tattcaacaa ccacgtgaca aacactggaa ttacaggatg  300
aagatgagat aatccgctcc ttggcagtgt tatactatta tataacctga aaaaacaaac  360
aggtaatttt cacacaaagt aatagatatc atgacacatt taaaataggg cactactgga  420
acacacagat aggacatcca ggttttgggt caatattgta gacttttttgg tggatgagat  480
atgcaggttg atrccagaag gacaacaaaa acatatgtca gatagaaggg aggagcaaat  540
gccaagagct ggagctgagg aagatcactg tgaaattcta tgtagtctag ttggctggat  600
gctagagcaa agaggtgg                                                618
```

<210> SEQ ID NO 72
<211> LENGTH: 806
<212> TYPE: DNA
<213> ORGANISM: Homo sapiens

<400> SEQUENCE: 72

```
tctacgatgg ccatttgctc attgtctttc ctctgtgtgt agtgagtgac cctggcagtg   60
tttgcctgct cagagtggcc cctcagaaca acagggctgg ccttggaaaa accccaaaac  120
aggactgtgg tgacaactct ggtcaggtgt gatttgacat gagggccgga ggcggttgct  180
gacggcagga ctggagaggc tgcgtgcccg gcactgcag cgaggctcgt gtgtccccca  240
ggcagatctg ggcactttcc caacccaggt ttatgccgtc tccagggaag cctcggtgcc  300
agagtggtgg gcagatctga ccatccccac agaccagaaa caaggaattt ctgggattac  360
ccagtccccc ttcaacccag ttgatgtaac cacctcattt tttacaaata cagaatctat  420
tctactcagg ctatgggcct cgtcctcact cagttattgc gagtgttgct gtccgcatgc  480
tccgggcccc acgtggctcc tgtgctctag atcatggtga ctccccgcc ctgtggttgg  540
aatcgatgcc acggattgca ggccaaattt cagatcgtgt ttccaaacac ccttgctgtg  600
ccctttaatg ggattgaaag cacttttacc acatggagaa atatatttt aatttgtgat  660
gcttttctac aagtccact atttctgagt ttaatgtgtt ccaacactt aaggagactc   720
taatgaaagc tgatgaattt tcttttctgt ccaaacaagt aaaataaaaa taaagtcta   780
tttagatgtt gaaaaaaaaa aaaaaa                                       806
```

<210> SEQ ID NO 73
<211> LENGTH: 301
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 73

```
actctggtaa gcttgttgtt gtccaagtga agctccctca gatgaggcgt gttggccana   60
gagccattgt caacagcaga gatgctgttg aaactcaatc ccaacttagc caaattattc  120
agtcctttca ggctagctgc atcaactctg ctgatttgt tgccatcaag atgtaattcc  180
gtaagggaag gaggaagacc ttgaggaatg ctggygatat tggyatcagc aatgcggatg  240
```

```
tasgaagagc ttcttcmttc cctggaaagc cccattttca atyccttgag ctcttcakcg    300
g                                                                     301
```

<210> SEQ ID NO 74
<211> LENGTH: 401
<212> TYPE: DNA
<213> ORGANISM: Homo sapiens

<400> SEQUENCE: 74

```
agtttacatg atccctgtaa cagccatggt ctcaaactca gatgcttcct ccatctgcca    60
agtgtgttct ggatacagag cacatcgtgg cttctggggt cacactcagc ttaggctgtg   120
ggtccacaga gcactcatct ggctgggcta tggtggtggt ggctctactc aagaagcaaa   180
gcagttacca gcacattcaa acagtgtatt gaacatcttt taaatatcaa agtgagaaac   240
aagaaggcaa cataataatg ttatcagaaa gatgttagga agtaaggaca gctgtgtaaa   300
gcttgaggct gaaaagtagc ttgccagctt catttctttg gtttcttggg tagtgggccg   360
ccggaacagc aagatgtgag gttctggttc atggatcata t                       401
```

<210> SEQ ID NO 75
<211> LENGTH: 612
<212> TYPE: DNA
<213> ORGANISM: Homo sapiens

<400> SEQUENCE: 75

```
ttattttca attttattt tggttttctt acaaaggttg acattttcca taacaggtgt      60
aagagtgttg aaaaaaaaat tcaaattttt ggggagcgag ggaaggagtt aatgaaactg   120
tattgcacaa tgctctgatc aatccttctt tttctctttt gcccacaatt taagcaagta   180
gatgtgcaga agaaatggaa ggattcagct ttcagttaaa aagaagaag aagaaatggc    240
aaagagaaag ttttttcaaa tttctttctt ttttaattta gattgagttc atttatttga   300
aacagactgg gccaatgtcc acaaagaatt cctggtcagc accaccgatg tccaaaggtg   360
caatatcaag gaagggcagg cgtgatggc tatttgtttt gtattcaatg attgtctttc    420
cccattcatt tgtcttttta gagcagccat ctacaagaac agtgtaagtg aacctgctgt   480
tgccctcagc aacaagttca acatcattag agccctgtag aatgacagcc tttttcaggt   540
tgccagtctc ctcatccatg tatgcaatgc tgttcttgca gtggtaggtg atgttctgag   600
aggcatagtt gg                                                       612
```

<210> SEQ ID NO 76
<211> LENGTH: 844
<212> TYPE: DNA
<213> ORGANISM: Homo sapiens

<400> SEQUENCE: 76

```
ggctttcgag cggccgcccg ggcaggtctg atggttctcg taaaacccc gctagaaact     60
gcagagacct gaaattctgc catcctgaac tcaagagtgg agaatactgg gttgaccta   120
accaaggatg caaattggat gctatcaagg tattctgtaa tatggaaact ggggaaacat   180
gcataagtgc caatcctttg aatgttccac ggaaacactg gtggacagat tctagtgctg   240
agaagaaaca cgtttggttt ggagagtcca tggatggtgg ttttcagttt agctacggca   300
atcctgaact tcctgaagat gtccttgatg tgcagcykgc attccttcga cttctctcca   360
gccgagcttc ccagaacatc acatatcact gcaaaaatac cattgcatac atggatcagg   420
ccagtggaaa tgtaaagaag gccctgaagc tgatgggtc aaatgaaggt gaattcaagg    480
ctgaaggaaa tagcaaattc acctacacag ttctggagga tggttgcacg aaacacactg   540
gggaatggag caaaacagtc tttgaatatc gaacacgcaa tgctgttcct tgacattgca   600
ccaccaatgt ccagaggtgc aatgtcaagg aacggcaggc gagatggctt attttgttttg  660
tattcaatga ttgtcttgcc ccattcattt gtcttttttgg agcagccatc gactaggaca   720
gagtaggtga acctgctgtt gccctcagca acaagttcca catcgttgga accctgcaga   780
agcacagcct tgttcaarct gcccgtctcc tcatccagat acctcggccg cgaccacgct   840
aatc                                                                844
```

<210> SEQ ID NO 77
<211> LENGTH: 314
<212> TYPE: DNA
<213> ORGANISM: Homo sapiens

<400> SEQUENCE: 77

```
ccagtcctcc acttggcctg atgagagtgg ggagtggcaa gggacgtttc tcctgcaata    60
gacacttaga tttctctctt gtgggaagaa accacctgtc catccactga ctcttctaca   120
ttgatgtgga aattgctgct gctaccacca cctcctgaag aggcttccct gatgccaatg   180
ccagccatcc tggcatcctg gccctcgagc aggctgcggt aagtagcgat ctcctgctcc   240
agccgtgtct ttatgtcaag cagcatcttg tactcctggt tctgagcctc catctcgcat   300
cggagctcac tcag                                                     314
```

```
<210> SEQ ID NO 78
<211> LENGTH: 548
<212> TYPE: DNA
<213> ORGANISM: Homo sapiens

<400> SEQUENCE: 78
accaagagcc aagtgttaca caggatattt taaaaataaa atgttttggg aatcctcacc    60
     tcccatgcta tcttctaaga taactacaaa tattcttcaa agatttaact gagttctgcc   120
     aaggacctcc caggactcta tccagaatga ttattgtaaa gctttacaaa tcccaccttg   180
     gccctagcga taattaggaa atcacaggca aacctcctct ctcggagacc aatgaccagg   240
     ccaatcagtc tgcacattgg ttttgttaga tactttgtgg agaaaaacaa aggctcgtga   300
     tagtgcagct ctgtgcctac agagagcctc ccttttggtt ctgaaattgc tgatgtgaca   360
     gagacaaagc tgctatgggt ctaaaaccct caataaagta actaatgaca ctcaaggtcc   420
     tgggactctg agacagacgg tggtaaaacc cacagctgcg attcacattt ccaatttatt   480
     ttgagctctt tctgaagctg ttgcttccta cctgagaatt cccatttaga gagctgcaca   540
     gcacagtc                                                            548

<210> SEQ ID NO 79
<211> LENGTH: 646
<212> TYPE: DNA
<213> ORGANISM: Homo sapiens

<400> SEQUENCE: 79
accccgtcac tatgtgaata aaggcagcta gaaaatggac tcaattctgc aagccttcat    60
     ggcaacagcc catattaaga cttctagaac aagttaaaaa aaatcttcca tttccatcca   120
     tgcatgggaa aagggcttta gtatagttta ggatggatgt gtgtataata ataaaatgat   180
     aagatatgca tagtggggga ataaagcctc agagtccttc cagtatgggg aatccattgt   240
     atcttagaac cgagggattt gtttagattg ttgatctact aattttttc ttcacttata   300
     tttgaatttt caatgatagg acttattgga aattggggat aattctgttg tggtattaaa   360
     taatattcat tttttaaaaa ctcatcttgg tattgagtta atgcattgac ttccaatgaa   420
     ttgacataag cccatatttc attttaacca gaaacaaaaa ctagaaaatg ttactcccta   480
     aataggcaac aatgtatttt ataagcactg cagagattta gtaaaaaaca tgtatagtta   540
     ctttagaaac aacttctgac acttgagggt tacccaatgg tctccttccc attctttata   600
     tgaggtaaat gcaaaccagg gagccaccga ataaacagcc ctgagt                   646

<210> SEQ ID NO 80
<211> LENGTH: 276
<212> TYPE: DNA
<213> ORGANISM: Homo sapiens
<220> FEATURE:
<221> NAME/KEY: misc_feature
<222> LOCATION: 16, 29, 32, 45, 53, 55, 58, 59, 65, 66, 75, 77, 85, 90, 97,
      109, 112, 163, 170
<223> OTHER INFORMATION: n = A,T,C or G

<400> SEQUENCE: 80
gtctgaatga gcttcnctgc gagatgggan ancataaccc agaantccaa aancntanng    60
     aacgnnaaaa cccgntngaa caagnaaacn gcaactnacg gccgcctgnt gnagggcgag   120
     gacgcccacc tctcctcctc ccagttctcc tctggatcgc agncatccan agatgtgacc   180
     tcttccagcc gccaaatccg caccaaggtc atggatgtgc acgatggcaa ggtgggtgtc   240
     cacccacgaa caggtccttc gcaccaagaa ctgagg                              276

<210> SEQ ID NO 81
<211> LENGTH: 647
<212> TYPE: DNA
<213> ORGANISM: Homo sapiens

<400> SEQUENCE: 81
gtcctgcctt tcatcttttc tttaaaaaaa ataaatgttt acaaaacatt tccctcagat    60
     tttaaaattc atggaagtaa taaacagtaa taaatatgg atactatgaa aactgacaca   120
     cagaaaaaca taaccataaa atattgttcc aggatacaga tattaattaa gagtgacttc   180
     gttagcaaca cgtagacatt catacatatc cggtggaaga ctggtttctg agatgcgatt   240
     gccatccaaa cgcaaatgct tgatcttgga gtaggrtaat ggccccagga tcttgcagaa   300
     gctctttatg tcaaacttct caagttgatt gacctccaga taatagtttt caaggttttc   360
     attgacagtt ggtatgtttt taagcttgtt ataggacaga tccagctcaa ccagggatga   420
     cacattgaaa gaatttccag gtattccact atcagccagt tcgttgtgag ataaacgcag   480
     atactgcaat gcattaaaac gcttgaaata tcatcaggg atgttgctga tcttattgtt   540
     gtctaagtag agagttagaa gagagacagg gagaccagaa ggcagtctgg ctatctgatt   600
     gaagctcaag tcaaggtatt cgagtgattt aagacctta aaagcag                  647

<210> SEQ ID NO 82
```

```
<211> LENGTH: 878
<212> TYPE: DNA
<213> ORGANISM: Homo sapiens

<400> SEQUENCE: 82
ccttctttcc ccactcaatt cttcctgccc tgttattaat taagatatct tcagcttgta    60
    gtcagacaca atcagaatya cagaaaaatc ctgcctaagg caaagaaata taagacaaga   120
    ctatgatatc aatgaatgtg ggttaagtaa tagatttcca gctaaattgg tctaaaaaag   180
    aatattaagt gtggacagac ctatttcaaa ggagcttaat tgatctcact tgttttagtt   240
    ctgatccagg gagatcaccc ctctaattat ttctgaactt ggttaataaa agtttataag   300
    atttttatga agcagccact gtatgatatt ttaagcaaat atgttattta aaatattgat   360
    ccttcccttg gaccaccttc atgttagttg ggtattataa ataagagata caaccatgaa   420
    tatattatgt ttatacaaaa tcaatctgaa cacaattcat aaagatttct cttttatacc   480
    ttcctcactg gcccctcca cctgcccata gtcaccaaat tctgttttaa atcaatgacc    540
    taagatcaac aatgaagtat tttataaatg tatttatgct gctagactgt gggtcaaatg   600
    tttccatttt caaattattt agaattctta tgagtttaaa atttgtaaat ttctaaatcc   660
    aatcatgtaa aatgaaactg ttgctccatt ggagtagtct cccacctaaa tatcaagatg   720
    gctatatgct aaaaagagaa aatatggtca agtctaaaat ggctaattgt cctatgatgc   780
    tattatcata gactaatgac atttatcttc aaaacaccaa attgtcttta gaaaaattaa   840
    tgtgattaca ggtagagaac ctcggccgcg accacgct                           878

<210> SEQ ID NO 83
<211> LENGTH: 645
<212> TYPE: DNA
<213> ORGANISM: Homo sapiens

<400> SEQUENCE: 83
acaaacattt tacaaaaaag aacattacca atatcagtgg cagtaagggc aagctgaaga    60
    ataaatagac tgagtttccg ggcaatgtct gtcctcaaag acatccaaac tgcgttcagg   120
    cagctgaaac aggcttcttt cccagtgaca agcatatgtg gtcagtaata caaacgatgg   180
    taaatgaggc tactacatag gcccagttaa caaactcctc ttctcctcgg gtaggccatg   240
    atacaagtgg aactcatcaa ataatttaaa cccaaggcga taacaacgct atttcccatc   300
    taaactcatt taagccttca caatgtcgca atggattcag ttacttgcaa acgatcccgg   360
    gttgtcatac agatacttgt ttttacacat aacgctgtgc catcccttcc ttcactgccc   420
    cagtcaggtt tcctgttgtt ggaccgaaag gggatacatt ttagaaatgc ttccctcaag   480
    acagaagtga gaaagaaagg agaccctgag gccaggatct attaaacctg gtgtgtgcgc   540
    aaaagggagg gggaaggcag gaatttgaaa ggataaacgt ctccttttgcg ccgaggaatc   600
    aggaagcgtg actcacttgg gtctgggacg ataccgaaat ccggt                   645

<210> SEQ ID NO 84
<211> LENGTH: 301
<212> TYPE: DNA
<213> ORGANISM: Homo sapiens
<220> FEATURE:
<221> NAME/KEY: misc_feature
<222> LOCATION: 270, 284
<223> OTHER INFORMATION: n = A,T,C or G

<400> SEQUENCE: 84
tctgatgtca atcacaactt gaaggatgcc aatgatgtac caatccaatg tgaaatctct    60
    cctcttatct cctatgctgg agaaggatta gaaggttatg tggcagataa agaattccat   120
    gcacctctaa tcatcgatga gaatggagtt catgggctgg tgaaaaatgg tatttgaacc   180
    agataccaag ttttgtttgc cacgatagga atagctttta ttttttgatag accaactgtg   240
    aacctacaag acgtcttgga caactgaagn ttaaatatcc acangggttt attttgcttg   300
    g                                                                   301

<210> SEQ ID NO 85
<211> LENGTH: 296
<212> TYPE: DNA
<213> ORGANISM: Homo sapiens
<220> FEATURE:
<221> NAME/KEY: misc_feature
<222> LOCATION: 16, 20, 240
<223> OTHER INFORMATION: n = A,T,C or G

<400> SEQUENCE: 85
agcgtgggtc gcggcncgan gtagagaacc gactgaaacg tttgagatga agaaagttct    60
    cctcctgatc acagccatct tggcagtggc tgttggtttc cagtctctc aagaccagga   120
    acgagaaaaa agaagtatca gtgacagcga tgaattagct tcagggtttt ttgtgttccc   180
    ttaccatat ccatttcgcc cacttccacc aattccattt ccaagatttc catggttan    240
    acgtaatttt cctattccaa tacctgaatc tgccctaca actcccttc ctagcg        296
```

<210> SEQ ID NO 86
<211> LENGTH: 806
<212> TYPE: DNA
<213> ORGANISM: Homo sapiens

<400> SEQUENCE: 86

```
tctacgatgg ccatttgctc attgtctttc ctctgtgtgt agtgagtgac cctggcagtg    60
tttgcctgct cagagtggcc cctcagaaca acagggctgg ccttggaaaa accccaaaac   120
aggactgtgg tgacaactct ggtcaggtgt gatttgacat gagggccgga ggcggttgct   180
gacggcagga ctggagaggc tgcgtgcccg gcactggcag cgaggctcgt gtgtccccca   240
ggcagatctg ggcactttcc caacccaggt ttatgccgtc tccagggaag cctcggtgcc   300
agagtggtgg gcagatctga ccatccccac agaccagaaa caaggaattt ctgggattac   360
ccagtccccc ttcaacccag ttgatgtaac cacctcattt tttacaaata cagaatctat   420
tctactcagg ctatgggcct cgtcctcact cagttattgc gagtgttgct gtccgcatgc   480
tccgggcccc acgtggctcc tgtgctctag atcatggtga ctcccccgcc ctgtggttgg   540
aatcgatgcc acggattgca ggcaaatttc agatcgtgt ttccaaacac ccttgctgtg   600
cccttttaatg ggattgaaag cacttttacc acatggagaa atatattttt aatttgtgat   660
gcttttctac aaggtccact atttctgagt ttaatgtgtt tccaacactt aaggagactc   720
taatgaaagc tgatgaattt tcttttctgt ccaaacaagt aaaataaaaa taaaagtcta   780
tttagatgtt gaaaaaaaaa aaaaaa                                         806
```

<210> SEQ ID NO 87
<211> LENGTH: 620
<212> TYPE: DNA
<213> ORGANISM: Homo sapiens

<400> SEQUENCE: 87

```
tttttgcatc agatctgaaa tgtctgagag taatagtttc tgttgaattt ttttttgttc    60
attttttctgc acagtccatt ctgtttttat tactatctag gcttgaaata tatagtttga   120
aattatgaca tccttcctct ttgttatttt cctcatgatt gctttggcta ttcaaagttt   180
attttagttt catgtaaatt tttgaattgt attttccatt attgtgaaaa tagtaccact   240
gcaattttaa taggaagttt attgaatcta tagattactt tggataatat ggcacttcaa   300
taatattcat gttttcaatt catagacaaa atatttttaaa atttatttgt atcttttcta   360
attttttcctt tttttattgt aaagatttac ctccttggtt aatatttttcc tcagaaattt   420
attatttaag gtatagtcaa taaaattttc ttcctctatt ttgtcagata gtttaagtgt   480
atgaaaccat agatatactt gtatgttaat tttatatttt gctaatttac tgagtgtatt   540
tattagttta gagaggtttt aatgtactgt ttatggtttt ttaaatataa gattacttat   600
tttttaaaaa aaaaaaaaa                                                 620
```

<210> SEQ ID NO 88
<211> LENGTH: 308
<212> TYPE: DNA
<213> ORGANISM: Homo sapiens
<220> FEATURE:
<221> NAME/KEY: misc_feature
<222> LOCATION: 9, 189, 194, 206, 238, 296
<223> OTHER INFORMATION: n = A,T,C or G

<400> SEQUENCE: 88

```
tagctgtgnt cagcaggccg aggtttttt ttttttgag atggagtctc gccctgtcac    60
ccaggctgga gtgcagtggc ctgatctcag ctcactgcaa gctccacctc ctggattcac   120
gctattctcc tgcctcagcc tcccaagtag ctgggactac aggcgcccgc caccacgccc   180
agctaattnt ttgnatttttt agtacnagat gcggtttcat cgtgttagcc agcatggnct   240
cgatctcctg acctcgtgaa ctgcccgcct cggcctccca aagacctgcc cgggcnggcc   300
gctcgaaa                                                            308
```

<210> SEQ ID NO 89
<211> LENGTH: 492
<212> TYPE: DNA
<213> ORGANISM: Homo sapiens
<220> FEATURE:
<221> NAME/KEY: misc_feature
<222> LOCATION: 448
<223> OTHER INFORMATION: n = A,T,C or G

<400> SEQUENCE: 89

```
agcggccgcc cggcaggtc tgttaagtaa catacatatc accttaataa aaatcaagat    60
gaaatgtttt agaaactatt ttatcaaaag tggctctgat acaaagactt gtacatgatt   120
gttcacagca gcactattaa tgccaaaaag tagacaaaac ctaaatgtcc attaactgat   180
aagcaaaatg tggtatatcc atacaatgga atattatgta gcccacaaca tggcatggag   240
tactacaaca tggatgagcc tcaaaaacgt tatgctaaat gaaaaaagtc agatatagga   300
```

```
    aaccacatgt catatgatcc catttatatg aaatagccag aaaaggcaag tcatagaaac    360
    aagatagatc ggaaaatggg ttggaggact acaaatggca ccagggatct tgaagttga     420
    tggaaatggt ctaaaatcag actgtggntg tggttgaaca agtctgtaaa tttaccaaaa    480
    tgcgttaata ca                                                        492
```

<210> SEQ ID NO 90
<211> LENGTH: 390
<212> TYPE: DNA
<213> ORGANISM: Homo sapiens
<220> FEATURE:
<221> NAME/KEY: misc_feature
<222> LOCATION: 106, 184, 206, 209, 234, 314
<223> OTHER INFORMATION: n = A,T,C or G

<400> SEQUENCE: 90

```
    tcgagcggcc gcccgggcag gtacaagctt tttttttttt tttttttttt ttttctaaca    60
    gttctctgtt ttattgcaat acagcaaagt ctggttaata ttaagngata tcaacataaa    120
    gtattggtga ggagtctttt gtgacatttt ttaccatccc accttaaata tttctgtgca    180
    aaanaatcca catcattgtt tggtancana ggatctctta aaaagttccc taanacactg    240
    agggcataaa accaaacaaa ataaaataag gagtgatagg ctaaagcagt atcttcccct    300
    ccatccacat ttgncaagca ttatattcta accaaaaaat gatcacacca ggccatgcaa    360
    aactgtccaa tattaccgag aaaaaaccct                                     390
```

<210> SEQ ID NO 91
<211> LENGTH: 192
<212> TYPE: DNA
<213> ORGANISM: Homo sapiens

<400> SEQUENCE: 91

```
    agcgtggtcg cggccgaggt ctgtcaatta atgctagtcc tcaggattta aaaaataatc    60
    ttaactcaaa gtccaatgca aaaacattaa gttggtaatt actcttgatc ttgaattact    120
    tccgttacga aagtccttca cattttcaa actaagctac tatatttaag gcctgcccgg     180
    gcggccgctc ga                                                        192
```

<210> SEQ ID NO 92
<211> LENGTH: 570
<212> TYPE: DNA
<213> ORGANISM: Homo sapiens
<220> FEATURE:
<221> NAME/KEY: misc_feature
<222> LOCATION: 519, 559
<223> OTHER INFORMATION: n = A,T,C or G

<400> SEQUENCE: 92

```
    agcgtggtcg cggccgaggt ctgacaacta acaaagaagc aaaaactggc atcttggaca    60
    tcctagtatt acacttgcaa gcaattagaa cacaaggagg gccaaggaaa aagtttagct    120
    ttgaatcact tccaaatcta ctgattttga ggttccgcag tagttctaac aaaacttttc    180
    agacaatgtt aactttcgat taagaaagaa aaaaacccca aacatcttca ggaattccat    240
    gccaggttca gtctcttcca gtgagcccgc ttgctaaaag tccacgtgca ccattaatta    300
    gctgggctgg cagcaccatg taaaaagaag cctattcacc accaaccaca cagactagac    360
    atgtaaagta ggatcaagta atggatgaca accatggtcg tggaatatgg tcaatgagag    420
    tcagaaaagt acaggcacca gtacaagcag cagataacag aattgacggg ccaaaggata    480
    aaaataggct tatttaaata ggatgctaca gaacacatnc acttctaatt ggaagctgct    540
    ttacactggg tggcattgna ccatatgcat                                     570
```

<210> SEQ ID NO 93
<211> LENGTH: 446
<212> TYPE: DNA
<213> ORGANISM: Homo sapiens
<220> FEATURE:
<221> NAME/KEY: misc_feature
<222> LOCATION: 328, 389
<223> OTHER INFORMATION: n = A,T,C or G

<400> SEQUENCE: 93

```
    tcgagcggcc gcccgggcag gtccaggttt ttatttagtt gtgtaatctt ggacaagtta    60
    cctaactttt ttgagtctga atatatttaa tctgcaaaat gagaatcatg ataatacgtc    120
    ataggcttaa ttaggaggat taaatgaaat aatttatagg tggtgccatg gttacataca    180
    agtattagta gttaattctt ttcctttgtt tacttttata gtataggttg gatgaaggtt    240
    ccagtatagg caaaaatact acttgggggt aaagtagagt gtgatacttt atttgaaatg    300
    ttccctgaat ctgatcttta cttttttgnta ctgctgcact acccaaatcc aaattttcat    360
```

```
          cccaacattc ttggatttgt gggacagcng tagcagcttt tccaatataa tctatactac   420
          atcttttctt actttggtgc tttttg                                        446
```

<210> SEQ ID NO 94
<211> LENGTH: 409
<212> TYPE: DNA
<213> ORGANISM: Homo sapiens

<400> SEQUENCE: 94

```
          cgagcggccg cccgggcagg tccatcagct cttctgctta gaatacgagg cagacagtgg    60
          agaggtcaca tcagttatcg tctatcaggg tgatgaccca agaaaggtga gtgagaaggt   120
          gtcggcacac acgcctctgg atccacccat gcgagaagcc tcaagttgc gtatccagga    180
          ggagattgca aagcgccaga gccaacactg accatgttga aggcgttctc tccaggctgg   240
          attcactgca ctcggaagaa ttctgcccag ggaatttagt gtggggtac caggaccagt    300
          ttgtcttgat cttgagaccc ccagagctgc tgcatccata gggtgttgca ggactacacc   360
          tggcctgcct tgcagtcatt ctttcttata tgttgaccca tttgcccaa              409
```

<210> SEQ ID NO 95
<211> LENGTH: 490
<212> TYPE: DNA
<213> ORGANISM: Homo sapiens
<220> FEATURE:
<221> NAME/KEY: misc_feature
<222> LOCATION: 486
<223> OTHER INFORMATION: n = A,T,C or G

<400> SEQUENCE: 95

```
          tcgagcggcc gcccgggcag gtcctacttg tttgcagctt ccacacactg cacctaccta    60
          ctacctctct tccatgctta actgggttta gaaaggtgag ctatgcgtag aagaactact   120
          tgggatattc aagtgctgta tttgaacgat aagcctatag ataacagtct gaagctgcaa   180
          gggagacttt gttagtacac tactataaac aggtaaacta cctgtttgta cttgatatag   240
          tgcatatgaa atgactgatt taatacaaaa ctacagaaca tgcaaaattt tttctgagat   300
          gttaagtatt acttcagtgg agaacaaaac ttacttaacc tttcgctaat gcatgtagta   360
          ccagaaagca aacatgtttt tagcttcctt tactcaaaat atgaacatta agtggttgtg   420
          aattttgtct gccaagtggt tcagaaaata cattataaat aacctaagtt aaaaaaaaga   480
          aactgngaac                                                          490
```

<210> SEQ ID NO 96
<211> LENGTH: 223
<212> TYPE: DNA
<213> ORGANISM: Homo sapiens

<400> SEQUENCE: 96

```
          agcgtggtcg cggccgaggt ctggaagccc accctaggac ttgaatggca ccttgtcctt    60
          tctctgccag taatgcaatc caacacaata tgctacaggg aaaacagaat ttccacggtg   120
          ccgccctctg gtacaaggga aacagcacgc aaagcaaaag gccacagagg gctccctgag   180
          aatccagtac aactaagcga ggacctgccc gggcggccgc tcg                     223
```

<210> SEQ ID NO 97
<211> LENGTH: 527
<212> TYPE: DNA
<213> ORGANISM: Homo sapiens
<220> FEATURE:
<221> NAME/KEY: misc_feature
<222> LOCATION: 404, 436, 451, 476
<223> OTHER INFORMATION: n = A,T,C or G

<400> SEQUENCE: 97

```
          tcgagcggcc gcccgggcag gtctgtgcag agacactga agtgggtagt gtccataatc    60
          tttttagcct gttgctgaaa ttccagttgt actccttcaa accaaaatgc ttacaggatc   120
          atgggaaagc ctcggttgca gaaatcaaga caggcaagtg ggaagataac tcggctttga   180
          ggttaaacag atctgggttc aaagcatagt ttcactctct gtcttgtgaa gtgtcctggg   240
          tgaagtcatt tcctctcttg aatttcagag aggatgaaaa tataaaaagt ataataacta   300
          tcttcataat ctttgtgagg attaaagaag acgaagtgtg tgaaaagcta agcacagagc   360
          aggcattcta caataagtag ttattatttt tggaaccatc ccgncctag ccccagccca    420
          attaccttct cttagnctct tcatatcgaa ngccgtaatc ttgaccttct cttgcnactg   480
          gattggtgct ggttgatgcc caaacttccc gagatgctgt ctgggaa                 527
```

<210> SEQ ID NO 98
<211> LENGTH: 514

<212> TYPE: DNA
<213> ORGANISM: Homo sapiens
<220> FEATURE:
<221> NAME/KEY: misc_feature
<222> LOCATION: 455
<223> OTHER INFORMATION: n = A,T,C or G

<400> SEQUENCE: 98

```
tcgagcggcc gcccgggcag gtctggctcc catggccctt ggggtggcct gactctgtca   60
ctattcctaa aaccttctag gacatctgct ccaggaagaa ctttcaacac caaaattcat  120
ctcaatttta cagatgggaa aagtgattct gagaccagac cagggtcagg ccaaggtcat  180
ccagcatcag tggctgggct gagactgggc ccaggaacc ctgtctgctc ctcttttcc    240
cagagctgtg agttctctag ccaaggctgc actcttgagg gagagccagg aagcatagct  300
gaggccatga caacctcact cttcacctga aaatttaacc cgtggcagag gatccaggca  360
catataggct tcggagccaa acaggacctc ggccgcgacc acgctaagcc gaattccagc  420
acactggcgg ccgttactag tggatcccga gcttnggtac caagcttggc gtaatcatgg  480
gcatagctgg ttcctggggt gaaaatggta tccg                              514
```

<210> SEQ ID NO 99
<211> LENGTH: 530
<212> TYPE: DNA
<213> ORGANISM: Homo sapiens
<220> FEATURE:
<221> NAME/KEY: misc_feature
<222> LOCATION: 430, 522
<223> OTHER INFORMATION: n = A,T,C or G

<400> SEQUENCE: 99

```
tcgagcggcc gcccgggcag gtctgaagaa acaggtataa atttggcagc cagtaatttt   60
gacagggaag ttacagcttg catgacttta aatatgtaaa tttgaaaata ctgaattcg  120
agtaatcatt gtgctttgtg ttgatctgaa aaatataaca ctggctgtcg aagaagcatg  180
ttcaaaaata tttaattcac ttcaaaatgt catacaaatt atggtggttt ctatgcaccc  240
ctaaagcttc aagtcattta gctcaggtac atactaaagt aatatattaa ttcttccagt  300
acagtggtgt ttcataccat tgacatttgc atacccctaga ataatttaag aaagacatgt  360
gtaatattca caatgttcag aaaagcaagc aaaaggtcaa ggaacctgct ttggttcttc  420
tggagatggn ctcatatcag cttcataaac attcattcta caaaatagta agctaaccat  480
ttgaaccca atttccagat taagcatatt ttctcataaa tnatgaagcc               530
```

<210> SEQ ID NO 100
<211> LENGTH: 529
<212> TYPE: DNA
<213> ORGANISM: Homo sapiens

<400> SEQUENCE: 100

```
agcgtggtcg cggccgaggt ccaggcacgg tggcttatgt gtgtaatccc agcacttggg   60
gaggctgagg gaggtggatc acttgagtcc aggagtttga ccagtctg ggcaacatgg    120
cgaaacttca tcactaccaa agaagaaaaa aattagccag gtgtggtggt gtatgcctgt  180
agtcccagat actctggtgg ctgaggtgag aggatagctt gagcccagga aattgaggct  240
gcagtgaact atgattgcac tactgtgctc cagcttgggc aacagagtga gatcttgtct  300
ccaaaagtcc ttgaaggatt ttaggaagtt gttaaaagtc ttgaaacgat gtttgggggc  360
atgttagggt tcttgaatgt ttaattcctc taataactgc ttattcaaga gaagcatttc  420
tgactgggtg cggggcagtg gcttcatgcc ccataatccc agtactttgg gaggctgaag  480
caggaacatt gcttgagccc aggacttcaa gaacagcctg ggtaacata               529
```

<210> SEQ ID NO 101
<211> LENGTH: 277
<212> TYPE: DNA
<213> ORGANISM: Homo sapiens

<400> SEQUENCE: 101

```
tcgagcggcc gcccgggcag gtcgcaggaa gaggatggaa actgaggagt ccaggaagaa   60
gagggaacga gatcttgagc tggaaatggg agatgattat attttggatc ttcagaagta  120
ctgggattta atgaatttgt ctgaaaaaca tgataagata ccagaaatct gggaaggcca  180
taatatagct gattatattg atccagccat catgaagaaa ttggaagaat tagaaaaaga  240
agaagagctg agaacagacc tcggccgcga ccacgct                           277
```

<210> SEQ ID NO 102
<211> LENGTH: 490
<212> TYPE: DNA
<213> ORGANISM: Homo sapiens

```
<400> SEQUENCE: 102
gcgtggtcgc ggccgaggtc tgacggcttt gctgtcccag agccgcctaa acgcaagaaa    60
    agtcgatggg acagttagag gggatgtgct aaagcgtgaa atcagttgtc cttaattttt   120
    agaaagattt tggtaactag gtgtctcagg gctgggttgg ggtccaaagt gtaaggaccc   180
    cctgcccctta gtggagagct ggagcttgga gacattaccc cttcatcaga aggaatttc   240
    ggatgttttc ttgggaagct gttttggtcc ttggaagcag tgagagctgg gaagcttctt   300
    ttggctctag gtgagttgtc atgtgggtaa gttgaggtta tcttggagca aaggtcttc   360
    tagggcacaa aactcactct aggtttatat tgtatgtagc ttatattttt tactaaggtg   420
    tcaccttata agcatctata aattgacttc ttttctttag ttgtatgacc tgccccgggc   480
    ggccgctcga                                                           490

<210> SEQ ID NO 103
<211> LENGTH: 490
<212> TYPE: DNA
<213> ORGANISM: Homo sapiens

<400> SEQUENCE: 103
gagcggccgc ccgggcaggt ccaaaccagc ttgctcataa gtcattaacc aaatccatta    60
    taggtaattt gttcagttca atgtttacaa ttcttatgga aaaaattagc aacacacaca   120
    tttaaaacgt gtgcatttac ctttgcgtga gtgcttaaaa tacatatttc tatttcaaga   180
    tgacatttaa aaattattct aatatatcag cagcaaaaat ataatttgca attacaaaaa   240
    actaaactag aatccttaag ttattctcat gtttacagtt gtgattcttt aataaatact   300
    attatgcagc tctattgttt aagctttctg gatttggttt aaacacatgc atatatattg   360
    tcaattgtgg gaagcttac aagttatatt ccatgcactt tttggacaga gttctaacag   420
    agccagccag tccacaaaac aggcaagaca aaagttgaat taactggggc aaaataggac   480
    tcttatgcaa                                                           490

<210> SEQ ID NO 104
<211> LENGTH: 489
<212> TYPE: DNA
<213> ORGANISM: Homo sapiens

<400> SEQUENCE: 104
cgtggtcgcg gccgaggtcc aggctggtct cgaactcctg accttgtgat ctgcccgcct    60
    cggcctccca agtgttggg attacaggca tgagccactg cgcccgaccg agttgaacat   120
    ttaatgtcag actaggccag agtttctcaa tcttttatt ctcacttccc aaaggagccg   180
    ttggagattt tccctcaat ctctctcctt catgaaattt cataccacaa atatagtatg   240
    ttttatttat gtactgtgac cctttgaagg atcacaaacc aatataatag ttttttcttt   300
    taacccgtca aggaccaagt ttttgcccct gttggaaatg cataaactga actgatgaat   360
    tggtatagat ggcttttatc atgaggatca gaaaaacttg aaattccttg gctacgacac   420
    tccatattta tcaccgtata gggaggacct tggtatgggg aagtagaaac acttctacac   480
    tttacagca                                                            489

<210> SEQ ID NO 105
<211> LENGTH: 479
<212> TYPE: DNA
<213> ORGANISM: Homo sapiens
<220> FEATURE:
<221> NAME/KEY: misc_feature
<222> LOCATION: 142, 453
<223> OTHER INFORMATION: n = A,T,C or G

<400> SEQUENCE: 105
gcgtggtcgc ggccgaggtc tgactggctt cagccccaga agttgagctg gcctttagac    60
    aaaataattg cacctccctc tgctgcttat tcccttccgt ttttcatttg agtgtgaaca   120
    gttagataaa atctgtggct gnctcttcca ccttgctcta gtttccattg ctgtgagcag   180
    gccctcctat gccccgcatt tagctacaat gctgtggact cacttgattc ttttttctccg   240
    agctttgtct agaaatatgt gaaggtgagg ttaagtgctt ctctgtgtag atccacttag   300
    ccctgtctgc tgtctcgatg ggcgttgctt cgtctctcct ctcttccatc ctttccattt   360
    gcttctcacc accttctggc ttcttttctt aatgcaataa aggcagtttc taacaaagaa   420
    agaatgtggg ctttggagtt agacagacct ggntttaaat tctgcttctg gctctccaa   479

<210> SEQ ID NO 106
<211> LENGTH: 511
<212> TYPE: DNA
<213> ORGANISM: Homo sapiens

<400> SEQUENCE: 106
tcgcggccga ggtccaaaac gtggattcca atgacctgcc ttgagcccgc ggttgccagg    60
    agttggacct gcagtagtat gggaagctca cggcctaaat accgactgcc ctctgacccc   120
```

```
accgtccagc gattctagaa catttctagt aggaaagaca tagcaaggga ttttcatgat    180
tgggaaatac tgggagacaa gctgaagatt tgttaagggc tatgcttctg tcatcttttta   240
ggtatttaag gctactcctt tagctagcta ctttgagctg tttaaagtga ctatctccct    300
acacagagtt acacaatgag catctctgaa agagaatatt accctggatt tccaaagatg    360
tactctaaca ggatgaccag gcaaaaggtg acccggggga ggagtctgtt ataacactcg    420
gacccacatg ttctcaaggc acttcagaac tttgggaaat cattttgtac cggatcctca    480
gaaagcattt atggaaatac acatccttta g                                   511

<210> SEQ ID NO 107
<211> LENGTH: 451
<212> TYPE: DNA
<213> ORGANISM: Homo sapiens

<400> SEQUENCE: 107
ggccgcccgg gcaggtccag aatatcaaat caaaaggtca caatgttca cttcctcctc     60
caccctctta catattggat cttcaattgc aatagggagt gtaagatggg catttagag    120
acgtagttgc atcagcagaa gcaaacccat cttatacaaa tgggttttgg ggataggaaa   180
aggctgctaa aaattcacaa gtcaccattc cccagaagca atgaatagcc gtagaagacc   240
aaggaagatc aacaagtttc caagtgctca agccagaga tttggcccctt ccaaaatacc   300
accaggacgc ctggacccgt gggctctccg catgtcacca ctgactgcca ggatgctgct   360
gcacctccct tccttgagac acaacagaga gacagtgaag tcacccaaga ctgggatcat   420
cagaggctcc tcatgcttgc tacagagaag c                                  451

<210> SEQ ID NO 108
<211> LENGTH: 461
<212> TYPE: DNA
<213> ORGANISM: Homo sapiens

<400> SEQUENCE: 108
ccgcccgggc aggtcctgaa acattcaga ctaatcaaaa tggtactact gtaacttctt     60
ataatacata atataaaagt ttttgaaaga tatagacaca attacccct aaacaacaca    120
ctatctgatt ctcaaaagca atggctattt aacaagatgt aaaaggacaa taacatatca   180
aagaacttc acacacctaa agatagcatt tagcagcaag ttagtcagac aaaacaaaca   240
caaatatttt cacatttcct atgtttgttt ttaactttac ttcataaagc cactgataat   300
tgaggtttct ttcaagtata agatttctaa aattaaaaac tgttttttgac atatttttat   360
aaagaaataa aaagcaaaac gcaatccaac tatttatatg agtccctctt ctccaacagc   420
tttagatggt tttctgagta ctttttttaca cagaatattt t                      461

<210> SEQ ID NO 109
<211> LENGTH: 441
<212> TYPE: DNA
<213> ORGANISM: Homo sapiens

<400> SEQUENCE: 109
ggccgcccgg gcaggtctga ttataagaga aagaaatcca gtgacacgag ggcaggcagg    60
ccccgctctg ctctgatcga gaaaagcttc ctgatgtcag gggagatgga ctgccaccat   120
cagaaccatg gcactttggg tgaaggtgtg tcagcgacca aggggggcagg aaatgggcag   180
tgactaaggg ggcaggaaac aggcaggcac atggcaaggt tctcccagcc catcagccca   240
gtgatggcct cgattttgaa gctgcactgt tgtctgaaaa gcacaattac tggtgactct   300
taacaaactt cagcatactg gggaaggaga ctgtcaagta actgaattgg aaagatgaaa   360
aagaaccatc tctaaaagtt gatgcttgtc agaagaataa cctcctttgt gcaagtcttg   420
caacatcttc attcaaccac a                                              441

<210> SEQ ID NO 110
<211> LENGTH: 451
<212> TYPE: DNA
<213> ORGANISM: Homo sapiens
<220> FEATURE:
<221> NAME/KEY: misc_feature
<222> LOCATION: 260, 361
<223> OTHER INFORMATION: n = A,T,C or G

<400> SEQUENCE: 110
ggtcgcggcc gaggtctggg aaggggtga gaatccctgg gccttgccca gtcctgagct      60
ctgggtgtct gcagggaagc acagtggtga gttagtgtta aagaaagcat ccagagaggt    120
aagagggggct tgggtagcac ccttttgcctc tgtcacttcc gcaaaaactt cttgttgagg   180
aggaagatga gaaggttgac attgactttg gccttgttga agagtttcat gacagccaca    240
ccctcatact ggagctgcan gagatcctga tagtgaagct tgaaatcgct ccatgtccac    300
acccaggaac ttggcattta cttcaaactt tcctgcctca tctcccggcg tgatgtcaaa    360
natgacgttt cttgaagtga gaggcggaaa agatcttcaa tttccaccaa agacacccctt   420
tttccaggaa gcttgagcaa caagtgtaat g                                   451
```

<210> SEQ ID NO 111
<211> LENGTH: 407
<212> TYPE: DNA
<213> ORGANISM: Homo sapiens
<220> FEATURE:
<221> NAME/KEY: misc_feature
<222> LOCATION: 26, 33, 36, 79, 105, 111, 133, 149, 186, 206, 220, 239, 245, 259, 336, 375, 383, 393
<223> OTHER INFORMATION: n = A,T,C or G

<400> SEQUENCE: 111

```
ggccgacgtt cgacctgact tctttngagc agntgncact acccgtcttg aggaatgccg    60
actgcagaca gtggcccang gcaaagagtg tgcgtcatcg atganattgg naagatggag   120
ctcttcagtc agntttttcat tcaagctgnt cgtcagacgc tgtctacccc agggactata  180
atcctnggca caatcccagt tcctanagga aagccactgn ctcttgtaga agaaatcana  240
cacanaaagg atgtgaacng tgtttaatgt caccaaggga aaacatgaaa ccaccttctg  300
ccagatatcg ggacgttgcg tgcagatcaa gcacgnaagt gaagacgcgt gcattccttg  360
ccttccgtga acgantgccc agntcaagaa gancctgatg gaaccct              407
```

<210> SEQ ID NO 112
<211> LENGTH: 401
<212> TYPE: DNA
<213> ORGANISM: Homo sapiens
<220> FEATURE:
<221> NAME/KEY: misc_feature
<222> LOCATION: 363
<223> OTHER INFORMATION: n = A,T,C or G

<400> SEQUENCE: 112

```
tcgcggccga ggtcggccga ggtctgacat ctgttgtctg tgataaccac ttctgtattg    60
cgtcttaacc acttctgtat tgtgtggttt taactgccta aggcggcaat gggcagtggg   120
cccctttccc ttaggatggg tatcaattca acaatatttta taaggcattt actgtgtgct  180
aagcatttgg aagacccagg ctacaaaata agacatagtt cctgccctcc aggccagcag  240
agggaggcac aaatacccag gaatctctga tgggtgtgaa gtgcggtcgt gggccacaga  300
aaatgaccgt catggagacc ctgctaaagg tcggaccctg agcccaaagg ggtattcaga  360
agnggagatg attttggccc cactcataga tgggtggcaa a                      401
```

<210> SEQ ID NO 113
<211> LENGTH: 451
<212> TYPE: DNA
<213> ORGANISM: Homo sapiens

<400> SEQUENCE: 113

```
gtcgcggccg aggtccatat taaaaagtcc atcataaaca aagactcctc ctcatggtat    60
gaatatgctc catatgccca taatggtgca taacggactt agaaattcca atgagtctta   120
gggttgaaat ttccaatgac ctgagcaagg cagctcccta tagcttctgg ataacatttt  180
acacccagag ttcaggctta aacagaccta tcaacacaat tattttcgga ttgtctgtct  240
agaaaacggc aatgctcaaa ggaatataaa taagggtggg gggacatatg cttccagcct  300
ggcctttctc catgtggtaa aaaacaatgg aatggctgtg ttaatttttt tttaatcttt  360
tctgaccttt actatgtttg gtaatgcaaa taagtcaggg aaaacaaaat gaacaggtct  420
catcacttaa ttaatactgg gttttcttct t                                  451
```

<210> SEQ ID NO 114
<211> LENGTH: 441
<212> TYPE: DNA
<213> ORGANISM: Homo sapiens

<400> SEQUENCE: 114

```
ggccgccgg gcaggtccat cctgtcagag atgggagaag tcacagacgg aatgatggat    60
acaaagatgg ttcactttct tacacactat gctgacaaga ttgaatctgt tcattttttca  120
gaccagttct ctggtccaaa aattatgcaa gaggaaggtc agcctttaaa gctacctgac  180
actaagagca cactgttgtt tacatttaat gtgcctggct caggtaacac ttacccaaag  240
gatatggagg cactgctacc cctgatgaac atggtgattt attctattga taaagccaaa  300
aagttccgac tcaacagaga aggcaaacaa aaagcagata agaaccgtcc ccgagtagaa  360
gagaacttct tgaaacttga cacatgtgca aagacaggaa gcagcacagt ctcggcggga  420
ggaagaaaaa aagaacagag a                                            441
```

<210> SEQ ID NO 115
<211> LENGTH: 431

```
<212> TYPE: DNA
<213> ORGANISM: Homo sapiens
<220> FEATURE:
<221> NAME/KEY: misc_feature
<222> LOCATION: 317
<223> OTHER INFORMATION: n = A,T,C or G

<400> SEQUENCE: 115
gccgcccggg cagtccatt  ggcggtgaca aaaggaaaag aagcaaagag actcagtcca   60
taatgctgat tagttagaag aaagggctag gattgagaaa gtaccaggaa cttttaatta  120
tttaaaagag aatgctgact gttaatgttt taaatcttac tgttcaaatg tactaatatg  180
aattttacc  ctttgtgcat gaatattcta aacaactaga agacctccac aatttagcag  240
ttatgaaagt taaactttt  attataaaaa ttctaaacct tactgctcct ttaccaggaa  300
catgacacac tatttancat cagttgcata cctcgccaat agtataattc aactgtcttg  360
cccgaacaat catctccatc tggaagacgt aagcctttag aaacacattt ttctattaat  420
ttctctagaa c                                                      431

<210> SEQ ID NO 116
<211> LENGTH: 421
<212> TYPE: DNA
<213> ORGANISM: Homo sapiens

<400> SEQUENCE: 116
gtcgcggccg aggtccagaa atgaagaaga agtttgcaga tgtatttgca aagaagacga   60
aggcagagtg gtgtcaaatc tttgacggca cagatgcctg tgtgactccg gttctgactt  120
ttgaggaggt tgttcatcat gatcacaaca aggaaccggg gctcgtttat caccagtgag  180
gagcaggacg tgagcccccg ccctgcacct ctgctgttaa acacccagc  catcccttct  240
ttcaaaaggg atcctttcat aggagaacac actgaggaga tacttgaaga atttggattc  300
agcccgcgaa gagatttatc aagcttaact cagataaaat cattgaaagt aataaggtaa  360
aagctaagtc tctaacttcc aggcccacgg ctcaagtgaa tttcgaatac tgcatttaca  420
g                                                                 421

<210> SEQ ID NO 117
<211> LENGTH: 489
<212> TYPE: DNA
<213> ORGANISM: Homo sapiens

<400> SEQUENCE: 117
agcgtggtcg cggccgaggt aaggctgcga ggttgtggtg tctgggaaac tccgaggaca   60
gagggctaaa tccatgaagt ttgtggatgg cctgatgatc cacagcggag accctgttaa  120
ctactacgtt gacactgctg tgcgccacgt gttgctcaga cagggtgtgc tgggcatcaa  180
ggtgaagatc atgctgccct gggaccccaa ctggtaagatt ggccctaaga agccctgcc  240
tgaccacgtg agcattgtgg aacccaaaga tgagtactg  cccaccaccc ccatctcaga  300
acagaagggt gggaagccag agccgcctgc catgccccag ccagtcccca cagcataaca  360
gggtctcctt ggcagacctg cccgggcggc cgctcgaaag cccgaattcc agcacactgg  420
cggccgttac tagtggatcc cagctcggta ccaagcttgg cgtaatcatg gtcatagctg  480
gtttcctgt                                                         489

<210> SEQ ID NO 118
<211> LENGTH: 489
<212> TYPE: DNA
<213> ORGANISM: Homo sapiens

<400> SEQUENCE: 118
tcgagcggcc gcccgggcag gtattgaata cagcaaaatt ctatatacaa agtgacctgg   60
acctgctgct tcaaaacatg atcctttctt actaatatct tgatagtcgg tccatagagc  120
attagaaagc aattgactct taaataaaca gaaagtgcc  taatgcacat taaatgaatg  180
gcctaactac tggaacttta gtagttctat aaggtgatta acataggtag gatccagttc  240
ctatgacagg ctgctgaaga acagatatga gcatcaagag gccattttgt gcactgccac  300
cgtgatgcca tcgtgtttct ggatcataat gttcccatta tctgattcta gacacaccac  360
aggaatatca gtggggtcag aggttagctt agctgcttgc tgggctagaa cagatatcac  420
tccagcatgc tcatctgaca gggtcccgcg gcaacccaga ttaagtcctt gtgaatctgt  480
gcacaggga                                                         489

<210> SEQ ID NO 119
<211> LENGTH: 181
<212> TYPE: DNA
<213> ORGANISM: Homo sapiens

<400> SEQUENCE: 119
```

```
            taggttccag agacttttgg cccaggagga atatttactt ttagctctgg acatcattac     60
            aaaaaggaat atttcccaaa cctcttcaga ccgagaatac atgggtaaaa ttattaaata    120
            gttgtataat aaaaataatt ttttccttaa aaaaaaaaaa aacctcggcc gcgaccacgc    180
            t                                                                   181
```

<210> SEQ ID NO 120
<211> LENGTH: 489
<212> TYPE: DNA
<213> ORGANISM: Homo sapiens
<220> FEATURE:
<221> NAME/KEY: misc_feature
<222> LOCATION: 422, 487
<223> OTHER INFORMATION: n = A,T,C or G

<400> SEQUENCE: 120

```
            gcgtggtcgc ggccgaggtc catttaaaac aaagaaaaat actaaagcca ctagtaaaca     60
            tctgatgtgc aaaatacaac atcctctagt tggctttatg ccattattac ataagctcca    120
            aatagctcat cttaaattaa aaagaaaaag tggctgtccc atctctgctg cataaatcag    180
            attttttttt aaaggtttag agtactttaa ggaagggaag ttcaaaactg ccagtgaaat    240
            tcacagagaa tacaaattta gcaatttaat ttcccaaagc tctttgaaga agcaagagag    300
            tctctcttct taatgcagtg ttctcccaag aggaactgta attttgcttg gtacttatgc    360
            tgggagatat gcaaaatgtg ttttcaatg tttgctagaa tataatggtt cctcttcagt    420
            gnctggttca tcctggaact catgggttaa gaaggacttc ttggagccga actgccggg    480
            cgggccntt                                                           489
```

<210> SEQ ID NO 121
<211> LENGTH: 531
<212> TYPE: DNA
<213> ORGANISM: Homo sapiens

<400> SEQUENCE: 121

```
            cgagcggccg cccgggcagg tggccagcgc tggtcccgca gacgccgaga tggaggaaat     60
            atttgatgat gcgtcacctg gaaagcaaaa ggaaatccaa gaaccagatc ctacctatga    120
            agaaaaaatg caaactgacc gggcaaatag attcgagtat ttattaaagc agacagaact    180
            ttttgcacat ttcattcaac ctgctgctca gaagactcca acttcaccttt tgaagatgaa    240
            accagggcgc ccacgaataa aaaagatga gaagcagaac ttactatccg ttggcgatta    300
            ccgacaccgt agaacagagc aagaggagga tgaagagcta ttaacagaaa gctccaaagc    360
            aaccaatgtt tgcactcgat ttgaagactc tccatcgtat gtaaaatggg gtaaactgag    420
            agattatcag gtcccgagga ttaaactggc tcattttcttt gtatgagaat ggcatcaatg    480
            gtatccttgc agatgaaatg ggcctaggaa agactcttca acaatttctc t              531
```

<210> SEQ ID NO 122
<211> LENGTH: 174
<212> TYPE: DNA
<213> ORGANISM: Homo sapiens

<400> SEQUENCE: 122

```
            tcgagcggcc gcccgggcag gtctgccaac agcagaggcg gggcctccgg catcttcaaa     60
            gcacctctga gcaggctcca gccctctggc tgcggagggg gtctggggtc tcctctgagc    120
            tcggcagcaa agcagatgtt atttctctcc cgcgacctcg gccgcgacca cgct          174
```

<210> SEQ ID NO 123
<211> LENGTH: 531
<212> TYPE: DNA
<213> ORGANISM: Homo sapiens
<220> FEATURE:
<221> NAME/KEY: misc_feature
<222> LOCATION: 152, 373, 482, 494, 496, 502
<223> OTHER INFORMATION: n = A,T,C or G

<400> SEQUENCE: 123

```
            agcgtggtcg cggccgaggt cctcaaccaa gagggttgat ggcctccagt caagaaactg     60
            tggctcatgc cagcagagct ctctcctcgt ccagcaggcg ccatgcaagg gcaggctaaa    120
            agacctccag tgcatcaaca tccatctagc anagagaaaa ggggcactga agcagctatg    180
            tctgccaggg gctagggggct cccttgcaga cagcaatgct acaataaagg acacagaaat    240
            gggggaggtg gggaagccc tattttata acaaagtcaa acagatctgt gccgttcatt    300
            ccccagaca cacaagtaga aaaaaaccaa tgcttgtggt ttctgccaag atgaatatt    360
            cctccttcct aanttccaca catggccgtt tgcaatgctc gacagcattg cactgggctg    420
            cttgtctctg tggtctgggc accagtagct tgggcccat atacacttct cagttccac    480
            anggcttatg gccnangggc angctccaat tttcaagcac cacgaaggaa g             531
```

```
<210> SEQ ID NO 124
<211> LENGTH: 416
<212> TYPE: DNA
<213> ORGANISM: Homo sapiens

<400> SEQUENCE: 124
tcgagcggcc gcccgggcag gtccatctat actttctaga gcagtaaatc tcataaattc   60
     acttaccaag cccaggaata atgactttta aagccttgaa tatcaactaa gacaaattat  120
     gccaattctg atttctcaca tatacttaga ttacacaaag ataaagcttt agatgtgatc  180
     attgttttaat gtagacttat ctttaaagtt tttaattaaa aactacagaa gggagtaaac  240
     agcaagccaa atgatttaac caaatgattt aagagtaaaa ctcactcaga aagcattata  300
     cgtaactaaa tatacatgag catgattata tacatacatg aaactgcaat tttatggcat  360
     tctaagtaac tcatttaagt acattttttgg catttaaaca aagatcaaat caagct      416

<210> SEQ ID NO 125
<211> LENGTH: 199
<212> TYPE: DNA
<213> ORGANISM: Homo sapiens
<220> FEATURE:
<221> NAME/KEY: misc_feature
<222> LOCATION: 112, 160, 195
<223> OTHER INFORMATION: n = A,T,C or G

<400> SEQUENCE: 125
agcgtggtcg cggccgaggt gcttttttttt tttttttttt tttttttttt gctattctaa   60
     aggggaaggc cccttttttat taaacttgta cattttactt tccttctttc anaatgctaa  120
     taaaaaactt ttgtttatac ttaaaaaaac cataaatcan acaaacaaaa gaaacgattc  180
     caacatcact tctgngatg                                                199

<210> SEQ ID NO 126
<211> LENGTH: 490
<212> TYPE: DNA
<213> ORGANISM: Homo sapiens

<400> SEQUENCE: 126
cgtggtcgcg gccgaggtcc agttgctcta agtggattgg atatggttgg agtggcacag   60
     actggatctg ggaaaacatt gtcttatttg cttcctgcca ttgtccacat caatcatcag  120
     ccattcctag agagaggcga tgggcctatt tgtttggtgc tgcaccaac tcgggaactg   180
     gcccaacagg tgcagcaagt agctgctgaa tattgtagag catgtcgctt gaagtctact  240
     tgtatctacg gtggtgctcc taagggacca caaatacgtg atttggagag aggtgtggaa  300
     atctgtattg caacacctgg aagactgatt gacttttttag agtgtggaaa aaccaatctg  360
     agaagaacaa cctaccttgt ccttgatgaa gcagatagaa tgcttgatat gggctttgaa  420
     ccccaaataa ggaagattgt ggatcaaata agacctgata ggcaaactct aatgtggagt  480
     gcgacttggc                                                         490

<210> SEQ ID NO 127
<211> LENGTH: 490
<212> TYPE: DNA
<213> ORGANISM: Homo sapiens

<400> SEQUENCE: 127
cgtggtcgcg gccgaggtcg gccgaggtct ggagatctga gaacggcag actgcctcct   60
     caagtgggtc cctgacccct gaccccgag cagcctaact ggaggcacc ccccagcagg   120
     ggcacactga cacctcacac ggcagggtat tccaacagac ctgaagctga gggtcctgtc  180
     tgttagaagg aaaactaaca agcagaaagg acagccacat caaaaccca tctgtacatc   240
     accatcatca aagaccaaaa gtaaataaaa ccacaaagat gggaaaaaaa cagaacagaa  300
     aaactggaaa ctctaaaaag cagagcacct ctcctcttcc aaaggaacgc agttcctcac  360
     cagcaatgga acaaagctgg atggagaatg actttgacga gctgagaaaa gaacgcttca  420
     gacgatcaaa ttactctgag ctacgggagg acattcaaac caaaggcaaa gaagttgaaa  480
     actttgaaaa                                                         490

<210> SEQ ID NO 128
<211> LENGTH: 469
<212> TYPE: DNA
<213> ORGANISM: Homo sapiens
<220> FEATURE:
<221> NAME/KEY: misc_feature
<222> LOCATION: 69, 106, 140, 152, 165, 196, 224, 233, 241, 258, 260, 267,
      291, 347, 395
<223> OTHER INFORMATION: n = A,T,C or G
```

<400> SEQUENCE: 128

```
cgtggtcgcg gccgaggtgc tttttttttt tttttttttt tttttttttt tgctgattta    60
tttttctnt ttattgttac atacaatgta taaacacata aaacanaaaa cagtagggat   120
cctctaggat ctctagggan acagtaaagt anaaagaggt ctcanaaaca tttttttaaa   180
gtacaagaca ttcagngctc ggcccaaagg cgtaaaaggt ttanagccag canatagctg   240
nactaaaggc tccgtctntn tccccanagc caggacaacc ccagggagct ntccattagc   300
agccagtcca cgcaggcagg atgctgcgga aaaagctcta tgctganaac attcccttg   360
atggaaagaa gggcaacaca aaagggtaa ctaanagctc cttcctctcg tgagggcgac   420
aactgaggaa cagaaaagga gtgtcccatg tcactttga ccccctccc                469
```

<210> SEQ ID NO 129
<211> LENGTH: 419
<212> TYPE: DNA
<213> ORGANISM: Homo sapiens

<400> SEQUENCE: 129

```
gcgtggtcgc ggccgaggtc tgattttcat ttaaatattt cagagctata gcatttgcct    60
ccatgctcaa atccacacca ttggggctta agccgctcat gccaacatta gcaaatgaca   120
tgcagtttaa tccagagatc actgcttctg ggctgatgca tgccaacaca ctggcgtgat   180
ccacgttatg tgcatttttc ttcactttag tgggagaatc aatttttact ccaaggcttc   240
ttagttgctt aagagttgca ttaaggacac aatctttgtc caccagtctt gaatgatgtg   300
ttttttctt tgtatggtaa acgttttggg ttctggtgca ttcatgactg ataattactg   360
ctttggtaga cggctgctca agtttccttg gaggaactat ttaataggtg ggttacttg    419
```

<210> SEQ ID NO 130
<211> LENGTH: 354
<212> TYPE: DNA
<213> ORGANISM: Homo sapiens

<400> SEQUENCE: 130

```
agcgtggtcg cggccgaggt ccatctgagg agataaccac atcactaaca aagtgggagt    60
gaccccgcag agcacgctgt ggaattccat agttggtctc atccctggtc agtttccaca   120
tgatgatggt cttatctcga gaggcggaga ggatcatgtc cgggaactgc ggggtagtag   180
cgatctgggt tacccagccg ttgtggccct tgagggtgcc acgaagggtc atctgctcag   240
tcatggcggc ggcgagagcg tgtgtcgctg cagcgacgag gatggcactg atggcttag   300
agaaactagc accacaacct tcctgccgc acctgcccgg gcggcccgct cgaa           354
```

<210> SEQ ID NO 131
<211> LENGTH: 474
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 131

```
cgagcggccg cccgggcagg tctggcagca gcttcctctg gaataattga cagctttgtg    60
ctgcctgact aaaatttgaa atgacaaccg ctgaatgtaa aatgatgtac ctacaatgag   120
agagatttag gaatactatc tgtcaatcca tagatgtgaa aacaaaacaa actacagaat   180
gaaaacaaac ttatttaaa ccaagaaac aaatgtatcc aaaatatagt ccatgatata   240
tttgattact agtataacca cagttgaaaa cttaaaaaaa aaattgaca ttttttgtaa   300
tgggtactaa tggattata aaaggtttct gtttccaaag atgttattgg ggtccacata   360
ttccttgaag acttcagcat cccaaagccc gacatcagag atactttcct ttagccattg   420
nttcccgtaa cttgcccact ccatggtgat gtgacaggct tcccttcatt agca          474
```

<210> SEQ ID NO 132
<211> LENGTH: 474
<212> TYPE: DNA
<213> ORGANISM: Homo sapiens
<220> FEATURE:
<221> NAME/KEY: misc_feature
<222> LOCATION: 403
<223> OTHER INFORMATION: n = A,T,C or G

<400> SEQUENCE: 132

```
ggccgaggtg gggaattcat gtggaggtca gagtggaagc aggtgtgaga gggtccagca    60
gaaggaaaca tggctgccaa agtgtttgag tccattggca agtttggcct ggccttagct   120
gttgcaggag gcgtggtgaa ctctgcctta tataatgtgg atgctgggca cagagctgtc   180
```

```
                   atctttgacc gattccgtgg agtgcaggac attgtggtag gggaagggac tcattttctc    240
                   atcccgtggg tacagaaacc aattatcttt gactgccgtt ctcgaccacg taatgtgcca    300
                   gtcatcactg gtagcaaaga tttacagaat gtcaacatca cactgcgcat cctcttccgg    360
                   cctgtcgcca gccagcttcc tcgcatcttc accagcatcg ganaggacta tgatgaaccg    420
                   tgtgctgccg tccatcacaa ctgagatcct caagtcagtg gtggctcgct ttga           474
```

<210> SEQ ID NO 133
<211> LENGTH: 387
<212> TYPE: DNA
<213> ORGANISM: Homo sapiens

<400> SEQUENCE: 133

```
                   tgctcgagcg gccgccagtg tgatggatat ctgcagaatt cggcttagcg tggtcgcggc     60
                   cgaggtctgc gggcccctta gcctgccctg cttccaagcg acggccatcc cagtagggga    120
                   ctttcccaca ctgtgccttt acgatcagcg tgacagagta gaagctggag tgcctcacca    180
                   cacggcccgg aaacagcggg aagtaactgg aaaagagcttt aggacagctt agatgccgag    240
                   tgggcgaatg ccagaccaat gatacccaga gctacctgcc gccaacttgt tgagatgtgt    300
                   gtttgactgt gagagagtgt gtgtttgtgt gtgtgttttg ccatgaactg tggccccagt    360
                   gtatagtgtt tcagtggggg agaactg                                         387
```

<210> SEQ ID NO 134
<211> LENGTH: 401
<212> TYPE: DNA
<213> ORGANISM: Homo sapiens

<400> SEQUENCE: 134

```
                   ggccgcccgg gcaggtctga tgaagaacac gggtgtgatc cttgccaatg acgccaatgc     60
                   tgagcggctc aagagtgttg tgggcaactt gcatcggctg ggagtcacca acaccattat    120
                   cagccactat gatgggcgcc agttccccaa ggtggtgggg ggctttgacc gagtactgct    180
                   ggatgctccc tgcagtggca ctggggtcat ctccaaggat ccagccgtga agactaacaa    240
                   ggatgagaag gacatcctgc gcttgtgctc acctccagaa ggaagttgct cctgagtgct    300
                   attgactctt gtcaatgcga ccttcaagac aggaggctac ctggtttact gcacctgttc    360
                   tatcacagtg agacctctgc catggcagaa caggggaagc t                         401
```

<210> SEQ ID NO 135
<211> LENGTH: 451
<212> TYPE: DNA
<213> ORGANISM: Homo sapiens

<400> SEQUENCE: 135

```
                   ggtcgcggcc gaggtctgtt cctgagaaca gcctgcattg gaatctacag agaggacaac     60
                   taatgtgagt gaggaagtga ctgtatgtgg actgtggaga aagtaagtca cgtgggccct    120
                   tgaggacctg gactgggtta ggaacagttg tactttcaga ggtgaggtgt cgagaaggga    180
                   aagtgaatgt ggtctggagt gtgtccttgg ccttggctcc acaggtgtg ctttcctctg     240
                   gggccgtcag ggagctcatc ccttgtgttc tgccagggtg gggtaccggg gtttgacact    300
                   gaggagggta acctgctggg tggagcggca aacagtggc cttgattgt cttttggaag      360
                   attttaaaaa ccaaaaagca taaacattct ggtccttcac aatgctttct ctgaagaaat    420
                   acttaacgga aggacttctc cattcaccat t                                   451
```

<210> SEQ ID NO 136
<211> LENGTH: 411
<212> TYPE: DNA
<213> ORGANISM: Homo sapiens

<400> SEQUENCE: 136

```
                   ggccgcccgg gcaggtctga atcacgtaga atttgaagat caagatgatg aagccagagt     60
                   tcagtatgag ggttttcgac ctgggatgta tgtccgcgtt gagattgaaa atgttccctg    120
                   tgaatttgtg cagaactttg accccctta ccccattatc ctggtgtggct tgggcaacag     180
                   tgagggaaat gttggacatg tgcaggtggg tcccttttgct gcgtatttgg tgcctgaggc    240
                   tctgtggatt tccctccat caatcatctt accctctcat cccctcaga tgcgtctgaa        300
                   gaaacatctc tggtataaga aaatcctcaa gtcccaagat ccaatcatat tttctgtagg    360
                   gtggaggaag tttcagacca tcctgctcta ttatatccga agaccacaat g             411
```

<210> SEQ ID NO 137
<211> LENGTH: 211
<212> TYPE: DNA
<213> ORGANISM: Homo sapiens
<220> FEATURE:
<221> NAME/KEY: misc_feature
<222> LOCATION: 186

```
<223> OTHER INFORMATION: n = A,T,C or G

<400> SEQUENCE: 137
cggccgcccg ggcaggtcgg ttggtgcggc ctccattgtt cgtgttttaa ggcgccatga   60
    ggggtgacag aggccgtggt cgtggtgggc gctttggttc cagaggaggc ccaggaggag  120
    ggttcaggcc ctttgcacca catatcccat ttgacttcta tttgtgtgaa atggcctttc  180
    cccggntcaa gccagcacct cgatgaaact t                                  211

<210> SEQ ID NO 138
<211> LENGTH: 471
<212> TYPE: DNA
<213> ORGANISM: Homo sapiens

<400> SEQUENCE: 138
gccgcccggg caggtctggg ctggcgactg gcatccaggc cgtaactgca aatctatgct   60
    aggcgggtc tcccttctgt gtgttcaagt gttctcgact tggattctta actatttaa   120
    aaaatgcact gagtttgggt taaaaaccaa ccaccaaaat ggatttcaac acagctctaa  180
    agccaagggc gtggccggct ctcccaacac agcgactcct ggaggccagg tgcccatggg  240
    cctacatccc ctctcagcac tgaacagtga gttgattttt cttttttacaa taaaaaaagc  300
    tgagtaatat tgcataggag taccaagaaa ctgcctcatt ggaaacaaaa actatttaca  360
    ttaaataaaa agcctggccg caggctgcgt ctgccacatt tacagcacgg tgcgatgcac  420
    acggtgacca aaccacgag gcaagcttct ggcactcaca ccacgacccg c            471

<210> SEQ ID NO 139
<211> LENGTH: 481
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 139
gtcgcggccg aggtctgttc tttagctcag atttaaacct gctgtctctt ctttatttgc   60
    agaatgaatt cccagttcct gagcagttca agaccctatg gaacgggcag aagttggtca  120
    ccacagtgac agaaattgct ggataagcga agtgccactg ggtctttgc cctcccttca   180
    caccatggga taaatctgta tcaagacggt tcttttctag atttcctcta ccttttttgct  240
    cttaaaactg cttctctgct ctgagaagca cagctacctg ccttcactga aatatacctc  300
    aggctgaaat tgggggtggg atagcaggtc agttgatctt ctgcaggaag gtgcagcttt  360
    tccatatcag ctcaaccacg ccgncagtcc attcttaagg aactgccgac taggactgat  420
    gatgcatttt agcttttgag cttttggggg gtattctacc aaccaacagt ccatttgaa   480
    a                                                                  481

<210> SEQ ID NO 140
<211> LENGTH: 421
<212> TYPE: DNA
<213> ORGANISM: Homo sapiens
<220> FEATURE:
<221> NAME/KEY: misc_feature
<222> LOCATION: 372
<223> OTHER INFORMATION: n = A,T,C or G

<400> SEQUENCE: 140
gtcgcggccg aggtttccca tttaagaaaa atagatcttg agattctgat tcttttccaa   60
    acagtcccct gctttcatgt acagcttttt ctttaccttta cccaaaattc tggccttgaa  120
    gcagttttcc tctatggctt tgcctttctg attttctcag aggctcgagt ctttaatata  180
    accccaaatg aaagaaccaa ggggagggt gggatggcac ttttttttgt tggtcttgtt   240
    ttgttttgtt ttttggttgg ttgggttccg ttatttttta agattagcca ttctctgctg  300
    ctatttccct acataatgtc aattttaac cataattttg acatgattga gatgtacttg   360
    aggctttttt gntttaattg agaaaagact ttgcaatttt ttttttagga tgagcctctc  420
    c                                                                  421

<210> SEQ ID NO 141
<211> LENGTH: 242
<212> TYPE: DNA
<213> ORGANISM: Homo sapiens
<220> FEATURE:
<221> NAME/KEY: misc_feature
<222> LOCATION: 4, 6, 20, 31, 35, 39, 72, 94, 141, 142, 211, 222
<223> OTHER INFORMATION: n = A,T,C or G
```

```
<400> SEQUENCE: 141
cgantngccc gcccgggcan gtctgtctaa ntttntcang gaccacgaac agaaactcgt   60
gcttcaccga anaacaatat cttaaacatc gaanaattta aatattatga aaaaaaacat  120
tgcaaaatat aaaataaata nnaaaaggaa aggaaacttt gaaccttatg taccgagcaa  180
atccaggtct agcaaacagt gctagtccta nattacttga tntacaacaa cacatgaata  240
ca                                                                 242

<210> SEQ ID NO 142
<211> LENGTH: 551
<212> TYPE: DNA
<213> ORGANISM: Homo sapiens
<220> FEATURE:
<221> NAME/KEY: misc_feature
<222> LOCATION: 15, 19, 32, 73, 110, 278, 405, 436, 473, 510
<223> OTHER INFORMATION: n = A,T,C or G

<400> SEQUENCE: 142
agcgtggtcg cggcncgang tccacagggc anatattctt ttagtgtctg gaattaaaat   60
gtttgaggtt tangtttgcc attgtctttc caaaaggcca ataattcan atgtaaccac   120
accaagtgca aacctgtgct ttctatttca cgtactgttg tccatacagt tctaaataca  180
tgtgcagggg attgtagcta atgcattaca cagtcgttca gtcttctctg cagacacact  240
aagtgatcat accaacgtgt tatacactca actagaanat aataagcttt aatctgaggg  300
caagtacagt cctgacaaaa gggcaagttt gcataataga tcttcgatca attctctctc  360
caaggggccc gcaactaggc tattattcat aaaacacaac tgaanagggg attggtttta  420
ctggtaaatc atgtgntgct aaatcattttt ctgaacagtg gggtctaaat cantcattga  480
tttagtggca gccacctgcc cggcggccgn tcgaagccca attctgcaga tatccatcac  540
actggcggcc g                                                       551

<210> SEQ ID NO 143
<211> LENGTH: 515
<212> TYPE: DNA
<213> ORGANISM: Homo sapiens
<220> FEATURE:
<221> NAME/KEY: misc_feature
<222> LOCATION: 5, 286, 498
<223> OTHER INFORMATION: n = A,T,C or G

<400> SEQUENCE: 143
cgagnggccc gcccgggcag gtatcttcac aaactcaaca aaggcactac atgagacttc   60
acattcccct agtccaaatag ctgacaaatt tttgcaacgt tctgcaatgc gaattaactc  120
ttcatcaagt ggccgtaatc catttgcaca cactactagt tcaaccagtc tagggcatgt  180
cattcccaca cggccaagca catctttgct tactgatctc ccaaagtaca gatgggtggc  240
aggtatttca tagcgaaaga aggggtcaaa ttcttcttca tataanaaaa aatacatcac  300
taagttcact ttgggtgaat gtctgatgaa agcatcccag ctactcttct gaatagtatg  360
gaagtgtgtc tgtccaggat tctcactgac tacatcaatg cgcaaatgtt ctaatcgaac  420
atgttttttca gaagacaatg caagtaacaa ctcatcactc aataagtggt aagttcaggg  480
ctagttctct taagccgnga cactgatcag cacac                             515

<210> SEQ ID NO 144
<211> LENGTH: 247
<212> TYPE: DNA
<213> ORGANISM: Homo sapiens
<220> FEATURE:
<221> NAME/KEY: misc_feature
<222> LOCATION: 11, 20, 42, 115, 152, 165, 181, 195, 208, 221
<223> OTHER INFORMATION: n = A,T,C or G

<400> SEQUENCE: 144
tgcattctct ntggatgcan acctgcccgt tggtagggac tntgctcaca cggaacatgg   60
acggttacac ctgtgccgtg ggtgacgtcc accagcttct ggatcatctc ggcgngggtg  120
ttgtggaagg gcagactatc cacctccatg cncacgatgc ccganacgcc actccggact  180
ntgtgctgca ccaanatgcc cagcattnta tcttcaagca nagcacttat cagggtcctt  240
ggcacac                                                            247

<210> SEQ ID NO 145
<211> LENGTH: 309
<212> TYPE: DNA
<213> ORGANISM: Homo sapiens
<220> FEATURE:
<221> NAME/KEY: misc_feature
<222> LOCATION: 18, 155, 247
```

-continued

<223> OTHER INFORMATION: n = A,T,C or G

<400> SEQUENCE: 145

```
cgtgggtcgc ggcccgangt ctgctgtaac aaaacaccat agtctgggca gctcatagac    60
aatggaattt tatttctcac gcttctggag gctggattcc aagatcaagg ttccaggaga   120
ctcagtgtct ggcaaggtct cggtttctgc ctcanagatg gtgccatctg gctgtgtcct   180
cacaagtagg aaggtgcaag aagctcccct caggctctgt ctgtaagaca ctgatcccat   240
tcatganggg gaaacgtaat gacctaatca gcccccagag accccacttc taacaccatc   300
accttgggg                                                           309
```

<210> SEQ ID NO 146
<211> LENGTH: 486
<212> TYPE: DNA
<213> ORGANISM: Homo sapiens
<220> FEATURE:
<221> NAME/KEY: misc_feature
<222> LOCATION: 16, 97, 154, 244, 275, 322, 347, 349, 352, 357, 449, 460, 472
<223> OTHER INFORMATION: n = A,T,C or G

<400> SEQUENCE: 146

```
agcgtgggtc gcggcncgac gtcctgtcca tatttcacag cccgagaact aatacaagat    60
gctgacatca tattttgtcc ctacaactat cttctanatg cacaaataag ggaaagtatg   120
gatttaaatc tgaaagaaca ggttgtcatt ttanatgaag ctcataacat cgaggactgt   180
gctcgggaat cagcaagtta cagtgtaaca gaagttcagc ttcggtttgc tcgggatgaa   240
ctanatagta tggtcaacaa taatataagg aaganagatc agaaccccct acgagctgtg   300
tgctgtagcc tcattaattg gntagaagca aacgctgaat atcttgnana angagantat   360
gaatcagctt gtaaaatatg gagtggaaat gaaatgctct taactttaca caaaatgggt   420
atcaccactg ctactttttcc cattttgcng gtaagatatn ttttctacct gngaaacgta   480
tttaag                                                              486
```

<210> SEQ ID NO 147
<211> LENGTH: 430
<212> TYPE: DNA
<213> ORGANISM: Homo sapiens
<220> FEATURE:
<221> NAME/KEY: misc_feature
<222> LOCATION: 13, 26, 28, 289, 299, 352, 390, 399
<223> OTHER INFORMATION: n = A,T,C or G

<400> SEQUENCE: 147

```
gccgcccggg cangttcgac attacntnga gttccatgat gtacaattct ttcacgaaaa    60
acaatgaatg caagaatttg aggatctcct tactcctccc ttttacagat ggtctctcaa   120
tcccttcttc ttcctcttca tcttcatctt cttctgaacg cgctgccggg taccacggct   180
ttctttgtct ttatcgtgag atgaaggtga tgcttctgtt tcttctacca taactgaaga   240
aatttcgctg caagtctctt gactggctgt ttctccgact tcgcctttnt gtcaaacgng   300
agtctttta cctcatgccc ctcagcttca cagcatcttc atctggatgt tnatttctca   360
aagggctcac tgaggaaact tctgattcan atgtcgaana gcactgtgaa gttttctctt   420
cattttgctg                                                          430
```

<210> SEQ ID NO 148
<211> LENGTH: 483
<212> TYPE: DNA
<213> ORGANISM: Homo sapiens
<220> FEATURE:
<221> NAME/KEY: misc_feature
<222> LOCATION: 20, 24, 53, 55, 374, 381, 423, 431, 459
<223> OTHER INFORMATION: n = A,T,C or G

<400> SEQUENCE: 148

```
cccgggcagg tctgtgttgn tttncaaccg gtgtcctccc cagcgtccag aananggaaa    60
tgtggagcgg gtgatgatga cccctcgctg tcctgtcacc tcctgcacag cttcgtatgt   120
gggtctggtc tgggaccacc cgtacaggtt gtgcacgttg tagtgctcca cgggggagct   180
gtccggcagg atctgctgac tctccatgca cagagtcttg ctgctcaggc ccttgtccct   240
agattccaaa tatggcatat agggtggggt tatttagcat ttcattgctg cagcccctga   300
cagatccatc cacaaaattt gatggctcat tcatatcaat ccacaatcca tcaaacttca   360
agctcttctc tggntctcga nggtttgcat agaactcttc tatctctttc ttccaccacg   420
canacctcgg ngcgaccac gctaagccga attctgcana tatccatcac actggcggcc   480
gct                                                                 483
```

<210> SEQ ID NO 149

```
<211> LENGTH: 439
<212> TYPE: DNA
<213> ORGANISM: Homo sapiens
<220> FEATURE:
<221> NAME/KEY: misc_feature
<222> LOCATION: 11, 359, 384, 402
<223> OTHER INFORMATION: n = A,T,C or G

<400> SEQUENCE: 149
ctttcacgaa nacaatgaat gcaagaattt gaggatctcc ttactcctcc cttttacaga   60
    tggtctctca atcccttctt cttcctcttc atcttcatct tcttctgaac gcgctgccgg  120
    gtaccacggc tttctttgtc tttatcgtga gatgaaggtg atgcttctgt ttcttctacc  180
    ataactgaag aaatttcgct gcaagtctct tgactggctg tttctccgac ttcgcctttt  240
    tgcaaacgtg agtctttta cctcatgccc ctcagcttcc acagcatctt catctggatg  300
    ttcatttctc aaagggctca ctgaggaaac ttctgactca catgtcgaag aagcactgng  360
    agtttctctt catttgctgc aaanttgctc tttgctggct gngctctcag accacccatt  420
    tggctgcatg ggggctgac                                               439

<210> SEQ ID NO 150
<211> LENGTH: 578
<212> TYPE: DNA
<213> ORGANISM: Homo sapiens
<220> FEATURE:
<221> NAME/KEY: misc_feature
<222> LOCATION: 4, 15, 260, 336, 371, 430, 461, 535, 572
<223> OTHER INFORMATION: n = A,T,C or G

<400> SEQUENCE: 150
ggcncgcccg ggcangtcca ctccactttt gagctctgag ggaataacctt caggagggac  60
    agggtcaggg agtcctggca gctccgcagc agagattcac attcattcag agacttgttg  120
    tccagtgcaa tgccattgat cgcaacgatc ctgtctccca cagcaaggga cccttctta  180
    gcggcagggc ttccaggcag cacagcggca gcatacactc cattctccag actgatgcca  240
    ctgtctttct gtccactgan gttgatgtgc agcggcgtga ccaccttccc acccagggac  300
    ttcctccgcc gcacgaccat gttgatgggc cccctnccca ttgaggagcg ccttgatggc  360
    ctgcttcttg nccttggtga tgaagtccac atcggtgatt ctcacagcca gtcattgacc  420
    cttaagcggn catcagcaat gcttcctttg gccactttag ngacaaatat gccacagtcc  480
    ccgggaaaca agggtcattc acaccttctg gcatatcaaa cacctcggcc gggancacta  540
    agccgaattc tgcagatatc catcacactg gnggcccg                           578

<210> SEQ ID NO 151
<211> LENGTH: 503
<212> TYPE: DNA
<213> ORGANISM: Homo sapiens
<220> FEATURE:
<221> NAME/KEY: misc_feature
<222> LOCATION: 392, 464
<223> OTHER INFORMATION: n = A,T,C or G

<400> SEQUENCE: 151
cgagcggccc gcccgggcag gtctgggaga tcagcgactg ctgccacgtg cccagaaatg   60
    gctcgtcctt tcactacagc ggaatgcaat gagggtgggt gagaagatga tgggtcggtt  120
    atttcattcc tttctttttt acaacttcac tttcagagac ttcagcgttc catgtctgct  180
    gtgctgtgga acccagagtg tctcttgcctg gatggctgag aatcccttgg accctggaag  240
    cacctactcc atgatggccc ggtatagtgc aggctcaata taatcttccc ggtatcttga  300
    gttgataact cgttgccgtt tcttttcttg cttaacctct ttctctgtga aaatctcatt  360
    gaagcgcatg tctgaagcta ctgacagtct anatttgact ctcttgggaa gctcttcatc  420
    cagtgtgtat acatcatctc tcttaaccac aagttggagc catncttaaa cttcacctgg  480
    tacatttgga tagggtggga ggc                                          503

<210> SEQ ID NO 152
<211> LENGTH: 553
<212> TYPE: DNA
<213> ORGANISM: Homo sapiens
<220> FEATURE:
<221> NAME/KEY: misc_feature
<222> LOCATION: 293, 432, 459, 481, 536
<223> OTHER INFORMATION: n = A,T,C or G

<400> SEQUENCE: 152
agcgtggtcg cggcccgagg tccactgagc tccgccttcc ccgggctccc tgaggaagca   60
    gagtcctgac ttccaggaag gacaggacac agaggcaaga actcagcctg tgaggctctg  120
    ggtggctcct gaggccagag gacgccttcc gcgatccatg gctcagcatc gtccttctgt  180
```

```
cttcccagcc ccgggccgaa cgttcgggtt aataagcaga gcagttattc ggctcctggc    240
aggagctccc ccgttagttt ccacgttgtg agcacattca tacttaagac tgnttctctt    300
tgtgttttaa gcgtctgtct ctgtagtaaa ctgaaatgtt aacagaaatg cagacctgcc    360
cgggcgccg ctcgaaagcc gaattctgca gatatccatc acactggcgg ccgctcgagc    420
atgcatctag anggcccaat tcgccctata gtgagtcgna ttacaattca ctgggccgcg    480
ntttacaacg tcgtgactgg gaaaaccctg cggtacccac ttaatcgcct tgcagnacat    540
cccccttttcg cca                                                      553
```

<210> SEQ ID NO 153
<211> LENGTH: 454
<212> TYPE: DNA
<213> ORGANISM: Homo sapiens
<220> FEATURE:
<221> NAME/KEY: misc_feature
<222> LOCATION: 198, 307, 325, 347, 386, 389, 392, 415, 425
<223> OTHER INFORMATION: n = A,T,C or G

<400> SEQUENCE: 153

```
tcgagcggct cgcccgggca ggtccaccta gcatggctcc tctaaacacg caactcagcg     60
aggggacccc cttcacctct ggcaagagag ctgggtagat cagaaacttg gtgacacctg    120
gctagcacag agcaggctca cttgtcttgg tcccactacc cagattcctg cagacattgc    180
aaaccaaatg aaggttgntg aatgacccct gtcccagcc acttgttttg gtatcatctg     240
ctctgcagtg gaatgcctgt gtgtttgagt tcactctgca tctgtatatt tgagtataga    300
aaccgantca agtgatctgt gcatncagac acactgggc acctgancac agaacaaatc    360
accttaacga tctggaatga aactgnganc antgcccgcc tgggtgggtc tgganaaact    420
gccgncttct tgttggacct tggccgcacc acct                                454
```

<210> SEQ ID NO 154
<211> LENGTH: 596
<212> TYPE: DNA
<213> ORGANISM: Homo sapiens
<220> FEATURE:
<221> NAME/KEY: misc_feature
<222> LOCATION: 19, 33, 37, 131, 377, 425, 439, 505
<223> OTHER INFORMATION: n = A,T,C or G

<400> SEQUENCE: 154

```
agcgtggtcg cggcccgang gcggcctcct gantganggg aagggacgtg ggggcggcca     60
cggcaggatt aacctccatt tcagctaatc atgggagaga ttaaagtctc tcctgattat    120
aactggttta naggtacagt tcccctaaaa aagattattg tggatgatga tgacagtaag    180
atatggtcgc tctatgacgc gggcccccga agtatcaggt gtcctctcat attcctgccc    240
cctgtcagtg gaactgcaga tgtcttttttc cggcagattt tgctctgac tggatggggt    300
taccgggtta tcgctttgca gtatccagtt tattgggacc atctcgagtt cttgtgatgt    360
attcacaaaa cttttanacc atttacaatt ggataaagtt catcttttttg gcgcttcttt    420
gggangcttt ttggcccana aatttgctga atacactcac aaatctccta gaagccattc    480
cctaatcctc tgcaattcct tcagngacac ctctatcttc aaccaacttg gactggaaac    540
agctttggct gatgcctgca tttatgctca aaaaatagtt cttggaaatt ttcatc        596
```

<210> SEQ ID NO 155
<211> LENGTH: 343
<212> TYPE: DNA
<213> ORGANISM: Homo sapiens
<220> FEATURE:
<221> NAME/KEY: misc_feature
<222> LOCATION: 6, 12, 23, 44, 58, 86, 99, 279, 310, 319
<223> OTHER INFORMATION: n = A,T,C or G

<400> SEQUENCE: 155

```
ctcganttgg cncgcccggg cangtctgcc tggttttttga ccgngcgagc tatttagnct     60
ctggctctgt ttccggagct caaggnaaaa atcttgaana actcgagcag cttcgtgtgga    120
tagccttggg tacacatact gccgagcata gccaatgtac tttctcaata gctggtggta    180
aatgggatct attgtttctc caggaaccac ctttagtctt tctgataatg gcttctcaga    240
aactacttca agtacggaag tatttgaatc ttgactatnc atacgagcta ctgtggcact    300
gctaatgggn tctctgctnt ccagctctta ttgcaatcac atg                       343
```

<210> SEQ ID NO 156
<211> LENGTH: 556
<212> TYPE: DNA
<213> ORGANISM: Homo sapiens
<220> FEATURE:
<221> NAME/KEY: misc_feature
<222> LOCATION: 34, 375, 530

-continued

<223> OTHER INFORMATION: n = A,T,C or G

<400> SEQUENCE: 156

```
tcgagcggcc cgcccgggca ggtctggcac cacncagatc gattaactgg ctcatctgat    60
ctcgtggccc ccaccctgga actgacttag cacaaaagga cacctcaatt ccttatgatt   120
tcatctccga cccaaccaat caacacccct gactcactgg ccttcccccct cccaccaaat   180
tatccttaaa aactctgatc cccgaatgct cagggagtg gatttgagta ctaataagac    240
tccagtctcc tgcacaagca gctctgtgta ctcttcctct attgcaattc ctgtcttgat    300
aaatcggctc tgtgtaggcg gcggaagaag tgaacctgtt gggcggttac cacctctgtc    360
gtgtgtgaca gttgntttga atctctaatt gctcagtaca gatccacatg caggttaagt    420
aagaagcttt tgaagaaaat ggaaagtctt aagtgatggc ttccaagaaa tcaaacctac    480
attaattagg gaacaacgga ctttacgtat cacaaatgaa gagactgacn aagtaaatca    540
acttggcctt ttctta                                                   556
```

<210> SEQ ID NO 157
<211> LENGTH: 333
<212> TYPE: DNA
<213> ORGANISM: Homo sapiens
<220> FEATURE:
<221> NAME/KEY: misc_feature
<222> LOCATION: 18, 40, 55, 57, 60, 91, 97, 103, 110, 161, 173, 193, 195,
      196, 214, 231, 233, 238, 263, 264, 266, 283, 284, 287, 297,
      298, 323, 331
<223> OTHER INFORMATION: n = A,T,C or G

<400> SEQUENCE: 157

```
ggtccacaaa aatatatnaa ataagctgga tatataaaan caaacactta acatngncan    60
cattccttca gttattcaaa ctcactgata nctaacnggg agnagttggn attctggaag   120
acttcctaag ctaaagtat atttacatat ttacaacaca ngtaaatata acngaagaac    180
tacttcaaat aangnngaaa ttccagaatt ctanagattt atagctatag ntnacaanta   240
tcaccaattg gtttgcaatc aanngnccag cactacttat gannaagntt taactannaa    300
accaaaaggg gagaaaacct ggnagggaaa nat                                 333
```

<210> SEQ ID NO 158
<211> LENGTH: 629
<212> TYPE: DNA
<213> ORGANISM: Homo sapiens
<220> FEATURE:
<221> NAME/KEY: misc_feature
<222> LOCATION: 345, 565
<223> OTHER INFORMATION: n = A,T,C or G

<400> SEQUENCE: 158

```
tcgagcggcc gcccgggcag gtctggtaca tttgtgcgag gtccggcact ctgttctcat    60
ccagtaagtg gtcgagccct ttctgcagaa ttgctgttaa atgttctcct aatagctgtt   120
tctccacaca agcaatcagt ggtttctgtg tgctgtggtc caagtaagtg attactctgt   180
ctccctcttc ttctaagcgt ttacttacat ggttaagata ttctggaacc tctctttcct    240
gcattaacct ttggccttcg gcagcatata agcaattagt ctcttccaaa aatttcagtt    300
caaatgaatc tttatacacc tgcaggtcag acagcatgcc caggnaggct ccgcaacagg    360
ctccggtcca cggcctcgcc gctcctctcg cgctcgatca gcagtaggat tccatcaatg    420
gtttttactct gaaccatttt atcactaata atatgggttc taaacagttc taatcccata   480
tcccagatgg agggcagcgt ggagttctgc agcacatagg tgcggtccaa gaacaggaag   540
atgcttctga tcatgaatca tttgnctggc aatggtcctg ccagcacgtg gtaatctttc    600
ttttaaaaat aaacccttat ctaaacgtc                                      629
```

<210> SEQ ID NO 159
<211> LENGTH: 629
<212> TYPE: DNA
<213> ORGANISM: Homo sapiens
<220> FEATURE:
<221> NAME/KEY: misc_feature
<222> LOCATION: 33, 546, 576
<223> OTHER INFORMATION: n = A,T,C or G

<400> SEQUENCE: 159

```
tcgagcggcc gcccgggcag gttctagagg ganaatctgg ctgatttggg aataaaatat    60
aatcgaatat tcaacaccat gaagataaat cttattttgg aaatctactg accttaatac   120
cccaagcttg ccctgaatac tttgattgga attggaatat atcaaaaaag gttagtattt   180
ttgttgtagt taggatacta aaaggatatt agttacccaa gagatccaat ttgtttttct    240
gatgaatagt gttcagtaaa atgaagcagt cttaagagtg actaataatt tcaaagtgat   300
ttttcgtcta ttcttaatat ttttaattta tttattttta agagtttat accttgagca    360
gatacaatga tccgctttag tgagaggaca atttctgatt gattgttttc tcttcaggcc   420
```

```
                    atctcacctc ttcattctct tgttacattt gaagcagttg atataatggg tttatacttt    480
                    aaaagataga catggtgcca tgaagtttgg ggaagttggg tgaattatcc cattctagtt    540
                    acagangagc tttccttaaa tgcccttttac ttctangttt ggtcaagaag tcattttctg    600
                    agtaaaagtt attttcatat atgttgggg                                       629
```

<210> SEQ ID NO 160
<211> LENGTH: 519
<212> TYPE: DNA
<213> ORGANISM: Homo sapiens
<220> FEATURE:
<221> NAME/KEY: misc_feature
<222> LOCATION: 46, 309, 397, 430, 434, 471, 497
<223> OTHER INFORMATION: n = A,T,C or G

<400> SEQUENCE: 160

```
                    tcgagcggcg cgcccgggca ggtctgctgg gattaatgcc aagttnttca gccataaggt    60
                    agcgaaatct agcagaatcc agattacatc cacttccaat cacgcggtgt ttgggtaatc    120
                    cacttagttt ccagataaca tacgtaagaa tgtccactgg gttggaaacc acaattatga    180
                    tgcaatcagg actgtacttg acgatctgag gaataatgaa tttgaagaca ttaacatttc    240
                    tctgcaccag attgagccga ctctccccctt cttgctgacg gactcctgca gttaccacta    300
                    caatcttana attgggcggg tcacagaata atctttatct gccacaattt taggtgctga    360
                    agaaataagc tcccatgctg cagatccatc atttctnctt taagcttatc ttccaaaaca    420
                    tccacaagan caangttcat cagccagaga ctttcccaga atgctgatag nacacgccat    480
                    accaacttgt ccaacancca ctacagcgat cttattggt                             519
```

<210> SEQ ID NO 161
<211> LENGTH: 446
<212> TYPE: DNA
<213> ORGANISM: Homo sapiens
<220> FEATURE:
<221> NAME/KEY: misc_feature
<222> LOCATION: 5, 32, 36, 269, 354, 381
<223> OTHER INFORMATION: n = A,T,C or G

<400> SEQUENCE: 161

```
                    cgagnggccc gcccgggcag gtccagtaag cntttnacga tgatgggaaa ggttatgcaa    60
                    ggtcccagcg gtacaacgag ctgtttctac atcatttgta ttctgcatgg tacgtacaat    120
                    agcagacacc atctgaggag aacgcatgat agcgtgtctg gaagcttcct ttttagaaag    180
                    ctgatggacc ataactgcag ccttattaac caccacctgg tcctcgtcat ttagcagttt    240
                    tgtcagttca gggattgcac gtgtggcang ttctgcatca tcttgatagt taatcaagtt    300
                    tacaactggc atgtttcagc atctgcgatg ggctcagcaa acgctggaca ttantgggat    360
                    gagcagcatc aaactgtgta natgggatct gcatgccctc atctaatgtc tcagggaaca    420
                    tagcagctcg taccctctga gctcga                                          446
```

<210> SEQ ID NO 162
<211> LENGTH: 354
<212> TYPE: DNA
<213> ORGANISM: Homo sapiens
<220> FEATURE:
<221> NAME/KEY: misc_feature
<222> LOCATION: 6, 19, 36, 116, 152, 174, 186, 196, 223, 249
<223> OTHER INFORMATION: n = A,T,C or G

<400> SEQUENCE: 162

```
                    agcgtngtcg cggcccgang tcctgggaag cctttnttgc tgagcctcac agcctctgtc    60
                    aggcggctgc ggatccagcg gtccaccagg ctctcatggc ctccgggctg ggaggnggg t    120
                    gagggcacaa aacccttccc aaggccacga anggcaaact tggtggcatt ccanagcttg    180
                    ttgcanaagt ggcggnaacc cagtatccgg ttcacatcca ggntgatgtc acgaccctgg    240
                    gacatgtang cacataatcc aaaccggaga gcatcggtgc acattcacg aatcccgct    300
                    gggaagtcag ctttctgccc ttctttggcc ttctccacct cgctgggatc cagg          354
```

<210> SEQ ID NO 163
<211> LENGTH: 258
<212> TYPE: DNA
<213> ORGANISM: Homo sapiens
<220> FEATURE:
<221> NAME/KEY: misc_feature
<222> LOCATION: 7, 24, 32, 153, 198, 205
<223> OTHER INFORMATION: n = A,T,C or G

<400> SEQUENCE: 163

```
tttttcncca agtcctcttg ccgngggatc tngactgcaa tttaagacac ttctaattag   60
ttatacccag gccctgcaaa attgctgggt ttatataata tattcttgct gcacgaagat  120
ttattattct gttggatgat tctattttaa ttntatttat tctggccaaa aaagaacctt  180
ctccgctcgt caagagangc caatntgtct tgaaggacaa gagaaagatg ctaacacaca  240
ctttcttctt cttgagga                                                258
```

<210> SEQ ID NO 164
<211> LENGTH: 282
<212> TYPE: DNA
<213> ORGANISM: Homo sapiens
<220> FEATURE:
<221> NAME/KEY: misc_feature
<222> LOCATION: 97, 130, 163, 178, 203, 204
<223> OTHER INFORMATION: n = A,T,C or G

<400> SEQUENCE: 164

```
ggaacatatt acttttaaat tacttgggtc aatgaaacat ttaataaaaa catttgcttc   60
tctatataat acgtatgtat aaaataagcc ttttcanaaa ctctggttct cataatcctc  120
tataaatcan atgatctgac ttcaagagg  aacaaattac agnaaggggt atacattnat  180
gaatactggt agtactagag ganngacgct aaaccactct actaccactt gcggaactct  240
cacagggtaa atgacaaagc caatgactga ctctaaaaac aa                     282
```

<210> SEQ ID NO 165
<211> LENGTH: 462
<212> TYPE: DNA
<213> ORGANISM: Homo sapiens
<220> FEATURE:
<221> NAME/KEY: misc_feature
<222> LOCATION: 10, 33, 36, 49, 198, 222, 243, 278, 357, 385, 399, 405, 437
<223> OTHER INFORMATION: n = A,T,C or G

<400> SEQUENCE: 165

```
gcccgggcan gtcctgtaat cccagctact cangangctg agtcatgana atcgcctgaa   60
tccgggaggt agaggccgca gcgagcaaag attaagccac tgcactccag tctgggtgac  120
agagtgagaa tctgtctgtt gctcctctgg cattggtctg aaatgggttt gtagaacatg  180
ccacagaagg accagcanca gcaacaaatg gatttgtgga angcgtagct ccaaatggag  240
cangcacact tgatgaagca cgctgtgtct gtgcagangc aaccactggc actgttccaa  300
aaacattgct gctagcatta cttgtggaag tatacgcatt actggaggtg gctgcanaac  360
tgaaaacgct gtctagttct gccanagctg catacttgnc tgaanatgca cttgactgac  420
tgggaactga accacanaac caacaggacc tttacctgtg ga                     462
```

<210> SEQ ID NO 166
<211> LENGTH: 365
<212> TYPE: DNA
<213> ORGANISM: Homo sapiens
<220> FEATURE:
<221> NAME/KEY: misc_feature
<222> LOCATION: 14, 18
<223> OTHER INFORMATION: n = A,T,C or G

<400> SEQUENCE: 166

```
cgtgggtcgc ggcncgangt ctgaaaccaa tccagaacta aacatcagca cacaaaaaat   60
accaggatag atggaatcaa aagactctga agccaaaagg aggctaggga gagcaactga  120
acttagcaag ctgaggactt cagtgtccat catccgatcc tgccctgtaa caacaggtct  180
atatgataga gatattccat ctgagctgga ggccattatc cttagcaaac taacacagaa  240
cagaaaacca aatacatgtt tcatttaga  agtaggagct aaatgatgag aactcaagga  300
cacaaagaaa ggaacaacag acactggggc ctacttgagg gtggagggtg ggaggaggga  360
gaaga                                                              365
```

<210> SEQ ID NO 167
<211> LENGTH: 364
<212> TYPE: DNA
<213> ORGANISM: Homo sapiens
<220> FEATURE:
<221> NAME/KEY: misc_feature
<222> LOCATION: 19, 342, 361
<223> OTHER INFORMATION: n = A,T,C or G

<400> SEQUENCE: 167

```
agcgtggtcg cggcgcgang tccagcccta gcttgcctgt gactccgcct tcactgggtg   60
ctctctctaa aagttgctga ctctttactg tatctcccaa ttccactcc  attggttcca  120
```

```
taaggggagg ggtgtctcac tcaacatggt gttcctggta ccaagaactg gctgacgaag   180
ctgggtgccg tggctcatgc ctgtaatccc agcactttg ggaggccaag aagggcggat    240
cacctgaggt ctggagttca agatcagcct gaccaacatg atgaaaccaa gtctccacta   300
aaaatataaa acaattagcc aggcatggtg gtgggtgcct gnaatcccag ctactgggga   360
ngct                                                                364
```

<210> SEQ ID NO 168
<211> LENGTH: 447
<212> TYPE: DNA
<213> ORGANISM: Homo sapiens
<220> FEATURE:
<221> NAME/KEY: misc_feature
<222> LOCATION: 407, 414, 437
<223> OTHER INFORMATION: n = A,T,C or G

<400> SEQUENCE: 168

```
cccgggcagg tcaaaaccca aaacctttca ttttagccca aaccagctca tgattaggta   60
tacaaggata acagaaccag ttgtcaggac gagcatttga caagtaaaag caattcttgc   120
aaagctgcag ttcatccagc tcatgcatg tgtctttata tagcatcctc gcaatgttgc    180
cttgctcact gtctgctcca tagaaaatca cggtattgtg gagaagcaat tgggcatcag   240
ctttgaactc ttcataactt cggtatttcc cttcattcac tttctcttga atggtgggaa   300
cgtccacaga cctcggccgc gaccacgcta agcccgaatt ctgcagatat ccatcacact   360
ggcggccgtt cgagcatggc atctagaagg cccaattcgc ctatagngag tcgnattacc   420
aattcactgg ccgtcgnttt acaacgc                                       447
```

<210> SEQ ID NO 169
<211> LENGTH: 524
<212> TYPE: DNA
<213> ORGANISM: Homo sapiens
<220> FEATURE:
<221> NAME/KEY: misc_feature
<222> LOCATION: 4, 6, 39, 40, 235, 248, 313, 340, 359, 382, 389, 420, 434,
       442, 453, 496
<223> OTHER INFORMATION: n = A,T,C or G

<400> SEQUENCE: 169

```
cgantngcgc gcccgggcag gtctgagcag cctttctgnn tgctggacta ttgggattgg   60
gttcatccaa cagagactgt atggatgtta gaatggaaga cacatcatag gttggactcc   120
aacggttctg aagtatgtcc agacatatac taccatctgc atagactaag aacaaagaag   180
taggtacatt aaacgtaaca agaccactaa ggttttaaca ttatagacaa aacanaaata   240
gtcaagnata ctttgctttt gaagtttaaa gattcctatg ttgcttccca gttaactgcc   300
taaaaagata agncataacc accactagtg aaataatcan gatgatcaga gaatgtcana   360
tgtgatcagt ataaaactgg angatattna gtgtcatcct ttggaaaagg ctgccctatn   420
atccaggaaa tcanaaacat tnttgaacag ggccctagc tatccacaga catgtgggaa    480
attcattccc caaatngtag gctggatccc ctatctgaaa taac                    524
```

<210> SEQ ID NO 170
<211> LENGTH: 332
<212> TYPE: DNA
<213> ORGANISM: Homo sapiens
<220> FEATURE:
<221> NAME/KEY: misc_feature
<222> LOCATION: 5, 10, 63, 66, 90, 93, 96, 186, 207, 261, 290, 324, 326
<223> OTHER INFORMATION: n = A,T,C or G

<400> SEQUENCE: 170

```
tcgancggcn cgcccgggca ggtgacaaac ctgttattga agatgttggt tctgatgagg   60
aanaanatca gaagggatgg tgacaagaan aanaanaaga agattaagga aaagtacatc   120
gatcaagaag agctcaacaa aacaaagccc atctggacca gaaatcccga cgatattact   180
aatgangagt acggagaatt ctataanagc ttgaccaatg actgggaaga tcacttggca   240
gtgaagcatt tttcagttga nggacagttg gaattcagag cccttctatn tgtcccacga   300
cgtgctcctt ttgatctgtt tganancaga aa                                 332
```

<210> SEQ ID NO 171
<211> LENGTH: 334
<212> TYPE: DNA
<213> ORGANISM: Homo sapiens
<220> FEATURE:
<221> NAME/KEY: misc_feature
<222> LOCATION: 5, 9, 200, 228, 232
<223> OTHER INFORMATION: n = A,T,C or G -continued

```
<400> SEQUENCE: 171
cgagnggcnc gcccgggcag gtctgttgat agcgacttaa cagaaaagtc tagacaaaca    60
     taagcataaa aaattacagt cttttctaccc ttgggaatgg ggagaaaaag gaatctctac   120
     cccaagacca gaaataataa gtcctgtttc tggtcctgaa catccagaat tatggaggct   180
     ttggcctgac accacattan aatttggtct ggaaatcaaa ctttagaac angagatcgt    240
     aagccatttt atactatcga cctaaattcc agtctaacgg ttcctttaca aagttgcgga   300
     aagccctctt atatgctagc tgtaggaaat atag                                334

<210> SEQ ID NO 172
<211> LENGTH: 439
<212> TYPE: DNA
<213> ORGANISM: Homo sapiens
<220> FEATURE:
<221> NAME/KEY: misc_feature
<222> LOCATION: 19, 375, 388, 390, 395, 409, 426, 434
<223> OTHER INFORMATION: n = A,T,C or G

<400> SEQUENCE: 172
agcgtggtcg cggcccgang tctgcctata aaactagact tctgacgctg ggctccagct    60
     tcattctcac aggtcatcat cctcatccgg gagagcagtt gtctgagcaa cctctaagtc   120
     gtgctcatac tgtgctgcca aagctgggtc catgacaact tctggtgggg cgagagcagg   180
     catggcaaca aattccaagt tagggtctcc aatgagcctg ctagcaagcc agaggaaggg   240
     cttttcaaag ttgtagttac ttttggcaga aatgtcgtag tactgaagat tcttctttcg   300
     gtggaagaca atggatttcg ccttcacttt ctgccttaat atccactttg gtgccacaca   360
     acacaatggg gatgntttca cacacttngn accanatctc tatgccagnt aggccatttt   420
     ggaagnactt cganggtac                                                 439

<210> SEQ ID NO 173
<211> LENGTH: 599
<212> TYPE: DNA
<213> ORGANISM: Homo sapiens
<220> FEATURE:
<221> NAME/KEY: misc_feature
<222> LOCATION: 5, 31
<223> OTHER INFORMATION: n = A,T,C or G

<400> SEQUENCE: 173
cgatnggccg cccgggcagg tcctgtaaaa naggaaattc agacatcgta cgactcgtaa    60
     ttgaatgtgg agctgactgc aatattttgt caaagcacca gaatagtgcc ctgcactttg   120
     cgaagcagtc taacaatgtg cttgtgtacg acttgctgaa gaaccattta gagacacttt   180
     caagagtagc agaagagaca ataaaggatt actttgaagc tcgccttgct ctgctagaac   240
     cagttttttcc aatcgcatgt catcgactct gtgagggtcc agattttca acagatttca    300
     attaccaacc cccacagaac ataccagaag gctctggcat cctgctgttt atcttccatg   360
     caaactttt gggtaaagaa gttattgctc ggctctgtgg accgtgtagt gtacaagctg    420
     tagttctgaa tgataaattt cagcttcctg ttttttctgg tctcgctctg ttgtccaggc   480
     tggagtgcag tggcgcggat tacagctcac tggagtcttg acttcccagg cacaagcaat   540
     cctcccacct cagcctccta actacctggg actaaaaatg caccgccacc acattccgg   599

<210> SEQ ID NO 174
<211> LENGTH: 458
<212> TYPE: DNA
<213> ORGANISM: Homo sapiens
<220> FEATURE:
<221> NAME/KEY: misc_feature
<222> LOCATION: 30, 32, 35, 51, 61, 213, 261, 327, 347, 359, 377, 418
<223> OTHER INFORMATION: n = A,T,C or G

<400> SEQUENCE: 174
tcgatttggc cgcccgggca ggtccatgcn gnttntgccc attcccatgg ngcccgacaa    60
     ncccatcccc gaggccgaca tccccatgtt catgttcatg ccaccatgc cctggctcat    120
     ccctgcgctg ttccccagag gggccattcc catggtgccc gtcattacac cgggcatgtt   180
     cataggcatg ggtcccccca ggagagggtt agnttgaggc cggacaggaa gcatgtttga   240
     tggagaactg aggttcacag nctccaaaac tttgagtcat cacattcata ggctgctgca   300
     tattctgtct gctgaatcca ttgtatncag tgatggcctg ctgggnttt ggaaggctga    360
     cataccaggt agtaagntcg tctaggctga tgtttacacc tggggtcaga ccaagtanga   420
     gggcaaggtt ttgctgactg attttctgga cccatatc                           458

<210> SEQ ID NO 175
<211> LENGTH: 1206
<212> TYPE: DNA
<213> ORGANISM: Homo sapiens
```

<400> SEQUENCE: 175

```
ggcacgagga agttttgtgt actgaaaaag aaactgtcag aagcaaaaga aataaaatca    60
cagttagaga accaaaaagt taaatgggaa caagagctct gcagtgtgag gtttctcaca   120
ctcatgaaaa tgaaaattat ctcttacatg aaaattgcat gttgaaaaag gaaattgcca   180
tgctaaaact ggaaatagcc acactgaaac accaatacca ggaaaaggaa aataaaatact  240
ttgaggacat taagatttta aaagaaaaga atgctgaact tcagatgacc ctaaaactga   300
aagaggaatc attaactaaa agggcatctc aatatagtgg gcagcttaaa gttctgatag   360
ctgagaacac aatgctcact tctaaattga aggaaaaaca agacaaagaa atactagagg   420
cagaaattga atcacaccat cctagactgg cttctgctgt acaagaccat gatcaaattg   480
tgacatcaag aaaaagtcaa gaacctgctt tccacattgc aggagatgct tgtttgcaaa   540
gaaaaatgaa tgttgatgtg agtagtacga tatataacaa tgaggtgctc catcaaccac   600
tttctgaagc tcaaggaaa tccaaaagcc taaaaattaa tctcaattat gccggagatg   660
ctctaagaga aaatacattg gtttcagaac atgcacaaag agaccaacgt gaaacacagt   720
gtcaaatgaa ggaagctgaa cacatgtatc aaaacgaaca agataatgtg aacaaacaca   780
ctgaacagca ggagtctcta gatcagaaat tatttcaact acaaagcaaa aatatgtggc   840
ttcaacagca attagttcat gcacataaga aagctgacaa caaaagcaag ataacaattg   900
atattcattt tcttgagagg aaaatgcaac atcatctcct aaaagagaaa atgaggaga   960
tatttaatta caataaccat ttaaaaaacc gtatatatca atatgaaaaa gagaaagcag  1020
aaacagaagt tatataatag tataacactg ccaaggagcg gattatctca tcttcatcct  1080
gtaattccag tgtttgtcac gtggttgttg aataaatgaa taaagaatga gaaaaccaga  1140
agctctgata cataatcata atgataatta tttcaatgca caactacggg tggtgctgct  1200
cgtgcc                                                             1206
```

<210> SEQ ID NO 176
<211> LENGTH: 317
<212> TYPE: PRT
<213> ORGANISM: Homo sapiens

<400> SEQUENCE: 176

```
Met Gly Thr Arg Ala Leu Gln Cys Glu Val Ser His Thr His Glu Asn
  1               5                  10                  15
Glu Asn Tyr Leu Leu His Glu Asn Cys Met Leu Lys Lys Glu Ile Ala
             20                  25                  30
Met Leu Lys Leu Glu Ile Ala Thr Leu Lys His Gln Tyr Gln Glu Lys
         35                  40                  45
Glu Asn Lys Tyr Phe Glu Asp Ile Lys Ile Leu Lys Glu Lys Asn Ala
     50                  55                  60
Glu Leu Gln Met Thr Leu Lys Leu Lys Glu Ser Leu Thr Lys Arg
 65                  70                  75                  80
Ala Ser Gln Tyr Ser Gly Gln Leu Lys Val Leu Ile Ala Glu Asn Thr
                 85                  90                  95
Met Leu Thr Ser Lys Leu Lys Glu Lys Gln Asp Lys Glu Ile Leu Glu
            100                 105                 110
Ala Glu Ile Glu Ser His His Pro Arg Leu Ala Ser Ala Val Gln Asp
        115                 120                 125
His Asp Gln Ile Val Thr Ser Arg Lys Ser Gln Glu Pro Ala Phe His
    130                 135                 140
Ile Ala Gly Asp Ala Cys Leu Gln Arg Lys Met Asn Val Asp Val Ser
145                 150                 155                 160
Ser Thr Ile Tyr Asn Asn Glu Val Leu His Gln Pro Leu Ser Glu Ala
                165                 170                 175
Gln Arg Lys Ser Lys Ser Leu Lys Ile Asn Leu Asn Tyr Ala Gly Asp
            180                 185                 190
Ala Leu Arg Glu Asn Thr Leu Val Ser Glu His Ala Gln Arg Asp Gln
        195                 200                 205
Arg Glu Thr Gln Cys Gln Met Lys Glu Ala Glu His Met Tyr Gln Asn
    210                 215                 220
Glu Gln Asp Asn Val Asn Lys His Thr Glu Gln Glu Ser Leu Asp
225                 230                 235                 240
Gln Lys Leu Phe Gln Leu Gln Ser Lys Asn Met Trp Leu Gln Gln Gln
                245                 250                 255
Leu Val His Ala His Lys Lys Ala Asp Asn Lys Ser Lys Ile Thr Ile
            260                 265                 270
Asp Ile His Phe Leu Glu Arg Lys Met Gln His His Leu Leu Lys Glu
        275                 280                 285
Lys Asn Glu Glu Ile Phe Asn Tyr Asn Asn His Leu Lys Asn Arg Ile
    290                 295                 300
Tyr Gln Tyr Glu Lys Glu Lys Ala Glu Thr Glu Val Ile
305                 310                 315
```

<210> SEQ ID NO 177
<211> LENGTH: 20
<212> TYPE: DNA
<213> ORGANISM: Artificial Sequence

```
<220> FEATURE:
<223> OTHER INFORMATION: Made in the lab

<400> SEQUENCE: 177
ccaatcatct ccacaggagc                                              20

<210> SEQ ID NO 178
<211> LENGTH: 1665
<212> TYPE: DNA
<213> ORGANISM: Homo sapiens

<400> SEQUENCE: 178
gcaaactttc aagcagagcc tcccgagaag ccatctgcct tcgagcctgc cattgaaatg   60
    caaaagtctg ttccaaataa agccttggaa ttgaagaatg aacaaacatt gagagcagat  120
    cagatgttcc cttcagaatc aaaacaaaag aaggttgaag aaaattcttg ggattctgag  180
    agtctccgtg agactgtttc acagaaggat gtgtgtgtac ccaaggctac acatcaaaaa  240
    gaaatggata aaataagtgg aaaattagaa gattcaacta gcctatcaaa aatcttggat  300
    acagttcatt cttgtgaaag agcaagggaa cttcaaaaag atcactgtga acaacgtaca  360
    ggaaaaatgg aacaaatgaa aaagaagttt tgtgtactga aaagaaact gtcagaagca  420
    aaagaaataa aatcacagtt agagaaccaa aaagttaaat gggaacaaga gctctgcagt  480
    gtgaggtttc tcacactcat gaaaatgaaa attatctctt acatgaaaat tgcatgttga  540
    aaaaggaaat tgccatgcta aaactggaaa tagccacact gaaacaccaa taccaggaaa  600
    aggaaaataa atactttgag gacattaaga ttttaaaaga aaagaatgct gaacttcaga  660
    tgaccctaaa actgaaagag gaatcattaa ctaaaagggc atctcaatat agtgggcagc  720
    ttaaagttct gatagctgag aacacaatgc tcacttctaa attgaaggaa aaacaagaca  780
    aagaaatact agaggcagaa attgaatcac accatcctag actggcttct gctgtacaag  840
    accatgatca aattgtgaca tcaagaaaaa gtcaagaacc tgctttccac attgcaggag  900
    atgcttgttt gcaaagaaaa atgaatgttg atgtgagtag tacgatatat aacaatgagg  960
    tgctccatca accactttct gaagctcaaa ggaaatccaa aagcctaaaa attaatctca 1020
    attatgccgg agatgctcta agagaaaata cattggtttc agaacatgca caaagagacc 1080
    aacgtgaaac acagtgtcaa atgaaggaag ctgaacacat gtatcaaaac gaacaagata 1140
    atgtgaacaa acacactgaa cagcaggagt ctctagatca gaaattattt caactacaaa 1200
    gcaaaatat gtggcttcaa cagcaattag ttcatgcaca taagaaagct gacaacaaaa 1260
    gcaagataac aattgatatt catttcttg agaggaaaat gcaacatcat ctcctaaaag 1320
    agaaaaatga ggagatattt aattacaata accatttaaa aaaccgtata tatcaaatatg 1380
    aaaaagagaa agcagaaaca gaaaactcat gagagacaag cagtaagaaa cttcttttgg 1440
    agaaacaaca gaccagatct ttactcacaa ctcatgctag gaggccagtc ctagcattac 1500
    cttatgttga aaatcttacc aatagtctgt gtcaacagaa tacttatttt agaagaaaaa 1560
    ttcatgattt cttcctgaag cctgggcgac agagcgagac tctgtctcaa aaaaaaaaaa 1620
    aaaaaagaa agaaagaaat gcctgtgctt acttcgcttc ccagg                   1665

<210> SEQ ID NO 179
<211> LENGTH: 179
<212> TYPE: PRT
<213> ORGANISM: Homo sapiens

<400> SEQUENCE: 179

Ala Asn Phe Gln Ala Glu Pro Glu Lys Pro Ser Ala Phe Glu Pro
    1               5                   10                  15
    Ala Ile Glu Met Gln Lys Ser Val Pro Asn Lys Ala Leu Glu Leu Lys
                    20                  25                  30
    Asn Glu Gln Thr Leu Arg Ala Asp Gln Met Phe Pro Ser Glu Ser Lys
                35                  40                  45
    Gln Lys Lys Val Glu Glu Asn Ser Trp Asp Ser Glu Ser Leu Arg Glu
            50                  55                  60
    Thr Val Ser Gln Lys Asp Val Cys Val Pro Lys Ala Thr His Gln Lys
    65                  70                  75                  80
    Glu Met Asp Lys Ile Ser Gly Lys Leu Glu Asp Ser Thr Ser Leu Ser
                    85                  90                  95
    Lys Ile Leu Asp Thr Val His Ser Cys Glu Arg Ala Arg Glu Leu Gln
                100                 105                 110
    Lys Asp His Cys Glu Gln Arg Thr Gly Lys Met Glu Gln Met Lys Lys
                115                 120                 125
    Lys Phe Cys Val Leu Lys Lys Leu Ser Glu Ala Lys Glu Ile Lys
                130                 135                 140
    Ser Gln Leu Glu Asn Gln Lys Val Lys Trp Glu Gln Leu Cys Ser
    145                 150                 155                 160
    Val Arg Phe Leu Thr Leu Met Lys Met Lys Ile Ile Ser Tyr Met Lys
                        165                 170                 175
    Ile Ala Cys

<210> SEQ ID NO 180
<211> LENGTH: 1681
```

-continued

```
<212> TYPE: DNA
<213> ORGANISM: Homo sapiens

<400> SEQUENCE: 180
gatacagtca ttcttgtgaa agagcaaggg aacttcaaaa agatcactgt gaacaacgta    60
caggaaaaat ggaacaaatg aaaagaagt tttgtgtact gaaaagaaa ctgtcagaag     120
caaaagaaat aaaatcacag ttagagaacc aaaaagttaa atgggaacaa gagctctgca   180
gtgtgagatt gactttaaac caagaagaag agaagagaag aaatgccgat atattaaatg   240
aaaaaattag ggaagaatta ggaagaatcg aagagcagca taggaaagag ttagaagtga   300
aacaacaact tgaacaggct ctcagaatac aagatataga attgaagagt gtagaaagta   360
atttgaatca ggtttctcac actcatgaaa atgaaaatta tctcttacat gaaaattgca   420
tgttgaaaaa ggaaattgcc atgctaaaac tggaaatagc cacactgaaa caccaatacc   480
aggaaaagga aaataaatac tttgaggaca ttaagatttt aaaagaaaag aatgctgaac   540
ttcagatgac cctaaaactg aagaggaat cattaactaa aagggcatct caatatagtg     600
ggcagcttaa agttctgata gctgagaaca caatgctcac ttctaaattg aaggaaaaac   660
aagacaaaga aatactagag gcagaaattg aatcacacca tcctagactg gcttctgctg   720
tacaagacca tgatcaaatt gtgacatcaa gaaaaagtca agaacctgct ttccacattg   780
caggagatgc ttgtttgcaa agaaaaatga atgttgatgt gagtagtacg atatataaca   840
atgaggtgct ccatcaacca ctttctgaag ctcaaaggaa atccaaaagc ctaaaaatta   900
atctcaatta tgccggagat gctctaagag aaaatacatt ggtttcagaa catgcacaaa   960
gagaccaacg tgaaacacag tgtcaaatga aggaagctga acacatgtat caaaacgaac  1020
aagataatgt gaacaaacac actgaacagc aggagtctct agatcagaaa ttatttcaac  1080
tacaaagcaa aaatatgtgg cttcaacagc aattagttca tgcacataag aaagctgaca  1140
acaaaagcaa gataacaatt gatattcatt ttcttgagag gaaaatgcaa catcatctcc  1200
taaaagagaa aaatgaggag atatttaatt acaataacca tttaaaaaac cgtatatatc  1260
aatatgaaaa agagaaagca gaaacagaaa actcatgaga gacaagcagt aagaaacttc  1320
ttttggagaa acaacagacc agatctttac tcacaactca tgctaggagg ccagtcctag  1380
cattaccta tgttgaaaaa tcttaccaat agtctgtgtc aacagaatac ttattttaga   1440
agaaaaattc atgatttctt cctgaagcct acagacataa aataacagtg tgaagaatta  1500
cttgttcacg aattgcataa aagctgccca ggatttccat ctaccctgga tgatgccgga  1560
gacatcattc aatccaacca gaatctcgct ctgtcactca ggctggagtg cagtgggcgc  1620
aatctcggct cactgcaact ctgcctccca ggttcacgcc attctctggc acagcctccc  1680
g                                                                  1681

<210> SEQ ID NO 181
<211> LENGTH: 432
<212> TYPE: PRT
<213> ORGANISM: Homo sapiens

<400> SEQUENCE: 181

Asp Thr Val His Ser Cys Glu Arg Ala Arg Glu Leu Gln Lys Asp His
  1               5                  10                  15
Cys Glu Gln Arg Thr Gly Lys Met Glu Gln Met Lys Lys Lys Phe Cys
                 20                  25                  30
Val Leu Lys Lys Lys Leu Ser Glu Ala Lys Glu Ile Lys Ser Gln Leu
             35                  40                  45
Glu Asn Gln Lys Val Lys Trp Glu Gln Leu Cys Ser Val Arg Leu
     50                  55                  60
Thr Leu Asn Gln Glu Glu Lys Arg Arg Asn Ala Asp Ile Leu Asn
 65                  70                  75                  80
Glu Lys Ile Arg Glu Glu Leu Gly Arg Ile Glu Glu Gln His Arg Lys
                 85                  90                  95
Glu Leu Glu Val Lys Gln Gln Leu Glu Gln Ala Leu Arg Ile Gln Asp
                100                 105                 110
Ile Glu Leu Lys Ser Val Glu Ser Asn Leu Asn Gln Val Ser His Thr
            115                 120                 125
His Glu Asn Glu Asn Tyr Leu Leu His Glu Asn Cys Met Leu Lys Lys
        130                 135                 140
Glu Ile Ala Met Leu Lys Leu Glu Ile Ala Thr Leu Lys His Gln Tyr
145                 150                 155                 160
Gln Glu Lys Glu Asn Lys Tyr Phe Glu Asp Ile Lys Ile Leu Lys Glu
                165                 170                 175
Lys Asn Ala Glu Leu Gln Met Thr Leu Lys Leu Lys Glu Ser Leu
            180                 185                 190
Thr Lys Arg Ala Ser Gln Tyr Ser Gly Gln Leu Lys Val Leu Ile Ala
        195                 200                 205
Glu Asn Thr Met Leu Thr Ser Lys Leu Lys Lys Gln Asp Lys Glu
    210                 215                 220
Ile Leu Glu Ala Glu Ile Glu Ser His His Pro Arg Leu Ala Ser Ala
225                 230                 235                 240
Val Gln Asp His Asp Gln Ile Val Thr Ser Arg Lys Ser Gln Glu Pro
                245                 250                 255
Ala Phe His Ile Ala Gly Asp Ala Cys Leu Gln Arg Lys Met Asn Val
            260                 265                 270
Asp Val Ser Ser Thr Ile Tyr Asn Asn Glu Val Leu His Gln Pro Leu
        275                 280                 285
```

-continued

```
      Ser Glu Ala Gln Arg Lys Ser Lys Ser Leu Lys Ile Asn Leu Asn Tyr
          290                 295                 300
      Ala Gly Asp Ala Leu Arg Glu Asn Thr Leu Val Ser Glu His Ala Gln
      305                 310                 315                 320
      Arg Asp Gln Arg Glu Thr Gln Cys Gln Met Lys Glu Ala Glu His Met
                      325                 330                 335
      Tyr Gln Asn Glu Gln Asp Asn Val Asn Lys His Thr Glu Gln Gln Glu
                  340                 345                 350
      Ser Leu Asp Gln Lys Leu Phe Gln Leu Gln Ser Lys Asn Met Trp Leu
              355                 360                 365
      Gln Gln Gln Leu Val His Ala His Lys Lys Ala Asp Asn Lys Ser Lys
          370                 375                 380
      Ile Thr Ile Asp Ile His Phe Leu Glu Arg Lys Met Gln His His Leu
      385                 390                 395                 400
      Leu Lys Glu Lys Asn Glu Glu Ile Phe Asn Tyr Asn Asn His Leu Lys
                      405                 410                 415
      Asn Arg Ile Tyr Gln Tyr Glu Lys Glu Lys Ala Glu Thr Glu Asn Ser
                  420                 425                 430
```

<210> SEQ ID NO 182
<211> LENGTH: 511
<212> TYPE: DNA
<213> ORGANISM: Homo sapiens

<400> SEQUENCE: 182

```
gaagtttcat gaggtttagc ttttctgggc tggggagtgg agagaaagaa gttgcagggc    60
ttacaggaaa tcccagagcc tgaggttttc tcccagattt gagaactcta gattctgcat   120
cattatcttt gagtctatat tctcttgggc tgtaagaaga tgaggaatgt aataggtctg   180
ccccaagcct tcatgccttc tgtaccaag cttgtttcct tgtgcatcct tcccaggctc    240
tggctgcccc ttattggaga atgtgatttc caagacaatc aatccacaag tgtctaagac   300
tgaatacaaa gaacttcttc aagagttcat agacgactaa gccactacaa atgccataga   360
tgaattgaag gaatgttttc ttaaccaaac ggatgaaact ctgagcaatg ttgaggtgtt   420
tatgcaatta atatatgaca gcagtctttg tgatttattt taactttctg caagaccttt   480
ggctcacaga actgcagggt atggtgagaa a                                  511
```

<210> SEQ ID NO 183
<211> LENGTH: 260
<212> TYPE: DNA
<213> ORGANISM: Homo sapiens

<400> SEQUENCE: 183

```
cacctcgcgg ttcagctcct ctgtcttggt gaagaaccat tcctcggcat ccttgcggtt    60
cttctctgcc atcttctcat actggtcacg catctcgttc agaatgcggc tcaggtccac   120
gccaggtgca gcgtccatct ccacattgac atctccaccc acctggcctc tcagggcatt   180
catctcctcc tcgtggttct tcttcaggta ggccagctcc tccttcaggc tctcaatctg   240
catctccagg tcagctctgg                                               260
```

<210> SEQ ID NO 184
<211> LENGTH: 461
<212> TYPE: DNA
<213> ORGANISM: Homo sapiens

<400> SEQUENCE: 184

```
gtctgatggg agaccaaaga atttgcaagt ggatggtttg gtatcactgt aaataaaaag    60
agggcctttt ctagctgtat gactgttact tgaccttctt tgaaaagcat tcccaaaatg   120
ctctatttta gatagattaa cattaaccaa cataatttt tttagatcga gtcagcataa    180
atttctaagt cagcctctag tcgtggttca tctctttcac ctgcattta tttggtgttt    240
gtctgaagaa aggaaagagg aaagcaaata cgaattgtac tatttgtacc aaatctttgg   300
gattcattgg caaataattt cagtgtggtg tattattaaa tagaaaaaaa aaattttgtt   360
tcctaggttg aaggtctaat tgataccgtt tgacttatga tgaccattta tgcactttca   420
aatgaatttg ctttcaaaat aaatgaagag cagacctcgg c                       461
```

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga    60
caggcagtga acttgacatg attagctggc atgattttt cttttttttc ccccaaacat   120
tgttttgtg gccttgaatt ttaagacaaa tattctacac ggcatattgc acaggatgga   180
```

```
      tggcaaaaaa aagtttaaaa acaaaaaccc ttaacggaac tgccttaaaa aggcagacgt    240
      cctagtgcct gtcatgttat attaaacata catacacaca atctttttgc ttattataat    300
      acagacttaa atgtacaaag atgttttcca cttttttcaa tttttaaaca caacagctat    360
      aaacctgaac acatatgcta tcatcatgcc ataagactaa aacaattata tttagcgaca    420
      agtagaaagg attaaatagt caaatacaag aatgaaaaac gcagtacata gtgtcgcgaa    480
      ctcaaatcgg catttagata gatccagtgg tttaaacggc acgttttgc t              531
```

<210> SEQ ID NO 186
<211> LENGTH: 441
<212> TYPE: DNA
<213> ORGANISM: Homo sapiens

<400> SEQUENCE: 186

```
      cattcctttc ctcgcgttgg ggtttctctg tgtcagcgag cctcggtaca ctgatttccg     60
      atcaaaagaa tcatcatctt taccttgact tttcaggtaa ttactgaact ttcttctcag    120
      aagatagggc acagccattg ccttggcctc acttgaaggg tctgcatttg ggtcctctgg    180
      tctcttgcca agtttcccaa ccactcgagg gagaaatatc gggaggtttg acttcctccg    240
      gggctttccc gagggcttca ccgtgagccc tgcggccctc agggctgcaa tcctggattc    300
      aatgtctgaa acctcgctct ctgcctgctg gacttctgag gccgtcactg ccactctgtc    360
      ctccagctct gacagctcct catctgtggt cctgttgtac tggacgdggt ccccagggtc    420
      ctggggcttt ttttcctgtc t                                              441
```

<210> SEQ ID NO 187
<211> LENGTH: 371
<212> TYPE: DNA
<213> ORGANISM: Homo sapiens

<400> SEQUENCE: 187

```
      aaaagtgaat gagtaactat tatattgttg gcaataataa gttgcaaaat catcaggctg     60
      caggctgctg atggtgagag tgaactctgt cccagatcca ctgccgctga accttgatgg    120
      gaccccagat tctaaactag acgccttatg gatcaggagc tttgggcctt tccctggttt    180
      ctgttgatac caggccaacc aactactaac actctgactg gcccggcaag tgatggtgac    240
      tctgtctcct acagttgcag acagggtgga aggagactgg gtcatctgga tgtcacattt    300
      ggcacctggg agccagagca gcaggagccc caggagctga gcggggaccc tcatgtccat    360
      gctgagtcct g                                                         371
```

<210> SEQ ID NO 188
<211> LENGTH: 226
<212> TYPE: DNA
<213> ORGANISM: Homo sapiens

<400> SEQUENCE: 188

```
      ggtatataaa ttgagatgcc cccccaggcc agcaaatgtt ccttttttgtt caaagtctat     60
      ttttattcct tgatatttt cttttttttt ttttgtgga tgggacttg tgaattttc         120
      taaaggtgct atttaacatg ggaggagagc gtgtgcggct ccagcccagc ccgctgctca    180
      ctttccaccc tctctccacc tgcctctggc ttctcaggac ctgccc                   226
```

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: 43, 112, 131, 156, 195, 208, 221, 317, 333, 367
<223> OTHER INFORMATION: n = A,T,C or G

<400> SEQUENCE: 189

```
      tgggtgaagt ttattctgtt ttcacatcta ggttgttggg ganagtgata gacaaagttc     60
      tggattctgg gcatcgtcgg cgcatgcttg taatcctact tgggaggttg anacaggaga    120
      cctcggccgc naccacgcta agggcgaatt ctgcanatat ccatcacact ggcggccgct    180
      cgagcatgca tctanagggc ccaattcncc ctatagtgag ncgtattaca attcactggc    240
      cgtcgtttta caacgtcgtg actgggaaaa ccctggcgtt acccaactta atcgccttgc    300
      agcacatccc cctttcncca gctggcttaa tancgaagag gcccgcaccg atcgcccttc    360
      ccaacanttg cgcagcctga atggcgaatg g                                   391
```

<210> SEQ ID NO 190
<211> LENGTH: 501
<212> TYPE: DNA
<213> ORGANISM: Homo sapiens

```
<400> SEQUENCE: 190
catcttggcc tttttgagct gtttccgctt cttctcatcc cggtcactgt caccctcatt    60
actgagggag ctggcagagg cgttgctgtc aaactcctct gccacatctt cctcctcttc   120
acctgggttg aatgactcat cggtttcttc tcctgagtca tcgctgctgt cattggcatt   180
ctcctcccgg atcttgcctt cctccttcat cctctccaag taggcatcat gctggtcctc   240
atcagagtca gcatattcat cgtagcttgg gttcatgccc tctttcaatc ctcggttttt   300
gatgtttgagc ttttttcgcgt tgacaaaatc aaacagtttc ccgtactcct ccctctcaat   360
gctgctgaag gtatactgag tgccctgctt ggtctcaatt tcaaagtcaa aggaacgagt   420
agtagtggta ccacgagcaa agttgacaaa ggagatctca tcgaagcgga tgtgcacagg   480
tggcttgtgg acgtagatga a                                             501
```

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

```
<400> SEQUENCE: 191
ggaaaaactg tgaaaaatat atctgaattt attaagtaca gtataaaana gggttgtggc    60
aacagaaagt aaaaactaac atggattgct ataaatatgc tgaagcctag ttgttcaaat   120
gatacaattc tctcatgcta ctctaaagtt tataaagaaa aaggatttac actttacaca   180
ctgtacacaa aaggaatacc ttctgagagc cagggagtgg ggaaggggga aggagacttg   240
a                                                                   241
```

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: 6, 17, 23, 26, 70, 227, 245
<223> OTHER INFORMATION: n = A,T,C or G

```
<400> SEQUENCE: 192
tggtcntgga ttcacanata aantanatcg actaaaactg gcagaaattg tgaagcaggt    60
gatagaagan caaaccacgt cccacgaatc ccaataatga cagcttcaga ctttgctttt   120
ttaacaattt gaaaaattat tctttaatgt ataaagtaat tttatgtaaa ttaataaatc   180
ataatttcat ttccacattg attaaagctg ctgtatagat ttagggngca ggacttaata   240
atagnggaaa tgaaattatg atttattaat c                                  271
```

<210> SEQ ID NO 193
<211> LENGTH: 351
<212> TYPE: DNA
<213> ORGANISM: Homo sapiens

```
<400> SEQUENCE: 193
agtcgaggcg ctgatcccta aaatggcgaa catgtgtttt catcatttca gccaaagtcc    60
taacttcctg tgcctttcct atcacctcga gaagtaatta tggatttggtt tggattttg   120
gaccaccgtt cagtcatttt gggttgccgt gctcccaaaa catttttaaat gaaagtattg   180
gcattcaaaa agacagcaga caaaatgaaa gaaaatgaga gcagaaagta agcatttcca   240
gcctatctaa tttctttagt tttctatttg cctccagtgc agtccatttc ctaatgtata   300
ccagcctact gtactattta aaatgctcaa tttcagcacc gatggacctg c             351
```

<210> SEQ ID NO 194
<211> LENGTH: 311
<212> TYPE: DNA
<213> ORGANISM: Homo sapiens

```
<400> SEQUENCE: 194
ctgagacaca gaggcccact gcgaggggga cagtggcggt gggactgacc tgctgacagt    60
caccctccct ctgctgggat gaggtccagg agccaactaa acaatggca gaggagacat    120
ctctggtgtt cccaccaccc tagatgaaaa tccacagcac agacctctac cgtgtttctc   180
ttccatccct aaaccacttc cttaaaatgt ttggatttgc aaagccaatt tggggcctgt   240
ggagcctggg gttggatagg gccatggctg gtcccccacc atacctcccc tccacatcac   300
tgacacagac c                                                        311
```

```
<210> SEQ ID NO 195
<211> LENGTH: 381
<212> TYPE: DNA
<213> ORGANISM: Homo sapiens

<400> SEQUENCE: 195
tgtcagagtg gcactggtag aagttccagg aaccctgaac tgtaagggtt cttcatcagt    60
     gccaacagga tgacatgaaa tgatgtactc agaagtgtcc tggaatgggg cccatgagat   120
     ggttgtctga gagagagctt cttgtcctgt ctttttcctt ccaatcaggg gctcgctctt   180
     ctgattattc ttcagggcaa tgacataaat tgtatattcg gttcccggtt ccaggccagt   240
     aatagtagcc tctgtgacac cagggcgggg ccgagggacc acttctctgg gaggagaccc   300
     aggcttctca tacttgatga tgtagccggt aatcctggca cgtggcggct gccatgatac   360
     cagcagggaa ttgggtgtgg t                                              381

<210> SEQ ID NO 196
<211> LENGTH: 401
<212> TYPE: DNA
<213> ORGANISM: Homo sapiens

<400> SEQUENCE: 196
cacaaacaag aggagcacca gacctcctct tggcttcgag atggcttcgc cacaccaaga    60
     gcccaaacct ggagacctga ttgagatttt ccgccttggc tatgagcact gggccctgta   120
     tataggagat ggctacgtga tccatctggc tcctccaagt gagtaccccg gggctggctc   180
     ctccagtgtc ttctcagtcc tgagcaacag tgcagaggtg aaacgggagc gcctggaaga   240
     tgtggtggga ggctgttgct atcgggtcaa caacagcttg gaccatgagt accaaccacg   300
     gcccgtggag gtgatcacca gttctgcgaa ggagatggtt ggtcagaaga tgaagtacag   360
     tattgtgagc aggaactgtg agcactttgt cacccagacc t                       401

<210> SEQ ID NO 197
<211> LENGTH: 471
<212> TYPE: DNA
<213> ORGANISM: Homo sapiens

<400> SEQUENCE: 197
ctgtaatgat gtgagcaggg agccttcctc cctgggccac ctgcagagag ctttcccacc    60
     aactttgtac cttgattgcc ttacaaagtt atttgtttac aaacagcgac catataaaag   120
     cctcctgccc caaagcttgt gggcacatgg gcacatacag actcacatac agacacacac   180
     atatatgtac agacatgtac tctcacacac acaggcacca gcatacacac gttttttctag   240
     gtacagctcc caggaacagc taggtgggaa agtcccatca ctgagggagc ctaaccatgt   300
     ccctgaacaa aaattgggca ctcatctatt cctttctct tgtgtccta ctcattgaaa    360
     ccaaactctg gaaaggaccc aatgtaccag tatttatacc tctagtgaag cacagagaga   420
     ggaagagagc tgcttaaact cacacaacaa tgaactgcag acacagacct g             471

<210> SEQ ID NO 198
<211> LENGTH: 201
<212> TYPE: DNA
<213> ORGANISM: Homo sapiens

<400> SEQUENCE: 198
ggtccattga ggctctgtcg gccatgccca cagttcgaag ctttgccaac gaggagggcg    60
     aagcccagaa gtttaggaa aagctgcaag aaataaagac actcaaccag aaggaggctg   120
     tggcctatgc agtcaactcc tggaccacta gtatttcagg tatgctgctg aaagtggaa   180
     tcctctacat tggtgggcag a                                              201

<210> SEQ ID NO 199
<211> LENGTH: 551
<212> TYPE: DNA
<213> ORGANISM: Homo sapiens

<400> SEQUENCE: 199
tctggcacag atcttcaccc acacggcggt ccacgtgctg atcatcttcc gggtctcacc    60
     gggcctggaa cacaccatct tccccatgag cccggtgccc agtctggtga cttccatctt   120
     ggcccctggc cttatgtccc agttatgacc cctgacttca actctggctc ttaccctgta   180
     actccagtcc atctctgaca tttttaacac ccggccttgt gaccgtggac atagctcctg   240
     acctcgattc ccatcttgag cccagtgtta gtccatgaga tcatgacctg actcctggtc   300
     tccaaccttg tgatcctaat tctgggacct caatcctagc ctctgaactt gggaccctgg   360
     agctcctgac cttagtcctg accgctaccc ttgattctga cctttgatcc tgtaacttag   420
     gggtggcccc tgaccttatt actgtcattt agctccttga ccttgccact tcaatcctgg   480
     ctttatgacc tcctactctc aattttaact ttaaccaaat gaccaaattt gtgacactaa   540
     atgaccacaa t                                                         551
```

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: 8, 36, 40, 78, 165, 170, 171, 173, 203, 207, 208
<223> OTHER INFORMATION: n = A,T,C or G

<400> SEQUENCE: 200

```
cagctcancg ggcgacatgc ccctacaagt tggcanaagn ggctgccact gctgggtttg    60
tgtaagagag gctgctgnca ccattacctg cagaaacctt ctcataggg ctacgatcgg   120
tactgctagg gggcacatag cgcccatggg tgtggtaggt ggggnactcn ntnataggat   180
ggtaggtatc ccgggctgga aanatgnnca g                                  211
```

<210> SEQ ID NO 201
<211> LENGTH: 111
<212> TYPE: DNA
<213> ORGANISM: Homo sapiens

<400> SEQUENCE: 201

```
ccagtgaaag gaaacaaaac tggcagtttg tccatttgaa tatcagacct agtttcttct    60
taatttccac actatttctc ccatattcct taaacttctt ggcatccacc t            111
```

<210> SEQ ID NO 202
<211> LENGTH: 331
<212> TYPE: DNA
<213> ORGANISM: Homo sapiens

<400> SEQUENCE: 202

```
tgaaaataca gaataccagg tggtcccaaa tgtttgaagt tctttgaaca gaaagagaga    60
ggagagagag agagaggaaa attccctaac ccttggttta aagacaatat tcatttattg   120
ctcaaatgat gcttttaagg gaggacagtg gaataaaata aactttttt ttctccctac   180
aatacataga agggttatca aaccactcaa gtttcaaaat cttttccaggg tccaatatca   240
ctttttttct ttcggttcaa tgaaaagcta aatgtaataa tactaattat agataaaatt   300
ttattttact ttttaaaaat ttgtccagac c                                  331
```

<210> SEQ ID NO 203
<211> LENGTH: 491
<212> TYPE: DNA
<213> ORGANISM: Homo sapiens

<400> SEQUENCE: 203

```
agtcacccag tctacttagt acctggttgc tgcctctgac cttttcagct tgatacctg     60
ggctttagtg taaccaataa atctgtagtg accttacctg tattccctgt gctatcctgt   120
gggaaggtag gaatgggcta agtatgatga atgtataggt tagggatctt ttggttttaa   180
atcacagaaa acctaattca aactggctta aaataaaag gatttattgg ttcatgtaac   240
tagaaagtcc ataggtagtg ctggctccag gtgaagactt gacccagtag ttcagtatgt   300
ctctaaatac cggactgact tttttctcac tgttgcatct tctgtaggac catttaagtc   360
tgggccactt aatggctgcc agcattccta agattacact tttcccatt tatgtccaat   420
cagaaaaga aggcatcttt gtaccagaaa tctcagcaaa gccctaata ttcacactga   480
ttaggacctg c                                                        491
```

<210> SEQ ID NO 204
<211> LENGTH: 361
<212> TYPE: DNA
<213> ORGANISM: Homo sapiens

<400> SEQUENCE: 204

```
tcccttcctc ccccatgtga taaatgggtc cagggctgat caaagaactc tgactgcaga    60
actgccgctc tcagtggaca gggcatctgt tatcctgaga cctgtggcag acacgtcttg   120
ttttcatttg attttttgtta agagtgcagt attgcagagt ctagaggaat ttttgtttcc   180
ttgattaaca tgattttcct ggttgttaca tccagggcat ggcagtggcc tcagccttaa   240
acttttgttc ctactccac cctcagcgaa ctgggcagca cggggagggt ttggctaccc   300
ctgcccatcc ctgagccagg taccaccatt gtaggaaac actttcagaa attcagacct   360
c                                                                   361
```

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: 2, 3
<223> OTHER INFORMATION: n = A,T,C or G

<400> SEQUENCE: 205

```
cnngtacagt tcttcctgga tggccgacac agatcctggg gaaaggcaat cctggcactg    60
ctctgaaacc agagctcctc ctccctcccc gggcagggtg gagctgagaa gggctgctct   120
agcgttggga ctccacctcc atacacctga tattttgata gggcaggtcc ctgctatggg   180
ccactgttct gggcagtata gtatgcttga cagcatcctt ggcatctatc caccagatcc   240
cagagcaccc gctactagct gtgacaacat cctccaaaca ttgcaaaatt tcccctggga   300
ggcaagattg cctcagatgg gagaatcacg ctctagggaa atctgctggt atgagaaccc   360
caactcccca ctccactgag cctccagatg gcgagcaggc tgcagctcca gcacagacac   420
gaagctccct ccagccactg acggtccatg gctggggtta cccaggacct c            471
```

<210> SEQ ID NO 206
<211> LENGTH: 261
<212> TYPE: DNA
<213> ORGANISM: Homo sapiens

<400> SEQUENCE: 206

```
tagagtattt agagtcctga gataacaagg aatccaggca tcctttagac agtcttctgt    60
tgtcctttct tcccaatcag agatttgtgg atgtgtggaa tgacaccacc accagcaatt   120
gtagccttga tgagagaatc caattcttca tctccacgaa tagcaagttg caagtgacga   180
ggggtaatac gctttacctt taagtctttt gatgcatttc ctgccagttc aagtacctct   240
gcggtgaggt actccaggat g                                             261
```

<210> SEQ ID NO 207
<211> LENGTH: 361
<212> TYPE: DNA
<213> ORGANISM: Homo sapiens

<400> SEQUENCE: 207

```
gctctccggg agcttgaaga agaaactggc tacaaagggg acattgccga atgttctcca    60
gcggtctgta tggacccagg cttgtcaaac tgtactatac acatcgtgac agtcaccatt   120
aacggagatg atgccgaaaa cgcaaggccg aagccaaagc caggggatgg agagtttgtg   180
gaagtcattt ctttacccaa gaatgacctg ctgcagaaga ttgatgctct ggtagctgaa   240
gaacatctca cagtggacgc cagggtctat tcctacgctc tagcactgaa acatgcaaat   300
gcaaagccat ttgaagtgcc cttcttgaaa ttttaagccc aaatatgaca ctggacctgc   360
c                                                                   361
```

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: 10, 27, 37, 46, 75, 95, 102, 137, 143, 202, 234, 278, 310, 351
<223> OTHER INFORMATION: n = A,T,C or G

<400> SEQUENCE: 208

```
agaggagatn tttgccatgc ctgaatnctt tcctatncca ccctancact taacatatta    60
cttagtctgc tttgntaaaa gcaagtatta ccttnaactt gnctcttact ctttgccctt   120
tagctaacta ataaagnttg atntaggcat tattatataa ttctgagtca ttcatggtat   180
ctctcatgtt tgatgtattt tncaaactaa gatctatgat agttttttt ccanagttcc   240
attaaatcat ttatttcctt tactttctca cctctgtnga aacatttaga aactggattt   300
gggaacccan ttttggaaaa ccagattcat agtcatgaaa atggaaactt ncatattctg   360
tttttgaaaa gatgtggacc t                                             381
```

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: 83

<223> OTHER INFORMATION: n = A,T,C or G

<400> SEQUENCE: 209

```
gtggagagca agtgatttat taaagcaaga cgttgaaacc tttacattct gcagtgaaga   60
tcaggtgtgtc attgaaagac agnggaaacc aggatgaaag ttttacatg tcacacacta  120
catttcttca atattttcac caggacttcc gcaatgaggc ttcgtttctg aagggacatc  180
tgatccgtgc atctcttcac tcctaacttg gctgcaacag cttccacctg c           231
```

<210> SEQ ID NO 210
<211> LENGTH: 371
<212> TYPE: DNA
<213> ORGANISM: Homo sapiens

<400> SEQUENCE: 210

```
tccatcctgg ttttgcagag atcaggttgt tgacagttcc tggttgaccc acagctaccc   60
atgtcagtta tctccactaa catatccaag aatctttgta ggacaatttc tccacctgca  120
aggtttttta ggtagaactc ttcttttaag gcaattagcc cattgccaaa aggttttact  180
gtcttaaagc tgtctttctg agatctaatt ccaagaactt ctccacagct aagtgagatg  240
cctcacacca ttaggtgatg ctttggacag aacagagtat tttcatcttg tgtttaaagc  300
aattccttgg cttcggctcc tcaccacttt ctatgccagt ctcccattta tgtccctagt  360
aatgcctatg c                                                        371
```

<210> SEQ ID NO 211
<211> LENGTH: 471
<212> TYPE: DNA
<213> ORGANISM: Homo sapiens

<400> SEQUENCE: 211

```
tttattttaa aagaaaaaaa ttaaaataga gccaacaaat gcaattaaga aaaaaaaagt   60
attgagacac aaggggacct acatgttctg gtctaagaag catgcaagta ttacaaagca  120
ttccagatac agtatgcacg aggaacagtg aacaagcatt ggaacgatgc tctttctttc  180
agaaacggga agtctaacag ttatgttttc acaatggtag tgattaaacc atctttattt  240
ttaaggaatt ttataggaag aattttagca ccatcattaa aggaaaaata ataatacctt  300
tttagccctg cctatctcca gtcttggaat aataacagaa gcatagcacc tttcagtatc  360
taaaatataa acaagaatag taagtccatc ccagcttcta gagatgaggt agctcatgct  420
aagaaatgtt gggtcatttt tcctatgaaa gttcaaaggc caaatggtca c            471
```

<210> SEQ ID NO 212
<211> LENGTH: 401
<212> TYPE: DNA
<213> ORGANISM: Homo sapiens

<400> SEQUENCE: 212

```
tggcctgtct ccttcacata gtccatatca ccacaaatca cacaacaaaa gggagaggat   60
atattttggg ttcaaaaaaa gtaaaaagat aatgtagctg catttctttg gttattttgg  120
gccccaaata tttcctcatc tttttgttgt tgtcatggat ggtggtgaca tggacttgtt  180
tatagaggac aggtcagctc tctggctcgg tgatctacat tctgaagttg tctgaaaatg  240
tcttcatgat taaattcagc ctaaacgttt tgccgggaac actgcagaga caatgctgtg  300
agtttccaac ctcagcccat ctgcgggcag agaaggtcta gtttgtccat caccattatg  360
atatcaggac tggttacttg gttaaggagg ggtctacctc g                      401
```

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: 239, 290, 358, 359, 391, 393
<223> OTHER INFORMATION: n = A,T,C or G

<400> SEQUENCE: 213

```
tgtgaagcat acataaataa atgaagtaag ccatactgat ttaatttatt ggatgttatt   60
ttccctaaga cctgaaaatg aacatagtat gctagttatt tttcagtgtt agccttttac  120
tttcctcaca caatttggaa tcatataata taggtacttt gtccctgatt aaataatgtg  180
acggatagaa tgcatcaagt gtttattatg aaaagagtgg aaaagtatat agctttttanc  240
aaaaggtgtt tgcccattct aagaaatgag cgaatatata gaaatagtgn gggcatttct  300
tcctgttagg tggagtgtat gtgttgacat ttctccccat ctcttccac tctgttttnnt  360
ccccattatt tgaataaagt gactgctgaa nangactttg aatccttatc cacttaattt  420
aatgttaaaa gaaaaaccta taatggaaag tgagactcct t                      461
```

<210> SEQ ID NO 214
<211> LENGTH: 181
<212> TYPE: DNA
<213> ORGANISM: Homo sapiens

<400> SEQUENCE: 214

```
cctgagcttc tactcctttc ccttaagatt cctccaaagc accagctcca taaaatcctt    60
cagctcccca gacccacacc aagaacccca catgttaatt ggatcagcca aatctacaag   120
cagataagtc ctaaggagaa tgccgaagcg ttttcttct tcctcaagcc tagcatgaga   180
c                                                                  181
```

<210> SEQ ID NO 215
<211> LENGTH: 581
<212> TYPE: DNA
<213> ORGANISM: Homo sapiens

<400> SEQUENCE: 215

```
ctgctttaag aatggttttc caccttttcc ccctaatctc taccaatcag acacatttta    60
ttatttaaat ctgcacctct ctctatttta tttgccaggg gcacgatgtg acatatctgc   120
agtcccagca cagtgggaca aaaagaattt agaccccaaa agtgtcctcg gcatggatct   180
tgaacagaac cagtatctgt catggaactg aacattcatc gatggtctcc atgtattcat   240
ttattcactt gttcattcaa gtatttattg aatacctgcc tcaagctaga gagaaaagag   300
agtgcgcttt ggaaatttat tccagttttc agcctacagc agattatcag ctcggtgact   360
tttctttctg ccaccattta ggtgatggtg tttgattcag agatggctga atttctattc   420
ttagcttatt gtgactgttt cagatctagt ttgggaacag attagaggcc attgtcctct   480
gtcctgatca ggtggcctgg ctgtttcttt ggatccctct gtcccagagc cacccagaac   540
cctgactctt gagaatcaag aaaacaccca gaaaggacct c                       581
```

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: 37, 38, 164, 176, 254
<223> OTHER INFORMATION: n = A,T,C or G

<400> SEQUENCE: 216

```
ccgatgtcct gcttctgtgg accaggggct cctctgnngg tggcctcaac cacggctgag    60
atccctagaa gtccaggagc tgtgggggaag agaagcactt agggccagcc agccgggcac   120
ccccacttgc gccccgaccc acgctcacgc accagacctg cccnggcggt cgctcnaaag   180
ggcgaattct gcagatatcc atcacactgg cggacgctcg agcatgcatc tagagggccc   240
aattcaccct atantgagtc gtattacaat tcactggccg t                       281
```

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: 33, 322
<223> OTHER INFORMATION: n = A,T,C or G

<400> SEQUENCE: 217

```
atagcaggtt tcaacaattg tcttgtagtt tgnagtaaaa agacataaga aagagaaggt    60
gtggtttgca gcaatccgta gttggtttct caccataccc tgcagttctg tgagccaaag   120
gtcttgcaga aagttaaaat aaatcacaaa gactgctgtc atatattaat tgcataaaca   180
cctcaacatt gctcagagtt tcatccgttt ggttaagaaa acattccttc aattcatcta   240
tggcatttgt agtggcattg tcgtctatga actcttgaag aagttctttg tattcagtct   300
tagacacttg tggattgatt gncttggaaa tcacattctc caataaggga cctcgg       356
```

<210> SEQ ID NO 218
<211> LENGTH: 321
<212> TYPE: DNA
<213> ORGANISM: Homo sapiens

<400> SEQUENCE: 218

```
ttgtccatcg ggagaaaggt gtttgtcagt tgtttcataa accagattga ggaggacaaa    60
ctgctctgcc aatttctgga tttctttatt ttcagcaaac actttcttta aagcttgact   120
```

```
              gtgtgggcac tcatccaagt gatgaataat catcaagggt tgttgcttg tcttggattt    180
              atatagagct tcttcatatg tctgagtcca gatgagttgg tcaccccaac ctctggagag    240
              ggtctgggc agtttgggtc gagagtcctt tgtgtccttt ttggctccag gtttgactgt     300
              ggtatctctg gacctgcctg g                                               321
```

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: 41
<223> OTHER INFORMATION: n = A,T,C or G

<400> SEQUENCE: 219

```
              ccggttaggt ccacgcgggg gcagtggagg cacaggctca nggtggccgg gctacctggc    60
              accctatggc ttacaaagta gagttggccc agtttccttc cacctgaggg gagcactctg    120
              actcctaaca gtcttccttg ccctgccatc atctgggggtg gctggctgtc aagaaaggcc    180
              gggcatgctt tctaaacaca gccacaggag gctgtaggg catcttccag gtggggaaac      240
              agtcttagat aagtaaggtg acttgtctaa g                                    271
```

<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: 32, 43
<223> OTHER INFORMATION: n = A,T,C or G

<400> SEQUENCE: 220

```
              gtcctacgac gaggaccagc ttttcttctt cnacttttcc canaacactc gggtgcctcg    60
              cctgcccgaa tttgctgact gggctcagga acaggagat gctcctgcca ttttatttga      120
              caaagagttc tgcgagtgga tgatccagca aatagggcca aaacttgatg gaaaatccc      180
              ggtgtccaga gggtttccta tcgctgaagt gttcacgctg aagcccctgg agtttggcaa     240
              gcccaacact ttggtctgtt ttgtcagtaa tctcttccca cccatgctga cagtgaactg     300
              gtagcatcat tccgtccctg tggaaggatt tgggcctact tttgtctcag a             351
```

<210> SEQ ID NO 221
<211> LENGTH: 371
<212> TYPE: DNA
<213> ORGANISM: Homo sapiens

<400> SEQUENCE: 221

```
              gtctgcagaa gcgtgtctga ggtgtccggt ggaggtggca gccgagctct gggactaatc    60
              accgtgctgg ggacggcacc gcgtcaggat gcaggcagat ccctgcagaa gtgtctaaaa    120
              ttcacactcc tcttctggag ggacgtcgat ggtattagga tagaagcacc agggggacccc   180
              acgaacggtg tcgtcgaaac agcagccctt atttgcacac tggagggcg tgacaccagg    240
              aaaaccacaa ttctgtcttt cacggggggc cactgtcac gtctctgtct gggcctcggc    300
              cagggtgccg agggccagca tggacaccag gaccagggcg cagatcacct tgttctccat    360
              ggtggacctc g                                                         371
```

<210> SEQ ID NO 222
<211> LENGTH: 471
<212> TYPE: DNA
<213> ORGANISM: Homo sapiens

<400> SEQUENCE: 222

```
              gtccatgttc catcattaat gttccaacat caccagggac acaaagctgc aaaaatgaga    60
              agggaaataa ggttagagaa aggatccggg caatcttaag gactgaggaa gacatgttcc    120
              ccaaccctg aactcacaaa ccctgaagct caaggattgc atccttcctc caaatctcac     180
              tcaacataat aagtgcagaa caacatgcca aagcactgta tgaagcacta gggacaaaga    240
              caaggtcaaa atccttgtaa ccaaatttaa tggtattgta atgcagtgtt aacacaggac    300
              agtaacgaaa cacccaagaa ccaaacagaa gagggtaggg ataagcataa atgaagtaac    360
              atgaaataaa cttccaaatg gaaaacttgt ccatacccc agggcaagtc aactacagtc      420
              tcccaaagga cataaattcc acttagggca cactagacag aaaacaatat t             471
```

<210> SEQ ID NO 223
<211> LENGTH: 411
<212> TYPE: DNA

<213> ORGANISM: Homo sapiens

<400> SEQUENCE: 223

```
agttgctcta caatgacaca caaatcccgt taaataaatt ataaacaagg gtcaattcaa    60
atttgaagta atgtttagt aaggagagat tagaagacaa caggcatagc aaatgacata   120
agctaccgat taactaatcg gaacatgtaa aacagttaca aaaataaacg aactctcctc   180
ttgtcctaca atgaaagccc tcatgtgcag tagagatgca gttttcatcaa agaacaaaca   240
tccttgcaaa tgggtgtgac gcggttccag atgtggattt ggcaaaacct catttaagta   300
aaaggttagc agagcaaagt gcggtgcttt agctgctgct tgtgccgctg tggcgtcggg   360
gaggctcctg cctgagcttc cttccccagc tttgctgcct gagaggaacc a            411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: 31
<223> OTHER INFORMATION: n = A,T,C or G

<400> SEQUENCE: 224

```
ggtctgaagt ttgataacaa agaaatatat ntaagacaaa aatagacaag agttaacaat    60
aaaaacacaa ctatctgttg acataacata tggaaacttt ttgtcagaaa gctacatctt   120
cttaatctga ttgtccaaat cattaaaata tggatgattc agtgccattt tgccagaaat   180
tcgtttggct ggatcataga ttaacatttt cgagagcaaa tccaagccat tttcatccaa   240
gttttttgaca tgggatgcta ggcttcctgg tttccatttg ggaaatgtat tcttatagtc   300
ctgtaaagat tccacttctg g                                              321
```

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: 34
<223> OTHER INFORMATION: n = A,T,C or G

<400> SEQUENCE: 225

```
atgtctgggg aaagagttca ttggcaaaag tgtnctccca agaatggttt acaccaagca    60
gagaggacat gtcactgaat ggggaaaggg aaccccgta tccacagtca ctgtaagcat   120
ccagtaggca ggaagatggc tttgggcagt ggctggatga aagcagattt gagatacccca  180
gctccggaac gaggtcatct tctacaggtt cttccttcac tgagacaatg aattcagggt   240
gatcattctc t                                                         251
```

<210> SEQ ID NO 226
<211> LENGTH: 331
<212> TYPE: DNA
<213> ORGANISM: Homo sapiens
<220> FEATURE:
<221> NAME/KEY: misc_feature
<222> LOCATION: 26, 34, 35, 36, 37, 39
<223> OTHER INFORMATION: n = A,T,C or G

<400> SEQUENCE: 226

```
gttaggtccc aggccccccg ccaagnggtt accnnnntna ccactcctga cccaaaaatc    60
aggcatggca ttaaaacgtt gcaaattcct ttactgttat ccccccacc accaggacca   120
tgtagggtgc agtctttact ccctaacccg tttcccgaaa aggtgctac ctcctttcca    180
gacagatgag agagggcagg acttcaggct ggatccacca ctgggctctc cctcccccag   240
cctggagcac gggaggggag gtgacggctg gtgactgatg gatgggtagt gggctgaaa   300
gaggggacta ggaagggcta ttccaggctc a                                   331
```

<210> SEQ ID NO 227
<211> LENGTH: 391
<212> TYPE: DNA
<213> ORGANISM: Homo sapiens

<400> SEQUENCE: 227

```
aggtctgccc ttgaagtata ggaaggaatc atagttggag gacttctgca ttatttgttg    60
gctgaagcta gaagtgcaac ccctcctga tttctgcagc aagatgaact gccttatccc   120
cagcccgcag gaatgttcat atctgagcaa tcaatgggca ctgtgttcaa ccacgccatt   180
```

```
          ttcaagattg gctccttaaa ccacccacaa ggcaccagct ctggagaaag ctgcagggag    240
          aagagaacaa agccctcgct gtgatcagga tgggtgtctc ataccttttc tctggggtca    300
          ttccaggtat gagacagagt tgaacctgcg catgagcgtg gaggccgaca tcaacggcct    360
          gcgcagggtg ctggatgagc tgaccctgga c                                   391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 228
gttgtccata gccacctcct gggatagaag ctttntagtt catagttcga ttagtgtgtc     60
          cttaggacat aggtccagcc ctacagatta gctgggtgaa gaaggcaagt gtctcgacag    120
          ggcttagtct ccaccctcag gcatggaacc attcaggtg aagcctggga tgtgggcaca    180
          ggagactcag gctgatataa aaataacaaa atcagtaata aaaaaattat aaaacctgtt    240
          gcttgtctga atagatttga gcaacagtct tgcttttgtt aaaatcctgg agccgttaag    300
          tcctgaatat tcttctggac atcattgctg gctggagaaa ggagcccag gcccggctcg    360
          gctgacatct gtcaggtttg gaagtctcat c                                   391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: 202
<223> OTHER INFORMATION: n = A,T,C or G

<400> SEQUENCE: 229
gtccatggct tctcacccag acagtctttc tgggcaactt ggggaagccc ctgttctgct     60
          caagtctcac cccatggaag aggtggggga aggggccctt ggttttcag gaagacgggt    120
          tggagagcac gagtcactac aaagcagtaa aagtgaatgg tgtctccagg ggctgggtcc    180
          agaacaccgc ggagagcccc anccataaag gtgtgttccg cctctggcct gcaggaatct    240
          cttgaatct ctttgattgg tggctcaag agcaatggga agtcaacagc caggaggctg    300
          gactgggttc cctgggaccc cgaggtccca gaggctgctg g                        341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg     60
          gggctaaagg aaatggacaa tgcaggacag ctagtgtttc tggctacaga aggggaccat    120
          cttcagttgt ctgaagaatg gttttatgcc cacatcatac cattccttgg atgaaacccg    180
          tatagttcac aatagagctc agggagcccc taactcttcc aaaccacatg ggagacagtt    240
          tccttcatgc ccaagcctga gctcagatcc agcttgcaac taatccttct atcatctaac    300
          atgccctact tggaaagatc taagatctga atcttatcct ttgccatctt ctgttaccat    360
          atggtgttga atgcaagttt aattaccatg gagattgttt tacaaacttt tgatgtggtc    420
          aagttcagtt ttagaaaagg gagtctgttc cagatcagtg ccagaactgt gcccaggccc    480
          aaaggagaca actaactaaa gtagtgagat a                                   511

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct     60
          cccctcgtgt cagctcaggc agctcgaggc cccgaccaa cacttgcagg ggtccctgct    120
          agttagcgcc caccgccgt ggagttcgta ccgcttcctt agaacttcta cagaagccaa    180
          gctccctgga gccctgttgg cagctctagc tttgcagtcg tgtaattggc ccaagtcatt    240
          gtttttctcg cctcactttc caccaagtgt ctagagtcat gtgagcctcg tgtcatctcc    300
          ggggtggacc t                                                         311

<210> SEQ ID NO 232
```

<211> LENGTH: 351
<212> TYPE: DNA
<213> ORGANISM: Homo sapiens

<400> SEQUENCE: 232

```
tcgtttagct aataatccct tccttgatga tacactccaa cttcttgttt ttctttattt   60
ctaaaaagcg gttctgtaac tctcaatcca gagatgttaa aaatgtttct aggcacggta  120
ttagtaaatc aagtaaattt catgtcctct taaaggacaa acttccagag atttgaatat  180
aaatttttat atgtgttatt gattgtcgtg taacaaatgg cccccacaaa ttagtagctt  240
aaaatagcat ttatgatgtc actgttttct ttgccttttc attaatgttc tgtacagacc  300
tatgtaaaca acttttgtat atgcatatag gatagctttt ttgagggtat a           351
```

<210> SEQ ID NO 233
<211> LENGTH: 511
<212> TYPE: DNA
<213> ORGANISM: Homo sapiens

<400> SEQUENCE: 233

```
aggtctggat gtaaggatgg atgctctcta tacatgctgg gttggggatg ctgggactgc   60
acagccaccc ccagtatgcc gctccaggac tctgggacta gggcgccaaa gtgtgcaaat  120
gaaaatacag gatacccagg gaactttgaa tttcagattg tgaaagaaa acaaatcttg   180
agactccaca atcaccaagc taaaggaaaa agtcaagctg ggaactgctt agggcaaagc  240
tgcctcccat tctattcaca gtcatccccc tgaggctcac ctgcatagct gattgcttcc  300
tttcccctat cgcttctgta aaaatgcaga ctcactgagc cagactaaat tgtgtgttca  360
gtggaaggct gatcaagaac tcaaagaat gcaaccttt gtctcttatc tactacaacc    420
aggaagcccc cacttaaggg ttgtcccacc ttactggact gaaccaaggt acatcttaca  480
cctactgatt gatgtctcat gtcccctaa g                                  511
```

<210> SEQ ID NO 234
<211> LENGTH: 221
<212> TYPE: DNA
<213> ORGANISM: Homo sapiens

<400> SEQUENCE: 234

```
caggtccagc gaagggcttt cataggctac accaagcatg tccacataac cgaggaagct   60
ctctccatca gcatagcctc cgatgaccat ggtgttccac aaagggttca tcttcgagcg  120
ccggctgtac atggccctgg tcagccatga atgaatagct ctaggactat agctgtgtcc  180
atctcccaga agctcctcat caatcaccat ctggccgaga c                      221
```

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: 33
<223> OTHER INFORMATION: n = A,T,C or G

<400> SEQUENCE: 235

```
ggtccaagaa agggacatct atgtgaaagt ganactgaga cagtgctggt cacaggtcat   60
gctgcagaat aatacattcc caggcactgt cacgtggggg acccaagagg cccaggagt   120
gacctataac ctctccagaa agaccactct gtgtggcatc acagtccaca cagtttaagg  180
aaatatttag acttaacaat cagacaccag ctcttactca cacttacact cacagcccac  240
acacaagtgt gcaaacatac acacacatat atatttcctg atacattcat ggaatatcag  300
agccctgccc tgaagtcgtt agtgtctctg ctccccaaac cgctgctccc acattggcta  360
agctccctca agagacctca g                                            381
```

<210> SEQ ID NO 236
<211> LENGTH: 441
<212> TYPE: DNA
<213> ORGANISM: Homo sapiens

<400> SEQUENCE: 236

```
aggtcctgtt gccccttct tttgcccaac ttcgccattt gggaattgga atatttaccc    60
aacacctgta ctgcattgaa tattggaagc aaataacttg gctttgatct tataggctca  120
cagatggagg aacgtacctt gaagttcaga tgagatttcg gacttttgag ttgatgctga  180
aacagcttga gattttggg gactactgag agatgataat tgtattgtgc aatatgagaa   240
ggacatgaga tttggtgggc ataggtgtga aatgcacattg tttgatgtg tttaccctcc   300
aaatctcttg ttgaatgtga tcttaaacgt tggtggtggg cctagtggaa ggtgttgaat  360
catgggggtg gactcttcat aatttgctta gctccatccc cttggtgatg agcaagtcct  420
```

```
          tgctctgttg tgtcacatga g                                          441
```

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: 81, 90, 194, 209, 210, 211, 219, 233
<223> OTHER INFORMATION: n = A,T,C or G

<400> SEQUENCE: 237

```
          tcctaaaaaa ttagctgacc ttgttaaaaa tgttggcgtg agcagtatat tattacctat  60
          cttttttttat tgtgtgtgtg ngtgtgtgtn ttaaactaat tggctgaaat atctgcctgt 120
          ttccctcttt acattttct tgtttctttc cttatttatc tttgtccatc ttgagatcta 180
          ctgtaaagtg aatnttttaa tgaaaacann nccaagttnt actctcactg ggnttgggac 240
          atcagatgta attgagaggc caacaggtaa gtcttcatgt c                      281
```

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: 30, 85
<223> OTHER INFORMATION: n = A,T,C or G

<400> SEQUENCE: 238

```
          gtctgcctcc tcctactgtt tccctctatn aaaaagcctc cttggcgcag gttccctgag  60
          ctgtgggatt ctgcactggt gcttnggatt ccctgatatg ttccttcaaa tccactgaga 120
          attaaataaa catcgctaaa g                                           141
```

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: 29, 30, 65, 86, 471, 489
<223> OTHER INFORMATION: n = A,T,C or G

<400> SEQUENCE: 239

```
          aacaatctaa acaaatccct cggttctann atacaatgga ttccccatat tggaaggact  60
          ctgangcttt attccccccac tatgcntatc ttatcatttt attattatac acatacccat 120
          cctaaactat actaaagccc ttttcccatg catggatgga aatggaagat ttttttttaa 180
          cttgttctag aagtcttaat atgggctgtt gccatgaagg cttgcagaat tgagtccatt 240
          ttctagctgc ctttattcac atagtgatgg ggtactaaaa gtactgggtt gactcagaga 300
          gtcgctgtca ttctgtcatt gctgctactc taacactgag caacactctc ccagtggcag 360
          atcccctgta tcattccaag aggagcattc atcccctttgc tctaatgatc aggaatgatg 420
          cttattagaa aacaaactgc ttgacccagg aacaagtggc ttagcttaag naaacttggc 480
          tttgctcana tccctgatcc t                                           501
```

<210> SEQ ID NO 240
<211> LENGTH: 451
<212> TYPE: DNA
<213> ORGANISM: Homo sapiens

<400> SEQUENCE: 240

```
          tgtcctgaaa ggccattact aatagaaaca cagcctttcc aatcctctgg aacatattct  60
          gtctgggttt ttaatgtctg tggaaaaaaa ctaaacaagt ctctgtctca gttaagagaa 120
          atctattggt ctgaaggttt ctgaacctct ttctggttct cagcagaagt aactgaagta 180
          gatcaggaag gggctgcctc aggaaaattc ctagatccta ggaattcagt gagaccctgg 240
          gaaggaccag catgctaatc agtgtcagtg aatccacagt ctttacttcc tgcctcataa 300
          agggccaggt ctccccagta ccaagtcctt tcctcatgaa gttgtgttgc ctcaggctgt 360
          ttagggacca ttgctgtct tggtcacatg agtctgtctc cttactttag tccctgggca 420
          atccttgctt aatgcttttg ttgactcaac g                                 451
```

<210> SEQ ID NO 241
<211> LENGTH: 411
<212> TYPE: DNA

<213> ORGANISM: Homo sapiens
<220> FEATURE:
<221> NAME/KEY: misc_feature
<222> LOCATION: 62, 82, 364, 370, 385
<223> OTHER INFORMATION: n = A,T,C or G

<400> SEQUENCE: 241

```
aatctccagt gtgatggtat cggggttaga gcttcaatct ccagtgtgat ggtactgcag   60
cnagagcttc aatctccagt gngatggtat tagggttaga tcttcaatct ccagtgtgat  120
ggtatcaggg ttagagcttc agcctccagt gtgatggtat cagggttaga gcttcagcct  180
ccagtgtgat ggtatcgggg ttagatcttc aatccccagt ggtggtggtt agagcttcaa  240
tctccagtgt gatggtattg gggttagagc ttcaatctcc agtctgatgg tgtttcggga  300
tggggctttt aagatgtaat tagggtttaa gatcataagg acctggtct gatggggatt   360
agtncgcttn tatgaagaga cacangaggg cttgctctat ctctgactct c           411
```

<210> SEQ ID NO 242
<211> LENGTH: 351
<212> TYPE: DNA
<213> ORGANISM: Homo sapiens

<400> SEQUENCE: 242

```
ttcccttca caacagtaga gacctacaca gtgaactttg gggacttctg agatcagcgt    60
cctaccaaga ccccagccca actcaagcta cagcagcagc acttcccaag cctgctgacc  120
acagtcacat cacccatcag cacatggaag gcccctggta tggacactga aaggaaggc   180
tggtcctgcc cctttgaggg ggtgcaaaca tgactgggac ctaagagcca gaggctgtgt  240
agaggctcct gctccacctg ccagtctcgt aagaaatggg gttgctgcag tgttggagta  300
ggggcagagg gagggagcca aggtcactcc aataaaacaa gctcatggca c           351
```

<210> SEQ ID NO 243
<211> LENGTH: 241
<212> TYPE: DNA
<213> ORGANISM: Homo sapiens

<400> SEQUENCE: 243

```
gtctgtgctt tatcaggaaa agcacaagaa tatgtttttc tacctaaaac cctcttctac    60
tttaaaaatg gtttgctgaa ttttctatg ttttttaaaat gtttttatgc ttttttttaa   120
acacgtaaag gatggaacct aatcctctcc cgagacgcct cctttgtgtt aatgcctatt  180
cttacaacag agaaacaagt acattaatat aaaaacgagt tgattattgg ggtataaaat  240
a                                                                    241
```

<210> SEQ ID NO 244
<211> LENGTH: 301
<212> TYPE: DNA
<213> ORGANISM: Homo sapiens

<400> SEQUENCE: 244

```
ggtccagagc aatagcgtct gtggtgaagc gcctgcactc ctcgggagac atgcctggct    60
tatatgctgc atccacataa ccatagataa aggtgctgcc ggagccacca atgcaaaag   120
gctgtcgagt cagcattcct cccagggttc catatacctg acctccttca cgttggtccc  180
agccagctac catgagatgt gcagacaagt cctctcgata tttatagctg atatttctca  240
ccacatttgc agcagccaaa acaagtggag gttcctccag ttctatccca tggagctcca  300
g                                                                    301
```

<210> SEQ ID NO 245
<211> LENGTH: 391
<212> TYPE: DNA
<213> ORGANISM: Homo sapiens

<400> SEQUENCE: 245

```
ctgacactgc tgatgtgggc cggggggcgc cgaggcacaa ctggtggccg gaccattgag    60
gcacctggag ggtaggcagc ttgtggtgca gacaccacag agagagaaaa gttggatgga  120
gtggtgggaa taatcagggt ggcacactgt gcctagaagc ttccagggcc accaagagaa  180
tgggaaggga aactacaaca ttcacaacag aaataggagt caattcactt agacccagaa  240
ctccagaaag ggggagtgta ggaatctaca atttcaaagc cagctcgtgt ctacctagag  300
cccccaaactg cataagcacc aggattgtac accttagtcc ctcaagatag tttcaagtga  360
gcgtgcaatt cactcttaca gaggagggcc t                                   391
```

<210> SEQ ID NO 246
<211> LENGTH: 291

```
<212> TYPE: DNA
<213> ORGANISM: Homo sapiens
<220> FEATURE:
<221> NAME/KEY: misc_feature
<222> LOCATION: 26, 80, 82, 185, 255, 259
<223> OTHER INFORMATION: n = A,T,C or G

<400> SEQUENCE: 246
tcctccacag gggaagcagg aagttngacc agcttcaggc tggaacgtgc ccagggcaca    60
     gagctggcaa ggtgcaaagn cntctgcaga atattcacca ggttgacaca gacctccaca   120
     ttcagacata ttccaagctt ctggggtctt cagggcccca gaatttcctg gtcttgggca   180
     tggtncacaa gtcatttgtc cttcctcatt ttggaaggtt ccatttggac ataaaatgca   240
     agcgttctcg tgctncatna taataggtcc cagcctgcac tgacacattt g            291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: 80, 110, 125, 245, 249, 279, 318, 336, 339, 455, 471
<223> OTHER INFORMATION: n = A,T,C or G

<400> SEQUENCE: 247
cactgagtga atgagtatat aatttatgaa aacagaaaag tgctttggaa aaaaaaaaag    60
     acaacaggag tacatacagn gaaccaaaaa gagtgtacca ggaggagcan accctgaaca   120
     gttanaacta tggaaatcgc tatgctttgt gttgtcacag gagttaaaat aggaataccc   180
     tgcatacaat aaatatttat tggataaata actaagcctg atacccttt caatgcgtta   240
     tacanactnt atcatccac cactaatcta agttctcana agttaaacat tacaagactt   300
     cagaacaaca taggcgtntt tggctccatt taacanaana aggaccatag tgatcattta   360
     atctctatga gtctgtctta tcttctggaa aagggcccta acaccatttc cttttgcaaa   420
     aaggtagctg ccttgcttcc agttctacca tcctntagca acccatcttt n             471

<210> SEQ ID NO 248
<211> LENGTH: 551
<212> TYPE: DNA
<213> ORGANISM: Homo sapiens

<400> SEQUENCE: 248
ccatgggatc aggaatgggg tcaggtcagt tgacctgagc atacccatta aacatgttca    60
     aatgtcccca tcccacccac tcacatgaca tggctcccga gccctgagat ctgtatccca   120
     agaacctcag ttgagaaata tttatggcag cttcactgtt gctcaagagc ctgggtattg   180
     tagcagcctg ggggcaggtt gtccctaatg ttctccaagt tcttcacatc agccagaatc   240
     ccatctatgc ttgtctccag caaatggagg tggcccctct gctgacgtgc cctctcttcc   300
     agctctgaca tcatgggccg cagttggctg ttgatctggg tcttggctcg ggaaagcttc   360
     tgctccagta agaccagccc ctcttcatct acactgagag gctggtccat cagatgcagg   420
     aggccgtcta atgtgttgag tgtgtcttgg attgtaaccc cagcgttctt ggctctggta   480
     tcaaccttct gggcttctgt aatcaccatc tgtactgcat ccatattcgt gtcgaactcc   540
     agctccttcc t                                                         551

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: 3, 96
<223> OTHER INFORMATION: n = A,T,C or G

<400> SEQUENCE: 249
atntccagag ggaccgtaag actggtacaa gtttacacca taagaggcga cgtggtcagc    60
     cacaatgtct tcacctccac aggggctcat cacggnggtc agggcaaggg cccccagcat   120
     cagagctttg tttaggatca tcctcttccc aaggcagcct tagcagttgc tgacctgccc   180
     g                                                                    181

<210> SEQ ID NO 250
<211> LENGTH: 551
<212> TYPE: DNA
<213> ORGANISM: Homo sapiens

<400> SEQUENCE: 250
```

```
tctgtagcta ggatgagctg gctctcaagc aaaagtttgt cttcctgggt ccatttgtgg    60
ttatcacttg ttattgaatg tacatcacaa attaaagtct gcattgttgg acgtaagaga   120
atgtgccgac tttggtaacc aggagatttc atgttactgg actgcctgta gtcacgtatt   180
tctgctatga cacatccgca atgaaaaata ttaacctgag attttttctag gagatcaacc   240
aaaataggag gtaattcttc tgcatccaaa tattcaagca actctccttc ttcatagggc   300
agtcgaatgg tctcggaatc tgatccgttt ttccctga gcatcagaga atatccctca   360
tttcctgggt atagattgac cactaaacat gacaaagtct cttgcataac aagcttctct   420
aacaagttca catttcttct taatttctta acttcaggtt ctttttcaca ttcttcaata   480
tacaagtcat aaagttttttg aaatacagat tttcttccac ttgataggta tttccttta   540
ggaggtctct g                                                        551
```

<210> SEQ ID NO 251
<211> LENGTH: 441
<212> TYPE: DNA
<213> ORGANISM: Homo sapiens

<400> SEQUENCE: 251

```
tgtctgctct cccatcctgg ttactatgag tcgctcttgg cagaaaggac cacagatgga    60
gagcttggca ctcgctccaa ctttgccgaa aagaggacaa ccaccaaagt agtaggtaaa   120
aacacaattt tagcagcagt gaaataaaaa gaggaagtga ggatggggcc aggccgcaac   180
tataattaaa ctgtctgttt aggagaagct gaatccagaa gaaacacaag ctgtaaagtg   240
agagaggaca gggagcaggg cctttggaga gcaggagagg acaggctgtc accaagcgct   300
gctcggactc tgccctgaaa gatttgaatt ggacactgtc cagtcacgtg tgtggcaaac   360
cgtactccaa gcactttcct cacggcagag gaaggagctg ccatgctgt acccctgaac   420
gtttgtgggg ccagcgatgt g                                            441
```

<210> SEQ ID NO 252
<211> LENGTH: 406
<212> TYPE: DNA
<213> ORGANISM: Homo sapiens

<400> SEQUENCE: 252

```
tttttttttg aacaagtaaa aatttcttta tttgctgaca ataagataac ctacagggaa    60
aacctgatga aatctattaa aaagttacta aaactaataa agaatttag gaaggttata   120
gaatgtaaga ccaagacaca aaaatcaatt acatttctat ataatagcaa tgaacagata   180
ctgaaatttt aaaaactaaa tcatttttaca aaagtatcaa aatatgaaac actccgggat   240
aaattggata aaagatgtgc aagactgtac aaaagctaca aaacatttat gaaggaaatt   300
ggaagataga aacaagatag aaaatgaaaa tattgtcaag agtttcagat agaaaatgaa   360
aaacaagcta agacaagtat tggagaagta tagaagatag aaaaat                  406
```

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: 224
<223> OTHER INFORMATION: n = A,T,C or G

<400> SEQUENCE: 253

```
gaaggagttc agtagcaaag tcacacctgt ccaattccct gagctttgct cactcagcta    60
atgggatggc aaaggtggtg gtgcttttcat cttcaggcag aagcctctgc ccatcccct   120
caagggctgc aggcccagtt ctcatgctgc ccttgggtgg gcatctgtta acagaggaga   180
acgtctgggt ggcggcagca gctttgctct gagtgcctac aaanctaatg cttggtgcta   240
gaaacatcat cattattaaa cttcagaaaa gcagcagcca tgttcagtca ggctcatgct   300
gcctcactgc ttaagtgcct gcaggagccg cctgccaagc tccccttcct acacctggca   360
cactggggtc tgcacaaggc tttgtcaacc aaagacagct tccccctttt gattgcctgt   420
agactttgga gccaagaaac actctgtgtg actctacaca cacttcaggt ggtttgtgct   480
tcaaagtcat tgatgcaact tgaaaggaaa cagtttaatg gtggaaatga actaccattt   540
ataa                                                                544
```

<210> SEQ ID NO 254
<211> LENGTH: 339
<212> TYPE: DNA
<213> ORGANISM: Homo sapiens

<400> SEQUENCE: 254

```
tggcattcag ggcagtgtct tctgcatctc ctaggaacct cgggagcggc agctccggcg    60
cctggtagcg agaggcgggt tccggagatc ccggcctcac ttcgtcccac tgtggttagg   120
ggtgagtcct gcaaatgtta agtgatttgc tcaaggtgcc catttcgcag gaattggagc   180
```

```
        ccaggccagt tctctgagcc tatcattagg gctaaaggag tgcgtgatca gaatggtgtc   240
        tggacggttc tacttgtcct gcctgctgct ggggtccctg ggctctatgt gcatcctctt   300
        cactatctac tggatgcagt actggcgtgg tggctttgc                          339
```

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: 11, 39, 70, 87, 103, 120, 177, 181, 220, 229, 233, 341, 345, 366, 380, 402
<223> OTHER INFORMATION: n = A,T,C or G

<400> SEQUENCE: 255

```
        gaggttttt nttttttttt tttttttttt caattaaana tttgatttat tcaagtatgt   60
        gaaaacattn tacaatggaa acttttntta aatgctgcat gtnctgtgct atgaccacn   120
        cacatacagc catgctgttt caaaaaactt gaaatgccat tgatagttta aaaactntac   180
        ncccgatgga aaatcgagga aaacaattta atgtttcatn tgaatccana ggngcatcaa   240
        attaaatgac agctccactt ggcaaataat agctgttact tgatggtatc caaaaaaaaa   300
        tggttgggga tggataaatt caaaaatgct tccccaaagg ngggnggttt ttaaaaagtt   360
        tcaggncaca acccttgcan aaaacactga tgcccaacac antga                   405
```

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: 6
<223> OTHER INFORMATION: n = A,T,C or G

<400> SEQUENCE: 256

```
        gggcangtct ggtcctctcc ccacatgtca cactctcctc agcctctccc ccaaccctgc   60
        tctccctcct ccctgccct agcccaggga cagagtctag gaggagcctg gggcagagct   120
        ggaggcagga agagagcact ggacagacag ctatggtttg gattggggaa gaggttagga   180
        agtaggttct taaagaccct tttttagta                                     209
```

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: 306, 311, 343
<223> OTHER INFORMATION: n = A,T,C or G

<400> SEQUENCE: 257

```
        tctggacacc ataatccctt ttaagtggct ggatggtcac acctctccca ttgacaagct   60
        gggttaagtc aataggttga ctaggatcaa cacgacccaa atcaataaga tactgcagtc   120
        tattgagact caaaggctta tactggcgtc tgaaactatg tccttcgtta aacccgtatt   180
        ttgggattcg gatgtaaaat ggagtctggc ctccctcaaa gcccaagcgg ggccgggttc   240
        ctctttgcct ttctccttta tggcctctgc cacattttct acctcttctc cgacctcttg   300
        gtcttntctc nggtttcttg gagccgggat tcggctttaa gtn                     343
```

<210> SEQ ID NO 258
<211> LENGTH: 519
<212> TYPE: DNA
<213> ORGANISM: Homo sapiens

<400> SEQUENCE: 258

```
        gcggcttctg acttctagaa gactaaggct ggtctgtgtt tgcttgtttg cccacctttg    60
        gctgataccc agagaacctg ggcacttgct gcctgatgcc caccctgcc agtcattcct    120
        ccattcaccc agcgggaggt gggatgtgag acagcccaca ttggaaaatc cagaaaaccg   180
        ggaacaggga tttgcccttc acaattctac tccccagatc ctctcccctg gacacaggag   240
        acccacaggg caggaccta agatctgggg aaaggaggtc ctgagaacct tgaggtaccc    300
        ttagatcctt ttctacccac tttcctatgg aggattccaa gtcaccactt ctctcaccgg   360
        cttctaccag ggtccaggac taaggcgttt tctccatagc ctcaacattt tgggaatctt   420
        cccttaatca cccttgctcc tcctgggtgc ctggaagatg gactggcaga gacctctttg   480
        ttgcgttttg tgctttgatg ccaggaatgc cgcctagtt                           519
```

<210> SEQ ID NO 259
<211> LENGTH: 371
<212> TYPE: DNA
<213> ORGANISM: Homo sapiens

<400> SEQUENCE: 259

```
attgtcaact atatacacag tagtgaggaa taaaatgcac acaaaacaat ggatagaata    60
tgaaaatgtc ttctaaatat gaccagtcta gcatagaacc ttcttctctt ccttctcagg   120
tcttccagct ccatgtcatc taacccactt aacaaacgtg gacgtatcgc ttccagaggc   180
cgtcttaaca actccatttc caaaagtcat ctccagaaga catgtatttt ctatgatttc   240
ttttaaacaa atgagaattt acaagatgtg taactttcta actctatttt atcatacgtc   300
ggcaacctct ttccatctag aagggctaga tgtgacaaat gttttctatt aaaaggttgg   360
ggtggagttg a                                                        371
```

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: 57, 189, 208, 256, 426
<223> OTHER INFORMATION: n = A,T,C or G

<400> SEQUENCE: 260

```
ttggattttt tgacttgcga tttcagtttt tttacttttt tttttttttt ttttganaaa    60
tactatattt attgtcaaag agtggtacat aggtgagtgt tcatcttccc tctcatgccg   120
gtatactctg cttcgctgtt tcagtaaaag ttttccgtag ttctgaacgt cccttgacca   180
caccataana caagcgcaag tcactcanaa ttgccactgg aaaactggct caactatcat   240
ttgaggaaag actganaaag cctatcccaa agtaatggac atgcaccaac atcgcggtac   300
ctacatgttc ccgttttttct gccaatctac ctgtgtttcc aagataaatt accacccagg   360
gagtcacttc ctgctatgtg aacaaaaacc cggtttcttt ctggaggtgc ttgactactc   420
tctcgngagc                                                          430
```

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: 178
<223> OTHER INFORMATION: n = A,T,C or G

<400> SEQUENCE: 261

```
tcctgacgat agccatggct gtaccactta actatgattc tattccaact gttcagaatc    60
atatcacaaa atgacttgta cacagtagtt tacaacgact cccaagagag gaaaaaaaaa   120
aaaaaagacg cctcaaaatt cactcaactt ttgagacagc aatggcaata ggcagcanag   180
aagctatgct gcaactgagg gcacatatca ttgaagatgt cacaggagtt taagagacag   240
gctggaaaaa atctcatact aagcaaacag tagtatctca taccaagcaa aaccaagtag   300
tatctgctca gcctgccgct aacagatctc acaatcacca actgtgcttt aggactgtca   360
ccaaa                                                               365
```

<210> SEQ ID NO 262
<211> LENGTH: 500
<212> TYPE: DNA
<213> ORGANISM: Homo sapiens

<400> SEQUENCE: 262

```
cctagatgtc atttgggacc cttcacaacc attttgaagc cctgtttgag tccctgggat    60
atgtgagctg tttctatgca taatggatat tcggggttaa caacagtccc ctgcttggct   120
tctattctga atccttttct ttcaccatgg ggtgcctgaa gggtggctga tgcatatggt   180
acaatggcac ccagtgtaaa gcagctacaa ttaggagtgg atgtgttctg tagcatccta   240
tttaaataag cctatttat cctttggccc gtcaactctg ttatctgctg cttgtactgg   300
tgcctgtact tttctgactc tcattgacca tattccacga ccatggttgt catccattac   360
ttgatcctac tttacatgtc tagtctgtgt ggttggtggt gaataggctt ctttttacat   420
ggtgctgcca gcccagctaa ttaatggtgc acgtggactt ttagcaagcg ggctcactgg   480
aagagactga acctggcatg                                               500
```

<210> SEQ ID NO 263
<211> LENGTH: 413
<212> TYPE: DNA

```
<213> ORGANISM: Homo sapiens

<400> SEQUENCE: 263
ctcagagagg ttgaaagatt tgcctacgaa agggacagtg atgaagctaa gctctagatc    60
    caggatgtct gacttcaaat tgaaactccc aaagtaatga gtttggaagg gtgggtgtg   120
    gcctttccag gatggggtc ttttctgctc ccagcggata gtgaaacccc tgtctgcacc   180
    tggttgggcg tgttgctttc ccaaaggttt ttttttttagg tccgtcgctg tcttgtggat   240
    taggcattat tatctttact ttgtctccaa ataacctgga gaatggagag agtagtgacc   300
    agctcagggc cacagtgcga tgaggaccat cttctcacct ctctaaatgc aggaagaaac   360
    gcagagtaac gtggaagtgg tccacaccta ccgccagcac attgtgaatg aca           413

<210> SEQ ID NO 264
<211> LENGTH: 524
<212> TYPE: DNA
<213> ORGANISM: Homo sapiens

<400> SEQUENCE: 264
tccaatgggg ccctgagagc tgtgacagga actcacactc tggcactggc agcaaaacac    60
    cattccaccc cactcatcgt ctgtgcacct atgttcaaac tttctccaca gttccccaat   120
    gaagaagact catttcataa gtttgtggct cctgaagaag tcctgccatt cacagaaggg   180
    gacattctgg agaaggtcag cgtgcattgc cctgtgtttg actacgttcc cccagagctc   240
    attaccctct ttatctccaa cattggtggg aatgcacctt cctacatcta ccgcctgatg   300
    agtgaactct accatcctga tgatcatgtt ttatgaccga ccacacgtgt cctaagcaga   360
    ttgcttaggc agatacagaa tgaagaggag acttgagtgt tgctgctgaa gcacatcctt   420
    gcaatgtggg agtgcacagg agtccaccta aaaaaaaaaa tccttgatac tgttgcctgc   480
    cttttagtc accccgtaac aagggcacac atccaggact gtgt                     524

<210> SEQ ID NO 265
<211> LENGTH: 344
<212> TYPE: DNA
<213> ORGANISM: Homo sapiens

<400> SEQUENCE: 265
tcctttcttc tacttcagga gatgattcaa agttacttgt ggacatttct ttaagttctg    60
    aagacaaatg agacaggatt tggcctgcgg gttcttcaga cttctctacc acctccatta   120
    actcttcatc ttggcttgac gtaggcaatg cactattttg ctctttttgtt tctggagatg   180
    acccagcacc acttctttct cttggcgggg ttctaagtgt gtctttgaat accagtgaag   240
    actcaggcct atcctgtact ggaaagggac taaatttgtc tttctgtcta ggaggtgatg   300
    cagtagcatc ctcctgaggg ggtaaggcca ttttctcttt ttga                    344

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: 78
<223> OTHER INFORMATION: n = A,T,C or G

<400> SEQUENCE: 266
ccacaatgtc cataacttga gcaggctttg gcatcccacc acccccttca gaccaataca    60
    cactatgttg gaggaacnac tttaaaatgt aaaatgagaa atgggcactg aacactccat   120
    cctcactccc aacagcccac ccacacacct cttcaactgc tatccaaaca tggaggagct   180
    cttgtggaag agaggctcaa caccaaataa                                    210

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: 5, 19, 31
<223> OTHER INFORMATION: n = A,T,C or G

<400> SEQUENCE: 267
tcggncctcc caccctctna ctgaaattct ntgaaattct cccctttggg atgaggatgg    60
    caaccccagg catgtaccct cccaacctgg gacccgacct aatacccctaa catcctgctg   120
    acagtggctg ttctcgctgg cgaggcgtcc caaagcacat cgagccagat tcaggcagag   180
    tggaactggc ccctcagcca tcagtggagg tggcctggga ggctctaccc tgaacggg    238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: 459
<223> OTHER INFORMATION: n = A,T,C or G

<400> SEQUENCE: 268

```
tcctcaagga catgccccctt gatagaaact cagttcctgt ctccagttcc ctcctggacc   60
tgatccccca aatgcagggc ctgggactat atccagttcc ttattttcag aggcccatgc  120
acaagatgca cagcaaataa gtgctgaata aagacccagc tactgctagc ttaccctgct  180
ccaaacattc accaagtcct cagcaaagag ggccatccat tcacctcttc taaaaacaca  240
ctgagctccc cagtctatac cccaagatat gcttggctcc caactatccc tcctctctca  300
tctccaagcc agtttcccct ttctaagtat actgatatta ccaaagcacac tgcaatctt   360
cttttcctac ctctccccag tgactaggtt tgcagcagga gctctataag tcctagtata  420
cagcagaagc tccataaatg tgtgctgacc taacattang c                       461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt   60
cccgctccca accagaatga ggaatgatca cttcatcgt caaggcatgc agtgcatggt   120
ccacaatctc cattttgatt gagtcatggg atgaaagatt ccacagggtt ccggtaataa  180
cttcagtaag gtccatatca cgagcctttc gaagcaatcg cacaagggca ggcacaccat  240
cacagttttt tatggcaatc ttgttatcct ggtcacgtcc aaaagagata ttcttgagag  300
ctccacaggc tccaaggtgc acttccttt tgggatggtc taacaatccc accagtactg  360
ggatgcccctt gagcttccgc acgtcagtct tcaccttgtc attgcggtag cataagtgtt  420
gcaggtatgc aaga                                                     434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggattt tgtatgctcc   60
ccagtagaac cagaatcaga caggtatgag ctagtcaaca gcaagtcttt gttggattcg  120
agtaggctca ggatctgctg aaggtcggag gagtta                             156
```

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: 100, 137, 383, 385, 411
<223> OTHER INFORMATION: n = A,T,C or G

<400> SEQUENCE: 271

```
ccactgtcac ggtctgtctg acacttactg ccaaacgcat ggcaaggaaa aactgcttag   60
tgaagaactt agaagctgtg gagaccttgg ggtccacgtn caccatctgc tctgataaaa  120
ctggaactct gactcanaac cggatgacga tggcccacat gtggtttgac aatcaaatcc  180
atgaagctga tacgacagag aatcagagtg gtgtctcttt tgacaagact tcagctacct  240
ggcttgctct gtccagaatt gcaggtctt gtaacagggc agtgtttcag gctaaccagg   300
aaaacctacc tattcttaag cgggcagttg caggagatgc ctctgagtca gcactcttaa   360
agtgcataga gctgtgctgt ggntncgtga aggagatgag agaaagatac nccaaaatcg  420
tcgagatacc cttcaactcc accaacaagt accagttgtc tattcataag aaccccaaca  480
catcggagcc ccaacacctg ttggtgatga agggcgcccc agaaaggatc cta          533
```

<210> SEQ ID NO 272
<211> LENGTH: 630
<212> TYPE: DNA
<213> ORGANISM: Homo sapiens

<400> SEQUENCE: 272

```
tggtatttt  ctttttcttt  tggatgtttt  atacttttt   ttctttttc   ttctctattc   60
ttttcttcgc  cttcccgtac  ttctgtcttc  cagttttcca  cttcaaactt  ctatcttctc  120
caaattgttt  catcctacca  ctcccaatta  atctttccat  tttcgtctgc  gtttagtaaa  180
tgcgttaact  aggctttaaa  tgacgcaatt  ctccctgcgt  catggatttc  aaggtctttt  240
aatcaccttc  ggtttaatct  ctttttaaaa  gatcgccttc  aaattatttt  aatcacctac  300
aactttaaa   ctaaacttta  agctgtttaa  gtcaccttca  tttaatcta   aaagcattgc  360
ccttctattg  gtattaattc  ggggctctgt  agtccttcc   ctcaattttt  ttttaaatac  420
attttttact  ccatgaagaa  gcttcatctc  aacctccgtc  atgttttaga  aaccttttat  480
cttttccttc  ctcatgctac  tcttctaagt  cttcatattt  tctcttaaaa  tcttaagcta  540
ttaaaattac  gttaaaaact  taacgctaag  caatatctta  gtaacctatt  gactatattt  600
tttaagtagt  tgtattaatc  tctatctttc                                      630
```

<210> SEQ ID NO 273
<211> LENGTH: 400
<212> TYPE: DNA
<213> ORGANISM: Homo sapiens

<400> SEQUENCE: 273

```
tctggtttgc  cctccagttc  attctgaatc  tagacttgct  cagcctaatc  aagttcctgt   60
acaaccagaa  gcgacacagg  ttcctttggt  atcatccaca  agtgaggggg  acacagcatc  120
tcaaccctg   taccagcctt  ctcatgctac  agagcaacga  ccacagaagg  aaccaattga  180
tcagattcag  gcaacaatc   ctttaaatac  agaccagact  acagcatcat  catcccttcc  240
tgctgcgtct  cagcctcaag  tatttcaggc  tgggacaagc  aaaccttac   atagcagtgg  300
aatcaatgta  aatgcagctc  cattccaatc  catgcaaacg  gtgttcaata  tgaatgcccc  360
agttcctcct  gttaatgaac  cagaaacttt  aaaacagcaa                          400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: 2
<223> OTHER INFORMATION: n = A,T,C or G

<400> SEQUENCE: 274

```
tntgagtatg  tcccagagaa  ggtgaagaaa  gcggaaaaga  aattagaaga  gaatccatat   60
gaccttgatg  cttggagcat  tctcattcga  gaggcacaga  atcaacctat  agacaaagca  120
cggaagactt  atgaacgcct  tgttgcccag  ttccccagtt  ctggcagatt  ctggaaactg  180
tacattgaag  cagaggttac  tattttattt  tattttttct  tatatcagta  ttgcagcatt  240
cactgtagtg  atagaaaaca  agttaggaac  atagccaatt  aggacaagga  ggatttaaat  300
gtgtcttacc  tttatttgt   aaaataggta  taaggagta   attaaaatga  a            351
```

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: 4, 11, 12, 13
<223> OTHER INFORMATION: n = A,T,C or G

<400> SEQUENCE: 275

```
gcgnggtcgc  nnncgaggtc  tgagaagccc  ataccactat  ttgttgagaa  atgtgtggaa   60
tttattgaag  atacaggggt  atgtaccgaa  ggactctacc  gtgtcagcgg  gaataaaact  120
gaccaagaca  atattcaaaa  gcagtttgat  caagatcata  atatcaatct  agtgtcaatg  180
gaagtaacag  taatgctgt   agctggagcc  cttaaagctt  tctttgcaga  tctgccagat  240
ccttttaattc catattctct tcatccagaa ctattggaag cagcaaaaat cccggataaa  300
acagaacgtc  ttcatgcctt  gaaagaaatt  gttaagaaat  ttcatcctgt  aaactatgat  360
gtattcagat  acgtgataac  a                                              381
```

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: 5
<223> OTHER INFORMATION: n = A,T,C or G

<400> SEQUENCE: 276

```
gctcngactc cggcgggacc tgctcggagg aatggcgccg ccgggttcaa gcactgtctt    60
cctgttggcc ctgacaatca tagccagcac ctgggctctg acgcccactc actacctcac   120
caagcatgac gtggagagac taaaagcctc gctggatcgc cctttcacaa atttggaatc   180
tgccttctac tccatcgtgg gactcagcag ccttggtgct caggtgccag atgcaaagaa   240
agcatgtacc tacatcgagt ctaaccttga tcccagcaat gtggattccc tcttctacgc   300
tgcccaggcc agccaggccc tctcaggatg tgagatctct atttcaaatg agaccaaaga   360
tctgcttctg gcagacctcg gccgcgacca                                    390
```

<210> SEQ ID NO 277
<211> LENGTH: 378
<212> TYPE: DNA
<213> ORGANISM: Homo sapiens

<400> SEQUENCE: 277

```
tgggaacttc tggggtagga cgttgtctgc tatctccagt tccacagacc caaccagtta    60
cgatggtttt ggaccattta tgccgggatt cgacatcatt ccctataatg atctgcccgc   120
actggagcgt gctcttcagg atccaaatgt ggctgcgttc atggtagaac caattcaggg   180
tgaagcaggc gttgttgttc cggatccagg ttacctaatg ggagtgcgag agctctgcac   240
caggcaccag gttctcttta ttgctgatga aatacagaca ggattggcca gaactggtag   300
atggctggct gttgattatg aaaatgtcag acctgatata gtcctccttg gaaaggccct   360
ttctgggggc ttataccc                                                 378
```

<210> SEQ ID NO 278
<211> LENGTH: 366
<212> TYPE: DNA
<213> ORGANISM: Homo sapiens

<400> SEQUENCE: 278

```
ggagggcaca ttcctttca cctcagagtc ggtcgggaa ggccacccag ataagatttg      60
tgaccaaacc agtgatgctg tccttgatgc ccaccttcag caggatcctg atgccaaagt   120
agcttgtgaa actgttgcta aaactggaat gatccttctt gctggggaaa ttacatccag   180
agctgctgtt gactaccaga aagtggttcg tgaagctgtt aaacacattg gatatgatga   240
ttcttccaaa ggttttgact acaagacttg taacgtgctg gtagccttgg agcaacagtc   300
accagatatt gctcaaggtg ttcatcttga cagaaatgaa gaagacattg gtgctggaga   360
ccaggg                                                              366
```

<210> SEQ ID NO 279
<211> LENGTH: 435
<212> TYPE: DNA
<213> ORGANISM: Homo sapiens

<400> SEQUENCE: 279

```
cctaagaact gagacttgtg acacaaggcc aacgacctaa gattagccca gggttgtagc    60
tggaagacct acaacccaag gatggaaggc ccctgtcaca aagcctacct agatggatag   120
aggacccaag cgaaaaagat atctcaagac taacgccgg aatctggagg cccatgaccc    180
agaacccagg aaggatagaa gcttgaagac ctggggaaat cccaagatga gaacccctaaa  240
ccctacctct tttctattgt ttacacttct tactcttaga tatttccagt tctcctgttt   300
atctttaagc ctgattcttt tgagatgtac ttttttgatgt tgccggttac ctttagattg   360
acaagtatta tgcctggcca gtcttgagcc agctttaaat cacagctttt acctatttgt   420
taggctatag tgttt                                                    435
```

<210> SEQ ID NO 280
<211> LENGTH: 435
<212> TYPE: DNA
<213> ORGANISM: Homo sapiens

<400> SEQUENCE: 280

```
tctggatgag ctgctaactg agcacaggat gacctgggac ccagcccagc caccccgaga    60
cctgactgag gccttcctgg caaagaagga gaaggccaag gggagccctg agagcagctt   120
caatgatgag aacctgcgca tagtggtggg taacctgttc cttgccggga tggtgaccac   180
ctcgaccacg ctggcctggg gcctcctgct catgatccta cacctggatg tgcagcgtga   240
gcccagacct gtccgggcgg ccgctcgaaa ttccagcaca gtcgcggccg ttactagtgg   300
atccgagctc ggtaccaagc ttggcgtaat catggtcata gctgtttcct gtgtgaaatt   360
gttatccgct cacaattcca cacaacatac gagccggaag cataaagtgt aaagcctggg   420
gtgcctaatg agtga                                                    435
```

<210> SEQ ID NO 281
<211> LENGTH: 440
<212> TYPE: DNA

<213> ORGANISM: Homo sapiens

<400> SEQUENCE: 281

```
catctgatct ataaatgcgg tggcatcgac aaaagaacca ttgaaaaatt tgagaaggag   60
gctgctgaga tgggaagggg ctccttcaag tatgcctggg tcttggataa actgaaagct  120
gagcgtgaac gtggtatcac cattgatatc tccttgtgga aatttgagac cagcaagtac  180
tatgtgacta tcattgatgc cccaggacac agagacttta tcaaaaacat gattacaggg  240
acatctcagg ctgactgtgc tgtcctgatt gttgctgctg tgttggtga atttgaagct   300
ggtatctcca agaatgggca gaccgagag catgcccttc tggcttacac actgggtgtg  360
aaacaactaa ttgtcggtgt taacaaaatg gattccactg agcccctac agccagaaga   420
gatatgagga aattgttaag                                                440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tccccggca gctctgacgt ctccaccgca gggactggtg    60
cttctcggag ctcccactcc tcagactccg gtggaagtga cgtggacctg gatcccactg  120
atgcaagct cttccccagc gatggttttc gtgactgcaa gaggggggat cccaagcacg   180
ggaagcgtga acgaggccgg ccccgaaagc tgagcaagta gtactgggac tgtctcgagg  240
gcaagaagag caagcacgcg cccagaggca cccacctgtg ggagttcatc cggacatcc   300
tcatccaccc ggagctcaac gagggcctca tgaagtggga gaatcggcat gaaggcgtct  360
tcaagttcct gcgctccgag gctgtggccc aactatgggg ccaaaagaaa agaacagca  420
acatgaccta cgagaagctg agccgggcca tgaggtacta ctacaaacgg gagatcctgg  480
aacgggtgga tggccggcga ct                                           502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: 130, 147, 221, 225, 242, 246, 261, 279, 292, 294, 298, 314,
      323, 332, 339, 342, 343, 350, 351, 356, 361, 362, 368, 372,
      375, 379, 380, 382, 387, 390, 392, 394, 401, 404, 406, 409,
      413, 423, 431, 433
<223> OTHER INFORMATION: n = A,T,C or G

<400> SEQUENCE: 283

```
ccatattaga ttactggaac atctaagcat cagtgtgtga ccatgcgaac aaaagacttc    60
ggggagtgtc tattttttaaa aaggtttatg tgtgtcgagg cagttgtaaa agatttactg  120
cagaatcaan cccactttta ggcttangac caggttctaa ctatctaaaa atattgactg  180
ataacaaaaa gtgttctaaa tgtggctatt ctgatccata nttgnttttt aaagaaaaaa   240
antgtntata cagaaagagt ntaaaagttc tgtgaattna atgcaaatta gncnccantc  300
ttgacttccc aaanacttga ttnataccct tnactcctnt cnnttcctgn ncttcnttaa   360
nntcaatnat tnggnagtnn anggccntcn gnanaacacc nttncncgnt ccncgcaatc  420
canccgcctt nan                                                       433
```

<210> SEQ ID NO 284
<211> LENGTH: 479
<212> TYPE: DNA
<213> ORGANISM: Homo sapiens

<400> SEQUENCE: 284

```
tctggaagga tcagggatct gagcaaagcc aagtttactt aagctaagcc acttgttcct    60
gggtcaagca gtttgttttc taataagcat cattcctgat cattagagca aagggatgaa  120
tgctcctctt ggaatgatac aggggatctg ccactgggag agtgttgctc agtgttagag  180
tagcagcaat gacagaatga cagcgactct ctgagtcaac ccagtacttt tagtacccg    240
tcactatgtg aataaaggca gctagaaaat ggactcaatt ctgcaagcct tcatggcaac  300
agcccatatt aagacttcta gaacaagtta aaaaaaaatc ttccatttcc atccatgcat  360
gggaaaaggg ctttagtata gtttaggatg gatgtgtgta taataataaa atgataagat  420
atgcatagtg ggggaataaa gcctcagagt ccttccagta tgggaatcc attgtatct    479
```

<210> SEQ ID NO 285
<211> LENGTH: 435
<212> TYPE: DNA
<213> ORGANISM: Homo sapiens
<220> FEATURE:
<221> NAME/KEY: misc_feature

```
<222> LOCATION: 27, 83, 90, 93, 96, 184, 207, 227, 232, 293, 306, 307, 328,
      331, 339, 343, 347, 349, 350, 370, 371, 382, 383, 414, 418,
      434
<223> OTHER INFORMATION: n = A,T,C or G

<400> SEQUENCE: 285 ttttttttt  ttttttttt  tcaatanaaa  tgccataatt  tattccattg  tataaaaag   60
      tcatccttat  gtaacaaaat  gtnttcttan  aanaanaaat  atattatttc  aggtcataaa 120
      taatcagcaa  acatacaact  gttggcaact  aaaaaaaaac  ccaacactgg  tattttccat 180
      cagngctgaa  aacaaacctg  cttaaanata  tatttacagg  gatagtncag  tnctcaaaaa 240
      caaaaattga  ggtattttgg  ttccttctagg  agtagacaat  gacattttgg  ganggcaga  300
      ccctnncc   aaaaaataaa  ataagggnat  nttcttcant  atngaanann  ggggcgccc  360
      cggggaaaan  naaaccttgg  gnngggggtt  tggcccaagc  ccttgaaaaa  aaantttntt 420
      tcccaaaaaa  aacng                                                     435

<210> SEQ ID NO 286
<211> LENGTH: 301
<212> TYPE: DNA
<213> ORGANISM: Homo sapiens

<400> SEQUENCE: 286
cctggtttct  ggtggcctct  atgaatccca  tgtagggtgc  agaccgtact  ccatccctcc  60
      ctgtgagcac  cacgtcaacg  gctcccggcc  cccatgcacg  ggggagggag  atacccccaa 120
      gtgtagcaag  atctgtgagc  ctggctacag  cccgacctac  aaacaggaca  agcactacgg 180
      atacaattcc  tacagcgtct  ccaatagcga  gaaggacatc  atggccgaga  tctacaaaaa 240
      cggccccgtg  gagggagctt  tctctgtgta  ttcggacttc  ctgctctaca  agtcaggagt 300
      g                                                                    301

<210> SEQ ID NO 287
<211> LENGTH: 432
<212> TYPE: DNA
<213> ORGANISM: Homo sapiens

<400> SEQUENCE: 287
tccagcttgt  tgccagcatg  agaaccgcca  ttgatgacat  tgaacgccgg  gactggcagg  60
      atgacttcag  agttgccagc  caagtcagcg  atgtggcggt  acaggggggac  cccttctcc  120
      acggcaccag  ctttgcagac  ggcaagggac  accccagaa   tggcgttcgc  accaaactta 180
      gatttatttt  ctgttccatc  catctcgatc  atcagtttgt  caatcttctc  ttgttctgtg 240
      acgttcagtt  tcttgctaac  cagggcaggc  gcaatagttt  tattgatgtg  ctcaacagcc 300
      tttgagacac  ccttccccat  atagcgagtc  ttatcattgt  cccggagctc  tagggcctca 360
      tagataccag  ttgaagcacc  actgggcaca  gcagctctga  agagaccttt  tgaggtgaag 420
      agatcaacct  ca                                                        432

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: 254
<223> OTHER INFORMATION: n = A,T,C or G

<400> SEQUENCE: 288
tctggctcaa  gtcaaagtcc  tggtcctctt  ctccgcctcc  ttcttcatca  tagtaataaa  60
      cgttgtcccg  ggtgtcatcc  tctgggggca  gtaagggctc  tttgaccacc  gctctcctcc 120
      gaagaaacag  caagagcagc  agaatcagaa  ttagcaaagc  aagaattcct  ccaagaatcc 180
      ccagaatggc  aggaatttgc  aatcctgctt  cgacaggctg  tgccttccta  cagacgccgg 240
      cggccccttc  acantcacac  acgctgacct  ctaaggtggt  cacttggtct  ttattctggt 300
      tatccatgag  cttgagattg  attttg                                        326

<210> SEQ ID NO 289
<211> LENGTH: 451
<212> TYPE: DNA
<213> ORGANISM: Homo sapiens

<400> SEQUENCE: 289
gtcccggtgt  ggctgtgccg  ttggtcctgt  gcggtcactt  agccaagatg  cctgaggaaa  60
      cccagaccca  agaccaaccg  atggaggagg  aggaggttga  gacgttcgcc  tttcaggcag 120
      aaattgccca  gttgatgtca  ttgatcatca  atacttcta   ctcgaacaaa  gagatctttc 180
      tgagagagct  catttcaaat  tcatcagatg  cattggacaa  aatccggtat  gaaagcttga 240
```

```
      cagatcccag taaattagac tctgggaaag agctgcatat taaccttata ccgaacaaac  300
      aagatcgaac tctcactatt gtggatactg gaattggaat gaccaaggct gactttgatca  360
      ataaccttgg tactatcgcc aagtctggga ccaaagcgtt catggaagct ttgcaggctg  420
      gtgcagatat ctctatgatt ggacctcggc c                                  451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: 421
<223> OTHER INFORMATION: n = A,T,C or G

<400> SEQUENCE: 290

```
      tttttttttt tcaaaacagt atattttatt ttacaatagc aaccaactcc ccagtttgtt  60
      tcaattgtga catctagatg gcttaagatt actttctggt ggtcacccat gctgaacaat  120
      attttttcaat cttccaaaca gcaaagactc aaaagagatt ctgcatttca catcagttca  180
      caagttcaag agtcttccat ttatcttagc ttttggaata aattatcttt gaggtagaag  240
      gacaatgacg aagccactta attccttgtg tctgcataaa agcagattta ttcatcacaa  300
      cttcatttat gtgaataaag cagatgatga taaaatgttc tcttattctt gtttaatcag  360
      tagtggtagt gatgccagaa acttgtaaat gcacttcaaa ccaattgtgg ctcaagtgta  420
      ngtggttccc caaggctggt accaatgaga ctggggtttg ggaattagtt ggtcatcatc  480
      cctcctgctg ccca                                                     494
```

<210> SEQ ID NO 291
<211> LENGTH: 535
<212> TYPE: DNA
<213> ORGANISM: Homo sapiens

<400> SEQUENCE: 291

```
      tcgcgtgctt aacatgaaaa caaactttgt gctgtttggt tcattgtatg cattgatgga  60
      gtcttgtctc tcatcatggg gtgtctgacc atccaacctg cagtactcat aatttctcca  120
      catgcaataa tcttccaaaa tgtccaatac ccttgtcatt tgactgaaga ttagtactcg  180
      tgaaccttgt tctttttaact tagggagcag cttgtctaaa accaccatt t tgccactgtt  240
      ggttactaga tgcatatctg ttgtataagg tggaccaggt tctgctccat caaagagata  300
      tggatgatta caacatttc tcaactgcat taggatgttc aataacctca ttttgtccat  360
      cttgcctgct gagttgagta tatctatatc cttcattaat atccgagtat accattccct  420
      ttgcattttg ctgaggccca catagatttt tacttccttc tttggaggca aactcttttc  480
      aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: 4, 348
<223> OTHER INFORMATION: n = A,T,C or G

<400> SEQUENCE: 292

```
      tacnagcccg tgctgatcga gatcctggtg gaggtgatgg atccttcctt cgtgtgcttg  60
      aaaattggag cctgcccctc ggcccataag cccttgttgg gaactgagaa gtgtatatgg  120
      ggcccaagct actggtgcca gaacacagag acagcagccc agtgcaaatgc tgtcgagcat  180
      tgcaaacgcc atgtgtgaa ctaggaggag gaatattcca tcttggcaga aaccacagca  240
      ttggttttt tctacttgtg tgtctgggg aatgaacgca cagatctgtt tgactttgtt  300
      ataaaaatag ggctccccca cctcccccat ttttgtgtcc tttattgnag cattgctgtc  360
      tgcaagggag cccta                                                    376
```

<210> SEQ ID NO 293
<211> LENGTH: 320
<212> TYPE: DNA
<213> ORGANISM: Homo sapiens

<400> SEQUENCE: 293

```
      tcggctgctt cctggtctgg cggggatggg tttgcttggg aaatcctcta ggaggctcct  60
      cctcgcatgg cctgcagtct ggcagcagcc ccgagttgtt tcctcgctga tcgatttctt  120
      tcctccaggt agagttttct ttgcttatgt tgaattccat tgcctctttt ctcatcacag  180
      aagtgatgtt ggaatcgttt cttttgtttg tctgatttat ggtttttta agtataaaca  240
      aaagtttttt attagcattc tgaaagaagg aaagtaaaat gtacaagttt aataaaaagg  300
      ggccttcccc tttagaatag                                               320
```

<210> SEQ ID NO 294
<211> LENGTH: 359
<212> TYPE: DNA
<213> ORGANISM: Homo sapiens

<400> SEQUENCE: 294

```
ctgtcataaa ctggtctgga gtttctgacg actccttgtt caccaaatgc accatttcct   60
gagacttgct ggcctctccg ttgagtccac ttggctttct gtcctccaca gctccattgc  120
cactgttgat cactagcttt ttcttctgcc cacaccttct tcgactgttg actgcaatgc  180
aaactgcaag aatcaaagcc aaggccaaga gggatgccaa gatgatcagc cattctggaa  240
tttggggtgt ccttatagga ccagaggttg tgtttgctcc accttcttga ctcccatgtg  300
agtgtccatc tgattcagat ccatgagtgg tatgggaccc cccactgggg tggaatgtg   359
```

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: 558
<223> OTHER INFORMATION: n = A,T,C or G

<400> SEQUENCE: 295

```
cctgagttgg gctgactgcc agagacagac ccctctgggt ctcggtgaac cagccaggca   60
tttacctcag tggttggcac ctggaacctg tccagggccc tcacctgact gaggagccgc  120
cgggcagtga agtaattgtc caggtctatg ctcttggggt ggataccata gccatccaag  180
gtattcctca ggttgtggaa ctgggtctga gtataggcag aactgggccc caggatgatc  240
tcccggagtg ggggaagctg tgaggtcagg taagtataca cgtccacccg taccccaatc  300
aaactcagca gaatggtgaa ctggagaagt ccttccgtta agtatttctt cagagaaagc  360
attgctgaag gaccagaatg tttatgcttt ttggttttta aaatcttcca aaagacaaat  420
caaggccact gctctgccgc tccagccagc aggttaccct cctcagtgtc aaacccgta   480
ccccaccctg gcagaacaca agggatgagc tccctgacgg ccccagagga aagcacaccc  540
tgtggagcca aggccaanga cacactccag accacattca cttt                   584
```

<210> SEQ ID NO 296
<211> LENGTH: 287
<212> TYPE: DNA
<213> ORGANISM: Homo sapiens

<400> SEQUENCE: 296

```
ccttatcatt cattcttagc tcttaattgt tcattttgag ctgaaatgct gcattttaat   60
tttaaccaaa acatgtctcc tatcctggtt tttgtagcct tcctccacat ccttttctaaa 120
caagattta aagacatgta ggtgtttgtt catctgtaac tctaaaagat ccttttaaa   180
ttcagtccta agaaagagga gtgcttgtcc cctaagagtg tttaatggca aggcagccct  240
gtctgaagga cacttcctgc ctaagggaga gtggtatttg cagacta                287
```

<210> SEQ ID NO 297
<211> LENGTH: 457
<212> TYPE: DNA
<213> ORGANISM: Homo sapiens

<400> SEQUENCE: 297

```
ccaattgaaa caaacagttc tgagaccgtt cttccaccac tgattaagag tggggtggca   60
ggtattaggg ataatattca tttagccttc tgagctttct gggcagactt ggtgaccttg  120
ccagctccag cagccttctt gtccactgct ttgatgacac ccaccgcaac tgtctgtctc  180
atatcacgaa cagcaaagcg acccaaaggt ggatagtctg agaagctctc aacacacatg  240
ggcttgccag gaaccatatc aacaatggca gcatcaccag acttcaagaa tttagggcca  300
tcttccagct ttttaccaga acggcgatca atctttttcct tcagctcagc aaacttgcat  360
gcaatgtgag ccgtgtggca atccaataca ggggcatagc cggcgcttat ttggcctgga  420
tggttcagga taatcacctg agcagtgaag ccagacc                           457
```

<210> SEQ ID NO 298
<211> LENGTH: 469
<212> TYPE: DNA
<213> ORGANISM: Homo sapiens

<400> SEQUENCE: 298

```
tctttgactt tccttgtcta cctcctctgg agatctcaaa ttctccaggt tccatgctcc   60
```

```
              cagagatctc aatgattcct gattctcctc ttccaggagt ctgaatgtct cttggttcac  120
              ttccacagac tccagtggtt cttgaatttc cttttctaga ggattcattg cccctgatt   180
              tatttcttct ggagtccaca gtggtgcttg agtttctgga gatttcagtg tttccaggtt  240
              ctcttgtccc gcagacttca gtgattctag gatctctgtt tctaaagatt ttactgcctc  300
              tatgctctct tctttgagtg actttaagaa ctcttgattc tcattttcaa gaggtctagc  360
              tatctcctgg tcaagagact tcagtggttc tagatccact ttttctgggg gtcttaatgt  420
              catctgatcc tgttccccta gagacctccg tcgctgttga gtctctttt             469
```

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: 37, 82, 144
<223> OTHER INFORMATION: n = A,T,C or G

<400> SEQUENCE: 299

```
              tctgtggaga ggatgaggtt gagggaggtg gggtatntcg ctgctctgac cttaggtaga   60
              gtcctccaca gaagcatcaa antggactgg cacatatgga ctcccttcac aggccacaat  120
              gatgtgtctc tccttcgggc tggnccggta tgcacagttg gggta                   165
```

<210> SEQ ID NO 300
<211> LENGTH: 506
<212> TYPE: DNA
<213> ORGANISM: Homo sapiens

<400> SEQUENCE: 300

```
              tctgaggaaa gtttgggctt attagtattt gctccagcga acctccaagt tttctccatt   60
              gcggacaacg taactaccag ctccttggct cagtggttcg cctccactca gaagttccca  120
              gtaggttctg tcattattgt tggcacatag gccctgaata caggtgatat agggccccca  180
              tgagcgctcc tccattgtga aaccaaatat agtatcattc attttctggg ctttctccat  240
              cacactgagg aagacagaac catttagcac agtgacattg tgaaatatg tttcattgat   300
              tctcacagag taattgacgg agatatatga ttgtgagtca ggaggtgtca cagttatagg  360
              ctcatcagcg gagatgttga agttacctga agcagagacg caagaagagt ctttgttaat  420
              atccaagaag gtctttccca tcagggcagg taagacctgg gctgcagcgt ttggattgct  480
              gaatgctcct tgagaaattt ccgtga                                        506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: 221, 223, 252, 275, 280
<223> OTHER INFORMATION: n = A,T,C or G

<400> SEQUENCE: 301

```
              tcctaaggca gagcccccat cacctcaggc ttctcagttc ccttagccgt cttactcaac   60
              tgcccctttc ctctccctca gaatttgtgt ttgctgcctc tatcttgttt tttgtttttt  120
              cttctggggg gggtctagaa cagtgcctgg cacatagtag gcgctcaata aatacttgtt  180
              tgttgaatgt ctcctctctc tttccactct gggaaaccta ngnttctgcc attctgggtg  240
              accctgtatt tntttctggt gcccattcca tttgnccagn taatacttcc tcttaaaaat  300
              ctcc                                                               304
```

<210> SEQ ID NO 302
<211> LENGTH: 492
<212> TYPE: DNA
<213> ORGANISM: Homo sapiens

<400> SEQUENCE: 302

```
              ttttcagtaa gcaactttc catgctctta atgtattcct ttttagtagg aatccggaag   60
              tattagattg aatggaaaag cacttgccat ctctgtctag gggtcacaaa ttgaaatggc  120
              tcctgtatca catacggagg tcttgtgtat ctgtggcaac agggagtttc cttattcact  180
              ctttatttgc tgctgtttaa gttgccaacc tcccctccca ataaaaattc acttacacct  240
              cctgcctttg tagttctggt attcacttta ctatgtgata gaagtagcat gttgctgcca  300
              gaatacaagc attgcttttg gcaaattaaa gtgcatgtca tttcttaata cactagaaag  360
              gggaaataaa ttaaagtaca caagtccaag tctaaaactt tagtactttt ccatgcagat  420
              ttgtgcacat gtgagaggt gtccagttt g tctagtgatt gttatttaga gagttggacc  480
              actattgtgt gt                                                       492
```

<210> SEQ ID NO 303
<211> LENGTH: 470
<212> TYPE: DNA
<213> ORGANISM: Homo sapiens

<400> SEQUENCE: 303

```
tctggggcag caggtactcc ctacggcact agtctacagg gggaaggacg ctctgtgctg    60
gcagcggtgg ctcacatggc ctgtctgcac tgtaaccaca ggctgggatg tagccaggac   120
ttggtctcct tggaagacag gtctgatgtt tggccaatcc agtccttcag accctgcctg   180
aaacttgtat cttacgtgaa cttaaagaat aaaatgcatt tctaccccga tctcgccccc   240
aggactggca cgacaggcc acggcagatt agatctttc ccagtactga tcggtgcgtg    300
gaattccagc caccacttct gattcgattc cacagtgatc ctgtcctctg agtatttaa   360
agaagccatt gtcaccccag tcagtgttcc aggagttggc aaccagccag tagggtgtgc  420
cattctccac tccccagccc aggatgcgga tggcatggac ctcggccgcg              470
```

<210> SEQ ID NO 304
<211> LENGTH: 79
<212> TYPE: DNA
<213> ORGANISM: Homo sapiens

<400> SEQUENCE: 304

```
tgtcccattg ttaactcagc ctcaaatctc aactgtcagg ccctacaaag aaaatggaga    60
gcctcttctg gtggatgcg                                                 79
```

<210> SEQ ID NO 305
<211> LENGTH: 476
<212> TYPE: DNA
<213> ORGANISM: Homo sapiens

<400> SEQUENCE: 305

```
tcactgagcc accctacagc cagaagagat atgaggaaat tgttaaggaa gtcagcactt    60
acattaagaa aattggctac aaccccgaca cagtagcatt tgtgccaatt tctggttgga   120
atggtgacaa catgctggag ccaagtgcta acgtaagtgg ctttcaagac cattgttaaa   180
aagctctggg aatggcgatt tcatgcttac acaaattggc atgcttgtgt ttcagatgcc   240
ttggttcaag ggatggaaag tcacccgtaa ggatggcaat gccagtggaa ccacgctgct   300
tgaggctctg gactgcatcc taccaccaac tcgtccaact gacaagccct tgcgcctgcc   360
tctccaggat gtctacaaaa ttggtggtaa gttggctgta aacaaagttg aatttgagtt   420
gatagagtac tgtctgcctt cataggtatt tagtatgctg taaatatttt taggta       476
```

<210> SEQ ID NO 306
<211> LENGTH: 404
<212> TYPE: DNA
<213> ORGANISM: Homo sapiens

<400> SEQUENCE: 306

```
tctgtctcgg agctcagggc gcagccagca cacacaggag cccacaggac agccacgtct    60
tcacagaaac tacagaagtc aggacccagg cgaggacctc aggaacaagt gcccctgca   120
gacagagaga cgcagtagca acagcttctg aacaactaca taataatgcg gggagaatcc   180
tgaagaccac tgcatcccac aagcactgac aaccacttca ggatttttatt cctccactc   240
taaccccag atccatttat gagaagtgag tgaggatggc aggggcatgg agggtgaagg   300
gacagcaagg atggtctgag ggcctggaaa caatagaaaa tcttcgtcct ttagcatatc   360
ctggactaga aaacaagagt tggagaagag gggggttgat acta                    404
```

<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: 10, 255, 257
<223> OTHER INFORMATION: n = A,T,C or G

<400> SEQUENCE: 307

```
tcctgcctan acatctgtga gggcctcaag ggctgctgcc tcgactttct ccctagctaa    60
gtccacccgt ccagggacac agccagggca ctgctctgtg ctgacttcca ctgcagccaa   120
gggtcaaaat gaagcatctg cggaggccag gactccttgg catcggacac agtcagggga   180
aaagccaccc tgactctgca ggacagaggg tctagggtca tttggcagga gaacactggt   240
gtgccaaggg aagcnancat                                                260
```

<210> SEQ ID NO 308
<211> LENGTH: 449
<212> TYPE: DNA
<213> ORGANISM: Homo sapiens

<400> SEQUENCE: 308

```
tctgtgctcc cgactcctcc atctcaggta ccaccgactg cactgggcgg ggccctctgg    60
ggggaaaggc tccacggggc agggatacat ctcgaggcca gtcatcctct ggaggcagcc   120
caatcaggtc aaagattttg cccaactggt cggcttcaga gtttccacag aagagaggct   180
ttcgacgaaa catctctgca aagatacagc caacactcca catgtccaca gtgttgcat   240
atgtggactg cagaagaact tcgggagctc ggtaccagag tgtaacaacc ttgatcgttt   300
cggctggcaa gcctggtggg ggtgccttgt ccagatatgt ccttaggtcc tggtctacat   360
gctcaaacac cagggttacc ttgatctccc ggtcagttcg ggatgtggca cagacgtcca   420
tcagccggac aacattggga tgctcaaaa                                     449
```

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: 384
<223> OTHER INFORMATION: n = A,T,C or G

<400> SEQUENCE: 309

```
ctgtggaaac ctggggtgcc gggtaaatgg agaactccag cttggatttc ttgccataat    60
caactgagag acgttccatg agcagggagg tgaacccaga accagttccc ccaccaaagc   120
tgtggaaaac caagaagccc tgaagaccgg tgcactggtc agccagcttc gaattcggt    180
ccaacacaag gtcaatgatc tccttgccaa tggtgtagtg ccctcgggca tagttattgg   240
cagcatcttc cttgcctgtg atgagctgct cagggtggaa gagctggcgg taggtgccag   300
tgcgaacttc atcaatgact gtgggttcca agtctacaaa cacagcccgg ggcacgtgct   360
tgccagcgcc cgtctcactt gaanaagggt gtttgaagga agtcatctcc t            411
```

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: 250
<223> OTHER INFORMATION: n = A,T,C or G

<400> SEQUENCE: 310

```
tcctcgtcca gcttgactcg attagtcctc ataaggtaag caaggcagat ggtggctgac    60
cgggaaatgc ctgcctggca gtgacaaac acccttcctc cagcattctt gatggagtct   120
atgaagtcaa tggcctcgtt gaaccaggag ctgatgtctg ccttgtggtt gtcctccaca   180
gggatgctct tgtactggta gtgaccctca aaatggttgg acaattggc tgagacgttg    240
atcaaggcan ttatgcccaa ggcatccagc atgtccttgc gggaagcgtg atacgcactg   300
cccaggtaca gaaagggcag                                               320
```

<210> SEQ ID NO 311
<211> LENGTH: 539
<212> TYPE: DNA
<213> ORGANISM: Homo sapiens

<400> SEQUENCE: 311

```
tctggcccat gaagctgaag ttgggagaga tgatgcttcg cctctgcttc acaaactcaa    60
aggcctcgtc cagcttgact cgattagtcc tcataaggta agcaaggcag atggtggctg   120
accgggaaat gcctgcctgg cagtgacaa acacccttcc tccagcattc ttgatggagt   180
ctatgaagtc aatggcctcg ttgaaccagg agctgatgtc tgccttgtgg ttgtcctcca   240
cagggatgct cttgtactgg tagtgaccct caaaatggtt gggacaattg gctgagacgt   300
tgatcaaggc agttatgccc aaggcatcca gcatgtcctt gcgggaagcg tgatacgcac   360
tgcccaggta cagaaagggc aggatttcca ccgggccacc ctgaaatcca gaaatatcca   420
acattcatca agcttgctca aagccaaggc cagtgcccat acccacaaaa actttctgct   480
ggaaaagtca atttcagata ccgagtgaac tcagttctgt tgctggagga taaataaat    539
```

<210> SEQ ID NO 312
<211> LENGTH: 475
<212> TYPE: DNA
<213> ORGANISM: Homo sapiens

<400> SEQUENCE: 312

```
tcaaggatct tcctaaagcc accatgtgag aggattcgga cgagagtctg agctgtatgg   60
cagaccatgt cctgctgttc tagggtcatg actgtgtgta ctctaaagtt gccactctca  120
caggggtcag tgatacccac tgaacctggc aggaacagtc ctgcagccag aatctgcaag  180
cagcgcctgt atgcaacgtt tagggcaaaa ggctgtctgg tggggttgtt catcacagca  240
taatggccta gtaggtcaag gatccagggt gtgagggget caaagccagg aaaacgaatc  300
ctcaagtcct tcagtagtct gatgagaact ttaactgtgg actgagaagc attttcctcg  360
aaccagcggg catgtcggat ggctgctaag gcactctgca atactttgat atccaaatgg  420
agttctggat ccagttttcg aagattgggt ggcactgttg taatgagaat cttca       475
```

<210> SEQ ID NO 313
<211> LENGTH: 456
<212> TYPE: DNA
<213> ORGANISM: Homo sapiens

<400> SEQUENCE: 313

```
tccacttaaa gggtgcctct gccaactggt ggaatcatcg ccacttccag caccacgcca   60
agcctaacat cttccacaag gatcccgatg tgaacatgct gcacgtgttt gttctgggcg  120
aatggcagcc catcgagtac ggcaagaaga agctgaaata cctgccctac aatcaccagc  180
acgaatactt cttcctgatt gggccgccgc tgctcatccc catgtatttc cagtaccaga  240
tcatcatgac catgatcgtc cataagaact gggtgggcc gtcagctact  300
acatccggtt cttcatcacc tacatccctt tctacggcat cctgggagcc ctccttttcc  360
tcaacttcat caggttcctg gagagccact ggtttgtgtg ggtcacacag atgaatcaca  420
tcgtcatgga gattgaccag gaggacctcg gcccgc                            456
```

<210> SEQ ID NO 314
<211> LENGTH: 477
<212> TYPE: DNA
<213> ORGANISM: Homo sapiens

<400> SEQUENCE: 314

```
tgcgtgggct tctggaagcc tggatctgga atcattcacc agattattct ggaaaactat   60
gcgtaccctg tgttcttct gattggcact gactcccaca cccccaatgg tggcggcctt  120
gggggcatct gcattggagt tggggtgcc gatgctgtgg atgtcatggc tgggatcccc  180
tgggagctga agtgccccaa ggtgattggc gtgaagctac cgggctctct ctccggttgg  240
tcctcaccca aagatgtgat cctgaaggtg gcaggcatcc tcacggtgaa aggtggcaca  300
ggtgcaatcg tggaatacca cgggcctggt gtagactcca tctcctgcac tggcatggcg  360
acaatctgca acatgggtgc agaaattggg gccaccactt ccgtgttccc ttacaaccac  420
aggatgaaga agtatctgag caagaccggc cgggaagaca ttgccaatct agctgat     477
```

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: 35
<223> OTHER INFORMATION: n = A,T,C or G

<400> SEQUENCE: 315

```
caggtactgg atgtcaggtc tgcgaaactt cttanatttt gacctcagtc cataaaccac   60
actatcacct cggccatcat atgtgtctac tgtggggaca actggagtga aaacttcggt  120
tgctgcaggt ccgtgggaaa atcagtgacc agttcatcag attcatcaga atggtgagac  180
tcatcagact ggtgagaatc atcagtgtca tctacatcat cagagtcgtt cgagtcaatg  240
g                                                                  241
```

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: 1, 4, 32, 39, 68, 77, 82, 94, 166, 172, 195, 196
<223> OTHER INFORMATION: n = A,T,C or G

<400> SEQUENCE: 316

```
nttntgtgat agtgtggttt atggactgag gncaaaatnt aagaagtttc gcagacctga   60
catccaancc tgcccgngcg gncgctcgaa aggncgaatt ctgcagatat ccatcacact  120
ggcggccgct cgagcatgca tctagagggc ccaattcgcc ctatantgag tnatattaca  180
```

```
attcactggc cgtcnnttta caacgtcgtg actgggaaaa ccctggcgtt acccaactta 240
a                                                                 241
```

<210> SEQ ID NO 317
<211> LENGTH: 241
<212> TYPE: DNA
<213> ORGANISM: Homo sapiens
<220> FEATURE:
<221> NAME/KEY: misc_feature
<222> LOCATION: 15, 25, 135, 154, 193
<223> OTHER INFORMATION: n = A,T,C or G

<400> SEQUENCE: 317

```
aggtaccctg ctcancagcc tgggngcctg ggttgtctcc ttgtccatcc actggtccat 60
tctgctctgc attttttgt tcctcttttg gaggttccac tttgggtttg ggctttgaaa 120
ttatagggct acaantacct cggccgaaac cacnctaagg gcgaattctg cagatatcca 180
tcacactggc ggncgctcga gcatgcatct agagggccca attcgccta tagtgagtcg 240
t                                                                 241
```

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: 3, 5, 10, 11, 24, 28, 31, 34, 40, 42, 47, 53, 74, 80, 96,
      101, 127, 129, 136, 138, 205, 241
<223> OTHER INFORMATION: n = A,T,C or G

<400> SEQUENCE: 318

```
cgngnacaan ntacattgat gganggtntg nggntctgan tntttantta cantggagca 60
ttaatatttt cttnaacgtn cctcaccttc ctgaantaaa nactctgggt tgtagcgctc 120
tgtgctnana accacntnaa ctttacatcc ctcttttgga ttaatccact gcgcggccac 180
ctctgccgcg accacgctaa gggcnaattc tgcagatatc catcacactg gcggccgctc 240
n                                                                 241
```

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: 24, 36, 39
<223> OTHER INFORMATION: n = A,T,C or G

<400> SEQUENCE: 319

```
caggtactga tcggtgcgtg gaantccagc caccanttnt gattcgattc cacagtgatc 60
ctgtcctctg agtattttaa agaagccatt gtcaccccag tcagtgttcc aggagttggc 120
aaccagccag tagggtgtgc cattctccac tccccagccc aggatgcgga tggcatggcc 180
acccatcatc tctccggtga cgtgttggta cctcggccgc gaccacgcta agggcgaatt 240
c                                                                 241
```

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: 27, 215, 216, 217, 220, 222, 235
<223> OTHER INFORMATION: n = A,T,C or G

<400> SEQUENCE: 320

```
ggcaggtacc aacagagctt agtaatntct aaaagaaaa aatgatctttt ttccgacttc 60
taaacaagtg actatactag cataaatcat tctagtaaaa cagctaaggt atagacattc 120
taataatttg ggaaaaccta tgattacaag tgaaaactca gaaatgcaaa gatgttggtt 180
ttttgtttct cagtctgctt tagcttttaa ctctnnnaan cncatgcaca cttgnaactc 240
t                                                                 241
```

<210> SEQ ID NO 321
<211> LENGTH: 241

```
<212> TYPE: DNA
<213> ORGANISM: Homo sapiens
<220> FEATURE:
<221> NAME/KEY: misc_feature
<222> LOCATION: 2, 25, 26, 228
<223> OTHER INFORMATION: n = A,T,C or G

<400> SEQUENCE: 321
angtaccaac agagcttagt aattnntaaa agaaaaaaat gatcttttc  cgacttctaa    60
    acaagtgact atactagcat aaatcattct agtaaaacag ctaaggtata gacattctaa   120
    taatttggga aaacctatga ttacaagtga aaactcagaa atgcaaagat gttggttttt   180
    tgtttctcag tctgctttag cttttaactc tggaagcgca tgcacacntg aactctgctc   240
    a                                                                   241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atcttttcc  gacttctaaa    60
    caagtgacta tactagcata aatcattctt ctagtaaaac agctaaggta tagacattct   120
    aataatttgg gaaaacctat gattacaagt aaaaactcag aaatgcaaag atgttggttt   180
    tttgtttctc agtctgcttt agcttttaac tctggaagcg catgcacact gaactctgct   240
    c                                                                   241

<210> SEQ ID NO 323
<211> LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta    60
    ggtctcaagt tatgagaatc tccatggctt tcaggggcta aacttttctg ccattcttt   120
    gctcttaccg ggctcagaag gacatgtcag gtgggatacg tgtttctctt tcagagctga   180
    agaaagggtc tgagctgcgg aatcagtaga gaaagccttg gtctcagtga ctccttggct   240
    t                                                                   241

<210> SEQ ID NO 324
<211> LENGTH: 241
<212> TYPE: DNA
<213> ORGANISM: Homo sapiens

<400> SEQUENCE: 324
aggtactgtc gtatcctcag ccttgttcta tttctttatt ttagctttac agagattagg    60
    tctcaagtta tgagaatctc catggctttc aggggctaaa cttttctgcc attcttttgc   120
    tcttaccggg ctcagaagga catgtcaggt gggatacgtg tttctcttc  agagctgaag   180
    aaagggtctg agctgcggaa tcagtagaga agccttggt  ctcagtgact ccttggcttt   240
    c                                                                   241

<210> SEQ ID NO 325
<211> LENGTH: 241
<212> TYPE: DNA
<213> ORGANISM: Homo sapiens

<400> SEQUENCE: 325
ggcaggtaca tttgttttgc ccagccatca ctcttttttg tgaggagcct aaatacattc    60
    ttcctggggt ccagagtccc cattcaaggc agtcaagtta agacactaac ttgcccctt   120
    cctgatggaa atatttcctc catagcagaa gttgtgttct gacaagactg agagagttac   180
    atgttgggaa aaaaaaagaa gcattaactt agtagaactg aaccaggagc attaagttct   240
    g                                                                   241

<210> SEQ ID NO 326
<211> LENGTH: 241
<212> TYPE: DNA
<213> ORGANISM: Homo sapiens

<400> SEQUENCE: 326
```

```
       gcaggtacat ttgttttgcc cagccatcac tcttttttgt gaggagccta aatacattct    60
       tcctggggtc cagagtcccc attcaaggca gtcaagttaa gacactaact tggcccttc    120
       ctgatggaaa tatttcctcc atagcagaag ttgtgttctg acaagactga gagagttaca   180
       tgttgggaaa aaaaagaagc attaacttag tagaactgat ccaggagcat taagttctga   240
       a                                                                   241

<210> SEQ ID NO 327
<211> LENGTH: 241
<212> TYPE: DNA
<213> ORGANISM: Homo sapiens

<400> SEQUENCE: 327
ggtaccagac caagtgaatg cgacagggaa ttatttcctg tgttgataat tcatgaagta    60
       gaacagtata atcaaaatca attgtatcat cattagtttt ccactgccct cacactagtga  120
       gctgtgccaa gtagtagtgt gacacctgtg ttgtcatttc ccacatcacg taagagcttc   180
       caaggaaagc caaatcccag atgagtctca gagagggatc aatatgtcca tgattatcag   240
       g                                                                   241

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: 6, 19, 66, 232, 240
<223> OTHER INFORMATION: n = A,T,C or G

<400> SEQUENCE: 328
ggtacnagac caaatgaang ccacagggaa ttatttcctg tgttgataat tcatgaagta    60
       gaacantata atcaaaatca attgtatcat cattagtttt ccactgcctc acactagtga   120
       gctgtgccaa gtagtagtgt gacacctgtg ttgtcatttc ccacatcacg taagagcttc   180
       caaggaaagc caaatcccag atgagtctca gagagggatc aatatgtcca tnatcatcan   240
       g                                                                   241

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: 33, 61, 220, 228, 229, 240, 241
<223> OTHER INFORMATION: n = A,T,C or G

<400> SEQUENCE: 329
ttcaggtcga gttggctgca gatttgtggt gcnttctgag ccgtctgtcc tgcgccaaaa    60
       ngcttcaaag tattattaaa aacatatgga tccccatgaa gccctactac accaaagttt   120
       accaggagat ttggatagga atggggctga tgggcttcat cgtttataaa atccgggctg   180
       ctgataagaa gtaaggcttt gaaagcttca gcgcctgctn ctggtcanna ctaaccatan   240
       n                                                                   241

<210> SEQ ID NO 330
<211> LENGTH: 241
<212> TYPE: DNA
<213> ORGANISM: Homo sapiens

<400> SEQUENCE: 330
ttttgtgcag atttgtggtg cgttctgagc cgtctgtcct gcgccaagat gcttcaaagt    60
       attattaaaa acatatggat ccccatgaag ccctactaca ccaaagttta ccaggagatt   120
       tggataggaa tggggctgat gggcttcatc gtttataaaa tccgggctgc tgataaaaga   180
       agtaaggctt tgaaagcttc agcgcctgct cctggtcatc actaaccaga tttacttgga   240
       g                                                                   241

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: 1, 9, 41, 60, 61, 119, 124, 132, 139, 141, 153, 168
<223> OTHER INFORMATION: n = A,T,C or G
```

```
<400> SEQUENCE: 331
nttttaggna ctttgggctc cagacttcac tggtcttagg nattgaaacc atcacctggn   60
      ntgcattcct catgactgag gttaacttaa aacaaaaatg gtaggaaagc tttcctatnc  120
      ttcnggtaag anacaaatnt nctttaaaaa aangtggaag gcatgacnta cgtgagaact  180
      gcacaaactg gccactgaca aaaatgaccc ccatttgtgt gacttcattg agacacatta  240
      c                                                                  241

<210> SEQ ID NO 332
<211> LENGTH: 241
<212> TYPE: DNA
<213> ORGANISM: Homo sapiens

<400> SEQUENCE: 332
tgtgaggaga gggaacatgc tgagaaactg atgaagctgc agaaccaacg aggtggccga   60
      atcttccttc aggatatcaa gaaaccagac tgtgatgact gggagagcgg gctgaatgca  120
      atggagtgtg cattacattt ggaaaaaaat gtgaatcagt cactactgga actgcacaaa  180
      ctggccactg acaaaaatga ccccccatttg tgtgacttca ttgagacaca ttacctgaat  240
      g                                                                  241

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: 44, 52, 60, 98, 104, 108, 124, 126, 190, 198, 206, 214
<223> OTHER INFORMATION: n = A,T,C or G

<400> SEQUENCE: 333
caggtacaag cttttttttt tttttttttt tttttttttt ttgnaaatac tntttattgn   60
      aaatattcta tcctaaattc catatagcca attaattntt acanaatntt ttgttaattt  120
      ttgngngtat aaattttaca aaaataaagg gtatgtttgt tgcacacaac ttacaaataa  180
      taataaactn tttattgnaa atattntttta ttgnaaatat tctttatcct aaattccata  240
      t                                                                  241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: 10, 16, 22, 24, 49, 158, 159, 237
<223> OTHER INFORMATION: n = A,T,C or G

<400> SEQUENCE: 334
tacctgctgn aggggntgaa gncntctctg ctgccccagg catctgcanc ccctgctgct   60
      ggttctgccc ctgctgcagc agaggagaag aaagatgaga agaaggagga gtctgaagag  120
      tcagatgatg acatgggatt tggccttttt gattaaannc ctgctcccct gcaaataaag  180
      ccttttttaca caaaaaaaaa aaaaaaaaaa aaaaaaaaaa aagcttgtac ctgcccnggc  240
      g                                                                  241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: 39
<223> OTHER INFORMATION: n = A,T,C or G

<400> SEQUENCE: 335
ctatgtgctg ggatgactat ggagacccaa atgtctcana atgtatgtcc cagaaacctg   60
      tggctgcttc aaccattgac agttttgctg ctgctggctt ctgcagacag tcaagctgca  120
      gctcccccaa aggctgtgct gaaacttgag cccccgtgga tcaacgtgct ccaggaggac  180
      tctgtgactc tgacatgcca gggggctcgc agccctgaga gcgactccat tcagtggttc  240
      c                                                                  241

<210> SEQ ID NO 336
```

```
<211> LENGTH: 241
<212> TYPE: DNA
<213> ORGANISM: Homo sapiens

<400> SEQUENCE: 336
taccaaccta tgcagccaag caacctcagc agttcccatc aaggccacct ccaccacaac   60
    cgaaagtatc atctcaggga aacttaattc ctgcccgtcc tgctcctgca cctcctttat  120
    atagttccct cacttgattt ttttaacctt cttttttgcaa atgtcttcag ggaactgagc  180
    taatactttt ttttttcttg atgttttctt gaaaagcctt tctgttgcaa ctatgaatga  240
    a                                                                   241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: 47, 56, 69, 228
<223> OTHER INFORMATION: n = A,T,C or G

<400> SEQUENCE: 337
ggtactgtat gtagctgcac tacaacagat tcttaccgtc tccacanagg tcatanattg   60
    taaatggtna atactgactt tttttttatt cccttgactc aagacagcta acttcattt   120
    cagaactgtt ttaaaccttt gtgtgctggt ttataaaata atgtgtgtaa tccttgttgc  180
    tttcctgata ccagactgtt tcccgtggtt ggttagaata tattttgntt tgatgcttat  240
    a                                                                   241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt   60
    ctcaaatgga gttttccact ttcctttgaa gtagacagca ttcaccagga tcatcctggt  120
    atccccatct acagaacctt caggtaacaa gtttgggatt ttgcctttgg tttgagtctt  180
    gacccaggaa ttaatctttt ttctagcttc ttctgcacat tctaggaagt ctactgcctg  240
    g                                                                   241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg   60
    aaagtgtctg caactccaaa gatcaaggcc ataaccagg agaccatcaa cggaagatta   120
    gttctttgtc aagtgaatga aatccaaaag cacgcatgag accaatgaaa gtttccgcct  180
    gttgtaaaat ctattttccc ccaaggaaag tccttgcaca gacaccagtg agtgagttct  240
    a                                                                   241

<210> SEQ ID NO 340
<211> LENGTH: 241
<212> TYPE: DNA
<213> ORGANISM: Homo sapiens

<400> SEQUENCE: 340
gtagccctca cacacacatg cccgtaacag gatttatcac aagcacgcc tgcatgtaga    60
    ccagacacag ggcgtatgga aagcacgtcc tcaagactgt agtattccag atgagctgca  120
    gatgcttacc taccacggcc gtctccacca gaaaaccatc gccaactcct gcgatcagct  180
    tgtgacttac aaaccttgtt taaaagctgc ttacatggac ttctgtcctt taaaagcttc  240
    c                                                                   241

<210> SEQ ID NO 341
<211> LENGTH: 241
<212> TYPE: DNA
<213> ORGANISM: Homo sapiens

<400> SEQUENCE: 341
```

```
gtaccgccta ctttcgtctc atgtctccga acttcttgct gatggccgtt ccaacgttgc    60
tgaaagctgc agttgccttt tgccctgcgt gactcagggt ttcatgtgtt ttccttgtagg  120
cagtggtagt ctgcatgtca tgccagcttt tgctgaagtt ctgttttaat tcattcatca   180
ggttcatgcc gagttttgtt ttatctcaac tagatgcctt tctttcgctg acaaaacttg   240
t                                                                   241
```

<210> SEQ ID NO 342
<211> LENGTH: 241
<212> TYPE: DNA
<213> ORGANISM: Homo sapiens

<400> SEQUENCE: 342

```
gtacattggt gctataaata taaatgctac ttatgaagca tgaaattaag cttctttttt    60
cttcaagttt tttctcttgt ctagcaatct gttaggcttc tgaaccaaga ccaaatgttt  120
acgttcctct gctgcatacc aacgttactc caaacaataa aaatctatca tttctgctct  180
gtgctgagga atggaaaatg aaaccccccac cccctgaccc ctaggactat acagtggaaa  240
c                                                                   241
```

<210> SEQ ID NO 343
<211> LENGTH: 241
<212> TYPE: DNA
<213> ORGANISM: Homo sapiens

<400> SEQUENCE: 343

```
gtacatgtgg tagcagtaat tttttttgaag caactgcact gacattcatt tgagttttct    60
ctcattatca gattctgttc caaacaagta ttctgtagat ccaaatggat taccagtgtg   120
ctacagactt cttattatag aacagcattc tattctacat caaaaatagt ttgtgtaagt   180
tagttttggt taccatctaa aatattttta aatgttcttt acataaaaat ttatgttgtg   240
t                                                                   241
```

<210> SEQ ID NO 344
<211> LENGTH: 241
<212> TYPE: DNA
<213> ORGANISM: Homo sapiens

<400> SEQUENCE: 344

```
ggtacaaaat tgttggaatt tagctaatag aaaaacatag taaatattta caaaaacgtt    60
gataacatta ctcaagtcac acacatataa caatgtagac aggtcttaac aaagtttaca  120
aattgaaatt atggagattt cccaaaatga atctaatagc tcattgctga gcatggttat  180
caatataaca tttaagatct tggatcaaat gttgtccccg agtcttctgc aatccagtcc  240
t                                                                   241
```

<210> SEQ ID NO 345
<211> LENGTH: 241
<212> TYPE: DNA
<213> ORGANISM: Homo sapiens

<400> SEQUENCE: 345

```
ggtacgaagc tgagcgcacg ggggttgccc cagcgtggag cctggacctc aaacttcacg    60
gaaaatgctc tctctctttg acaggcttcc agctgtctcc taatttcctg gatgaactct  120
ccccggcgat ttaactgatc ctgaaaagtg gtgagaggac tgaggaagac aaccaggtca  180
gcgttagatc ggcctctgag ggtggtgccc ttgcctgagg agccacccct taccaccttg  240
g                                                                   241
```

<210> SEQ ID NO 346
<211> LENGTH: 241
<212> TYPE: DNA
<213> ORGANISM: Homo sapiens

<400> SEQUENCE: 346

```
caggtaccac tgagcctgag atggggatga gggcagagag aggggagccc cctcttccac    60
tcagttgttc ctactcagac tgttgcactc taaacctagg gaggttgaag aatgagaccc  120
ttaggttttta acacgaatcc tgacaccacc atctataggg tcccaacttg gttattgtag  180
gcaaccttcc ctctctcctt ggtgaagaac atcccaagcc agaaagaagt taactacagt  240
g                                                                   241
```

<210> SEQ ID NO 347

<211> LENGTH: 241
<212> TYPE: DNA
<213> ORGANISM: Homo sapiens

<400> SEQUENCE: 347

```
aggtacatct aaaggcatga agcactcaat tgggcaatta acattagtgt ttgttctctg   60
atggtatctc tgagaatact ggttgtagga ctggccagta gtgccttcgg gactgggttc  120
accccaggt ctgcggcagt tgtcacagcg ccagccccgc tggcctccaa agcatgtgca  180
ggagcaaatg gcaccgagat attccttctg ccactgttct cctacgtggt atgtcttccc  240
a                                                                  241
```

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: 2, 18, 29, 35, 56, 57, 64, 76, 77, 85, 102, 103, 104, 189, 232
<223> OTHER INFORMATION: n = A,T,C or G

<400> SEQUENCE: 348

```
angtacttgg caagattnga tgctcttgng ctcantgaca tcattcataa cttgtnngtg   60
tgancagagg aggagnncat catcntgtcc tcattcgtca gnnncctctc ctctctgaat  120
ctcaaacaag ttgataatgg agaaaaattt gaattctcag gattgaggct ggactggttc  180
cgcctacang catacactag cgtggctaag gcccctctgc accctgcatg anaaccctga  240
c                                                                  241
```

<210> SEQ ID NO 349
<211> LENGTH: 241
<212> TYPE: DNA
<213> ORGANISM: Homo sapiens

<400> SEQUENCE: 349

```
gcaggtacca tttgtctgac ctctgtaaaa aatgtgatcc tacagaagtg gagctggata   60
atcagatagt tactgctacc cagagcaata tctgtgatga agacagtgct acagagacct  120
gctacactta tgacagaaac aagtgctaca cagctgtggt cccactcgta tatggtggtg  180
agaccaaaat ggtggaaaca gccttaaccc cagatgcctg ctatcctgac taatttaagt  240
c                                                                  241
```

<210> SEQ ID NO 350
<211> LENGTH: 241
<212> TYPE: DNA
<213> ORGANISM: Homo sapiens

<400> SEQUENCE: 350

```
aggtactgtg gatatttaaa atatcacagt aacaagatca tgcttgttcc tacagtattg   60
cgggccagac acttaagtga aagcagaagt gtttgggtga ctttcctact taaaattttg  120
gtcatatcat ttcaaaacat ttgcatcttg gttggctgca tatgctttcc tattgatccc  180
aaaccaaatc ttagaatcac ttcatttaaa atactgagcg gtattgaata cttcgaagca  240
g                                                                  241
```

<210> SEQ ID NO 351
<211> LENGTH: 241
<212> TYPE: DNA
<213> ORGANISM: Homo sapiens

<400> SEQUENCE: 351

```
tacagaaatc atttggagcc gttttgagac agaagtagag gctctgtcaa gtcaatactg   60
cattgcagct tggtccactg aagaagccac gcctgagata caaaagatgc actacacttg  120
acccgcttta tgttcgcttc ctctcccctt ctctctcatc aactttatta ggttaaaaca  180
ccacatacag gctttctcca aatgactccc tatgtctggg gtttggttag aattttatgc  240
c                                                                  241
```

<210> SEQ ID NO 352
<211> LENGTH: 241
<212> TYPE: DNA
<213> ORGANISM: Homo sapiens
<220> FEATURE:

<221> NAME/KEY: misc_feature
<222> LOCATION: 10, 28, 29, 49, 54, 59, 72, 127, 148, 150, 160, 166, 182
<223> OTHER INFORMATION: n = A,T,C or G

<400> SEQUENCE: 352

```
gtaccctgtn gagctgcacc aagattannt ggggccatca tgactgcanc cacnacgang  60
acgcaggcgt gnagtgcatc gtctgacccg gaaacccttt cacttctctg ctcccgaggt 120
gtcctcnggc tcatatgtgg gaaggcanan gatctctgan gagttncctg gggacaactg 180
ancagcctct ggagagggc cattaataaa gctcaacatc attggcaaaa aaaaaaaaa  240
a                                                                 241
```

<210> SEQ ID NO 353
<211> LENGTH: 241
<212> TYPE: DNA
<213> ORGANISM: Homo sapiens

<400> SEQUENCE: 353

```
aggtaccagt gcattaattt gggcaaggaa agtgtcataa tttgatactg tatctgtttt  60
ccttcaaagt atagagcttt tggggaagga aagtattgaa ctggggggttg gtctggccta 120
ctgggctgac attaactaca attatgggaa atgcaaaagt tgtttggata tggtagtgtg 180
tggttctctt ttggaatttt tttcaggtga tttaataata atttaaaact actataaaaa 240
c                                                                 241
```

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 354

```
ngcaggtccg ggcaggtacc aagattcatt ctcatcaaaa actagaaaca gaagggcaaa  60
ttccagtttc cttctgggat tgaatacttt caagtaaggt cttcgacaaa caatcagggg 120
gccaattaat ccactgtaga ggtccttaac ttgatccaca gttgaataat aagcccatgg 180
aatacaagca gaatcctctg ttccagctcc agatctttct gggattttcc atacgtaagt 240
g                                                                 241
```

<210> SEQ ID NO 355
<211> LENGTH: 241
<212> TYPE: DNA
<213> ORGANISM: Homo sapiens

<400> SEQUENCE: 355

```
ggtacccacc ctaaatttga actcttatca agaggctgat gaatctgacc atcaaatagg  60
ataggatgga ccttttttg agttcattgt ataaacaaat tttctgattt ggacttaatt 120
cccaaaggat taggtctact cctgctcatt cactctttca aagctctgtc cactctaact 180
tttctccagt gtcatagata gggaattgct cactgcgtgc ctagtctttc ttcacttacc 240
t                                                                 241
```

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: 27
<223> OTHER INFORMATION: n = A,T,C or G

<400> SEQUENCE: 356

```
aggtactgta attgagcatc cggaatntgg agaagtaatt tagctacagg gtgaccaacg  60
caagaacata tgccagttcc tcgtagagat tggactggct aaggacgatc agctgaaggt 120
tcatgggttt taagtgcttg tggctcactg aagcttaagt gaggatttcc ttgcaatgag 180
tagaatttcc cttctctccc ttgtcacagg tttaaaaacc tcacagcttg tataatgtaa 240
c                                                                 241
```

<210> SEQ ID NO 357
<211> LENGTH: 241

```
<212> TYPE: DNA
<213> ORGANISM: Homo sapiens

<400> SEQUENCE: 357
ttttgtacca ccgatatgat caaggaaaat tctgcccatt tttatggctg aagttctaaa    60
     aacctaattc aaagttcttc catgatccta cactgcctcc aagatggtcc aggctggcat   120
     aaggcctgag cggcggtgag atccgcggct gccagcagct tgtcgctctt cagctggtat   180
     gaagccctc ggccacccga gtctccagga cctgcccggg cgccgctcga aagggcgaat    240
     t                                                                  241

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: 25, 57
<223> OTHER INFORMATION: n = A,T,C or G

<400> SEQUENCE: 358
aggtacgggg agtggggtg aagcntgttc tctacatagg caacacagcc gcctaantca     60
     caaagtcagt ggtcggccgc ttcgaccaac atgtggtagg cattccacgg gcgcatgaag   120
     tctgggtgct gtgctcgagt ctctgaatat tttgatagga agcgacaaga aaattcaaac   180
     tgctctttgc tgactactgg aaagtgaaaa gatgctcaag tttaccattc aaagaaacca   240
     t                                                                  241

<210> SEQ ID NO 359
<211> LENGTH: 241
<212> TYPE: DNA
<213> ORGANISM: Homo sapiens

<400> SEQUENCE: 359
gaggtacaca aaaggaatac cttctgagag ccagggagtg aggaaagggg aaggagactt    60
     gacgtcaagg gtgcttttga ggaacatgac gggccagcca gcctgcccca actttgaggc   120
     cctgctgggc tcttgtgact ataaatatac tgtctatttc taatgcaatc cgtctttcct   180
     gaaagatctt gttatctttt actattgaga catgctttca tttttgtggt cctgtttcca   240
     a                                                                  241

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 360
ngtactctat actaattctg ccttttata cttaattcta aatttctccc ctctaattta     60
     caacaaattt tgtgattttt ataagaatct atgcctcccc aattctcaga ttcttctctt   120
     ttctccttta tttctttgct taaattcagt ataagctttc ttggtatttt aggcttcatg   180
     cacattctta ttcctaaaca ccagcagttc ttcagagacc taaaatccag tataggaata   240
     a                                                                  241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc    60
     ccactttgta cttttcttac tatcctgtct agaatcatgt cttatgattt taacagatat   120
     agaaccactc ctagaaaatg ttctttcact ttctcgtttc ctttttaatc tatcatcctg   180
     actactgaac ttaaaatctt tttcttccct tttttgtttc tcttttcttt tatcctgttc   240
     a                                                                  241

<210> SEQ ID NO 362
<211> LENGTH: 241
<212> TYPE: DNA
```

```
<213> ORGANISM: Homo sapiens
<220> FEATURE:
<221> NAME/KEY: misc_feature
<222> LOCATION: 17, 23
<223> OTHER INFORMATION: n = A,T,C or G

<400> SEQUENCE: 362
aggtactttt atacctngct tangtcagtg acagatttac caatgacaac acaattttaa      60
aattccaaca catatattac tttgtcctat gaagggcaaa aagtcaatat attttaaatt    120
ttaaaaacag aatggatata atgacctttt tacacatcag tgatatttaa aagacttaaa    180
gagacaatac tatggttgag acactggctt cctattccag ccctaattaa agaaaaaata    240
g                                                                    241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 363
ttangtacta aaaacaaaat cctaattctg ttttaaagag ctgggagatg ttaatcatat      60
gctcagtttt tccacgttat aatttcctaa atgcaaactt ttcaatcagg gcagttcaaa    120
ttcattacat cacagtaaat aacagtagcc aactttgatt ttatgcttat aggaaaaaaa    180
atcctgtaga tataaaaaca gcaaattttg caaataaaaa ctcaaaccat tcatccctaa    240
a                                                                    241

<210> SEQ ID NO 364
<211> LENGTH: 241
<212> TYPE: DNA
<213> ORGANISM: Homo sapiens

<400> SEQUENCE: 364
ggtacaagca gttagtcctg aaggccsctg ataagaatgt catcttctcc ccactgagca      60
tctccaccgc cttggccttc ctgtctctgg gggcccataa taccaccctg acagagattc    120
tcaaaggcct caagttcaac ctcacggaga cttctgaggc agaaattcac cagagcttcc    180
agcacctcct gcgcaccctc aatcagtcca gcgatgagct gcagctgagt atgggaaatg    240
c                                                                    241

<210> SEQ ID NO 365
<211> LENGTH: 241
<212> TYPE: DNA
<213> ORGANISM: Homo sapiens

<400> SEQUENCE: 365
cgaggtactg agattacagg catgagccac cacgcccggc caaaaacatt taaaaaatga      60
ctgtccctgc tcaaatactg cagtaggaaa tgtaatttga catatatcac ttccagaaaa    120
aaactttaaa tctttctata aaatgaattt gatacatcat cagcatgaag tgaagttaaa    180
atctcttaca aagtaaattc aggtatatca acaatgagat ccaaaagtat cggttcaaga    240
t                                                                    241

<210> SEQ ID NO 366
<211> LENGTH: 241
<212> TYPE: DNA
<213> ORGANISM: Homo sapiens

<400> SEQUENCE: 366
ggcaggtaca catcaaacac ttcattgcct aaatgcaggg acatgcttcc atctgaccac      60
ttgactatcc gagcattgct ttctttaatt tcatttcctt cttcatctcg gcgtatcctc    120
catcttatag tattttctac ctttaatttt aacctggttc taccttcttc atccagcatt    180
tcttcatctt caaattcatc ttcataatac tgggctctac acttgagaaa gttgggcagt    240
t                                                                    241

<210> SEQ ID NO 367
<211> LENGTH: 241
<212> TYPE: DNA
<213> ORGANISM: Homo sapiens
```

```
<220> FEATURE:
<221> NAME/KEY: misc_feature
<222> LOCATION: 25
<223> OTHER INFORMATION: n = A,T,C or G

<400> SEQUENCE: 367
gcaggtacaa ataattcctg ttgtnacatt tagtggacgc gattatctgt atacctcaaa    60
     ttttaattta agaaagtatc acttaaagag catctcattt tctatagatt gaggcttaat   120
     tactgaaaag tgactcaacc aaaaagcaca taaccttta aaggagctac acctaccgca    180
     gaaagtcaga tgccctgtaa ataactttgg tctttcaaaa tagtggcaat gcttaagata   240
     c                                                                  241

<210> SEQ ID NO 368
<211> LENGTH: 241
<212> TYPE: DNA
<213> ORGANISM: Homo sapiens

<400> SEQUENCE: 368
tttgtacatt gttaatagtg accctcggag gaaatggatt tctcttctat taaaaactct    60
     atggtatata agcattacat aataatgcta cttaaccacc ttttgtctca agaattatca   120
     ccaaagtttt ctggaaataa gtccacataa gaattaaata tttaaaaggt gaaatgttcc   180
     ttattttaac tttagcaaga tcttttcttt ttcattaaga aacactttaa taattttaaa   240
     g                                                                  241

<210> SEQ ID NO 369
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat    60
     aaacaaaaca ccaaccagcc acagcagttg tgtcaagcat gacaattggt ctagtcttca   120
     cattttatta gtaagtctat caagtaagag atgaagggtc tagaaaacta gacacaaagc   180
     aaccagggtc caaatcacca aggtagatct gtgcttagct aaagggaaac acccgaagat   240
     t                                                                  241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 370
ngttcacagt gcccctccgg cctcgccatg aggctcttcc tgtcgctccc ggtcctggtg    60
     gtggttctgt cgatcgtctt ggaaggccca gccccagccc aggggacccc agacgtctcc   120
     agtgccttgg ataagctgaa ggagtttgga aacacactgg aggacaaggc tcgggaactc   180
     atcagccgca tcaaacagag tgaactttct gccaagatgc gggagtggtt ttcagaagac   240
     a                                                                  241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: 227
<223> OTHER INFORMATION: n = A,T,C or G

<400> SEQUENCE: 371
ggcaggtcat cttgagcctt gcacatgata ctcagattcc tcacccttgc ttaggagtaa    60
     aacaatatac tttacagggt gataataatc tccatagtta tttgaagtgg cttgaaaaag   120
     gcaagattga cttttatgac attggataaa atctacaaat cagccctcga gttattcaat   180
     gataactgac aaactaaatt atttccctag aaaggaagat gaaaggnagt ggagtgtggt   240
     t                                                                  241

<210> SEQ ID NO 372
```

```
<211> LENGTH: 241
<212> TYPE: DNA
<213> ORGANISM: Homo sapiens
<220> FEATURE:
<221> NAME/KEY: misc_feature
<222> LOCATION: 26, 27, 59
<223> OTHER INFORMATION: n = A,T,C or G

<400> SEQUENCE: 372
aggtacagca aagcgaccct tggtgnnata gatcagacgg aaattctctc ccgtcttgnc   60
aatgctgatg acatccatga atccagcagg gtaggttata tcagttcgga ccttgccatc  120
gattttaatg aaccgctgca tgcaaatctt ctttacttca tctcctgtca gggcatactt  180
aagtctgttc ctcaggaaaa tgatgagggg gagacactct ctcaacttgt ggggaccggt  240
g                                                                  241

<210> SEQ ID NO 373
<211> LENGTH: 241
<212> TYPE: DNA
<213> ORGANISM: Homo sapiens

<400> SEQUENCE: 373
tactgaaaca gaaaaaatgt attcccacaa aagctgttac acagcggttt cccgtcccca   60
gaagcagtag aaaatcttag cattccaatg gaaggcatgt atttgtaaaa tattctaaaa  120
tcagctctat agtttccttg tcctctttga taagggatca dacagagggt gtgtcccccct 180
tcagcagcta cccttcttga caaactggtc tccaataata cctttcagaa acttacaaga  240
c                                                                  241

<210> SEQ ID NO 374
<211> LENGTH: 241
<212> TYPE: DNA
<213> ORGANISM: Homo sapiens

<400> SEQUENCE: 374
caggtactaa aacttacaat aaatatcaga gaagccgtta gtttttacag catcgtctgc   60
ttaaaagcta agttgaccag gtgcataatt tcccatcagt ctgtccttgt agtaggcagg  120
gcaatttctg ttttcatgat cggaatactc aaatatatcc aaacatcttt taaaactttt  180
gatttatagc tcctagaaag ttatgttttt taatagtcac tctactctaa tcaggcctag  240
c                                                                  241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt   60
gaagaccatc acctccgtgg ccatgaccag tgctctgccc atcatccaga agctagagcc  120
gcaaattgca gttgccaata cctatgcctg taaggggcta dacaggattg aggagagact  180
gcctattctg aatcagccat caactcagat tgttgccaat gccaaaggcg ctgtgactgg  240
g                                                                  241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa acttttgttt atacttaaaa   60
aaaccataaa tcagacaaac aaaagaaacg attccaacat cacttctgtg atgagaaaag  120
aggcaatgga attcaacata agcaaagaaa actctacctg gaggaaagaa atcgatcagc  180
gaagaaacaa ctcggggctg ctgccagact gcaggccatg cgaggaggag cctcctagag  240
g                                                                  241

<210> SEQ ID NO 377
<211> LENGTH: 241
<212> TYPE: DNA
<213> ORGANISM: Homo sapiens
<220> FEATURE:
<221> NAME/KEY: misc_feature
```

<222> LOCATION: 234
<223> OTHER INFORMATION: n = A,T,C or G

<400> SEQUENCE: 377

```
tcctttctgt ccaggtgatt cacagactag acctttctta tcctcctcct agagttttga    60
cttgggactc tagtgttaag atgatgagcc cgtgcatcag gtccttctgc actttggtgg   120
aagtctccca gggtaggttt cctatttgaa acagtggaat catgtttcca gtgataaagt   180
ttaatgacct catccttttt tttttttttc tcatctgcca tttgtgtgtc ttanatgggt   240
t                                                                   241
```

<210> SEQ ID NO 378
<211> LENGTH: 241
<212> TYPE: DNA
<213> ORGANISM: Homo sapiens

<400> SEQUENCE: 378

```
aggtcagcga tcaggtcctt tatgggcagc tgctgggcag ccccacaagc ccagggccag    60
ggcactatct ccgctgcgac tccactcagc ccctcttggc gggcctcacc cccagcccca   120
agtcctatga gaacctctgg ttccaggcca gccccttggg gaccctggta accccagccc   180
caagccagga ggacgactgt gtctttgggc cactgctcaa cttccccctc ctgcagggga   240
t                                                                   241
```

<210> SEQ ID NO 379
<211> LENGTH: 241
<212> TYPE: DNA
<213> ORGANISM: Homo sapiens

<400> SEQUENCE: 379

```
tacggagcaa tcgaagaggc atatccacac ttggggtggc tatagggctg gaaaatgctg    60
aagatgactg ctttcactga ggtcaaggat tgtaatattg ccagctttgt aaagccatta   120
aagcagaagt ttcttcagtg atcttctctc taagaaacac catcacctcc atgtgcctta   180
cagaggcccc ctgcgttctg ctgcattgct tttgcgcaat cccttgatga tgaagatggt   240
c                                                                   241
```

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: 24, 25, 26, 34, 36, 56, 113, 129, 137, 184, 185, 208, 210,
      237, 240
<223> OTHER INFORMATION: n = A,T,C or G

<400> SEQUENCE: 380

```
acgtacacgc agaccgacat gggnnnttca ggcntnagat caaactcaaa acctgnaatg    60
atatccactc tcttttttctt aagctcaggg aaatattcca agtagaagtc canaaagtca   120
tcggctaana tgcttcngaa tttgaattca tgcacatagg ccttgaaaaa actgtcaaac   180
tgannctgat cacccaccaa gtgggccntn tatgacacaa agcagaaacc tttctcntan   240
g                                                                   241
```

<210> SEQ ID NO 381
<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg    60
tctaaagaga gggtatttca tatggctttt agttcacttg tttgtatttc atcttgattt   120
ttttctttgg aaaataaagc attctatttg gttcagattt ctcgatttg aaaaaggctc   180
tatctcagat gtagtaaatt atttcctttc agtttgtgaa agcaggattt gactctgaaa   240
g                                                                   241
```

<210> SEQ ID NO 382
<211> LENGTH: 241
<212> TYPE: DNA
<213> ORGANISM: Homo sapiens

<400> SEQUENCE: 382
```

```
gtactgctat aatcaatacg tctgatagac aggtttatcc actatattga ccctacctct    60
aaaaggattg tcataattta tatgctttat gtttacacct atgatacagt tgccttggaa   120
cacaaaattt ttcattgtaa ttaaaaaaag aagagttgtg cagacagaag aaatcaaatc   180
taagaaaatc acaggagtag ataaatactc tagaattcat atacccttgg aagatgggtt   240
t                                                                   241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact    60
gtatttaagt ctgtgcaaat aatccttcag aagaaatatc caagattctg tttgcagagg   120
tcattttgtc tctcaaagat gattaaatga gtttgtcttc agataaagtg ctcctgtcca   180
gcagaactca aaaggccttc aagctgttca gtaagtgtag ttcagataag actccgtcat   240
a                                                                   241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag    60
attctataaa atcagttata tcaacatata aaggagtgtg attttcagtt tgttttttta   120
agtaaaatatg accaaactga ctaaataaga aggcaaaaca aaaaattatg cttccttgac   180
aaggcctttg gagtaaacaa aatgctttaa ggctcctggt gaatgggtt gcaaggatga   240
a                                                                   241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc    60
tggtccctga ccccacagtg agctgtttag atgatccttc acatcttcct gatcaactgg   120
aagacactcc aatcctcagt gaagactctc tggagccctt caactctctg gcaccaggta   180
ggtttggagg ctatgtccct ttaacttatc catgcagagt agccaaactt tacctgaaag   240
a                                                                   241
```

<210> SEQ ID NO 386
<211> LENGTH: 241
<212> TYPE: DNA
<213> ORGANISM: Homo sapiens

<400> SEQUENCE: 386

```
aggtaccttt ttcctctcca aaggaacagt ttctaaagtt ttctgggggg aaaaaaaact    60
tacatcaaat ttaaaccata tgttaaactg catattagtt gtgttacacc aaaaaattgc   120
ctcagctgat ctacacaagt ttcaaagtca ttaatgcttg atataaattt actcaacatt   180
aaattatctt aaattattaa ttaaaaaaaa aactttctaa gggaaaaata aacaaatgta   240
g                                                                   241
```

<210> SEQ ID NO 387
<211> LENGTH: 241
<212> TYPE: DNA
<213> ORGANISM: Homo sapiens

<400> SEQUENCE: 387

```
accccactgg ccgctgtgga gtatctccac tctccctcg tgagggccgc tcccaccgac    60
cagtcgaact ttcgtaaatg gagttaatgt gtttccactc ccctttccc ctttctggcc   120
ttttggtcca gaatttcctg gccttccggc atatcctggg agtcctgac ttccaggaaa   180
gccaattgct ccccgatcac ctttaagacc cggaggacct attggacctg gaaatcctcg   240
t                                                                   241
```

<210> SEQ ID NO 388

```
<211> LENGTH: 241
<212> TYPE: DNA
<213> ORGANISM: Homo sapiens

<400> SEQUENCE: 388
tttgtactct tgtccacagc agagacattg agtataccat tggcatcaat gtcaaaagtg   60
acttcaatct gaggaacacc tcggggtgca ggaggtatgc ctgtgagttc aaacttgcca  120
agcaggttgt tatcctttgt catggcacgc tcgccttcat aaacctgaat aagtacacca  180
ggctggttgt cagaataggt agtgaaggtc tgtgtctgct tggtaggaat ggtggtatta  240
c                                                                  241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: 6, 28, 38, 43
<223> OTHER INFORMATION: n = A,T,C or G

<400> SEQUENCE: 389
tacctntgtt agtgagcacc ttgtcttntg tgcttatntc ttnaagataa atacatggaa   60
ggatgtgaaa atcgaacac  caactatgtg tctcactgca tctaagtgaa gcagccacag  120
ctgtgagagt tttcaaagca gaaagatgct gatgtgacct ctggaattca gacatactga  180
gctatgggtc agaagtgttt tacttaaaaa gcaaacaatc cccaggaaat actgaatagg  240
a                                                                  241

<210> SEQ ID NO 390
<211> LENGTH: 241
<212> TYPE: DNA
<213> ORGANISM: Homo sapiens

<400> SEQUENCE: 390
gcaggtacat ccacatgttc ctccaaatga cgtttggggt cctgcttgcc aacattcttt   60
attgccagct gttcaggtgt catcttatct tcttcttcta cagccttatt gtaattcttg  120
gctaattcca acatctcttt taccactgat tcattgcgtt acaatgttca actgtagtcc  180
tgaagtgtca aaccttccat ccaactcttc ttatgcaaat ttagcaacat cttctgttcc  240
a                                                                  241

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: 2, 10, 14, 22, 23, 25, 40, 50, 57, 59, 65, 71, 72, 73, 76,
       77, 78, 82, 83, 84, 95, 98, 100, 101, 102, 107, 148, 152,
       155, 158, 163, 169, 170, 172, 180, 182, 192, 193, 198, 200,
       202, 203, 206, 207, 208, 213, 214, 218, 220, 224, 225
<223> OTHER INFORMATION: n = A,T,C or G
<221> NAME/KEY: misc_feature
<222> LOCATION: 235, 236
<223> OTHER INFORMATION: n = A,T,C or G

<400> SEQUENCE: 391
cnggcacaan cttntgtttt tnntntttt ttttttttn tctttatttn ttttttantnt   60
taaanaaaaa nnntannnaa annngggttt aaatnctntn nncagancat taaaactgaa  120
ggggaaaaaa aaaccaaaaa cgagcttntt anttnacntg ggnttgggnn gntgctgatn  180
tnaagaagca anntttanan cnngcnnnat ganngagngn tcannttgaa atttnnaccc  240
t                                                                  241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gttttttcta   60
cattagaaat aagatgccac acaggaact  acattccaga tttaagaaa tgaaaggata  120
ccattagtgt gtataacaga ttattgttca tacttgtaaa gcatcttatg tcattgagaa  180
```

```
       tataaagaac agtgccttag aagacagtga aaggtaagct ctagcttaat gtctatgatt   240
       t                                                                   241
```

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: 57, 75, 224
<223> OTHER INFORMATION: n = A,T,C or G

<400> SEQUENCE: 393

```
       ggcaggtaca taagcataat cagttatgga cagcttcttg tataaattgc tattcancaa   60
       tacataaact gcctnaaaga tttatgctta caggtagaca ttcaatttac caataaaaca   120
       gcatgttctg aaaatatggg cacattttaa aacatattaa gacagttctg ttaaccataa   180
       tagtcccaca gtatgactga gtaataagaa tctacttcaa aagnaaaaaa aaaattaatc   240
       a                                                                   241
```

<210> SEQ ID NO 394
<211> LENGTH: 241
<212> TYPE: DNA
<213> ORGANISM: Homo sapiens

<400> SEQUENCE: 394

```
       aggtacagca gcagtagatg gctgcaacaa ccttcctcct accccagccc agaaaatatt   60
       tctgccccac cccaggatcc gggaccaaaa taaagagcaa gcaggccccc ttcactgagg   120
       tgctgggtag ggctcagtgc cacattactg tgctttgaga aagaggaagg ggatttgttt   180
       ggcactttaa aaatagagga gtaagcagga ctggagaggc cagagaagat accaaaattg   240
       g                                                                   241
```

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: 1, 5, 8, 9, 14, 24, 26, 28, 32, 42, 54
<223> OTHER INFORMATION: n = A,T,C or G

<400> SEQUENCE: 395

```
       nggcnggnnc caanatatga aatntnanta tnatacatga tnaaaagctt tatntattt t  60
       agtgagtaat taagtttaca ctgtgaataa ggattaattc ccagatgacc atctacagtt   120
       actaccacat agagggtata cacggatgga tcgattacaa gaatataaaa cttatttt cc  180
       ttcctgtatc cacatttctt tgcaatgtga atttgcaggc cctctcaaga agtggagtc   240
       a                                                                   241
```

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 396

```
       gaggtacacc ttgaatgaca atgctnggag ccccctgtg gtcatcgacg cctccactgc   60
       cattgatgca ccatccaacc tgcgtttcct ggccaccaca cccaattcct tgctggtatc   120
       atggcagccg ccacgtgcca ggattaccgg ctacatcatc aagtatgaga agcctgggtc   180
       tcctcccaga gaagtggtcc ctcggccccg ccctggtgtc acagaggcta ctattactgg   240
       c                                                                   241
```

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: 90

<223> OTHER INFORMATION: n = A,T,C or G

<400> SEQUENCE: 397

```
ggcaggtacc agcaggggga tgtgtttctg gggaattgtg gctctggaag cttcacggtt    60
tcccagaatg tggaaaatat atctgtgcan gatagaaatc ctgcccagag gctgtttctg   120
tctcatttga gctctccttc atgtggcaga gctgactgtg gcggtttagg agcctacatt   180
ttagaaaagc ttacctcaaa gttctgcatt gagcctgagc actggaaagg agataaaata   240
a                                                                   241
```

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: 3, 11, 22, 27, 38, 41, 53, 59, 63, 69, 77, 78, 94, 131, 133, 137, 149, 154, 162, 166, 167, 172, 175, 176, 179, 191, 230
<223> OTHER INFORMATION: n = A,T,C or G

<400> SEQUENCE: 398

```
gangtgacca ngacatcacc tnacacntgg aaagcganga nttgaatggt gcntacaang    60
ccntacccnt tgcccannac ctgaacgcgc cttntgattg ggacagccgt gggaaggaca   120
gttatgaaac nantcanctg gatgaccana gtgntgaaac cnacanncac angcnntcna   180
cattatataa ncggaaagct aatgatgaga gcaatgatca ttccgatgtn attgatagtc   240
a                                                                   241
```

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: 212, 226
<223> OTHER INFORMATION: n = A,T,C or G

<400> SEQUENCE: 399

```
cagagtgaga tgggagtggg agggccaatc tgatacagaa gggggtgaag ggtagggccc    60
ctgagcagcc caccccttac cctgacgaag gcaatcctcc tctggaatgt ctcttccctc   120
ttcagtctgg gttctgcctc agccacgaac tgggaaggag tgaggaacat cccaacggca   180
atgagagtat cccagtgact ccaaacagga angaatcagt gttcanaaag tcagggccct   240
t                                                                   241
```

<210> SEQ ID NO 400
<211> LENGTH: 241
<212> TYPE: DNA
<213> ORGANISM: Homo sapiens

<400> SEQUENCE: 400

```
ggtactcttg ctcttttagc tagagtgtat gtgaaaataa agaaatacat cattgtattc    60
acaaccatgt gtcttcattt ataactttt gtttaaaaaa ttttagttc aagtttagtt    120
cattgatatt atcctctgaa tgcagttaag gctgggcaga aattctactc atgtgacatc   180
tgccacaggt ctatttgaa gcttttcttc taatgggcaa tgtttgtcct taccaggatt   240
t                                                                   241
```

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: 1, 2
<223> OTHER INFORMATION: n = A,T,C or G

<400> SEQUENCE: 401

```
nncaggtact ttgtagagca gagagaggct ttggttcctc ctttcttcaa tcacgtggag    60
atgtgtcatc acctgggatt tcatctgggc cgccttttct gggtcaacag ccaacacatg   120
ctggtaatga cggatggtat gtaagcgatc tttgttctca gcacggacat aacgccgtaa   180
ggcctggaga atgcgatgag gccgtggcgg gtcagactgc aaggcagcca ggtagttctc   240
c                                                                   241
```

```
<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: 26, 27
<223> OTHER INFORMATION: n = A,T,C or G

<400> SEQUENCE: 402
ggcaggtcca aaaaaaacct aaaaanngtt tcaggaatgt agagaaatat ccaacttaaa    60
tagcgaaaaa gtgcaccata attactgctg cactgcagtc atttctgcaa ttcccatgtt   120
tcttaaataa ctatcttgtc agataacaca caatataaag agcaattatg aaaaacagac   180
atttacatat acttctaaag tcttattggg aatatcctgt ttggccattg ggataaccaa   240
t                                                                   241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: 49
<223> OTHER INFORMATION: n = A,T,C or G

<400> SEQUENCE: 403
aggtgttaac tacccgctcc gagacgggat tgatgacgag tcctatgang ccattttcaa    60
gccggtcatg tccaaagtaa tggagatgtt ccagcctagt gcggtggtct tacagtgtgg   120
ctcagactcc ctatctgggg atcggttagg ttgcttcaat ctaactatca aggacacgc    180
caagtgtgtg gaatttgtca agagctttaa cctgcctatg ctgatgctgg gaggcggtgg   240
t                                                                   241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt    60
ttctgtcttc ttttcacggc attcaaagta ggaataaact ttgcttgtgt tgggtggata   120
ttgtttatag tgagtaacct tgtaggagtc ggtggccagg aggatgttga actcggcttc   180
tgccgcagga ttcatctcgg gccggaggac aaggggcccg cgcgccgcga gctccctgac   240
c                                                                   241

<210> SEQ ID NO 405
<211> LENGTH: 266
<212> TYPE: DNA
<213> ORGANISM: Homo sapiens

<400> SEQUENCE: 405
ttctgggctg gggagtggag agaaagaagt tgcagggctt acaggaaatc ccagagcctg    60
aggttttctc ccagatttga gaactctaga ttctgcatca ttatctttga gtctatattc   120
tcttggctg taagaagatg aggaatgtaa taggtctgcc ccaagccttt catgccttct   180
gtaccaagct tgtttccttg tgcatccttc ccaggtctg gctgcccctt attggagaat   240
gtgatttcca agacaatcaa tccaca                                        266

<210> SEQ ID NO 406
<211> LENGTH: 231
<212> TYPE: DNA
<213> ORGANISM: Homo sapiens

<400> SEQUENCE: 406
ttggtgaaga accattcctc ggcatccttg cggttcttct ctgccatctt ctcatactgg    60
tcacgcatct cgttcagaat gcggctcagg tccacgccag gtgcagcgtc catctccaca   120
ttgacatctc cacccacctg gcctctcagg gcattcatct cctcctcgtg gttcttcttc   180
aggtaggcca gctcctcctt caggctctca atctgcatct ccaggtcagc t            231

<210> SEQ ID NO 407
```

```
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt   60
    ttgtgccata atgcagcagt atggagggag gattttatgg agaaatgggg atagtcttca  120
    tgaccacaaa taaataaagg aaaactaagc tgcattgtgg gttttgaaaa ggttattata  180
    cttcttaaca attcttttt tcagggactt ttctagctgt atgactgtta cttgaccttc   240
    tttgaaaagc attcccaaaa tgctct                                        266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg   60
    actttcagg gaattactga actttcttct cagaagatag ggcacagcca ttgccttggc  120
    ctcacttgaa gggtctgcat ttgggtcctc tggtctcttg ccaagtttcc cagccactcg  180
    agggagtaat atctggaggg caaagaagag acttatgtta ttgttgaacc tccagccaca  240
    gggaggagca tgggcatggg t                                            261

<210> SEQ ID NO 409
<211> LENGTH: 266
<212> TYPE: DNA
<213> ORGANISM: Homo sapiens

<400> SEQUENCE: 409
gctgacagta atacactgcc acatcttcag cctgcaggct gctgatggtg agagtgaaat   60
    ctgtcccaga cccgctgcca ctgaatcggt cagggatccc ggattcccgg gtagatgccc  120
    agtaaatgag cagtttagga ggctgtcctg gtttctgctg gtaccaagct aagtagttct  180
    tattgttgga gctgtctaaa acactctggg tggtcttgca gttgatggtg ccctctcgc   240
    ccagagacac agccaggag tgtgga                                        266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: 9, 17, 24, 26, 65, 97, 98, 99, 100, 103, 105, 106, 107, 108,
      120, 121, 123, 142, 145, 149, 162, 177
<223> OTHER INFORMATION: n = A,T,C or G

<400> SEQUENCE: 410
caaaaggtnc tttttgntca aaancnattt ttattccttg atattttct tttttttt    60
    tttgnggatg gggacttgtg aattttttcta aaggggnnnn ttnannnngg aagaaaaccn  120
    ngntccggtt ccagccaaac cngtngctna cttccacct tntttccacc tccctcngt    180
    t                                                                  181

<210> SEQ ID NO 411
<211> LENGTH: 261
<212> TYPE: DNA
<213> ORGANISM: Homo sapiens

<400> SEQUENCE: 411
gcccctgcag tacttggccg atgtggacac ctctgatgag gaaagcatcc gggctcacgt   60
    gatggcctcc caccattcca agcggagagg ccgggcgtct tctgagagtc agggtctagg  120
    tgctggagtg cgcacggagg ccgatgtaga ggaggaggcc ctgaggagga agctggagga  180
    gctggccagc aacgtcagtg accaggagac ctcgtccgag gaggaggaag ccaaggacga  240
    aaaggcagag cccaacaggg a                                            261

<210> SEQ ID NO 412
<211> LENGTH: 171
<212> TYPE: DNA
<213> ORGANISM: Homo sapiens
<220> FEATURE:
<221> NAME/KEY: misc_feature
```

```
<222> LOCATION: 1, 6, 53, 79, 91, 96, 114, 132
<223> OTHER INFORMATION: n = A,T,C or G

<400> SEQUENCE: 412
nttttntctt tacaattcag tcttcaacaa cttgagagct ttcttcatgt tgncaagcaa    60
    cagagctgta tctgcaggnt cgtaagcata nagacngttt gaatatcttc cagngatatc   120
    ggctctaact gncagagatg ggtcaacaaa cataatcctg gggacatact g            171

<210> SEQ ID NO 413
<211> LENGTH: 266
<212> TYPE: DNA
<213> ORGANISM: Homo sapiens

<400> SEQUENCE: 413
ttaggaccaa agatagcatc aactgtattt gaaggaactg tagtttgcgc attttatgac    60
    attttataa agtactgtaa ttctttcatt gagggctat gtgatggaga cagactaact    120
    cattttgtta tttgcattaa aattattttg ggtctctgtt caaatgagtt tggagaatgc   180
    ttgacttgtt ggtctgtgta aatgtgtata tatatatacc tgaatacagg aacatcggag   240
    acctattcac tcccacacac tctgct                                        266

<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: 86, 153, 162, 178, 184, 205
<223> OTHER INFORMATION: n = A,T,C or G

<400> SEQUENCE: 414
tttgccataa ttgagtgaaa agtggcagat ggcattaact ctgctccgct tcaagctggc    60
    tccatgacca ctcaaggcct cccancctg ttcgtcaagt tgtcctcaag tccaagcaat   120
    ggaatccatg tgtttgcaaa aaaagtgtgc tanttttaag gncttctcgta taagaataa   180
    tganacaatt ttcctaccaa aggangaaca aaaggataaa tataatacaa aatatatgta   240
    tatggttgtt tgacaaatta tataac                                        266

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: 37, 103, 223
<223> OTHER INFORMATION: n = A,T,C or G

<400> SEQUENCE: 415
cctccatcca gtctattaat tgttgccggg aagctanagt aagtagttcg ccagttaata    60
    gtttgcgcaa cgttgttgcc attgctacag gcatcgtggt gtnacgctcg tcgattggta   120
    tggcttcatt cagctccggt tcccaacgat caaggcgagt tacatgatcc cccatgttgt   180
    gcaaaaaagc ggttagctcc ttcggtcctc cgatcgttgt canaagtaag ttggccgcag   240
    tgttatcact catggttatg gcagca                                        266

<210> SEQ ID NO 416
<211> LENGTH: 878
<212> TYPE: DNA
<213> ORGANISM: Homo sapiens

<400> SEQUENCE: 416
cctgacgata gccatggctg taccacttaa ctatgattct attccaactg ttcagaatca    60
    tatcacaaaa tgacttgtac acagtagttt acaacgactc ccaagagagg aaaaaaaaaa   120
    aaaagacgc ctcaaaattc actcaacttt tgagacagca atggcaatag gcagcagaga    180
    agctatgctg caactgaggg cacatatcat tgaagatgtc acaggagttt aagagacagg   240
    ctggaaaaaa tctcatacta agcaaacagt agtatctcat accaagcaaa accaagtagt   300
    atctgctcag cctgccgcta acagatctca caatcaccaa ctgtgcttta ggactgtcac   360
    caaagtcaga ttcggtgcta accaggtggc atctatgatc aacgtcgccc tcttatttta   420
    acaaagggct ctgaaggagg tgttctccaa gcaacaagga gactgcttca gtacaagact   480
    ttgcaccttg aattcaattg catcaagtgt ggatagcaaa ataagtatct taccattgaa   540
    atatgtgttc agcctaagat tttaccacc agcagaacaa aagtgagggt gagagggatg   600
    ggcagtgag gggatggggg agaaaaaaaa atcacaggat taccaccaaa gccttgtttt   660
    aaaagggctc ccttcactat tcaggaaggg aagtggaagg agaaattaac caattcctgc   720
```

<210> SEQ ID NO 417
<211> LENGTH: 514
<212> TYPE: DNA
<213> ORGANISM: Homo sapiens

<400> SEQUENCE: 417

```
ttctgacttc tagaagacta aggctggtct gtgtttgctt gtttgcccac ctttggctga    60
tacccagaga acctgggcac ttgctgcctg atgcccaccc ctgccagtca ttcctccatt   120
cacccagcgg gaggtgggat gtgagacagc ccacattgga aaatccagaa aaccgggaac   180
agggatttgc ccttcacaat tctactcccc agatcctctc ccctggacac aggagaccca   240
cagggcagga ccctaagatc tggggaaagg aggtcctgag aaccttgagg taccctaaga   300
tccttttcta cccactttcc tatggaggat tccaagtcac cacttctctc accggcttct   360
accagggtcc aggactaagg cgttttctcc atagcctcaa cattttggga atcttccctt   420
aatcacccct gctcctcctg ggtgcctgga agatggactg gcagagacct ctttgttgcg   480
ttttgtgctt tgatgccagg aatgccgcct agtt                               514
```

<210> SEQ ID NO 418
<211> LENGTH: 352
<212> TYPE: DNA
<213> ORGANISM: Homo sapiens

<400> SEQUENCE: 418

```
ctgcaccagc gattaccagt ggcattcaaa tactgtgtga ctaaggattt tgtatgctcc    60
ccagtagaac cagaatcaga caggtatgag ctagtcaaca gcaagtcttt gttggattcg   120
agtaggctca ggatctgctg aaggtcggag gagttagtcc ccgcaatcaa gagcctgtct   180
tcctgaagcc cttggtgata ttttgccact cagccaagaa tgaggatgca tccttcagat   240
tctctatgtc ccgaacctgg aacccatcca cgccagcttg cagccaaaac tccagagcat   300
ccttcacctt ggtggaaaaa aaaaaaaaaa aaaaaaaaaa aaaaaaaaaa aa            352
```

<210> SEQ ID NO 419
<211> LENGTH: 344
<212> TYPE: DNA
<213> ORGANISM: Homo sapiens

<400> SEQUENCE: 419

```
ctggacacca taatcccttt taagtggctg gatggtcaca cctctcccat tgacaagctg    60
ggttaagtca ataggttgac taggatcaac acgacccaaa tcaataagat actgcagtct   120
attgagactc aaaggcttat actggcgtct gaaactatgt ccttcgttaa acccgtattt   180
tgggattcgg atgtaaaatg gagtctggcc tccctcaaag cccaagcggg gccgggttcc   240
tcttttgcctt tctcctttat ggcctctgcc acattttcta cctcttctcc gacctcttgg   300
tcttctctcc ggtttcttgg agccgggatt cggctttaag ttgg                    344
```

<210> SEQ ID NO 420
<211> LENGTH: 935
<212> TYPE: DNA
<213> ORGANISM: Homo sapiens

<400> SEQUENCE: 420

```
cgaaagtcaa cgttaagggg ctcaggtgaa ccatgatgat gaccttctgt tgactttgaa    60
atattggctc ttgtgggtga caaaagccag acaagctgtg gctgtggtcc gattttaaga   120
cgaggttctc aaagatccaa aggaggaaa  gggtattgga aacactgtgt atcatctgag   180
acacacgtgt cctcatgatc ttaaatgcct actttaaagc cacctaatac tgcccttcat   240
tgtggtcaga agagatttct acaaaagcac tcagaattct ggaggcagtt gtgattttgc   300
catgtggcag ttggtttgtg gagttgggca ggtgtgaaag ggtaaaactc cacttctgaa   360
tgctgcttct gcccctgggg acccagcaca ttgttagacc atcttcttga ctgaaaattc   420
tctcctgatg ctgagccctg caccaccacc ttccttttcc taactatgaa ttgatggcaa   480
agtccactca aaacaaccag ttaagtgctc acgagagagt agtcaagcac ctccagaaag   540
aaaccgggtt tttgttcaca tagcaggaag tgactccctg ggtggtaatt tatcttggaa   600
acacaggtag attggcagaa aaacggaaac atgtaggtac gcgatgttg gtgcatgtcc   660
attactttgg gataggcttt ctcagtcttt cctcaaatga tagttgagcc agttttccag   720
tggcaattct gagtgacttg cgcttgtctt atggtgtggt caagggacgt tcagaactac   780
ggaaaacttt tactgaaaca gcgaagcaga gtataccggc atgagaggga agatgaaaac   840
tcacctatgt accactcttt gacaataaat atagtatttc tcaaaaaaaa aaaaaaaaaa   900
agtaaaaaaa ctgaaatcgc aagtcaaaaa atcca                              935
```

<210> SEQ ID NO 421

```
<211> LENGTH: 745
<212> TYPE: DNA
<213> ORGANISM: Homo sapiens

<400> SEQUENCE: 421
ggcttcgagc ggccgcccgg gcaggtccta gatgtcattt gggaccttc  acaaccattt   60
     tgaagccctg tttgagtccc tgggatatgt gagctgtttc tatgcataat ggatattcgg  120
     ggttaacaac agtcccctgc ttggcttcta ttctgaatcc ttttctttca ccatggggtg  180
     cctgaagggt ggctgatgca tatggtacaa tggcacccag tgtaaagcag ctacaattag  240
     gagtggatgt gttctgtagc atcctattta aataagccta ttttatcctt tggcccgtca  300
     actctgttat ctgctgcttg tactggtgcc tgtacttttc tgactctcat tgaccatatt  360
     ccacgaccat ggttgtcatc cattacttga tcctacttta catgtctagt ctgtgtggtt  420
     ggtggtgaat aggcttcttt ttacatggtg ctgccagccc agctaattaa tggtgcacgt  480
     ggacttttag caagcgggct cactggaaga gactgaacct ggcatggaat tcctgaagat  540
     gtttggggtt tttttctttc ttaatcgaaa gttaacattg tctgaaaagt tttgttagaa  600
     ctactgcgga acctcaaaat cagtagattt ggaagtgatt caaagctaaa cttttcctt   660
     ggccctcctt gtgttctaat tgcttgcaag tgtaatacta ggatgtccaa gatgccagtt  720
     tttgcttctt tgttagttgt cagac                                        745

<210> SEQ ID NO 422
<211> LENGTH: 764
<212> TYPE: DNA
<213> ORGANISM: Homo sapiens

<400> SEQUENCE: 422
gagttcagta gcaaagtcac acctgtccaa ttccctgagc tttgctcact cagctaatgg   60
     gatggcaaag gtggtggtgc tttcatcttc aggcagaagc ctctgcccat cccctcaag   120
     ggctgcaggc ccagttctca tgctgccctt gggtgggcat ctgttaacag aggagaacgt  180
     ctggggtggcg gcagcagctt tgctctgagt gcctacaaag ctaatgcttg gtgctagaaa  240
     catcatcatt attaaacttc agaaaagcag cagccatgtt cagtcaggct catgctgcct  300
     cactgcttaa gtgcctgcag gagccgcctg ccaagctccc ttcctacac  ctggcacact  360
     ggggtctgca caaggctttg tcaaccaaag acagcttccc ccttttgatt gcctgtagac  420
     tttggagcca agaaacactc tgtgtgactc tacacacact tcaggtggtt tgtgcttcaa  480
     agtcattgat gcaacttgaa aggaaacagt ttaatggtgg aaatgaacta ccatttataa  540
     cttctgtttt tttattgaga aaatgattca cgaattccaa atcagattgc caggaagaaa  600
     taggacgtga cggtactggg ccctgtgatt ctcccagccc ttgcagtccg ctaggtgaga  660
     ggaaaagctc tttacttccg cccctggcag ggacttctgg gttatgggag aaaccagaga  720
     tgggaatgag gaaaatatga actacagcag aagcccctgg gcag                   764

<210> SEQ ID NO 423
<211> LENGTH: 1041
<212> TYPE: DNA
<213> ORGANISM: Homo sapiens

<400> SEQUENCE: 423
ctcagagagg ttgaaagatt tgcctacgaa agggacagtg atgaagctaa gctctagatc   60
     caggatgtct gacttcaaat tgaaactccc aaagtaatga gtttggaagg gtgggggtgtg  120
     gcctttccag gatgggggtc ttttctgctc ccagcggata gtgaaacccc tgtctgcacc  180
     tggttgggcg tgttgctttc ccaaaggttt ttttttttagg tccgtcgctg tcttgtggat  240
     taggcattat tatctttact ttgtctccaa ataacctgga gaatgcgagag agtagtgacc  300
     agctcaggc  cacagtgcga tgaggaccat cttctcacct ctctaaatgc aggaagaaac  360
     gcagagtaac gtggaagtgg tccacaccta ccgccagcac attgtgaatg acatgaaccc  420
     cggcaacctg cacctgttca tcaatgccta caacaggtat tgggatgtag ttcagccaca  480
     tcattgctat ttatgaggtg tcttctgtag atccgaaatg tgggacagat gagagggaga  540
     gtataaaatg agcggaagag gcaggctctg agtttgagca aatagattaa taggacaggt  600
     gtccccagga aggacacctg gcctgtaagc tggttcctgg cattcagctc gccttgcagg  660
     gatctgaaca aacactccag accactgggg gtgcagacgt gagagggacg cagtcgcaca  720
     ctcagagggt tgagagtaaa tatgtgtgcc cgctgctgac cttcacgaaa ggccaaatgt  780
     aagaagagct aagtgagaga gcagcaaagc actcctggag gccggggata atccaggcag  840
     gcttctggga gtttgtcatt ccaaggataa ggaggacctg aacatggcct ttgcctaagg  900
     cgtggccctc tcaaccagca ctaggtgctt atctgagct  cagctagggg aggagacagc  960
     tcagggccat tggtgtcagc cagagactct gtaatcttcc agggagctcg ctcaacctgc 1020
     tgagctcgct ctgccacgca c                                           1041

<210> SEQ ID NO 424
<211> LENGTH: 1288
<212> TYPE: DNA
<213> ORGANISM: Homo sapiens

<400> SEQUENCE: 424
ctaagaactg agacttgtga cacaaggcca acgacctaag attagcccag ggttgtagct   60
     ggaagaccta caacccaagg atggaaggcc cctgtcacaa agcctaccta gatggataga  120
```

-continued

```
      ggacccaagc gaaaaaggta tctcaagact aacggccgga atctggaggc ccatgaccca   180
      gaacccagga aggatagaag cttgaagacc tggggaaatc ccaagatgag aaccctaaac   240
      cctacctctt ttctattgtt tacacttctt actcttagat atttccagtt ctcctgttta   300
      tctttaagcc tgattctttt gagatgtact ttttgatgtt gccggttacc tttagattga   360
      cagtattatg cctgggccag tcttgagcca gctttaaatc acagcttttt cctatttgtt   420
      aggctatagt gttttgtaaa cttctgtttc tattcacatc ttctccactt gagagagaca   480
      ccaaaatcca gtcagtatct aatctggctt ttgttaactt ccctcaggag cagacattca   540
      tataggtgat actgtatttc agtcctttct tttgacccca gaagccctag actgagaaga   600
      taaatggtc aggttgttgg ggaaaaaaaa gtgccaggct ctctagagaa aaatgtgaag    660
      agatgctcca ggccaatgag aagaattaga caagaaatac acagatgtgc cagacttctg   720
      agaagcacct gccagcaaca gcttccttct ttgagcttag tccatccctc atgaaaaatg   780
      actgaccact gctgggcagc aggagggatg atgaccaact aattcccaaa ccccagtctc   840
      attggtacca gccttgggga accacctaca cttgagccac aattggtttt gaagtgcatt   900
      tacaagtttc tggcatcact accactactg attaaacaag aataagagaa catttatca    960
      tcatctgctt tattcacata aatgaagttg tgatgaataa atctgctttt atgcagacac  1020
      aaggaattaa gtggcttcgt cattgtcctt ctacctcaaa gataatttat tccaaaagct  1080
      aagataaatg gaagactctt gaacttgtga actgatgtga aatgcagaat ctcttttgag  1140
      tctttgctgt ttggaagatt gaaaaatatt gttcagcatg ggtgaccacc agaaagtaat  1200
      cttaagccat ctagatgtca caattgaaac aaactgggga gttggttgct attgtaaaat  1260
      aaaatatact gttttgaaaa aaaaaaac                                     1288
```

<210> SEQ ID NO 425
<211> LENGTH: 446
<212> TYPE: DNA
<213> ORGANISM: Homo sapiens

<400> SEQUENCE: 425

```
      ccactaaag ggtgcctctg ccaactggtg gaatcatcgc cacttccagc accacgccaa     60
      gcctaacatc ttccacaagg atcccgatgt gaacatgctg cacgtgtttg ttctgggcga   120
      atggcagccc atcgagtacg gcaagaagaa gctgaaatac ctgccctaca atcaccagca   180
      cgaatacttc ttcctgattg ggccgccgct gctcatcccc atgtatttcc agtaccagat   240
      catcatgacc atgatcgtcc ataagaactg ggtggacctg gcctgggccg tcagctacta   300
      catccggttc ttcatcaccct acatccctttt ctacggcatc ctgggagccc tccttttcct   360
      caacttcatc aggttcctgg agagccactg gtttgtgtgg gtcacacaga tgaatcacat   420
      cgtcatggag attgaccagg aggacc                                        446
```

<210> SEQ ID NO 426
<211> LENGTH: 874
<212> TYPE: DNA
<213> ORGANISM: Homo sapiens

<400> SEQUENCE: 426

```
      tttttttttt tttttttttt tttttcaat taaagatttg atttattcaa gtatgtgaaa     60
      acattctaca atggaaactt ttattaaatg ctgcatgtac tgtgctatgg accacgcaca   120
      tacagccatg ctgtttcaga agacttgaaa tgccattgat agtttaaaaa ctctacaccc   180
      gatggagaat cgaggaagac aatttaatgt ttcatctgaa tccagaggtg catcaaatta   240
      aatgacagct ccacttggca aataatagct gttacttgat ggtatccaag aagaaatggt   300
      tggtgatgga taaattcaga atgcttccc caaggtgggg tggtttttaa aaagttttca   360
      ggtcacaacc cttgcagaaa acactgatgc ccaacacact gattcgcggt ccaggaaaca   420
      cgggtcttcc aagttccaag gggctgggt tccccaacga tcaagttcct gtgctgtaat    480
      caagagggtc ctttggactg gatagggagc acttgggagc tgtacaccat cagtcataat   540
      ggatggcagt gtaaagatg atccaaatga cctgagatgc tcctgaggag tggtgcacca    600
      gacccaggag tgccactgta gggctgcttc tttgctttag tcatcacaca cacacacagc   660
      tccagagcag caatggcctt tcctgtaaca ggaaaagaac ctcctgctat tcccaagaac   720
      cctcgtaatg gcaaaactcc ccaaatgaca cccaggacca cagcaatgat ctgtcggaac   780
      cagtagatca catctaaaaa ttcatcctta tcctcccagg ccgcgtcgct ccgcagcacc   840
      ttactccaga cggagacttt gagggccccg ttgg                               874
```

<210> SEQ ID NO 427
<211> LENGTH: 638
<212> TYPE: DNA
<213> ORGANISM: Homo sapiens

<400> SEQUENCE: 427

```
      acttgtaatt agcacttggt gaaagctgga aggaagataa ataacactaa actatgctat     60
      ttgatttttc ttccttgaaag agtaaggttt acctgttaca ttttcaagtt aattcatgta   120
      aaaaatgata gtgattttga tgtaattta tctcttgtttg aatctgtcat tcaaaggcca   180
      ataatttaag ttgctatcag ctgatattag tagctttgca accctgatag agtaaataaa   240
      ttttatgggc gggtgccaaa tactgctgtg aatctatttg tatagtatcc atgaatgaat   300
      ttatggaaat agatatttgt gcagctcaat ttatgcagag attaaatgac atcataatac   360
      tggatgaaaa cttgcataga attctgatta aatagtgggt ctgttttcaca tgtgcagttt   420
      gaagtattta aataaccact ccttttcacag tttattttct tctcaagcgt tttcaagatc   480
      tagcatgtgg attttaaaag atttgccctc attaacaaga ataacattta aaggagattg   540
```

```
                                         -continued tttcaaaata tttttgcaaa ttgagataag gacagaaaga ttgagaaaca ttgtatattt   600
    tgcaaaaaca agatgtttgt agctgtttca gagagagt                           638

<210> SEQ ID NO 428
<211> LENGTH: 535
<212> TYPE: DNA
<213> ORGANISM: Homo sapiens

<400> SEQUENCE: 428
acaagatgat tcttcctcct caatttgaca gatcaaagaa gtatcccttg ctaattcaag    60
    tgtatggtgg tccctgcagt cagagtgtaa ggtctgtatt tgctgttaat tggatatctt   120
    atcttgcaag taaggaaggg atggtcattg cctggtggaa tggtcgagga acagctttcc   180
    aaggtgacaa actcctctat gcagtgtatc gaaagctggg tgtttatgaa gttgaagacc   240
    agattacagc tgtcagaaaa ttcatagaaa tgggtttcat tgatgaaaaa agaatagcca   300
    tatggggctg gtcctatgga ggatacgttt catcactggc ccttgcatct ggaactggtc   360
    ttttcaaatg tggtatagca gtggctccag tctccagctg gaatattac gcgtctgtct    420
    acacagagag attcatgggt ctcccaacaa aggatgataa tcttgagcac tataagaatt   480
    caactgtgat ggcaagagca gaatatttca gaaatgtaga ctatcttctc atcca         535

<210> SEQ ID NO 429
<211> LENGTH: 675
<212> TYPE: DNA
<213> ORGANISM: Homo sapiens

<400> SEQUENCE: 429
actattttca accctgagca ttaacactgc ataccaaggg ggggtgggtc aagaagctgg    60
    ttagatcgaa gcacaagcac aagccactga tattctctat gtgatcaggt ttttacaaaa   120
    aaatacatag ttttcaataa ataatgctta attttacaac tttgatacag caatgtcata   180
    caccgtttca acacactaca ctctgcatgc tagatagtct acgagaagac gaaactttgc   240
    catgcatttt ctttcccccc tagtgctatc aaacacttca tcctccagcg cactgcctca   300
    ggtagcttta ccttctctct gtttcacagc aataggccgt gcgctggcat gcaaactcta   360
    aaaaaggtcc cccccacaaa ccactcagac ttctacacaa aagggttttt cagcttttct   420
    gctcccaaac ctggagtggc taagaaagta agtttcatgt ggccttggaa aatacacact   480
    tgttaacagt gtcatgctga aaactgctct aaaacatcag gtggttctgt cctggtggcc   540
    gtcacgaagc attatgggat gccataacca ctaggagtcc caaaccggaa aaaataggcc   600
    tccgttttaa aacagtcaat tcaaaaaagg tgtcacagaa caaatgcaaa agactcttaa   660
    acccacaaca tatgt                                                     675

<210> SEQ ID NO 430
<211> LENGTH: 434
<212> TYPE: DNA
<213> ORGANISM: Homo sapiens

<400> SEQUENCE: 430
acctctgcca gaagtccagc gagaggacct cacagtagag cacaggccac tccgggagtg    60
    catcagaaga ttcatcctca tggaggaaga aggcttcaaa cgtgaatggg taggagaagt   120
    gagccacctt gtccattgcc agggacttgg tggtgcaggt ctgtgttact cctgagagct   180
    gctggaatgc tgggcttgac cagtgagcag ttggcaattc tacaaagaag tggacgtaga   240
    gattgtcata ctcatagcct tgggctgaaa cgacctctcc atttacaaag agccggaggg   300
    cacctgggac agtcatctca aagtcggtgc ctacgaggct gctgagatac tccttgtgcc   360
    ggccataaag atccttgaac actcgccgtt cccgctcctc ctcctccggc tgtgcgtggg   420
    gggaaacatt gtcg                                                      434

<210> SEQ ID NO 431
<211> LENGTH: 581
<212> TYPE: DNA
<213> ORGANISM: Homo sapiens

<400> SEQUENCE: 431
acacaagcct ccagcccgac ccagcggcct aatgaaactc tggcaaccta tcctgggcgt    60
    ggccacgagt atccagctcc aagcccaagt gaggcgggga gtcaacttcc ccatgattgc   120
    caagtgacca agaccagaag cagggacgat taggctagtt ctgcggcaag gtgaactgga   180
    gaccctgtct ctgccctcct tccctggcct gtcccacaga catcccgttg tttaacccac   240
    tgcctttgca aggacctgct ctgtccactc caaatcaaag gatacttgca tccttcttac   300
    acagactccc atctctctgc tcatagtggt cccaggctgc ccgagaaaaa gaaacttggg   360
    tcagtagaag gctcattagt gtgaaggagt gagaggccag gccttcctgt gacataatgc   420
    ttctatgctt gtttcctaaa cacttggtcc acacacaata cctgggcagg aagagagaac   480
    caagcaccac tggatggctc tggagccagg ggacttctat gcacatacaa ccaacatcac   540
    cccactctgc tcatctgtgc ctccaccctg aacagcagag t                        581
```

```
<210> SEQ ID NO 432
<211> LENGTH: 532
<212> TYPE: DNA
<213> ORGANISM: Homo sapiens

<400> SEQUENCE: 432
actccaactc aagtttacaa gttacacctt tgccacagcc ttggctaaat cttgaactag   60
    tgcagaattc agctgtggta gagtgctgat cttagcatgc ttcgatgtgg catacttgtt  120
    cttgacagtc atgtgctttg taagtccttg atttaccatg actacattct tagccaggtg  180
    ctgcataact ggaagaagag attcttcagt atatgacagg taatgttgta gagttggtgt  240
    ccattcacca ttatccagaa ttttcagtgc taagcaaaaa gtcctgctg caatttgaga  300
    aggaggaaag tgcaccatgt catagtccaa catagttagt tccatcaggt atttggccaa  360
    agtatgttgc tcgacatcaa cctctccaat cttagatgct ctccgaagga agtgcaaagg  420
    tagaggccga cccagaccaa agtttaaagc tcttagaatc ttcatttcca tctgtctgat  480
    ttggtgctta gtataagtgt tgtcagtcac aaaagcaaag tcaccaattt ct            532

<210> SEQ ID NO 433
<211> LENGTH: 531
<212> TYPE: DNA
<213> ORGANISM: Homo sapiens

<400> SEQUENCE: 433
acttggtttt acagctcctt tgaaaactct gtgtttggaa tatctctaaa aacatagaaa   60
    acactacagt ggtttagaaa ttactaattt tacttctaag tcattcataa accttgtcta  120
    tgaaatgact tcttaaatat ttagttgata gactgctaca ggtaataggg acttagcaag  180
    ctctttttata tgctaaagga gcatctatca gattaagtta gaacatttgc tgtcagccac  240
    atattgagat gacactaggt gcaatagcag ggatagattt tgttggtgag tagtctcatg  300
    ccttgagatc tgtggtggtc ttcaaaatgg tggccagcca gatcaaggat gtagtatctc  360
    atagttccca ggtgatattt ttcttattag aaaaatatta taactcattt gttgtttgac  420
    acttatagat tgaaatttcc taatttattc taaattttaa gtggttcttt ggttccagtg  480
    ctttatgttg ttgttgtttt tggatggtgt tacatattat atgttctaga a             531

<210> SEQ ID NO 434
<211> LENGTH: 530
<212> TYPE: DNA
<213> ORGANISM: Homo sapiens

<400> SEQUENCE: 434
acaagagaaa acccctaaaa aaaggatggc tttagatgac aagctctacc agagagactt   60
    agaagttgca ctagctttat cagtgaagga acttccaaca gtcaccacta atgtgcagaa  120
    ctctcaagat aaaagcattg aaaaacattg cagtagtaaa atagaaacaa tgaataagtc  180
    tcctcatatc tctaattgca gtgtagccag tgattattta gatttggata agattactgt  240
    ggaagatgat gttggtggtg ttcaagggaa aagaaagca gcatctaaag ctgcagcaca  300
    gcagaggaag attcttctgg aaggcagtga tggtgatagt gctaatgaca ctgaaccaga  360
    cttttgcacct ggtgaagatt ctgaggatga ttctgatttt tgtgagagtg aggataatga  420
    cgaagacttc tctatgagaa aaagtaaagt taaagaaatt aaaaagaaag aagtgaaggt  480
    aaaatcccca gtagaaaaga aagagaagaa atctaaatcc aaatgtaatg                 530

<210> SEQ ID NO 435
<211> LENGTH: 677
<212> TYPE: DNA
<213> ORGANISM: Homo sapiens

<400> SEQUENCE: 435
accttatgat ctaattaata gatattagaa acagtagaaa gacaagttac acgtcaatgc   60
    ccaatgacta gagtcaacat taaagagttg taatttaagt aatccaaact gacatctaat  120
    tccaaaatca tttataaaat gtatttggct ttggaatcca caggacttca aacaagcaaa  180
    gtttcactgc agatagtcac aaagatgcag atacactgaa atacttaaga gccttattaa  240
    tgattttttgt tattttggat cttctgttt tttcttatta tggtccgaag cctccttaat  300
    accaatttat cagacagaag catgtcatct tgttgttcaa gataatccag taaattttca  360
    gtccattcaa gtgccgcttt atggctaata cgcttctctg gattcagttc tgttttttcta  420
    ctcttactgg aaggcttttg ctcagcagcc ttggtctggt cctcagcact ttcactgtca  480
    gtcagcacct gacagcttga gtcactgctc cgagagtcga accactgatc aatattctca  540
    atgtcaacat gttcacattc ttctgtgttc tgtaaaactg ttgctaaatt agctgctaaa  600
    atggctcctt catcaatgtt catacctgaa ttctcttcat tgccagggaa aagtttttc   660
    catgctttgg ttatggt                                                     677

<210> SEQ ID NO 436
<211> LENGTH: 573
<212> TYPE: DNA
<213> ORGANISM: Homo sapiens
```

```
<400> SEQUENCE: 436
acctcttagg gtgggagaaa tggtgaagag ttgttcctac aacttgctaa cctagtggac    60
      agggtagtag attagcatca tccggataga tgtgaagagg acggctgttt ggataataat   120
      taaggataaa atttggccag ttgacagatt ctgtttccag cagttttac agcaacagtg   180
      gagtgcttca gtattgtgtt cctgtaaatt taattttgat ccgcaatcat ttgtataca   240
      atgctgtttg aagttttgtc ctattggaaa agtcttgtgt tgcaggggtg cagttaagat   300
      ctttgtgatg aggaatggga tgggctaatt ttttgccgtt ttccttggaat tggggcatg   360
      gcaaatacag tagggtagtt tagttcttta cacagaacat gataaactac acctgttgat   420
      gtcaccgtct gtcaatgaat attatagaag gtatgaaggt gtaattacca taataacaaa   480
      acaccctgtc tttagggctg accttcgtc ctttgacctc ctcagcctcc attcccatct   540
      tcgctcagac tgcaagtatg tttgtattaa tgt                                573

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: 605
<223> OTHER INFORMATION: n = A,T,C or G

<400> SEQUENCE: 437
acaattggta tccatatctt gttgaaattg taatgggaaa acaatatatt tcaatctcta    60
      tgtagatagt gggtttttgt tttcataata tattctttta gtttactgta tgagttttgc   120
      aggactgcat aatagatcac cacaatcata acatcttagg accacagaca tttatgagat   180
      catggcttct gtgggttaga agtatgctca tgtcttaact gggtcctctg ctcagtctta   240
      tctggctgca atcaaggtgt cagctgggct gaattttcat ttggaatctt gactgggaaa   300
      gagtctgctt ccaaggtcat gaagtttgct ggcaaaatgt atgttttat gacagtatga   360
      ctgaaatccc aagctatctc ctgactttta gctgggtaat ctcaggccct aaatgttgcc   420
      tacagttcct agaggctggt cacagttctt agccatgtgg atttcctcaa catggctgct   480
      tgcttcatca agtcagcaag aatagcctgt catatcagtg tatatcaggc tcactcagga   540
      taatttccct actgatgagc caaaactaca ctgattttag agcttaacta catctgcaaa   600
      attcngttca ccagaggcaa gtcatattca gggaaggaga agtgt                  645

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat    60
      atttctgatg aaaatgaagg aaaagaaatg tgtgttctgc gaatgactcg agctagacgt   120
      tcccaggtag aacagcagca gctcatcact gttgaaaagg ctttggcaat tctttctcag   180
      cctacaccct cacttgttgt ggatcatgag cgattaaaaa atcttttgaa gactgttgtt   240
      aaaaaaagtc aaaactacaa catatttcag ttggaaaatt tgtatgcagt aatcagccaa   300
      tgtatttatc ggcatcgcaa ggaccatgat aaaacatcac ttattcagaa aatggagcaa   360
      gaggtagaaa acttcagttg ttccagatga tgatgtcatg gtatcgagta ttctttatat   420
      tcagttccta tttaagtcat ttttgtcatg tccgcctaat tgatgtagta tgaaaccctg   480
      catct                                                              485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc    60
      aggttcaaca gtatggctcc aaatgatgaa atttcattct gattttctgg ctgaagacta   120
      ttctgtttgt gtatgtccac cacagttact ttatcccttc atctgtggat gggcagaatg   180
      aaacatatat ggaaatgttc tgtgcaataa aaacagcagt ggtaacacag atgtaggctc   240
      tgagtgtctc actgagagct gaagtccaca gatatgcaac aaagcctttg tctccctgat   300
      gttttttgcct cctgctggtc atgtgctttc acacatcaag agaggacatt taacatttga   360
      gccacagtgt catttgctgt tgtctgatgg ttggttggca ggaatttga actggagatg   420
      aactttatta tccaggacgc tgagagtata acatgcatga cagagcttt agagcactgt   480
      gatgtaacat gtcaagcaga aatagggagc atgtttacag ccattctatg aaa          533

<210> SEQ ID NO 440
<211> LENGTH: 341
<212> TYPE: DNA
<213> ORGANISM: Homo sapiens
```

```
<400> SEQUENCE: 440
catggggtag ggggtcggg gattcattga attgtggttg gcaggagcaa gccctgctca   60
    cactctcaca ctcgcaccca gaattgtcaa agatacagat tgtaaaaatc tacgatccct  120
    cagtctcact cacaaaaaat aaaatctcat gtccccaacg aacccagagt cagacgacag  180
    ctggagcatt ggcagggaca gtcagaaagg agacaagtga aaacggtcag atggacacag  240
    gcggaggaga aaagacagag ggagagagac catcgggaac aatcagaggg gccgagacga  300
    tcagaaaagg gtcagcccga gacaggctga gccagagttt c                      341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: 53, 84, 132, 138, 148
<223> OTHER INFORMATION: n = A,T,C or G

<400> SEQUENCE: 441
aagtttgggg ataatttatt atgcagcaag agataataca caggacttct canagcactt   60
    aatatgttaa tataaatctc caanaaaaaa gatatacaat gaaacattcc tcttagttat  120
    ctggccaagg anactttntt tttttganaa tattcttcaa aaagctgatc taatgatatg  180
    gctctggtcc tacaattcca tgtaacttct aaccttgatt ttatctcatg agcaaatcat  240
    ttatccttcc agaacctcaa cttttcccct ttacaaagta gaaataaacc atctgccttt  300
    acataaatca ttaatacagc cctggatggg cagattctga gctattttg gctgggggt   360
    gggaaatagc ctgtggaggt cctaaaaaga tctacgggggc tcgagatggt tctctgcaag  420
    gtagcaggtg ggctcaggc ccatttcagt cttgttccc caggccattt ccacaaaatg  480
    gtgagaaata gtgtcttctt ttagcttgct cataactcaa agatgggggg catggacctg  540
    ggccttttcta ggctagggca tgaacctcct cc                                572

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: 34, 67
<223> OTHER INFORMATION: n = A,T,C or G

<400> SEQUENCE: 442
tcccagctgc actgcttaca cgtcttcctt cgtnttcacc taccccgagg ctgactcctt   60
    ccccagntgt gcagctgccc accgcaaggg cagcagcagc aatgagcctt cctctgactc  120
    gctcagctca cccacgctgc tggccctgtg aggggcagg gaaggggagg cagccggcac  180
    ccacaagtgc cactgcccga gctggtgcat tacagagagg agaaacacat cttccctaga  240
    gggttcctgt agacctaggg aggaccttat ctgtgcgtga aacacaccag gctgtgggcc  300
    tcaaggactt gaaagcatcc atgtgtggac tcaagtcctt acctcttccg gagatgtagc  360
    aaaacgcatg gagtgtgta                                                379

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: 444
<223> OTHER INFORMATION: n = A,T,C or G

<400> SEQUENCE: 443
acatgccccc aaaggctcgc ttcattgcta cgattctcta cttaaatcca cattcacagc   60
    tattgcctca gaccctctgg aggaggggcc aggggttagc tggctttgaa tagcatgtag  120
    agcacaggca gtgtggccac aaatgtcaca caggtgacca gggtgctata gatggtgttc  180
    ctgttgactt gggcttctag tctctgctcc gtgtctgaca gtgccaagat catgctcccc  240
    tgctccagca agaagctggg catagccccg tctgctggtt ccaccaggcc tgggtgtgct  300
    gcagacttta caagctgaac caccccagcc atttggctac aagtcttttc taggccatca  360
    agctgctctc gtaagccttc tagacatgaa tggacttgcc tggaatgact aagctgctct  420
    ttcaaggcag ctgaaaggac atcnacatct ctgtctctgg tcggggact acctgcctgt  480
    gacccagagt cctgccctgg cccagcagca t                                  511

<210> SEQ ID NO 444
<211> LENGTH: 612
<212> TYPE: DNA
```

```
<213> ORGANISM: Homo sapiens
<220> FEATURE:
<221> NAME/KEY: misc_feature
<222> LOCATION: 547
<223> OTHER INFORMATION: n = A,T,C or G

<400> SEQUENCE: 444
acaggaagaa ttctacagtt aatctatcac agtgttccag caaagcatat gttgaaaact    60
     acagttttca atctaacatc taaattttaa aaagtagcat ttcagcaaca aacaagctca   120
     gagaggctca tggcaaaagt gaaataacag aactattgct cagatgtctg caaagtcaag   180
     ctgctgccct cagctccgcc cacttgaagg cttaggcaga cacgtaaggt ggcggtggct   240
     ccttggcagc accattcaca gtggcatcat catacggagg tagcagcacc gtagtgtcat   300
     tgctggtaac ataaaccagg acatcagagg agttcctacc attgatgtat cggtagcagt   360
     tccaaacaca gctaatcaag taacccttaa aagtcaagat aatgctaata acagaagaa   420
     taataaggac caaacaggta ggattcactg acatgacata atctctgtag ggaaaattag   480
     gaggcagttg ccgtatgtat tcctgaatgg agtttggata aataagcaca gtgattgcaa   540
     ccaacanctt cagggcaaag tcaaagatct ggtaacagaa gaatgggatg atccaggctg   600
     cgcgttgctt gt                                                       612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: 643, 676
<223> OTHER INFORMATION: n = A,T,C or G

<400> SEQUENCE: 445
accatcctgt tccaacagag ccattgccta ttcctaaatt gaatctgact gggtgtgccc    60
     ctcctcggaa cacaacagta gaccttaata gtggaaacat cgatgtgcct cccaacatga   120
     caagctgggc cagctttcat aatggtgtgg ctgctggcct gaagatagct cctgcctccc   180
     agatcgactc agcttggatt gtttacaata agcccaagca tgctgagttg gccaatgagt   240
     atgctggctt tctcatggct ctgggtttga atgggcacct taccaagctg gcgactctca   300
     atatccatga ctacttgacc aagggccatg aaatgacaag cattggactg ctacttggtg   360
     tttctgctgc aaaactaggc accatggata tgtctattac tcggcttgtt agcattcgca   420
     ttcctgctct cttaccccca acgtccacag agttggatgt tcctcacaat gtccaagtgg   480
     ctgcagtggt tggcattggc ctttgtatatc aagggacagc tcacagacat actgcagaag   540
     tcctgttggc tgagatagga cggcctcctg gtcctgaaat ggaatactgc actgacagag   600
     agtcatactc cttagctgct ggcttggccc tgggcatggt ctncttgggg catggcagca   660
     atttgatagg tatgtntgat ctcaatgtgc ctgagcagct ctatcagt                708

<210> SEQ ID NO 446
<211> LENGTH: 612
<212> TYPE: DNA
<213> ORGANISM: Homo sapiens

<400> SEQUENCE: 446
acaagcaacg cgcagcctgg atcatcccat tcttctgtta ccagatcttt gactttgccc    60
     tgaacatgtt ggttgcaatc actgtgctta tttatccaaa ctccattcag gaatacatac   120
     ggcaactgcc tcctaatttt ccctacagag atgatgtcat gtcagtgaat cctacctgtt   180
     tggtccttat tattcttctg tttattagca ttatcttgac ttttaagggt tacttgatta   240
     gctgtgtttg gaactgctac cgatacatca atggtaggaa ctcctctgat gtcctggttt   300
     atgttaccag caatgacact acggtgctgc tacccccgta tgatgatgcc actgtgaatg   360
     gtgctgccaa ggagccaccg ccaccttacg tgtctgccta agccttcaag tgggcggagc   420
     tgagggcagc agcttgactt tgcagacatc tgagcaatag ttctgttatt tcactttgc   480
     catgagcctc tctgagcttg tttgttgctg aaatgctact ttttaaaatt tagatgttag   540
     attgaaaact gtagttttca acatatgctt tgctggaaca ctgtgataga ttaactgtag   600
     aattcttcct gt                                                       612

<210> SEQ ID NO 447
<211> LENGTH: 642
<212> TYPE: DNA
<213> ORGANISM: Homo sapiens

<400> SEQUENCE: 447
actgaaagaa ttaaagtcag aagtcttccc aaaacaaaaa gaactgccca cagagaaaat    60
     cctttctgat actttctcatt gctaaaataa aacaggcggg aaatgtggaa aagaaattca   120
     acaaaataat gtagcaccag aagaacaagt cctagatgat tcaagttcaa aaggtaagct   180
     ccagcaatgt ggaagaggta aagaccaatg tagacaagct gacgaggaat atcttctttt   240
     ttggttttct ggaagtagag ttcaggaaaa gcatgaagcc agtaagccag ctgtgatatg   300
     tagaaaaact tcatttgaaa tgtcatcagg ttatggggat aagccctcca taagatagtt   360
```

```
                gggtctgaga tgtagttttc agagatgaga atgaatgtgc cccaaacaca ggcaaaaagg   420
                tagaacgcac taagctgacc agattcatta aacttgctgt gttttgtttt ggagaagtgc   480
                attcgcctgt taattttatc caacatatac tcttgaatta cggcatgaat aattatcgcc   540
                actagcatgt agaagaaaac agtagccaaa tctttgatgc catagtaata aagggacact   600
                gattcagtag cttgttcttc tgttgctggg agggtgacat tg                         642

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 448
accagaagac cttagaaaaa ggaggaaagg aggagaggca gataatttgg atgaattcct    60
                caaagngttt gaaaatccag aggttcctag agaggaccag caacagcagc atcagcagcg   120
                tgatgttatc gatgagccca ttattgaaga gccaagccgc ctccaggagt cagtgatgga   180
                ggccagcaga acaaacatag atgagtcagc tatgcctcca ccaccacctc agggagttaa   240
                gcgaaaagct ggacaaattg acccagagcc tgtgatgcct cctcagcagg tagagcagat   300
                ggaaatacca cctgtagagc ttcccccaga agaacctcca aatatctgtc agctaatacc   360
                agagttagaa cttctgccag aaaagagaa ggag                                 394

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 449
acaaaaaaca caaggaatac aacccaatag aaaatagtcc tgggaatgtg gtcagaagca    60
                aaggcntgag tgtctttctc aaccgtgcaa aagccgtgtt cttcccggga aaccaggaaa   120
                aggatccgct actcaaaaac caagaattta aaggagtttc ttaaatttcg accttgtttc   180
                tgaagctcac ttttcagtgc cattgatgtg agatgtgctg gagtggctat taacctttt    240
                ttcctaaaga ttattgttaa atagatattg tggttttgggg aagttgaatt ttttataggt   300
                taaatgtcat tttagagatg gggagaggga ttatactgca ggcagcttca gccatgttgt   360
                gaaactgata aaagcaactt agcaaggctt cttttcatta ttttttatgt ttcactttata   420
                aagtcttagg taactagtag gatagaaaca ctgtgtcccg agagtaagga gagaagctac   480
                tattgattag agcc                                                       494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct    60
                tcatgactga ggttaactta aaacaaaaat ggtaggaaag ctttcctatg cttcgggtaa   120
                gagacaaatt tgcttttgta gaattggtgg ctgagaaagg cagacagggc ctgattaaag   180
                aagacatttg tcaccactag ccaccaagtt aagttgtgga acccaaaggt gacggccatg   240
                gaaacgtaga tcatcagctc tgctaagtag ttaggggaag aaacatattc aaaccagtct   300
                ccaaatggga tcctgtggtt acagtgaatg gccactcctg ctttattttt cctgagattg   360
                ccgagaataa catggcactt atactgatgg gcagatgacc agatgaacat catcatccca   420
                agaatatgga accaccgtgc ttgcatcaat agatttttcc ctgttatgta ggcattcctg   480
                ccatccattg gcacttggct cagcacagtt aggccaacaa ggacataata gacaagtcca   540
                aaacagt                                                               547

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: 8, 9, 19, 41
<223> OTHER INFORMATION: n = A,T,C or G

<400> SEQUENCE: 451
```

```
actacttnnt ggttaaaang ccactggtag agtcatctga ntgtaaacaa tgtccctgca    60
ctgctggaaa aatccactgg ctcccaagaa aagaaaatgg tctgaagcct ctgttgtggc   120
tctcacaact catctttccc taagtcatca agctccacat cactgaggtc aatgtcatcc   180
tccacgggaa gctcgccatc cctgccgtcc caaggctctc tctcaacgat ggtagggaaa   240
gccccgcctc ctacaggtgc cgtggagcca cgcccaaaag agagctccct gagaaactcg   300
ttgatgcctt gctcactgaa ggagcctttt agcagagcaa atttcatctt gcgtgcattg   360
atggcggcca tggcggggta ccca                                         384
```

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: 291, 341, 368
<223> OTHER INFORMATION: n = A,T,C or G

<400> SEQUENCE: 452

```
actctaaagt tgccactctc acagggtca gtgatacca ctgaacctgg caggaacagt    60
cctgcagcca gaatctgcaa gcagcgcctg tatgcaacgt ttagggccaa aggctgtctg   120
gtgggttgt tcatcacagc ataatggcct agtaggtcaa ggatccaggg tgtgagggc   180
tcaaagccag gaaaacgaat cctcaagtcc ttcagtagtc tgatgagaac tttaactgtg   240
gactgagaag cattttcctc gaaccagcgg gcatgtcgga tggctgctaa ngcactctgc   300
aatactttga tatccaaatg gagttctgga tccagttttc naagattggg tggcactgtt   360
gtaatganaa tcttcactgt a                                            381
```

<210> SEQ ID NO 453
<211> LENGTH: 455
<212> TYPE: DNA
<213> ORGANISM: Homo sapiens

<400> SEQUENCE: 453

```
actgtgctaa acagcctata gccaagtttt aaagagttac aggaacaact gctacacatt    60
caaagaacag gcattcactg cagcctcctg atttgacctg atgggaggga caggagaatg   120
agtcactctg ccaccacttt tcctgccttg gatttgtaga ggatttgttt tgctctaatt   180
tgttttcct atatctgccc tactaaggta cacagtctgg gcactttgaa aatgttaaag   240
tttttaacgt ttgactgaca gaagcagcac ttaaaggctt catgaatcta ttttccaaaa   300
aaagtatgct ttcagtaaaa cattttacca ttttatctaa ctatgcactg acatttttgt   360
tcttcctgaa aaggggattt atgctaacac tgtattttta atgtaaaaat atacgtgtag   420
agatatttta acttcctgag tgacttatac ctcaa                             455
```

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: 9
<223> OTHER INFORMATION: n = A,T,C or G

<400> SEQUENCE: 454

```
acagagcanc tttacaagtt gtcacatttc tttataaatt tttttaaagc tacagtttaa    60
tacaaaatga attgcggttt tattacatta ataaccttc acctcagggt tttatgaaga   120
ggaaagggtt ttatgcaaaa gaaagtgcta caattcctaa tcatttaga cactttagga   180
ggggtgaag ttgtatgata aagcagatat tttaattatt tgttatcttt ttgtattgca   240
agaaatttct tgctagtgaa tcaagaaaac atccagattg acagtctaaa atggctactg   300
gtattttagt taattcaaaa atgaaacttt tcagtgattc actttactaa cattctattt   360
gagaaggctt attggtaaag ttt                                          383
```

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: 10
<223> OTHER INFORMATION: n = A,T,C or G

<400> SEQUENCE: 455

```
actcctttan gacaaggaaa caggtatcag catgatggta gcagaaacct tatcaccaag    60
gtgcaggagc tgacttcttc caaagagttg tggttccggg cagcggtcat gccgtgccc   120
```

```
      attgctggag ggctgatttt agtgttgctt attatgttgg ccctgaggat gcttcgaagt    180
      gaaaataaga ggctgcagga tcagcggcaa cagatgctct cccgtttgca ctacagcttt    240
      cacggacacc attccaaaaa ggggcaggtt gcaaagttag acttggaatg catggtgccg    300
      gtcagtgggc acgagaactg ctgtctgacc tgtgataaaa tgagacaagc agacctcagc    360
      aacgataaga tcctctcgct tgt                                            383
```

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: 64
<223> OTHER INFORMATION: n = A,T,C or G

<400> SEQUENCE: 456

```
      acaaacattt tacaaaaaag aacattacca atatcagtgg cagtaagggc aagctgaaga    60
      atangtagac tgagtttccg ggcaatgtct gtcctcaaag acatccaaac tgcgttcagg   120
      cagctgaaac aggcttcttt cccagtgaca agcatatgtg gtcagtaata caaacgatgg   180
      taaatgaggc tactacatag gcccagttaa caaactcctc ttctcctcgg gtaggccatg   240
      atacaagtgg aactcatcaa ataatttaaa cccaagcgaa taacaacact atttcccatc   300
      taaactcatt taagccttca caatgtcgca atggattcag ttacttgcaa acgatcccgg   360
      gttgtcatac agatacttgt ttttacaca taacgctgtg ccatcccttc cttcactgcc    420
      ccagtcaggt ttcctgttgt tggaccgaaa ggggatacat tttagaaatg cttccctcaa   480
      gacagaagtg agaaagaaag gagaccctga ggccaggatc tattaaacct ggtgtgtgcg   540
      caa                                                                 543
```

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: 17
<223> OTHER INFORMATION: n = A,T,C or G

<400> SEQUENCE: 457

```
      actggtgcca atattgncat ggtgagctcc tctctaatgt cttccagggc accaatatct    60
      gcccatgtca cattagggac agtgacaaag cctttccttt ggcagaggg ttggactgag    120
      gatagagcaa caatgaaatc attcagttca atgcacagtc cttgcatctg ctcctctgag   180
      aggggatctt ggtctcttag caacccagc agcctttgta attcatcctg tgtttcagaa    240
      gtgggctcag ttcccagcct ttcctcctgg actccttag atggcaaatc ttccatttca    300
      ggattttct tctgctgttc ctgtagcttc attaagactc tattgactgc acacattgct   360
      gcctctcggc acagtgccat gagatcagca ccaacaaagc ctggagttag gtgtgctaag   420
      tgacagaaat caaaagcttg aggaagcctc agttttctgc acaatgtttg aagtattctt   480
      tccctggatg cttcatctgg gataccagtt gcatttctc ggtcgaacct tcccgcacgt    540
      ctca                                                                544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: 5, 23
<223> OTHER INFORMATION: n = A,T,C or G

<400> SEQUENCE: 458

```
      acctntaggc tcaacggcag aancttcacc acaaaagcga aatgggcaca ccacagggag    60
      aaaactggtt gtcctggatg tttgaaaagt tggtcgttgt catggtgtgt tacttcatcc   120
      tatctatcat taactccatg gcacaaagtt atgccaaacg aatccagcag cggttgaact   180
      cagaggagaa aactaaataa gtagagaaag ttttaaactg cagaaattgg agtggatggg   240
      ttctgcctta aattgggagg actccaagcc gggaaggaaa attccctttt ccaacctgta   300
      tcaattttta caactttttt cctgaaagca gtttagtcca tactttgcac tgacatactt   360
      tttccttctg tgctaaggta ag                                            382
```

<210> SEQ ID NO 459
<211> LENGTH: 168
<212> TYPE: DNA
<213> ORGANISM: Homo sapiens

<400> SEQUENCE: 459

-continued

```
     ctcgtactct agccaggcac gaaaccatga agtagcctga tccttcttag ccatcctggc  60
     cgccttagcg gtagtaactt tgtgttatga atcacatgaa agcatggaat cttatgaact 120
     taatcccttc attaacagga gaaatgcaaa taccttcata tccccta                168
```

<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: 4
<223> OTHER INFORMATION: n = A,T,C or G

<400> SEQUENCE: 460

```
     acanctgcta ccagggagcc gagagctgac tatcccagcc tcggctaatg tattctacgc  60
     catggatgga gcttcacacg atttcctcct gcggcagcgg cgaaggtcct ctactgctac 120
     acctggcgtc accagtggcc cgtctgcctc aggaactcct ccgagtgagg gaggaggggg 180
     ctcctttccc                                                        190
```

<210> SEQ ID NO 461
<211> LENGTH: 495
<212> TYPE: DNA
<213> ORGANISM: Homo sapiens

<400> SEQUENCE: 461

```
     acagacaggc ttctctgcta tcctccaggc agtgtaatag tcaaggaaaa gggcaacagt  60
     attggatcat tccttagaca ctaatcagct gggggaaagag ttcattggca aaagtgtcct 120
     cccaagaatg gtttacacca agcagagagg acatgtcact gaatgggggaa agggaaccca 180
     cgtatccaca gtcactgtaa gcatccagta ggcaggaaga tggctttggg cagtggctgg 240
     atgaaagcag atttgagata cccagctccg gaacgaggtc atcttctaca ggttcttcct 300
     tcactgagac aatgaattca gggtgatcat tctctgaggg gctgagaggt gcttcctcga 360
     ttttcactac cacattagct tggctctctg tctcagaggg tatctctaag actaggggct 420
     tggtatatat gtggtcaaaa cgaattagtt cattaatggc ttccagcttg gctgatgacg 480
     tccccactga cagag                                                  495
```

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: 68
<223> OTHER INFORMATION: n = A,T,C or G

<400> SEQUENCE: 462

```
     acactgaaac ataaatccgc aagtcaccac acatacaaca cccggcagga aaaaaacaaa  60
     aacagggngt ttacatgatc cctgtaacag ccatggtctc aaactcagat gcttcctcca 120
     tctgccaagt gtgttttgga tacagagcac atcgtggctt ctggggtcac actcagctta 180
     ggctgtgggt ccacagagca ctcatctggc tggctatgg tggtggtggc tctactcaag 240
     aagcaaagca gttaccagca cattcaaaca gtgtattgaa catcttttaa atatcaaagt 300
     gagaaacaag aaggcaacat aataatgtta tcagaaagat gttaggaagt aaggacagct 360
     gtgtaaagct tgaggctgaa aagtagcttg ccagcttcat ttctttggtt tcttgggtag 420
     tgggcgccgg aacagcaaga tgtgaggttc tggttcatgg atcatataat ggacccatcc 480
     ctgactctgc tga                                                    493
```

<210> SEQ ID NO 463
<211> LENGTH: 3681
<212> TYPE: DNA
<213> ORGANISM: Homo sapiens

<400> SEQUENCE: 463

```
     tccgagctga ttacagacac caaggaagat gctgtaaaga gtcagcagcc acagccctgg  60
     ctagctggcc ctgtgggcat ttattagtaa agttttaatg acaaaagctt tgagtcaaca 120
     cacccgtggg taattaacct ggtcatcccc accctgagag gccatcctgc ccatgggtga 180
     tcaaagaagg aacatctgca ggaacacctg atgaggctgc acccttggcg gaaagaacac 240
     ctgacacagc tgaaagcttg gtggaaaaaa cacctgatga ggctgcaccc ttggtggaaa 300
     gaacacctga cacggctgaa agcttggtgg aaaaaacacc tgatgaggct gcatccttgg 360
     tggagggaac atctgacaaa attcaatgtt tggagaaagc gacatctgga aagttcgaac 420
     agtcagcaga agaaacacct agggaaatta cgagtcctgc aaaagaaaca tctgagaaat 480
     ttacgtggcc agcaaaagga agacctagga agatcgcatg ggagaaaaaa gaagacacac 540
```

-continued

```
      ctagggaaat tatgagtccc gcaaaagaaa catctgagaa atttacgtgg gcagcaaaag   600
      gaagacctag gaagatcgca tgggagaaaa aagaaacacc tgtaaagact ggatgcgtgg   660
      caagagtaac atctaataaa actaaagttt tggaaaaagg aagatctaag atgattgcat   720
      gtcctacaaa agaatcatct acaaaagcaa gtgccaatga tcagaggttc ccatcagaat   780
      ccaaacaaga ggaagatgaa gaatattctt gtgattctcg gagtctcttt gagagttctg   840
      caaagattca agtgtgtata cctgagtcta tatatcaaaa agtaatggag ataaatagag   900
      aagtagaaga gcctcctaag aagccatctg ccttcaagcc tgccattgaa atgcaaaact   960
      ctgttccaaa taaagccttt gaattgaaga atgaacaaac attgagagca gatccgatgt  1020
      tcccaccaga atccaaacaa aaggactatg aagaaaattc ttgggattct gagagtctct  1080
      gtgagactgt ttcacagaag gatgtgtgtt tacccaaggc tacacatcaa aaagaaatag  1140
      ataaaataaa tggaaaatta gaagagtctc ctaataaaga tggtcttctg aaggctacct  1200
      gcggaatgaa agtttctatt ccaactaaag ccttagaatt gaaggacatg caaactttca  1260
      aagcagagcc tccggggaag ccatctgcct tcgagcctgc cactgaaatg caaaagtctg  1320
      tcccaaataa agccttggaa ttgaaaaatg aacaaacatt gagagcagat gagatactcc  1380
      catcagaatc caaacaaaag gactatgaag aaagttcttg ggattctgag agtctctgtg  1440
      agactgtttc acagaaggat gtgtgtttac ccaaggctrc rcatcaaaaa gaaatagata  1500
      aaataaatgg aaaattagaa gggtctcctg ttaaagatgg tcttctgaag gctaactgcg  1560
      gaatgaaagt ttctattcca actaaagcct tagaattgat ggacatgcaa actttcaaag  1620
      cagagcctcc cgagaagcca tctgccttcg agcctgccat tgaaatgcaa aagtctgttc  1680
      caaatcaaagc cttggaattg aagaatgaac aaacattgag agcatgatga atactcccat  1740
      cagaatccaa acaaaaggac tatgaagaaa gttcttggga ttctgagagt ctctgtgaga  1800
      ctgtttcaca gaaggatgtg tgtttaccca aggctrcrca tcaaaaagaa atagataaaa  1860
      taaatggaaa attagaagag tctcctgata tgatggtttt tctgaaggct ccctgcagaa  1920
      tgaaagtttc tattccaact aaagccttag aattgatgga catgcaaact ttcaaagcag  1980
      agcctcccga gaagcctcct gccttcgagc ctgccattga aatgcaaaag tctgttccaa  2040
      ataaagcctt ggaattgaag aatgaacaaa cattgagagc agatcagatg ttcccttcag  2100
      aatcaaaaca aaagaagtt gaagaaaatt cttgggattc tgagagtctc cgtgagactg  2160
      tttcacagaa ggatgtgtgt gtacccaagg ctacacatca aaagaaatg gataaaataa  2220
      gtggaaaatt agaagattca actagcctat caaaaatctt ggatacagtt cattcttgtg  2280
      aaagagcaag ggaacttcaa aaagatcact gtgaacaacg tacaggaaaa atggaacaaa  2340
      tgaaaaagaa gttttgtgta ctgaaaaaga aactgtcaga agcaaaagaa ataaaatcac  2400
      agttagagaa ccaaaagtt aaatgggaac aagagctctg cagtgtgagg tttctcacac  2460
      tcatgaaaat gaaaattatc tcttacatga aaattgcaat ttgaaaaagg aaattgccat  2520
      gctaaaactg gaaatagcca cactgaaaca ccaataccag gaaaaggaaa ataaatactt  2580
      tgaggacatt aagatttaa aagaaaagaa tgctgaactt cagatgaccc taaaactgaa  2640
      agaggaatca ttaactaaaa gggcatctca atatagtggg cagcttaaag ttctgatagc  2700
      tgagaacaca atgctcactt ctaaattgaa ggaaaaacaa gacaaagaaa tactagaggc  2760
      agaaattgaa tcacaccatc ctagactggc ttctgctgta caagaccatg atcaaattgt  2820
      gacatcaaga aaaagtcaag aacctgcttt ccacattgca ggagatgctt gtttgcaaag  2880
      aaaaatgaat gttgatgtga gtagtacgat atataacaat gaggtgctcc atcaaccact  2940
      ttctgaagct caaaggaaat ccaaaagcct aaaaattaat ctcaattatg cmggagatgc  3000
      tctaagagaa aatacattgg tttcagaaca tgcacaaaga gaccaacgtg aaacacagtg  3060
      tcaaatgaag gaagctgaac acatgtatca aaacgaacaa gataatgtga caaacacac  3120
      tgaacagcag gagtctctag atcagaaatt attcaacta caaagcaaaa atatgtggct  3180
      tcaacagcaa ttagttcatg cacataagaa agctgacaac aaaagcaaga taacaattga  3240
      tattcatttt cttgagagga aaatgcaaca tcatctccta aaagagaaaa atgaggagat  3300
      atttaattac aataaccatt taaaaaccg tatatatcaa tatgaaaaag agaaagcaga  3360
      aacagaaaac tcatgagaga caagcagtaa gaaacttctt ttggagaaac aacagaccag  3420
      atctttactc acaactcatg ctaggaggcc agtcctagca tcaccttatg ttgaaaatct  3480
      taccaatagt ctgtgtcaac agaatactta ttttagaaga aaaattcatg attcttcct  3540
      gaagcctaca gacataaaat aacagtgtga agaattactt gttcacgaat tgcataaagc  3600
      tgcacaggat tcccatctac cctgatgatg cagcagacat cattcaatcc aaccagaatc  3660
      tcgctctgtc actcaggctg g                                            3681
```

<210> SEQ ID NO 464
<211> LENGTH: 1424
<212> TYPE: DNA
<213> ORGANISM: Homo sapiens

<400> SEQUENCE: 464

```
      tccgagctga ttacagacac caaggaagat gctgtaaaga gtcagcagcc acagccctgg    60
      ctagctggcc ctgtgggcat ttattagtaa agttttaatg acaaaagctt tgagtcaaca   120
      caccgtgggg taattaacct ggtcatcccc accctggaga gccatcctgc ccatgggtga   180
      tcaaagaagg aacatctgca ggaacacctg atgaggctgc acccttggcg gaaagaacac   240
      ctgacacagc tgaaagcttg gtgaaaaaa cacctgatga ggctgcaccc ttggtggaaa   300
      gaacacctga cacggctgaa agcttggtgg aaaaaacacc tgatgaggct gcatccttgg   360
      tggagggaac atctgacaaa attcaatgtt tggagaaagc gacatctgga aagttcgaac   420
      agtcagcaga agaaacacct agggaaatta cgagtcctgc aaaagaaaca tctgagaaat   480
      ttacgtggcc agcaaaagga agacctagga agatccgcat ggagaaaaaa gaagacacac   540
      ctagggaaat tatgagtccc gcaaaagaaa catctgagaa atttacgtgg gcagcaaaag   600
      gaagacctag gaagatcgca tgggagaaaa aagaaacacc tgtaaagact ggatgcgtgg   660
      caagagtaac atctaataaa actaaagttt tggaaaaagg aagatctaag atgattgcat   720
      gtcctacaaa agaatcatct acaaaagcaa gtgccaatga tcagaggttc ccatcagaat   780
      ccaaacaaga ggaagatgaa gaatattctt gtgattctcg gagtctcttt gagagttctg   840
      caaagattca agtgtgtata cctgagtcta tatatcaaaa agtaatggag ataaatagag   900
      aagtagaaga gcctcctaag aagccatctg ccttcaagcc tgccattgaa atgcaaaact   960
      ctgttccaaa taaagccttt gaattgaaga atgaacaaac attgagagca gatccgatgt  1020
```

-continued

```
     tcccaccaga  atccaaacaa  aaggactatg  aagaaaattc  ttgggattct  gagagtctct  1080
     gtgagactgt  ttcacagaag  gatgtgtgtt  tacccaaggc  tacacatcaa  aaagaaatag  1140
     ataaaataaa  tggaaaatta  gaaggtaaga  accgttttt   atttaaaaat  cagttgaccg  1200
     aatatttctc  taaactgatg  aggagggata  tcctctagta  gctgaagaaa  attacctcct  1260
     aaatgcaaac  catggaaaaa  aagagaagtg  caatggtcgt  aagttgtatg  tctcatcagg  1320
     tgttggcaac  agactatatt  gagagtgctg  aaaaggagct  gaattattag  tttgaattca  1380
     agatattgca  agacctgaga  gaaaaaaaaa  aaaaaaaaaa  aaaa                    1424
```

<210> SEQ ID NO 465
<211> LENGTH: 674
<212> TYPE: DNA
<213> ORGANISM: Homo sapiens

<400> SEQUENCE: 465

```
     attccgagct  gattacagac  accaaggaag  atgctgtaaa  gagtcagcag  ccacagccct   60
     ggctagctgg  ccctgtgggc  atttattagt  aaagttttaa  tgacaaaagc  tttgagtcaa  120
     cacaccgtg   ggtaattaac  ctggtcatcc  ccaccctgga  gagccatcct  gcccatgggt  180
     gatcaaagaa  ggaacatctg  caggaacacc  tgatgaggct  gcacccttgg  cggaaagaac  240
     acctgacaca  gctgaaagct  tggtggaaaa  aacacctgat  gaggctgcac  ccttggtgga  300
     aagaacacct  gacacggctg  aaagcttggt  ggaaaaaaca  cctgatgagg  ctgcatcctt  360
     ggtggaggga  acatctgaca  aaattcaatg  tttggagaaa  gcgacatctg  gaaagttcga  420
     acagtcagca  gaagaaacac  ctagggaaat  tacgagtcct  gcaaaagaaa  catctgagaa  480
     atttacgtgg  ccagcaaaag  gaagacctag  gaagatcgca  tgggagaaaa  aagatgactc  540
     agttaaggca  aaaaaaaaaa  aaaaaaaaaa  aaaaaaaaaa  aaaaaaaaaa  aaaaaaaaaa  600
     aaaaaaaaaa  aaaaaaaaaa  aaaaaaaaaa  aaaaaaaaaa  aaaaaaaaaa  aaaaaaaaaa  660
     aaaaaaaaaa  aaaa                                                         674
```

<210> SEQ ID NO 466
<211> LENGTH: 1729
<212> TYPE: DNA
<213> ORGANISM: Homo sapiens
<220> FEATURE:
<221> NAME/KEY: misc_feature
<222> LOCATION: 11, 1128
<223> OTHER INFORMATION: n = A,T,C or G

<400> SEQUENCE: 466

```
     gaaagttcga  ncagtcagca  gaagaaacac  ctagggaaat  tacgagtcct  gcaaaagaaa   60
     catctgagaa  atttacgtgg  ccagcaaaag  gaagacctag  gaagatcgca  tgggagaaaa  120
     aagaagacac  acctaggaa   attatgagtc  ccgcaaaaga  aacatctgag  aaatttacgt  180
     gggcagcaaa  aggaagacct  aggaagatcg  catgggagaa  aaaagaaaca  cctgtaaaga  240
     ctggatgcgt  ggcaagagta  acatctaata  aaactaaagt  tttggaaaaa  ggaagatcta  300
     agatgattgc  atgtcctaca  aaagaatcat  ctacaaaagc  aagtgccaat  gatcagaggt  360
     tcccatcaga  atccaaacaa  gaggaagatg  aagaatattc  ttgtgattct  cggagtctct  420
     ttgagagttc  tgcaaagatt  caagtgtgta  tacctgagtc  tatatatcaa  aaagtaatgg  480
     agataaatag  agaagtagaa  gagcctccta  agaagccatc  tgccttcaag  cctgccattg  540
     aaatgcaaaa  ctctgttcca  aataaagcct  ttgaattgaa  gaatgaacaa  acattgagag  600
     cagatccgat  gttcccacca  gaatccaaac  aaaaggacta  tgaagaaaat  tcttgggatt  660
     ctgagagtct  ctgtgagact  gttttcacaga  aggatgtgtg  tttacccaag  gctacacatc  720
     aaaaagaaaa  agataaaaata  aatggaaaat  tagaagagtc  tcctaataaa  gatggtcttc  780
     tgaaggctac  ctgcggaatg  aaagtttcta  ttccaactaa  agccttagaa  ttgaaggaca  840
     tgcaaacttt  caaagcgag   cctccgggga  agccatctgc  cttcgagcct  gccactgaaa  900
     tgcaaaagtc  tgtcccaaat  aaagccttgg  aattgaaaaa  tgaacaaaca  ttgagagcag  960
     atgagatact  cccatcagaa  tccaaacaaa  aggactatga  agaaaattct  tgggatactg  1020
     agagtctctg  tgagactgtt  tcacagaagg  atgtgtgttt  acccaaggct  gcgcatcaaa  1080
     aagaaataga  taaaataaat  ggaaaattag  aagggtctcc  tggtaaanat  ggtcttctga  1140
     aggctaactg  cggaatgaaa  gtttctattc  caactaaagc  cttagaattg  atggacatgc  1200
     aaacttcaa   agcaggcct   cccgagaagc  catctgcctt  cgagcctgcc  attgaaatgc  1260
     aaaagtctgt  tccaaataaa  gccttggaat  tgaagaatga  acaaacattg  agagcagatg  1320
     agatactccc  atcagaatcc  aaacaaaagg  actatgaaga  aagttcttgg  gattctgaga  1380
     gtctctgtga  gactgtttca  cagaaggatg  tgtgtttacc  caaggctgcg  catcaaaaag  1440
     aaatagataa  aataaatgga  aaattagaag  gtaagaacct  tttttttattt  aaaaatcatt  1500
     tgaccaaata  tttctctaaa  ttgatgagga  aggatatcct  ctagtagctg  aagaaatta   1560
     cctcctaaat  gcaaaccatg  gaaaaaaaga  gaagtgcaat  ggtcataagc  tatgtgtctc  1620
     atcaggcatt  ggcaacagac  tatattgtga  gtgctgaaga  ggagctgaat  tactagttta  1680
     aattcaagat  attccaagac  gtgaggaaaa  tgagaaaaaa  aaaaaaaaa                1729
```

<210> SEQ ID NO 467
<211> LENGTH: 1337
<212> TYPE: DNA
<213> ORGANISM: Homo sapiens

<400> SEQUENCE: 467

-continued

```
aaaagaaat agataaaata aatggaaaat tagaagggtc tcctgttaaa gatggtcttc   60
tgaaggctaa ctgcggaatg aaagtttcta ttccaactaa agccttagaa ttgatggaca  120
tgcaaacttt caaagcagag cctcccgaga agccatctgc cttcgagcct gccattgaaa  180
tgcaaaagtc tgttccaaat aaagccttgg aattgaagaa tgaacaaaca ttgagagcag  240
atgagatact cccatcagaa tccaaacaaa aggactatga agaaagttct tgggattctg  300
agagtctctg tgagactgtt tcacagaagg atgtgtgttt acccaaggct gcgcatcaaa  360
aagaaataga taaataaat ggaaaattag aagagtctcc tgataatgat ggttttctga  420
aggctccctg cagaatgaaa gtttctattc caactaaagc cttagaattg atggacatgc  480
aaactttcaa agcagagcct cccgagaagc catctgcctt cgagcctgcc attgaaatgc  540
aaaagtctgt tccaaataaa gccttggaat tgaagaatga acaaacattg agagcagatc  600
agatgttccc ttcagaatca aaacaaaaga aggttgaaga aaattcttgg gattctgaga  660
gtctccgtga gactgtttca cagaaggatg tgtgtgtacc caaggctaca catcaaaaag  720
aaatggataa aataagtgga aaattagaag attcaactag cctatcaaaa atcttggata  780
cagttcattc ttgtgaaaga gcaagggaac ttcaaaaaga tcactgtgaa caacgtacag  840
gaaaaatgga acaaatgaaa aagaagtttt gtgtactgaa aaagaaactg tcagaagcaa  900
aagaaataaa atcacagtta gagaaccaaa aagttaaatg ggaacaagag ctctgcagtg  960
tgagattgac tttaaaccaa gaagaagaga agagaagaaa tgccgatata ttaaatgaaa 1020
aaattaggga agaattagga agaatcgaag agcagcatag gaaagagtta gaagtgaaac 1080
aacaacttga acaggctctc agaatacaag atatagaatt gaagagtgta gaaagtaatt 1140
tgaatcaggt ttctcacact catgaaaatg aaaattatct cttacatgaa aattgcatgt 1200
tgaaaaagga aattgccatg ctaaaactgg aaatagccac actgaaacac caataccagg 1260
aaaaggaaaa taaatacttt gaggacatta gattttaaaa agaaaagaat gctgaacttc 1320
agatgacccc tcgtgcc                                                1337
```

<210> SEQ ID NO 468
<211> LENGTH: 2307
<212> TYPE: DNA
<213> ORGANISM: Homo sapiens

<400> SEQUENCE: 468

```
attgagagca gatgagatac tcccatcaga atccaaacaa aaggactatg agaaaagttc   60
ttgggattct gagagtctct gtgagactgt ttcacagaag gatgtgtgtt tacccaaggc  120
tacacatcaa aaagaaatag ataaaataaa tggaaaatta gaagggtctc ctgttaaaga  180
tggtcttctg aaggctaact gcggaatgaa agtttctatt ccaactaaag ccttagaatt  240
gatggacatg caaactttca aagcagagcc tcccgagaag ccatctgcct tcgagcctgc  300
cattgaaatg caaaagtctg ttccaaataa agccttggaa ttgaagaatg aacaaacatt  360
gagagcagat gagatactcc catcagaatc aaacaaaag gactatgaag aaagttcttg  420
ggattctgag agtctctgtg agactgtttc acagaaggat gtgtgtttac ccaaggctac  480
acatcaaaaa gaaatagata aaataaatgg aaaattagaa gagtctcctg ataatgatgg  540
ttttctgaag tctcccctgca gaatgaaagt ttctattcca actaaagcct tagaattgat  600
ggacatgcaa actttcaaag cagagcctcc cgagaagcca tctgccttcg agcctgccat  660
tgaaatgcaa aagtctgttc caaataaagc cttggaattg aagaatgaac aaacattgag  720
agcagatcag atgttccctt cagaatcaaa acaaaagaag gttgaagaaa attcttggga  780
ttctgagagt ctccgtgaga ctgtttcaca gaaggatgtg tgtacccca aggctacaca  840
tcaaaaagaa atggataaaa taagtggaaa attagaagat tcaactagcc tatcaaaaat  900
cttggataca gttcattctt gtgaaagagc aagggaactt caaaaagatc actgtgaaca  960
acgtacagga aaaatggaac aaatgaaaaa gaagttttgt gtactgaaaa agaaactgtc 1020
agaagcaaaa gaaataaaat cacagttaga gaaccaaaa gttaaatggg aacaagagct 1080
ctgcagtgtg aggtttctca cactcatgaa aatgaaaatt atctcttaca tgaaaattgc 1140
atgttgaaaa aggaaattgc catgctaaaa ctggaaatag ccacactgaa acaccaatac 1200
caggaaaagg aaaataaata ctttgaggac attaagattt taaagaaaa gaatgctgaa 1260
cttcagatga ccctaaaact gaaagaggaa tcattaacta aaagggcatc tcaatatagt 1320
gggcagctta aagttctgat agctgagaac acaatgctca cttctaaatt gaaggaaaaa 1380
caagacaaag aaatactaga ggcagaaatt gaatcacacc atcctagact ggcttctgct 1440
gtacaagacc atgatcaaat tgtgacatca agaaaaagtc aagaacctgc tttccacatt 1500
gcaggagatg cttgtttgca aagaaaaatg aatgttgatg tgagtagtac gatatataac 1560
aatgaggtgc tccatcaacc actttctgaa gctcaaagga aatccaaaag cctaaaaatt 1620
aatctcaatt atgcaggaga tgctctaaga gaaatacat tggtttcaga acatgcacaa 1680
agagaccaac gtgaaacaca gtgtcaaatg aaggaagctg aacacatgta tcaaaacgaa 1740
caagataatg tgaacaaaca cactgaacag caggagtctc tagatcagaa attatttcaa 1800
ctacaaagca aaaatatgtg gcttcaacag caattagttc atgcacataa gaaagctgac 1860
aacaaaagca agataacaat tgatattcat tttcttgaga ggaaaatgca acatcatctc 1920
ctaaaagaga aaaatgagga gatatttaat acaataacc atttaaaaaa ccgtatatat 1980
caatatgaaa aagagaaagc agaaacagaa aactcatgag agcaagcag taagaaactt 2040
cttttggaga aacaacagac cagatctttta ctcacaactc atgctaggag gccagtccta 2100
gcatcacctt atgttgaaaa tcttaccaat agtctgtgtc aacagatac ttattttaga 2160
agaaaaattc atgatttctt cctgaagcct acagacataa aataacagtg tgaagaatta 2220
cttgttcacg aattgcataa agctgcacag gattcccatc taccctgatg atgcagcaga 2280
catcattcaa tccaaccaga atctcgc                                     2307
```

<210> SEQ ID NO 469
<211> LENGTH: 650
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
1               5                   10                  15
Gly Arg Pro Arg Lys Ile Ala Trp Glu Lys Glu Thr Pro Val Lys
            20                  25                  30
Thr Gly Cys Val Ala Arg Val Thr Ser Asn Lys Thr Lys Val Leu Glu
        35                  40                  45
Lys Gly Arg Ser Lys Met Ile Ala Cys Pro Thr Lys Glu Ser Ser Thr
    50                  55                  60
Lys Ala Ser Ala Asn Asp Gln Arg Phe Pro Ser Glu Ser Lys Gln Glu
65                  70                  75                  80
Glu Asp Glu Glu Tyr Ser Cys Asp Ser Arg Ser Leu Phe Glu Ser Ser
                85                  90                  95
Ala Lys Ile Gln Val Cys Ile Pro Glu Ser Ile Tyr Gln Lys Val Met
            100                 105                 110
Glu Ile Asn Arg Glu Val Glu Pro Pro Lys Lys Pro Ser Ala Phe
            115                 120                 125
Lys Pro Ala Ile Glu Met Gln Asn Ser Val Pro Asn Lys Ala Phe Glu
130                 135                 140
Leu Lys Asn Glu Gln Thr Leu Arg Ala Asp Pro Met Phe Pro Pro Glu
145                 150                 155                 160
Ser Lys Gln Lys Asp Tyr Glu Glu Asn Ser Trp Asp Ser Glu Ser Leu
                165                 170                 175
Cys Glu Thr Val Ser Gln Lys Asp Val Cys Leu Pro Lys Ala Thr His
            180                 185                 190
Gln Lys Glu Ile Asp Lys Ile Asn Gly Lys Leu Glu Glu Ser Pro Asn
        195                 200                 205
Lys Asp Gly Leu Leu Lys Ala Thr Cys Gly Met Lys Val Ser Ile Pro
210                 215                 220
Thr Lys Ala Leu Glu Leu Lys Asp Met Gln Thr Phe Lys Ala Glu Pro
225                 230                 235                 240
Pro Gly Lys Pro Ser Ala Phe Glu Pro Ala Thr Glu Met Gln Lys Ser
                245                 250                 255
Val Pro Asn Lys Ala Leu Glu Leu Lys Asn Glu Gln Thr Leu Arg Ala
            260                 265                 270
Asp Glu Ile Leu Pro Ser Glu Ser Lys Gln Lys Asp Tyr Glu Glu Ser
        275                 280                 285
Ser Trp Asp Ser Glu Ser Leu Cys Glu Thr Val Ser Gln Lys Asp Val
    290                 295                 300
Cys Leu Pro Lys Ala Xaa His Gln Lys Glu Ile Asp Lys Ile Asn Gly
305                 310                 315                 320
Lys Leu Glu Gly Ser Pro Val Lys Asp Gly Leu Lys Ala Asn Cys
                325                 330                 335
Gly Met Lys Val Ser Ile Pro Thr Lys Ala Leu Glu Leu Met Asp Met
            340                 345                 350
Gln Thr Phe Lys Ala Glu Pro Pro Glu Lys Pro Ser Ala Phe Glu Pro
        355                 360                 365
Ala Ile Glu Met Gln Lys Ser Val Pro Asn Lys Ala Leu Glu Leu Lys
    370                 375                 380
Asn Glu Gln Thr Leu Arg Ala Asp Glu Ile Leu Pro Ser Glu Ser Lys
385                 390                 395                 400
Gln Lys Asp Tyr Glu Glu Ser Ser Trp Asp Ser Glu Ser Leu Cys Glu
                405                 410                 415
Thr Val Ser Gln Lys Asp Val Cys Leu Pro Lys Ala Xaa His Gln Lys
            420                 425                 430
Glu Ile Asp Lys Ile Asn Gly Lys Leu Glu Glu Ser Pro Asp Asn Asp
        435                 440                 445
Gly Phe Leu Lys Ala Pro Cys Arg Met Lys Val Ser Ile Pro Thr Lys
    450                 455                 460
Ala Leu Glu Leu Met Asp Met Gln Thr Phe Lys Ala Glu Pro Pro Glu
465                 470                 475                 480
Lys Pro Ser Ala Phe Glu Pro Ala Ile Glu Met Gln Lys Ser Val Pro
                485                 490                 495
Asn Lys Ala Leu Glu Leu Lys Asn Glu Gln Thr Leu Arg Ala Asp Gln
            500                 505                 510
Met Phe Pro Ser Glu Ser Lys Gln Lys Xaa Val Glu Glu Asn Ser Trp
        515                 520                 525
Asp Ser Glu Ser Leu Arg Glu Thr Val Ser Gln Lys Asp Val Cys Val
    530                 535                 540
Pro Lys Ala Thr His Gln Lys Glu Met Asp Lys Ile Ser Gly Lys Leu
545                 550                 555                 560
Glu Asp Ser Thr Ser Leu Ser Lys Ile Leu Asp Thr Val His Ser Cys
                565                 570                 575
Glu Arg Ala Arg Glu Leu Gln Lys Asp His Cys Glu Gln Arg Thr Gly
            580                 585                 590
```

```
        Lys Met Glu Gln Met Lys Lys Phe Cys Val Leu Lys Lys Leu
            595                 600                 605
        Ser Glu Ala Lys Glu Ile Lys Ser Gln Leu Glu Asn Gln Lys Val Lys
        610                 615                 620
        Trp Glu Gln Glu Leu Cys Ser Val Arg Phe Leu Thr Leu Met Lys Met
        625                 630                 635                 640
        Lys Ile Ile Ser Tyr Met Lys Ile Ala Cys
                        645                 650
```

<210> SEQ ID NO 470
<211> LENGTH: 228
<212> TYPE: PRT
<213> ORGANISM: Homo sapiens

<400> SEQUENCE: 470

```
        Met Ser Pro Ala Lys Glu Thr Ser Glu Lys Phe Thr Trp Ala Ala Lys
        1               5                   10                  15
        Gly Arg Pro Arg Lys Ile Ala Trp Glu Lys Lys Glu Thr Pro Val Lys
                        20                  25                  30
        Thr Gly Cys Val Ala Arg Val Thr Ser Asn Lys Thr Lys Val Leu Glu
                    35                  40                  45
        Lys Gly Arg Ser Lys Met Ile Ala Cys Pro Thr Lys Glu Ser Ser Thr
        50                  55                  60
        Lys Ala Ser Ala Asn Asp Gln Arg Phe Pro Ser Glu Ser Lys Gln Glu
        65                  70                  75                  80
        Glu Asp Glu Glu Tyr Ser Cys Asp Ser Arg Ser Leu Phe Glu Ser Ser
                        85                  90                  95
        Ala Lys Ile Gln Val Cys Ile Pro Glu Ser Ile Tyr Gln Lys Val Met
                        100                 105                 110
        Glu Ile Asn Arg Glu Val Glu Pro Pro Lys Lys Pro Ser Ala Phe
                    115                 120                 125
        Lys Pro Ala Ile Glu Met Gln Asn Ser Val Pro Asn Lys Ala Phe Glu
        130                 135                 140
        Leu Lys Asn Glu Gln Thr Leu Arg Ala Asp Pro Met Phe Pro Pro Glu
        145                 150                 155                 160
        Ser Lys Gln Lys Asp Tyr Glu Glu Asn Ser Trp Asp Ser Glu Ser Leu
                        165                 170                 175
        Cys Glu Thr Val Ser Gln Lys Asp Val Cys Leu Pro Lys Ala Thr His
                        180                 185                 190
        Gln Lys Glu Ile Asp Lys Ile Asn Gly Lys Leu Glu Gly Lys Asn Arg
                    195                 200                 205
        Phe Leu Phe Lys Asn Gln Leu Thr Glu Tyr Phe Ser Lys Leu Met Arg
        210                 215                 220
        Arg Asp Ile Leu
        225
```

<210> SEQ ID NO 471
<211> LENGTH: 154
<212> TYPE: PRT
<213> ORGANISM: Homo sapiens
<220> FEATURE:
<221> NAME/KEY: VARIANT
<222> LOCATION: 148
<223> OTHER INFORMATION: Xaa = Any Amino Acid

<400> SEQUENCE: 471

```
        Met Arg Leu His Pro Trp Arg Lys Glu His Leu Thr Gln Leu Lys Ala
        1               5                   10                  15
        Trp Trp Lys Lys His Leu Met Arg Leu His Pro Trp Trp Lys Glu His
                        20                  25                  30
        Leu Thr Arg Leu Lys Ala Trp Trp Lys Lys His Leu Met Arg Leu His
                    35                  40                  45
        Pro Trp Trp Arg Glu His Leu Thr Lys Phe Asn Val Trp Arg Lys Arg
                50                  55                  60
        His Leu Glu Ser Ser Asn Ser Gln Gln Lys His Leu Gly Lys Leu
        65                  70                  75                  80
        Arg Val Leu Gln Lys Lys His Leu Arg Asn Leu Arg Gly Gln Gln Lys
                        85                  90                  95
        Glu Asp Leu Gly Arg Ser His Gly Arg Lys Met Thr Gln Leu Arg
                    100                 105                 110
        Gln Lys Lys Lys Lys Lys Lys Lys Lys Lys Lys Lys Lys Lys Lys
                115                 120                 125
        Lys Lys Lys Lys Lys Lys Lys Lys Lys Lys Lys Lys Lys Lys Lys
        130                 135                 140
        Lys Lys Lys Xaa Lys Lys Lys Lys Lys Lys
```

145                 150

<210> SEQ ID NO 472
<211> LENGTH: 466
<212> TYPE: PRT
<213> ORGANISM: Homo sapiens
<220> FEATURE:
<221> NAME/KEY: VARIANT
<222> LOCATION: 329
<223> OTHER INFORMATION: Xaa = Any Amino Acid

<400> SEQUENCE: 472

```
Met Ser Pro Ala Lys Glu Thr Ser Glu Lys Phe Thr Trp Ala Ala Lys
 1               5                  10                  15
Gly Arg Pro Arg Lys Ile Ala Trp Glu Lys Lys Glu Thr Pro Val Lys
             20                  25                  30
Thr Gly Cys Val Ala Arg Val Thr Ser Asn Lys Thr Lys Val Leu Glu
         35                  40                  45
Lys Gly Arg Ser Lys Met Ile Ala Cys Pro Thr Lys Glu Ser Ser Thr
     50                  55                  60
Lys Ala Ser Ala Asn Asp Gln Arg Phe Pro Ser Glu Ser Lys Gln Glu
 65                  70                  75                  80
Glu Asp Glu Glu Tyr Ser Cys Asp Ser Arg Ser Leu Phe Glu Ser Ser
                 85                  90                  95
Ala Lys Ile Gln Val Cys Ile Pro Glu Ser Ile Tyr Gln Lys Val Met
            100                 105                 110
Glu Ile Asn Arg Glu Val Glu Glu Pro Pro Lys Lys Pro Ser Ala Phe
        115                 120                 125
Lys Pro Ala Ile Glu Met Gln Asn Ser Val Pro Asn Lys Ala Phe Glu
    130                 135                 140
Leu Lys Asn Glu Gln Thr Leu Arg Ala Asp Pro Met Phe Pro Pro Glu
145                 150                 155                 160
Ser Lys Gln Lys Asp Tyr Glu Glu Asn Ser Trp Asp Ser Glu Ser Leu
                165                 170                 175
Cys Glu Thr Val Ser Gln Lys Asp Val Cys Leu Pro Lys Ala Thr His
            180                 185                 190
Gln Lys Glu Ile Asp Lys Ile Asn Gly Lys Leu Glu Glu Ser Pro Asn
        195                 200                 205
Lys Asp Gly Leu Leu Lys Ala Thr Cys Gly Met Lys Val Ser Ile Pro
    210                 215                 220
Thr Lys Ala Leu Glu Leu Lys Asp Met Gln Thr Phe Lys Ala Glu Pro
225                 230                 235                 240
Pro Gly Lys Pro Ser Ala Phe Glu Pro Ala Thr Glu Met Gln Lys Ser
                245                 250                 255
Val Pro Asn Lys Ala Leu Glu Leu Lys Asn Glu Gln Thr Leu Arg Ala
            260                 265                 270
Asp Glu Ile Leu Pro Ser Glu Ser Lys Gln Lys Asp Tyr Glu Glu Asn
        275                 280                 285
Ser Trp Asp Thr Glu Ser Leu Cys Glu Thr Val Ser Gln Lys Asp Val
    290                 295                 300
Cys Leu Pro Lys Ala Ala His Gln Lys Glu Ile Asp Lys Ile Asn Gly
305                 310                 315                 320
Lys Leu Glu Gly Ser Pro Gly Lys Xaa Gly Leu Leu Lys Ala Asn Cys
                325                 330                 335
Gly Met Lys Val Ser Ile Pro Thr Lys Ala Leu Glu Leu Met Asp Met
            340                 345                 350
Gln Thr Phe Lys Ala Glu Pro Pro Glu Lys Pro Ser Ala Phe Glu Pro
        355                 360                 365
Ala Ile Glu Met Gln Lys Ser Val Pro Asn Lys Ala Leu Glu Leu Lys
    370                 375                 380
Asn Glu Gln Thr Leu Arg Ala Asp Glu Ile Leu Pro Ser Glu Ser Lys
385                 390                 395                 400
Gln Lys Asp Tyr Glu Glu Ser Ser Trp Asp Ser Glu Ser Leu Cys Glu
                405                 410                 415
Thr Val Ser Gln Lys Asp Val Cys Leu Pro Lys Ala Ala His Gln Lys
            420                 425                 430
Glu Ile Asp Lys Ile Asn Gly Lys Leu Glu Gly Lys Asn Arg Phe Leu
        435                 440                 445
Phe Lys Asn His Leu Thr Lys Tyr Phe Ser Lys Leu Met Arg Lys Asp
    450                 455                 460
Ile Leu
465
```

<210> SEQ ID NO 473
<211> LENGTH: 445
<212> TYPE: PRT

-continued

<213> ORGANISM: Homo sapiens

<400> SEQUENCE: 473

```
Lys Glu Ile Asp Lys Ile Asn Gly Lys Leu Glu Gly Ser Pro Val Lys
  1               5                  10                  15
Asp Gly Leu Leu Lys Ala Asn Cys Gly Met Lys Val Ser Ile Pro Thr
             20                  25                  30
Lys Ala Leu Glu Leu Met Asp Met Gln Thr Phe Lys Ala Glu Pro Pro
         35                  40                  45
Glu Lys Pro Ser Ala Phe Glu Pro Ala Ile Glu Met Gln Lys Ser Val
     50                  55                  60
Pro Asn Lys Ala Leu Glu Leu Lys Asn Glu Gln Thr Leu Arg Ala Asp
 65                  70                  75                  80
Glu Ile Leu Pro Ser Glu Ser Lys Gln Lys Asp Tyr Glu Glu Ser Ser
                 85                  90                  95
Trp Asp Ser Glu Ser Leu Cys Glu Thr Val Ser Gln Lys Asp Val Cys
            100                 105                 110
Leu Pro Lys Ala Ala His Gln Lys Glu Ile Asp Lys Ile Asn Gly Lys
        115                 120                 125
Leu Glu Glu Ser Pro Asp Asn Asp Gly Phe Leu Lys Ala Pro Cys Arg
    130                 135                 140
Met Lys Val Ser Ile Pro Thr Lys Ala Leu Glu Leu Met Asp Met Gln
145                 150                 155                 160
Thr Phe Lys Ala Glu Pro Pro Glu Lys Pro Ser Ala Phe Glu Pro Ala
                165                 170                 175
Ile Glu Met Gln Lys Ser Val Pro Asn Lys Ala Leu Glu Leu Lys Asn
            180                 185                 190
Glu Gln Thr Leu Arg Ala Asp Gln Met Phe Pro Ser Glu Ser Lys Gln
        195                 200                 205
Lys Lys Val Glu Glu Asn Ser Trp Asp Ser Glu Ser Leu Arg Glu Thr
    210                 215                 220
Val Ser Gln Lys Asp Val Cys Val Pro Lys Ala Thr His Gln Lys Glu
225                 230                 235                 240
Met Asp Lys Ile Ser Gly Lys Leu Glu Asp Ser Thr Ser Leu Ser Lys
                245                 250                 255
Ile Leu Asp Thr Val His Ser Cys Glu Arg Ala Arg Glu Leu Gln Lys
            260                 265                 270
Asp His Cys Glu Gln Arg Thr Gly Lys Met Glu Gln Met Lys Lys Lys
        275                 280                 285
Phe Cys Val Leu Lys Lys Lys Leu Ser Glu Ala Lys Glu Ile Lys Ser
    290                 295                 300
Gln Leu Glu Asn Gln Lys Val Lys Trp Glu Gln Glu Leu Cys Ser Val
305                 310                 315                 320
Arg Leu Thr Leu Asn Gln Glu Glu Lys Arg Arg Asn Ala Asp Ile
                325                 330                 335
Leu Asn Glu Lys Ile Arg Glu Glu Leu Gly Arg Ile Glu Glu Gln His
            340                 345                 350
Arg Lys Glu Leu Glu Val Lys Gln Gln Leu Glu Gln Ala Leu Arg Ile
        355                 360                 365
Gln Asp Ile Glu Leu Lys Ser Val Glu Ser Asn Leu Asn Gln Val Ser
    370                 375                 380
His Thr His Glu Asn Glu Asn Tyr Leu Leu His Glu Asn Cys Met Leu
385                 390                 395                 400
Lys Lys Glu Ile Ala Met Leu Lys Leu Glu Ile Ala Thr Leu Lys His
                405                 410                 415
Gln Tyr Gln Glu Lys Glu Asn Lys Tyr Phe Glu Asp Ile Lys Ile Leu
            420                 425                 430
Lys Glu Lys Asn Ala Glu Leu Gln Met Thr Pro Arg Ala
        435                 440                 445
```

<210> SEQ ID NO 474
<211> LENGTH: 3865
<212> TYPE: DNA
<213> ORGANISM: Homo sapiens

<400> SEQUENCE: 474

```
tccgagctga ttacagacac caaggaagat gctgtaaaga gtcagcagcc acagccctgg    60
ctagctggcc ctgtgggcat ttattagtaa agttttaatg acaaaagctt tgagtcaaca   120
cacccgtggg taattaacct ggtcatcccc accctggaga gccatcctgc ccatgggtga   180
tcaaagaagg aacatctgca ggaacacctg atgaggctgc acccttggcg gaaagaacac   240
ctgacacagc tgaaagcttg gtggaaaaaa cacctgatga ggctgcaccc ttgtggaaaa   300
gaacacctga cacggctgaa agcttggtgg aaaaacacc tgatgaggct gcatccttgg   360
tggagggaac atctgacaaa attcaatgtt tggagaaagc gacatctgga aagttcgaac   420
agtcagcaga gaaaacacct agggaaatta cgagtcctgc aaaagaaaca tctgagaaat   480
ttacgtggcc agcaaaagga agacctagga gatcgcatg ggagaaaaaa gaagacacac   540
ctagggaaat tatgagtccc gcaaaagaaa catctgagaa atttacgtgg gcagcaaaag   600
```

-continued

```
gaagacctag gaagatcgca tgggagaaaa aagaaacacc tgtaaagact ggatgcgtgg   660
caagagtaac atctaataaa actaaagttt tggaaaaagg aagatctaag atgattgcat   720
gtcctacaaa agaatcatct acaaaagcaa gtgccaatga tcagaggttc ccatcagaat   780
ccaaacaaga ggaagtgaa gaatattctt gtgattctcg gagtctcttt gagagttctg   840
caaagattca agtgtgtata cctgagtcta tatatcaaaa agtaatggag ataaatagag   900
aagtagaaga gcctcctaag aagccatctg ccttcaagcc tgccattgaa atgcaaaact   960
ctgttccaaa taaagccttt gaattgaaga atgaacaaac attgagagca gatccgatgt  1020
tcccaccaga atccaaacaa aaggactatg aagaaaattc ttgggattct gagagtctct  1080
gtgagactgt ttcacagaag gatgtgtgtt tacccaaggc tacacatcaa aaagaaatag  1140
ataaaataaa tgaaaatta aagagtctc ctaataaaga tggtcttctg aaggctaccct  1200
gcggaatgaa agtttctatt ccaactaaag ccttagaatt gaaggacatg caaactttca  1260
aagcagagcc tccggggaag ccatctgcct tcgagcctgc cactgaaatg caaaagtctg  1320
tcccaaataa agccttggaa ttgaaaaatg aacaaacatt gagagcagat gagatactcc  1380
catcagaatc caaacaaaag gactatgaag aaagttcttg ggattctgag agtctctgtg  1440
agactgtttc acagaaggat gtgtgtttac ccaaggctrc rcatcaaaaa gaaatagata  1500
aaataaatgg aaaattgaa gggtctcctg ttaaagatgg tcttctgaag gctaactgcg  1560
gaatgaaagt ttctattcca actaaagcct tagaattgat ggacatgcaa actttcaaag  1620
cagagcctcc cgagaagcca tctgccttcg agcctgccat tgaaatgcaa aagtctgttc  1680
caaataaagc cttggaattg aagaatgaac aaacattgag agcagatgag atactcccat  1740
cagaatccaa acaaaaggac tatgaagaaa gttcttggga ttctgagagt ctctgtgaga  1800
ctgtttcaca gaaggatgtg tgtttaccca aggctrcrca tcaaaaagaa atagataaaa  1860
taaatggaaa attagaagag tctcctgata tgatggtttt tctgaaggct ccctgcagaa  1920
tgaaagtttc tattccaact aaagccttag aattgatgga catgcaaact ttcaaagcag  1980
agcctcccga gaagccatct gccttcgagc ctgccattga aatgcaaaag tctgttccaa  2040
ataaagcctt ggaattgaag aatgaacaaa cattgagagc agatcagatg ttcccttcag  2100
aatcaaaaca aaagaasgtt gaagaaaatt cttgggattc tgagagtctc cgtgagactg  2160
tttcacagaa ggatgtgtgt gtacccaagg ctacacatca aaaagaaatg gataaaataa  2220
gtggaaaatt agaagattca actagcctat caaaaatctt ggatacagtt cattcttgtg  2280
aaagagcaga ggaacttcaa aaagatcact gtgaacaacg tacaggaaaa atggaacaaa  2340
tgaaaaagaa gttttgtgta ctgaaaaaga aactgtcaga agcaaaagaa ataaaatcac  2400
agttagagaa ccaaaaagtt aaatgggaac aagagctctg cagtgtgaga ttgactttaa  2460
accaagaaga agagaagaga agaaatgccg atatattaaa tgaaaaaatt agggaagaat  2520
taggaagaat cgaagagcag cataggaaag agttagaagg gaaacaacaa cttgaacagg  2580
ctctcagaat acaagatata gaattgaaga gtgtagaaag taatttgaat caggtttctc  2640
acactcatga aaatgaaaat tatctcttac atgaaaattg catgttgaaa aaggaaattg  2700
ccatgctaaa actggaaata gccacactga acaccaata ccaggaaaag gaaaataaat  2760
actttgagga cattaagatt ttaaaagaaa agaatgctga acttcagatg accctaaaac  2820
tgaaagagga atcattaact aaaagggcat ctcaatatag tgggcagctt aaagttctga  2880
tagctgagaa cacaatgctc acttctaaat tgaaggaaaa acaagacaaa gaaatactag  2940
aggcagaaat tgaatcacac catcctagac tggcttctgc tgtacaagac catgatcaaa  3000
ttgtgacatc aagaaaaagt caagaacctg ctttccacat tgcaggaagt gcttgtttgc  3060
aaagaaaaat gaatgttgat gtgagtagta cgatataataa caatgaggtg ctccatcaac  3120
cactttctga agctcaaagg aaatccaaaa gcctaaaaat taatctcaat tatgcmggag  3180
atgctctaag agaaaataca ttggtttcag aacatgcaca aagagaccaa cgtgaaacac  3240
agtgtcaaat gaaggaagct gaacacatgt atcaaaacga acaagataat gtgaacaaca  3300
acactgaaca gcaggagtct ctagatcaga aattatttca actacaaagc aaaaatatgt  3360
ggcttcaaca gcaattagtt catgcacata agaaagctga caacaaaagc aagataacaa  3420
ttgatattca ttttcttgag aggaaaatgc aacatcatct cctaaaagag aaaaatgagg  3480
agatatttaa ttcaataac catttaaaaa accgtatata tcaatatgaa aaagagaaag  3540
cagaaacaga aaactcatga gagacaagca gtaagaaact tcttttggag aaacaacaga  3600
ccagatcttt actcacaact catgctagga ggccagtcct agcatcacct tatgttgaaa  3660
atcttaccaa tagtctgtgt caacagaata cttatttag aagaaaaatt catgatttct  3720
tcctgaagcc tacagacata aaataacagt gtgaagaatt acttgttcac gaattgcata  3780
aagctgcaca ggattcccat ctaccctgat gatgcagcag acatcattca atccaaccag  3840
aatctcgctc tgtcactcag gctgg                                        3865
```

<210> SEQ ID NO 475
<211> LENGTH: 1002
<212> TYPE: PRT
<213> ORGANISM: Homo sapiens
<220> FEATURE:
<221> NAME/KEY: VARIANT
<222> LOCATION: 310, 429, 522
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
 1               5                  10                  15
Gly Arg Pro Arg Lys Ile Ala Trp Glu Lys Glu Thr Pro Val Lys
                20                  25                  30
Thr Gly Cys Val Ala Arg Val Thr Ser Asn Lys Thr Lys Val Leu Glu
                35                  40                  45
Lys Gly Arg Ser Lys Met Ile Ala Cys Pro Thr Lys Glu Ser Ser Thr
         50                  55                  60
Lys Ala Ser Ala Asn Asp Gln Arg Phe Pro Ser Glu Ser Lys Gln Glu
 65                  70                  75                  80
Glu Asp Glu Glu Tyr Ser Cys Asp Ser Arg Ser Leu Phe Glu Ser Ser
```

-continued

```
            85                  90                  95
Ala Lys Ile Gln Val Cys Ile Pro Glu Ser Ile Tyr Gln Lys Val Met
            100                 105                 110
Glu Ile Asn Arg Glu Val Glu Glu Pro Pro Lys Pro Ser Ala Phe
            115                 120                 125
Lys Pro Ala Ile Glu Met Gln Asn Ser Val Pro Asn Lys Ala Phe Glu
            130                 135                 140
Leu Lys Asn Glu Gln Thr Leu Arg Ala Asp Pro Met Phe Pro Pro Glu
145                 150                 155                 160
Ser Lys Gln Lys Asp Tyr Glu Glu Asn Ser Trp Asp Ser Glu Ser Leu
                165                 170                 175
Cys Glu Thr Val Ser Gln Lys Asp Val Cys Leu Pro Lys Ala Thr His
                180                 185                 190
Gln Lys Glu Ile Asp Lys Ile Asn Gly Lys Leu Glu Glu Ser Pro Asn
            195                 200                 205
Lys Asp Gly Leu Leu Lys Ala Thr Cys Gly Met Lys Val Ser Ile Pro
    210                 215                 220
Thr Lys Ala Leu Glu Leu Lys Asp Met Gln Thr Phe Lys Ala Glu Pro
225                 230                 235                 240
Pro Gly Lys Pro Ser Ala Phe Glu Pro Ala Thr Glu Met Gln Lys Ser
                245                 250                 255
Val Pro Asn Lys Ala Leu Glu Leu Lys Asn Glu Gln Thr Leu Arg Ala
            260                 265                 270
Asp Glu Ile Leu Pro Ser Glu Lys Gln Lys Asp Tyr Glu Glu Ser
    275                 280                 285
Ser Trp Asp Ser Glu Ser Leu Cys Glu Thr Val Ser Gln Lys Asp Val
    290                 295                 300
Cys Leu Pro Lys Ala Xaa His Gln Lys Glu Ile Asp Lys Ile Asn Gly
305                 310                 315                 320
Lys Leu Glu Gly Ser Pro Val Lys Asp Gly Leu Leu Lys Ala Asn Cys
                325                 330                 335
Gly Met Lys Val Ser Ile Pro Thr Lys Ala Leu Glu Leu Met Asp Met
                340                 345                 350
Gln Thr Phe Lys Ala Glu Pro Pro Glu Lys Pro Ser Ala Phe Glu Pro
            355                 360                 365
Ala Ile Glu Met Gln Lys Ser Val Pro Asn Lys Ala Leu Glu Leu Lys
    370                 375                 380
Asn Glu Gln Thr Leu Arg Ala Asp Glu Ile Leu Pro Ser Glu Ser Lys
385                 390                 395                 400
Gln Lys Asp Tyr Glu Glu Ser Ser Trp Asp Ser Glu Ser Leu Cys Glu
                405                 410                 415
Thr Val Ser Gln Lys Asp Val Cys Leu Pro Lys Ala Xaa His Gln Lys
                420                 425                 430
Glu Ile Asp Lys Ile Asn Gly Lys Leu Glu Glu Ser Pro Asp Asn Asp
            435                 440                 445
Gly Phe Leu Lys Ala Pro Cys Arg Met Lys Val Ser Ile Pro Thr Lys
    450                 455                 460
Ala Leu Glu Leu Met Asp Met Gln Thr Phe Lys Ala Glu Pro Pro Glu
465                 470                 475                 480
Lys Pro Ser Ala Phe Glu Pro Ala Ile Glu Met Gln Lys Ser Val Pro
                485                 490                 495
Asn Lys Ala Leu Glu Leu Lys Asn Glu Gln Thr Leu Arg Ala Asp Gln
                500                 505                 510
Met Phe Pro Ser Glu Ser Lys Gln Lys Xaa Val Glu Glu Asn Ser Trp
            515                 520                 525
Asp Ser Glu Ser Leu Arg Glu Thr Val Ser Gln Lys Asp Val Cys Val
    530                 535                 540
Pro Lys Ala Thr His Gln Lys Glu Met Asp Lys Ile Ser Gly Lys Leu
545                 550                 555                 560
Glu Asp Ser Thr Ser Leu Ser Lys Ile Leu Asp Thr Val His Ser Cys
                565                 570                 575
Glu Arg Ala Glu Leu Gln Lys Asp His Cys Glu Gln Arg Thr Gly
            580                 585                 590
Lys Met Glu Gln Met Lys Lys Phe Cys Val Leu Lys Lys Lys Leu
    595                 600                 605
Ser Glu Ala Lys Glu Ile Lys Ser Gln Leu Glu Asn Gln Lys Val Lys
    610                 615                 620
Trp Glu Gln Glu Leu Cys Ser Val Arg Leu Thr Leu Asn Gln Glu Glu
625                 630                 635                 640
Glu Lys Arg Arg Asn Ala Asp Ile Leu Asn Glu Lys Ile Arg Glu Glu
                645                 650                 655
Leu Gly Arg Ile Glu Glu Gln His Arg Lys Glu Leu Glu Val Lys Gln
            660                 665                 670
Gln Leu Glu Gln Ala Leu Arg Ile Gln Asp Ile Glu Leu Lys Ser Val
    675                 680                 685
Glu Ser Asn Leu Asn Gln Val Ser His Thr His Glu Asn Glu Asn Tyr
            690                 695                 700
Leu Leu His Glu Asn Cys Met Leu Lys Lys Glu Ile Ala Met Leu Lys
705                 710                 715                 720
```

-continued

```
        Leu Glu Ile Ala Thr Leu Lys His Gln Tyr Gln Glu Lys Glu Asn Lys
                    725                 730                 735
        Tyr Phe Glu Asp Ile Lys Ile Leu Lys Glu Lys Asn Ala Glu Leu Gln
                        740                 745                 750
        Met Thr Leu Lys Leu Lys Glu Glu Ser Leu Thr Lys Arg Ala Ser Gln
                    755                 760                 765
        Tyr Ser Gly Gln Leu Lys Val Leu Ile Ala Glu Asn Thr Met Leu Thr
                770                 775                 780
        Ser Lys Leu Lys Glu Gln Asp Lys Glu Ile Leu Glu Ala Glu Ile
        785                 790                 795                 800
        Glu Ser His His Pro Arg Leu Ala Ser Ala Val Gln Asp His Asp Gln
                        805                 810                 815
        Ile Val Thr Ser Arg Lys Ser Gln Glu Pro Ala Phe His Ile Ala Gly
                    820                 825                 830
        Asp Ala Cys Leu Gln Arg Lys Met Asn Val Asp Val Ser Ser Thr Ile
                    835                 840                 845
        Tyr Asn Asn Glu Val Leu His Gln Pro Leu Ser Glu Ala Gln Arg Lys
                    850                 855                 860
        Ser Lys Ser Leu Lys Ile Asn Leu Asn Tyr Ala Gly Asp Ala Leu Arg
        865                 870                 875                 880
        Glu Asn Thr Leu Val Ser Glu His Ala Gln Arg Asp Gln Arg Glu Thr
                        885                 890                 895
        Gln Cys Gln Met Lys Glu Ala Glu His Met Tyr Gln Asn Glu Gln Asp
                    900                 905                 910
        Asn Val Asn Lys His Thr Glu Gln Gln Glu Ser Leu Asp Gln Lys Leu
                    915                 920                 925
        Phe Gln Leu Gln Ser Lys Asn Met Trp Leu Gln Gln Gln Leu Val His
        930                 935                 940
        Ala His Lys Lys Ala Asp Asn Lys Ser Lys Ile Thr Ile Asp Ile His
        945                 950                 955                 960
        Phe Leu Glu Arg Lys Met Gln His His Leu Leu Lys Glu Lys Asn Glu
                        965                 970                 975
        Glu Ile Phe Asn Tyr Asn Asn His Leu Lys Asn Arg Ile Tyr Gln Tyr
                    980                 985                 990
        Glu Lys Glu Lys Ala Glu Thr Glu Asn Ser
                    995                 1000
```

<210> SEQ ID NO 476
<211> LENGTH: 356
<212> TYPE: DNA
<213> ORGANISM: Homo sapiens

<400> SEQUENCE: 476

```
    aggtctgccg gaaatgttag gcaccccaac tcaagtccca ggccccaggc atctttcctg    60
    ccctgccttg cttggcccat ccagtccagg cgcctggagc aagtgctcag ctacttctcc   120
    tgcactttga agacccctc ccactcctgg cctcacattt ctctgtgtga tccccactt    180
    ctgggctctg ccaccccaca gtgggaaagg ccaccctaga aagaagtccg ctggcaccca   240
    taggaagggg cctcaggagc aggaagggcc aggaccagaa ccttgcccac ggcaactgcc   300
    ttcctgcctc tccccttcct cctctgctct tgatctgtgt ttcaataaat aatgt        356
```

<210> SEQ ID NO 477
<211> LENGTH: 1876
<212> TYPE: DNA
<213> ORGANISM: Homo sapiens

<400> SEQUENCE: 477

```
    atgacctgcg gatcaggatt tggtgggcgc gccttcagct gcatctcggc ctgcgggccg    60
    cgccccggcc gctgctgcat caccgccgcc cctaccgtg gcatctcctg ctaccgcggc   120
    ctcaccgggg gcttcggcag ccacagcgtg tgcggaggct ttcgggccgg ctcctgcgga   180
    cgcagcttcg gctaccgctc cggggcgtg tgcgggccca gtccccatg catcaccacc   240
    gtgtcggtca cgagagcct cctcacgccc tcaacctgg agatcgaccc caacgcgcag   300
    tgcgtgaagc aggaggagaa ggagcagatc aagtccctca acaggaggtt cgcggccttc   360
    atcgacaagg tgcgcttcct ggagcagcag aacaaactgc tggagacaaa gctgcagttc   420
    taccagaacc gcgagtgttg ccagagcaac ctggagcccc tgttttgaggg ctacatcgag   480
    actctgcggc gggaggccga gtcgtggag gccgacagcg ggaggctggc ctcagagctt   540
    aaccacgtgc aggaggtgct ggagggctac aagaagaagt atgaggagga gttctctctg   600
    agagcaacag ctgaagaacga gtttgtggct ctgaagaggcg agtcctggta ccgcgcaag   660
    cgcaagtcag acctggaggc caacgtggag gccctgatcc aggagatcga cttcctgagg   720
    cggctgtatg aggaggagat ccgcattctc cagtcgcaca tctcagacac ctccgtggtt   780
    gtcaagctgg acaacagccg ggacctgaac atggactgca tcattgccga gattaaggca   840
    cagtatgacg acattgtcac ccgcagccgg gccgaggccg agtccggta ccgcgcaag   900
    tgtgaggaga tgaaggccc ggtgatcagg cacggggaga ccctgcgccc caccaaggag   960
    gagatcaatg agctgaaccg catgatccaa aggctgacgg ccgaggtgga gaatgccaag  1020
    tgccagaact ccaagctgga ggccgcggtg gctcagtctg agcagcaggg tgaggcagcc  1080
    ctcagtgatg cccgctgcaa gctggccgag ctggagggcg ccctgcagaa ggccaagcag  1140
```

```
                                                                -continued gacatggcct gcctgatcag ggagtaccag gaggtgatga actccaagct gggcctggac  1200
    atcgagatcg ccacctacag gcgcctgctg gagggcgagg agcagaggct atgtgaaggc  1260
    attggggctg tgaatgtctg tgtcagcagc tcccggggcg gggtcgtgtg cggggacctc  1320
    tgcgtgtcag gctcccggcc agtgactggc agtgtctgca gcgctccgtg caacgggaac  1380
    gtggcggtga gcaccggcct gtgtgcgccc tgcggccaat tgaacaccac ctgcggaggg  1440
    ggttcctgcg gcgtgggctc ctgtggtatc agctccctgg gtgtggggtc ttgcggcagc  1500
    agctgccgga aatgttaggc accccaactc aagtcccagg ccccaggcat ctttcctgcc  1560
    ctgccttgct tggcccatcc agtccaggcg cctggagcaa gtgctcagct acttctcctg  1620
    cactttgaaa gaccctcccc actcctggcc tcacatttct ctgtgtgatc ccccacttct  1680
    gggctctgcc accccacagt gggaaaggcc accctagaaa gaagtccgct ggcacccata  1740
    ggaaggggcc tcaggagcag gaagggccag gaccagaacc ttgcccacgg caactgcctt  1800
    cctgcctctc cccttcctcc tctgctcttg atctgtgttt caataaatta atgtagccaa  1860
    aaaaaaaaaa aaaaa                                                   1876

<210> SEQ ID NO 478
<211> LENGTH: 505
<212> TYPE: PRT
<213> ORGANISM: Homo sapiens

<400> SEQUENCE: 478

Met Thr Cys Gly Ser Gly Phe Gly Gly Arg Ala Phe Ser Cys Ile Ser
    1               5                   10                  15
    Ala Cys Gly Pro Arg Pro Gly Arg Cys Ile Thr Ala Ala Pro Tyr
                20                  25                  30
    Arg Gly Ile Ser Cys Tyr Arg Gly Leu Thr Gly Gly Phe Gly Ser His
                35                  40                  45
    Ser Val Cys Gly Gly Phe Arg Ala Gly Ser Cys Gly Arg Ser Phe Gly
            50                  55                  60
    Tyr Arg Ser Gly Gly Val Cys Gly Pro Ser Pro Cys Ile Thr Thr
    65                  70                  75                  80
    Val Ser Val Asn Glu Ser Leu Leu Thr Pro Leu Asn Leu Glu Ile Asp
                    85                  90                  95
    Pro Asn Ala Gln Cys Val Lys Gln Glu Glu Lys Glu Gln Ile Lys Ser
                100                 105                 110
    Leu Asn Ser Arg Phe Ala Ala Phe Ile Asp Lys Val Arg Phe Leu Glu
                115                 120                 125
    Gln Gln Asn Lys Leu Leu Glu Thr Lys Leu Gln Phe Tyr Gln Asn Arg
            130                 135                 140
    Glu Cys Cys Gln Ser Asn Leu Glu Pro Leu Phe Glu Gly Tyr Ile Glu
    145                 150                 155                 160
    Thr Leu Arg Arg Glu Ala Glu Cys Val Glu Ala Asp Ser Gly Arg Leu
                    165                 170                 175
    Ala Ser Glu Leu Asn His Val Gln Glu Val Leu Glu Gly Tyr Lys Lys
                180                 185                 190
    Lys Tyr Glu Glu Glu Val Ser Leu Arg Ala Thr Ala Glu Asn Glu Phe
                195                 200                 205
    Val Ala Leu Lys Lys Asp Val Asp Cys Ala Tyr Leu Arg Lys Ser Asp
            210                 215                 220
    Leu Glu Ala Asn Val Glu Ala Leu Ile Gln Glu Ile Asp Phe Leu Arg
    225                 230                 235                 240
    Arg Leu Tyr Glu Glu Glu Ile Arg Ile Leu Gln Ser His Ile Ser Asp
                    245                 250                 255
    Thr Ser Val Val Lys Leu Asp Asn Ser Arg Asp Leu Asn Met Asp
                260                 265                 270
    Cys Ile Ile Ala Glu Ile Lys Ala Gln Tyr Asp Asp Ile Val Thr Arg
                275                 280                 285
    Ser Arg Ala Glu Ala Glu Ser Trp Tyr Arg Ser Lys Cys Glu Glu Met
            290                 295                 300
    Lys Ala Thr Val Ile Arg His Gly Glu Thr Leu Arg Arg Thr Lys Glu
    305                 310                 315                 320
    Glu Ile Asn Glu Leu Asn Arg Met Ile Gln Arg Leu Thr Ala Glu Val
                    325                 330                 335
    Glu Asn Ala Lys Cys Gln Asn Ser Lys Leu Glu Ala Val Ala Gln
                340                 345                 350
    Ser Glu Gln Gln Gly Glu Ala Ala Leu Ser Asp Ala Arg Cys Lys Leu
                355                 360                 365
    Ala Glu Leu Glu Gly Ala Leu Gln Lys Ala Lys Gln Asp Met Ala Cys
            370                 375                 380
    Leu Ile Arg Glu Tyr Gln Glu Val Met Asn Ser Lys Leu Gly Leu Asp
    385                 390                 395                 400
    Ile Glu Ile Ala Thr Tyr Arg Arg Leu Leu Glu Gly Glu Glu Gln Arg
                    405                 410                 415
    Leu Cys Glu Gly Ile Gly Ala Val Asn Val Cys Val Ser Ser Arg
                420                 425                 430
    Gly Gly Val Val Cys Gly Asp Leu Cys Val Ser Gly Ser Arg Pro Val
                435                 440                 445
    Thr Gly Ser Val Cys Ser Ala Pro Cys Asn Gly Asn Val Ala Val Ser
```

```
                  450                 455                 460
        Thr Gly Leu Cys Ala Pro Cys Gly Gln Leu Asn Thr Thr Cys Gly Gly
        465                 470                 475                 480
        Gly Ser Cys Gly Val Gly Ser Cys Gly Ile Ser Ser Leu Gly Val Gly
                            485                 490                 495
        Ser Cys Gly Ser Ser Cys Arg Lys Cys
                        500                 505

<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: 22
<223> OTHER INFORMATION: n = A,T,C or G

<400> SEQUENCE: 479
ggtccattcc tttcctcgcg tngggtttc tctgtgtcag cgagcctcgg tacactgatt    60
    tccgatcaaa agaatcatca tctttacctt gacttttcag ggaattactg aactttcttc   120
    tcagaagata gggcacagcc attgccttgg cctcacttga agggtctgca tttgggtcct   180
    ctggtctctt gccaagtttc ccagccactc gagggagaaa t                       221

<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480
cggcgaattc accatgggaa caagagctct gcagtg                              36

<210> SEQ ID NO 481
<211> LENGTH: 62
<212> TYPE: DNA
<213> ORGANISM: Artificial Sequence
<220> FEATURE:
<223> OTHER INFORMATION: PCR primer

<400> SEQUENCE: 481
cggcaagctt ttaatggtga tggtgatgat gtataacttc tgtttctgct ttctcttttt    60
    ca                                                                   62

<210> SEQ ID NO 482
<211> LENGTH: 972
<212> TYPE: DNA
<213> ORGANISM: Homo sapiens

<400> SEQUENCE: 482
atgggaacaa gagctctgca gtgtgaggtt tctcacactc atgaaaatga aaattatctc    60
    ttacatgaaa attgcatgtt gaaaaggaa attgccatgc taaaactgga aatagccaca   120
    ctgaaacacc aataccagga aaaggaaaat aaatactttg aggacattaa gatttttaaaa   180
    gaaaagaatg ctgaacttca gatgacccta aaactgaaag aggaatcatt aactaaaagg   240
    gcatctcaat atagtgggca gcttaaagtt ctgatagctg agaacacaat gctcacttct   300
    aaattgaagg aaaaacaaga caaagaaata ctagaggcag aaattgaatc acaccatcct   360
    agactggctt ctgctgtaca agaccatgat caaattgtga catcaagaaa agtcaagaa   420
    cctgctttcc acattgcagg agatgcttgt ttgcaaagaa aatgaatgt tgatgtgagt   480
    agtacgatat ataacaatga ggtgctccat caaccacttt ctgaagctca aaggaaatcc   540
    aaaagcctaa aaattaatct caattatgcc ggagatgctc taagagaaaa tacattggtt   600
    tcagaacatg cacaaagaga ccaacgtgaa acacagtgtc aaatgaagga agctgaacac   660
    atgtatcaaa acgaacaaga taatgtgaac aaacacactg aacagcagga gtctctagat   720
    cagaaattat ttcaactaca aagcaaaaat atgtggcttc aacagcaatt agttcatgca   780
    cataagaaag ctgacaacaa aagcaagata acaattgata ttcattttct tgagaggaaa   840
    atgcaacatc atctcctaaa agagaaaaat gaggagatat ttaattacaa taaccattta   900
    aaaaaccgta tatatcaata tgaaaaagag aaagcagaaa cagaagttat acatcatcac   960
    catcaccatt aa                                                       972

<210> SEQ ID NO 483
<211> LENGTH: 323
```

```
<212> TYPE: PRT
<213> ORGANISM: Homo sapiens

<400> SEQUENCE: 483

Met Gly Thr Arg Ala Leu Gln Cys Glu Val Ser His Thr His Glu Asn
    1               5                   10                  15
    Glu Asn Tyr Leu Leu His Glu Asn Cys Met Leu Lys Lys Glu Ile Ala
                20                  25                  30
    Met Leu Lys Leu Glu Ile Ala Thr Leu Lys His Gln Tyr Gln Glu Lys
                35                  40                  45
    Glu Asn Lys Tyr Phe Glu Asp Ile Lys Ile Leu Lys Glu Lys Asn Ala
            50                  55                  60
    Glu Leu Gln Met Thr Leu Lys Leu Lys Glu Glu Ser Leu Thr Lys Arg
    65                  70                  75                  80
    Ala Ser Gln Tyr Ser Gly Gln Leu Lys Val Leu Ile Ala Glu Asn Thr
                    85                  90                  95
    Met Leu Thr Ser Lys Leu Lys Glu Lys Gln Asp Lys Glu Ile Leu Glu
                100                 105                 110
    Ala Glu Ile Glu Ser His His Pro Arg Leu Ala Ser Ala Val Gln Asp
                115                 120                 125
    His Asp Gln Ile Val Thr Ser Arg Lys Ser Gln Glu Pro Ala Phe His
            130                 135                 140
    Ile Ala Gly Asp Ala Cys Leu Gln Arg Lys Met Asn Val Asp Val Ser
    145                 150                 155                 160
    Ser Thr Ile Tyr Asn Asn Glu Val Leu His Gln Pro Leu Ser Glu Ala
                    165                 170                 175
    Gln Arg Lys Ser Lys Ser Leu Lys Ile Asn Leu Asn Tyr Ala Gly Asp
                180                 185                 190
    Ala Leu Arg Glu Asn Thr Leu Val Ser Glu His Ala Gln Arg Asp Gln
                195                 200                 205
    Arg Glu Thr Gln Cys Gln Met Lys Glu Ala Glu His Met Tyr Gln Asn
            210                 215                 220
    Glu Gln Asp Asn Val Asn Lys His Thr Glu Gln Gln Glu Ser Leu Asp
    225                 230                 235                 240
    Gln Lys Leu Phe Gln Leu Gln Ser Lys Asn Met Trp Leu Gln Gln Gln
                    245                 250                 255
    Leu Val His Ala His Lys Lys Ala Asp Asn Lys Ser Lys Ile Thr Ile
                260                 265                 270
    Asp Ile His Phe Leu Glu Arg Lys Met Gln His His Leu Leu Lys Glu
                275                 280                 285
    Lys Asn Glu Glu Ile Phe Asn Tyr Asn Asn His Leu Lys Asn Arg Ile
            290                 295                 300
    Tyr Gln Tyr Glu Lys Glu Lys Ala Glu Thr Glu Val Ile His His His
    305                 310                 315                 320
    His His His

<210> SEQ ID NO 484
<211> LENGTH: 1518
<212> TYPE: DNA
<213> ORGANISM: Homo sapiens

<400> SEQUENCE: 484
atgacctgcg gatcaggatt tggtgggcgc gccttccgct gcatctcggc ctgcgggccg   60
        cggcccggcc gctgctgcat caccgccgcc ccctaccgtg gcatctcctg ctaccgcggc  120
        ctcaccgggg gcttcggcag ccacagcgtg tgcggaggct ttcgggccgg ctcctgcgga  180
        cgcagcttcg gctaccgctc cgggggcgtg tgcgggccca gtccccatg catcaccacc  240
        gtgtcggtca acgagagcct cctcacgccc ctcaacctgg agatcgaccc caacgcgcag  300
        tgcgtgaagc aggaggagaa ggagcagatc aagtccctca cagcaggtt cgcggccttc  360
        atcgacaagg tgcgcttcct ggagcagcag aacaaactgc tggagacaaa gctgcagttc  420
        taccagaacc gcgagtgttg ccagagcaac ctggagcccc tgtttgaggg ctacatcgag  480
        actctgcggc gggaggccga gtgcgtggag gccgacagcg ggaggctggc ctcagagctt  540
        aaccacgtgc aggaggtgct ggagggctac aagaagaagt atgaggagga ggtttctctg  600
        agagcaacag ctgagaacga gtttgtggct ctgaagaagg atgtggactg cgcctacctc  660
        cgcaagtcag acctggaggc caacgtggag gccctgatcc aggagatcga cttcctgagg  720
        cggctgtatg aggaggagat ccgcattctc cagtcgcaca ctcagacac ctccgtggtt  780
        gtcaagctgg acaacagccg ggacctgaac atggactgca tcattgccga gattaaggca  840
        cagtatgacg acattgtcac ccgcagccgg gccgaggccg agtcctggta ccgcagcaag  900
        tgtgaggaga tgaaggccac ggtgatcagg cacgggggaga ccctgcgccg caccaaggag  960
        gagatcaatg agctgaaccg catgatccaa aggctgacgg ccgaggtgga gaatgccaag 1020
        tgccagaact ccaagctgga ggccgcggtg gccagtctg agcagcaggg tgaggcagcc 1080
        ctcagtgatg cccgctgcaa gctggccgag ctggagggcg ccctgcagaa ggccaagcag 1140
        gacatggcct gcctgatcag ggagtaccag gaggtgatga actccaagct gggcctggac 1200
        atcgagatcg ccacctacag gcgcctgctg gagggcgagg agcagaggct atgtgaaggc 1260
        attggggctg tgaatgtctg tgtcagcagc tcccggggcg gggtcgtgtg cggggacctc 1320
        tgcgtgtcag gctcccggcc agtgactggc agtgtctgca gcgctccgtg caacgggaac 1380
        gtggcggtga gcaccggcct tgtgcgcccc tgcggccaat tgaacaccac ctgcggaggg 1440
```

-continued

```
      ggttcctgcg gcgtgggctc ctgtggtatc agctccctgg gtgtggggtc ttgcggcagc  1500
      agctgccgga aatgttag                                                 1518
```

<210> SEQ ID NO 485
<211> LENGTH: 505
<212> TYPE: PRT
<213> ORGANISM: Homo sapiens

<400> SEQUENCE: 485

```
Met Thr Cys Gly Ser Gly Phe Gly Gly Arg Ala Phe Arg Cys Ile Ser
 1               5                  10                  15
Ala Cys Gly Pro Arg Pro Gly Arg Cys Cys Ile Thr Ala Ala Pro Tyr
             20                  25                  30
Arg Gly Ile Ser Cys Tyr Arg Gly Leu Thr Gly Gly Phe Gly Ser His
         35                  40                  45
Ser Val Cys Gly Gly Phe Arg Ala Gly Ser Cys Gly Arg Ser Phe Gly
     50                  55                  60
Tyr Arg Ser Gly Gly Val Cys Gly Pro Ser Pro Pro Cys Ile Thr Thr
 65                  70                  75                  80
Val Ser Val Asn Glu Ser Leu Leu Thr Pro Leu Asn Leu Glu Ile Asp
                 85                  90                  95
Pro Asn Ala Gln Cys Val Lys Gln Glu Lys Glu Gln Ile Lys Ser
            100                 105                 110
Leu Asn Ser Arg Phe Ala Ala Phe Ile Asp Lys Val Arg Phe Leu Glu
        115                 120                 125
Gln Gln Asn Lys Leu Leu Glu Thr Lys Leu Gln Phe Tyr Gln Asn Arg
    130                 135                 140
Glu Cys Cys Gln Ser Asn Leu Glu Pro Leu Phe Glu Gly Tyr Ile Glu
145                 150                 155                 160
Thr Leu Arg Arg Glu Ala Glu Cys Val Glu Ala Asp Ser Gly Arg Leu
                165                 170                 175
Ala Ser Glu Leu Asn His Val Gln Glu Val Leu Glu Gly Tyr Lys Lys
            180                 185                 190
Lys Tyr Glu Glu Val Ser Leu Arg Ala Thr Ala Glu Asn Glu Phe
        195                 200                 205
Val Ala Leu Lys Lys Asp Val Asp Cys Ala Tyr Leu Arg Lys Ser Asp
    210                 215                 220
Leu Glu Ala Asn Val Glu Ala Leu Ile Gln Glu Ile Asp Phe Leu Arg
225                 230                 235                 240
Arg Leu Tyr Glu Glu Glu Ile Arg Ile Leu Gln Ser His Ile Ser Asp
                245                 250                 255
Thr Ser Val Val Val Lys Leu Asp Asn Ser Arg Asp Leu Asn Met Asp
            260                 265                 270
Cys Ile Ile Ala Glu Ile Lys Ala Gln Tyr Asp Asp Ile Val Thr Arg
        275                 280                 285
Ser Arg Ala Glu Ala Glu Ser Trp Tyr Arg Ser Lys Cys Glu Glu Met
    290                 295                 300
Lys Ala Thr Val Ile Arg His Gly Glu Thr Leu Arg Arg Thr Lys Glu
305                 310                 315                 320
Glu Ile Asn Glu Leu Asn Arg Met Ile Gln Arg Leu Thr Ala Glu Val
                325                 330                 335
Glu Asn Ala Lys Cys Gln Asn Ser Lys Leu Glu Ala Ala Val Ala Gln
            340                 345                 350
Ser Glu Gln Gln Gly Glu Ala Ala Leu Ser Asp Ala Arg Cys Lys Leu
        355                 360                 365
Ala Glu Leu Glu Gly Ala Leu Gln Lys Ala Lys Gln Asp Met Ala Cys
    370                 375                 380
Leu Ile Arg Glu Tyr Gln Glu Val Met Asn Ser Lys Leu Gly Leu Asp
385                 390                 395                 400
Ile Glu Ile Ala Thr Tyr Arg Arg Leu Leu Glu Gly Glu Glu Gln Arg
                405                 410                 415
Leu Cys Glu Gly Ile Gly Ala Val Asn Val Cys Val Ser Ser Ser Arg
            420                 425                 430
Gly Gly Val Val Cys Gly Asp Leu Cys Val Ser Gly Ser Arg Pro Val
        435                 440                 445
Thr Gly Ser Val Cys Ser Ala Pro Cys Asn Gly Asn Val Ala Val Ser
    450                 455                 460
Thr Gly Leu Cys Ala Pro Cys Gly Gln Leu Asn Thr Thr Cys Gly Gly
465                 470                 475                 480
Gly Ser Cys Gly Val Gly Ser Cys Gly Ile Ser Ser Leu Gly Val Gly
                485                 490                 495
Ser Cys Gly Ser Ser Cys Arg Lys Cys
            500                 505
```

<210> SEQ ID NO 486
<211> LENGTH: 827

```
<212> TYPE: DNA
<213> ORGANISM: Homo sapiens

<400> SEQUENCE: 486
gcattctcca gtcgcacatc tcagacacct ccgtggttgt caagctggac aacagccggg     60
      acctgaacat ggactgcatc attgccgaga ttaaggcaca gtatgacgac attgtcaccc    120
      gcagccgggc cgaggccgag tcctggtacc gcagcaagtg tgaggagatg aaggccacgg    180
      tgatcaggca cggggagacc ctgcgccgca ccaaggagga gatcaatgag ctgaaccgca    240
      tgatccaaag gctgacggcc gaggtggaga atgccaagtg ccagaactcc aagctggagg    300
      ccgcggtggc ccagtctgag cagcagggtg aggcagccct cagtgatgcc cgctgcaagc    360
      tggccgagct ggagggcgcc ctgcagaagg ccaagcagga catggcctgc ctgatcaggg    420
      agtaccagga ggtgatgaac tccaagctgg gcctggacat cgagatcgcc acctacagga    480
      gcctgctgga gggcgaggag cagaggctat gtgaaggcat tggggctgtg aatgtctgtg    540
      tcagcagctc ccggggcggg gtcgtgtgcg gggacctctg cgtgtcaggc tcccggccag    600
      tgactggcag tgtctgcagc gctccgtgca acgggaacgt ggcggtgagc accggcctgt    660
      gtgcgccctg cggccaattg aacaccacct gcggagggg ttcctgcggc gtgggctcct    720
      gtggtatcag ctccctgggt gtggggtctt gcggcagcag ctgccggaaa tgttaggcac    780
      cccaactcaa gtcccaggcc ccaggcatct ttcctgccct gccttgc                 827

<210> SEQ ID NO 487
<211> LENGTH: 235
<212> TYPE: PRT
<213> ORGANISM: Homo sapiens

<400> SEQUENCE: 487

Met Asp Cys Ile Ile Ala Glu Ile Lys Ala Gln Tyr Asp Asp Ile Val
       1               5                   10                  15
      Thr Arg Ser Arg Ala Glu Ala Glu Ser Trp Tyr Arg Ser Lys Cys Glu
                      20                  25                  30
      Glu Met Lys Ala Thr Val Ile Arg His Gly Glu Thr Leu Arg Arg Thr
                  35                  40                  45
      Lys Glu Glu Ile Asn Glu Leu Asn Arg Met Ile Gln Arg Leu Thr Ala
              50                  55                  60
      Glu Val Glu Asn Ala Lys Cys Gln Asn Ser Lys Leu Glu Ala Ala Val
      65                  70                  75                  80
      Ala Gln Ser Glu Gln Gln Gly Glu Ala Ala Leu Ser Asp Ala Arg Cys
                      85                  90                  95
      Lys Leu Ala Glu Leu Glu Gly Ala Leu Gln Lys Ala Lys Gln Asp Met
                  100                 105                 110
      Ala Cys Leu Ile Arg Glu Tyr Gln Glu Val Met Asn Ser Lys Leu Gly
              115                 120                 125
      Leu Asp Ile Glu Ile Ala Thr Tyr Arg Arg Leu Leu Glu Gly Glu Glu
          130                 135                 140
      Gln Arg Leu Cys Glu Gly Ile Gly Ala Val Asn Val Cys Val Ser Ser
      145                 150                 155                 160
      Ser Arg Gly Gly Val Val Cys Gly Asp Leu Cys Val Ser Gly Ser Arg
                      165                 170                 175
      Pro Val Thr Gly Ser Val Cys Ser Ala Pro Cys Asn Gly Asn Val Ala
                  180                 185                 190
      Val Ser Thr Gly Leu Cys Ala Pro Cys Gly Gln Leu Asn Thr Thr Cys
              195                 200                 205
      Gly Gly Gly Ser Cys Gly Val Gly Ser Cys Gly Ile Ser Ser Leu Gly
          210                 215                 220
      Val Gly Ser Cys Gly Ser Ser Cys Arg Lys Cys
      225                 230                 235

<210> SEQ ID NO 488
<211> LENGTH: 9
<212> TYPE: PRT
<213> ORGANISM: Homo sapiens

<400> SEQUENCE: 488

Ser Leu Thr Lys Arg Ala Ser Gln Tyr
       1               5

<210> SEQ ID NO 489
<211> LENGTH: 27
<212> TYPE: DNA
<213> ORGANISM: Homo sapiens

<400> SEQUENCE: 489
tcattaacta aagggcatc tcaatat                                         27
```

<210> SEQ ID NO 490
<211> LENGTH: 3288
<212> TYPE: DNA
<213> ORGANISM: Homo sapiens

<400> SEQUENCE: 490

```
atgaagttgc tgatggtcct catgctggcg gccctctccc agcactgcta cgcaggctct   60
ggctgcccct tattggagaa tgtgatttcc aagacaatca atccacaagt gtctaagact  120
gaatacaaag aacttcttca agagttcata gacgacaatg ccactacaaa tgccatagat  180
gaattgaagg aatgtttttct taaccaaacg gatgaaactc tgagcaatgt tgaggtgttt  240
atgcaattaa tatatgacag cagtctttgt gatttattta tgagtcccgc aaaagaaaca  300
tctgagaaat ttacgtgggc agcaaaagga agacctagga agatcgcatg ggagaaaaaa  360
gaaacacctg taaagactgg atgcgtggca agagtaacat ctaataaaac taaagttttg  420
gaaaaaggaa gatctaagat gattgcatgt cctacaaaag aatcatctac aaaagcaagt  480
gccaatgatc agaggttccc atcagaatcc aaacaagagg aagatgaaga atattcttgt  540
gattctcgga gtctctttga gagttctgca aagattcaag tgtgtatacc tgagtctata  600
tatcaaaaag taatgggagat aaatagaaga gtagaagagc ctcctaagaa gccatctgcc  660
ttcaagcctg ccattgaaat gcaaaactct gttccaaata aagcctttga attgaagaat  720
gaacaaacat tgagagcaga tccgatgttc ccaccagaat ccaaacaaaa ggactatgaa  780
gaaaattctt gggattctga gagtctctgt gagactgttt cacgaaggga tgtgtgttta  840
cccaaggcta cacatcaaaa agaaatagat aaaataaatg gaaaattaga agagtctcct  900
aataaagatg gtcttctgaa ggctacctgc ggaatgaaaa tttctattcc aactaaagcc  960
ttagaattga aggacatgca aactttcaaa gcagagcctc cggggaagcc atctgccttc 1020
gagcctgcca ctgaaatgca aaagtctgtc ccaataaaag ccttggaatt gaaaatgaa  1080
caaacattga gagcagatga gatactccca tcagaatcca aacaaaagga ctatgaagaa 1140
agttcttggg attctgagag tctctgtgag actgttttcac agaaggatgt cgtttaccc  1200
aaggctcrcrc atcaaaaaga aatagataaa ataaatgaa aattagaagg gtctcctgtt 1260
aaagatggtc ttctgaaggc taactgcgga atgaaagttt ctattccaac taaagcctta 1320
gaattgatgg acatgcaaac tttcaaagca gagcctccg agaagccatc tgccttcgag 1380
cctgccattg aaatgcaaaa gtctgttcca aataaagcct tggaattgaa gaatgaacaa 1440
acattgagag cagatgagat actcccatca gaatccaaac aaaaggacta tgaagaaagt 1500
tcttgggatt ctgagagtct ctgtgagact gtttcacaga aggatgtgtg tttacccaag 1560
gctrcrcatc aaaaagaaat agataaaata aatggaaaat tagaagagtc tcctgataat 1620
gatggttttc tgaaggctcc ctgcagaatg aaagtttcta ttccaactaa agccttagaa 1680
ttgatggaca tgcaaacttt caaagcagag cctcccgaga gccatctgc cttcgagcct 1740
gccattgaaa tgcaaaagtc tgttccaaat aaagccttgg aattgaagaa tgaacaaaca 1800
ttgagagcag atcagatgtt cccttcagaa tcaaaacaaa gaagttgaa gaaaaattct 1860
tgggattctg agagtctccg tgagactgtt tcacagaagg atgtgtgtgt acccaaggct 1920
acacatcaaa aagaaatgga taaataagt ggaaaattag aagattcaac tagcctatca 1980
aaaatcttgg atacagttca ttcttgtgaa agagcaaggg aacttcaaaa agatcactgt 2040
gaacaacgta caggaaaaat ggaacaaatg aaaaagaagt tttgtgtact gaaaaagaaa 2100
ctgtcagaag caaaagaaat aaaatcacag ttagagaacc aaaaagttaa atgggaacaa 2160
gagctctgca gtgtgagatt gactttaaac caagaagaag agaagagaag aaatgccgat 2220
atattaaatg aaaaaattag ggaagaatta ggaagaatcg aagagcagca taggaaagag 2280
ttagaagtga acaacaact tgaacaggct ctcagaatac aagatataga attgaagagt 2340
gtagaaagta atttgaatca ggtttctcac actcatgaaa atgaaaatta tctcttacat 2400
gaaaattgca tgttgaaaaa ggaaattgcc atgctaaaac tggaaatagc cacactgaaa 2460
caccaatacc aggaaaagga aaataaatac tttgaggaca ttaagatttt aaaagaaaag 2520
aatgctgaac ttcagatgac cctaaaactg aaagaggaat cattaactaa aagggcatct 2580
caatatagtg ggcagcttaa agttctgata gctgagaaca caatgctcac ttctaaattg 2640
aaggaaaaac aagacaaaga aatactagag gcagaaattg aatcaccaca tcctagactg 2700
gcttctgctg tacaagacca tgatcaaatt gtgacatcaa gaaaaagtca agaacctgct 2760
ttccacattg caggagatgc ttgtttgcaa agaaaaatga atgttgatgt gagtagtacg 2820
atatataaca atgaggtgct ccatcaacca ctttctgaag ctcaaggaa atccaaaagc 2880
ctaaaaaatta atctcaatta tgcmggagat gctctaagaa aaatacatt ggtttcagaa 2940
catgcacaaa gagaccaacg tgaaacacag tgtcaaatga aggaagctga acacatgtat 3000
caaaacgaac aagataatgt gaacaaacac actgaacagc aggagtctct agatcagaaa 3060
ttatttcaac tacaaagcaa aaatatgtgg cttcaacagc aattagttca tgcacataag 3120
aaagctgaca acaaaagcaa gataacaatt gatatttcatt ttcttgagag gaaaatgcaa 3180
catcatctcc taaaagagaa aaatgaggag atatttaatt acaataacca tttaaaaaac 3240
cgtatatatc aatatgaaaa agagaaagca gaaacagaaa actcatga                3288
```

<210> SEQ ID NO 491
<211> LENGTH: 2232
<212> TYPE: DNA
<213> ORGANISM: Homo sapiens

<400> SEQUENCE: 491

```
atgaagttgc tgatggtcct catgctggcg gccctctccc agcactgcta cgcaggctct   60
ggctgcccct tattggagaa tgtgatttcc aagacaatca atccacaagt gtctaagact  120
gaatacaaag aacttcttca agagttcata gacgacaatg ccactacaaa tgccatagat  180
gaattgaagg aatgtttttct taaccaaacg gatgaaactc tgagcaatgt tgaggtgttt  240
atgcaattaa tatatgacag cagtctttgt gatttattta tgagtcccgc aaaagaaaca  300
tctgagaaat ttacgtgggc agcaaaagga agacctagga agatcgcatg ggagaaaaaa  360
```

```
                gaaacacctg taaagactgg atgcgtggca agagtaacat ctaataaaac taaagttttg  420
                gaaaaaggaa gatctaagat gattgcatgt cctacaaaag aatcatctac aaaagcaagt  480
                gccaatgatc agaggttccc atcagaatcc aaacaagagg aagatgaaga atattcttgt  540
                gattctcgga gtctctttga gagttctgca aagattcaag tgtgtatacc tgagtctata  600
                tatcaaaaag taatggagat aaatagagaa gtagaagagc ctcctaagaa gccatctgcc  660
                ttcaagcctg ccattgaaat gcaaaactct gttccaaata aagcctttga attgaagaat  720
                gaacaaacat tgagagcaga tccgatgttc ccaccagaat ccaaacaaaa ggactatgaa  780
                gaaaattctt gggattctga gagtctctgt gagactgttt cacagaagga tgtgtgttta  840
                cccaaggcta cacatcaaaa agaaatagat aaaataaatg gaaaattaga agagtctcct  900
                aataaagatg gtcttctgaa ggctacctgc ggaatgaaag tttctattcc aactaaagcc  960
                ttagaattga aggacatgca aactttcaaa gcagagcctc cggggaagcc atctgccttc 1020
                gagcctgcca ctgaaatgca aaagtctgtc ccaaatgaag ccttggaatt gaaaaatgaa 1080
                caaacattga gagcagatga gatactccca tcagaatcca aacaaaagga ctatgaagaa 1140
                agttcttggg attctgagag tctctgtgag actgtttcac agaaggatgt gtgtttaccc 1200
                aaggctrcrc atcaaaaaga aatagataaa ataaatggaa aattagaagg gtctcctgtt 1260
                aaagatggtc ttctgaaggc taactgcgga atgaaagttt ctattccaac taaagcctta 1320
                gaattgatgg acatgcaaac tttcaaagca gagcctcccg agaagccatc tgccttcgag 1380
                cctgccattg aaatgcaaaa gtctgttcca aataaagcct tggaattgaa gaatgaacaa 1440
                acattgagag cagatgagat actcccatca gaatccaaac aaaaggacta tgaagaaagt 1500
                tcttgggatt ctgagagtct ctgtgagact gtttcacaga aggatgtgtg tttacccaag 1560
                gctrcrcatc aaaaagaaat agataaaata aatggaaaat tagaagactc tcctgataat 1620
                gatggttttc tgaaggctcc ctgcagaatg aaagtttcta ttccaactaa agccttagaa 1680
                ttgatggaca tgcaaacttt caaagcagag cctcccgaga agccatctgc cttcgagcct 1740
                gccattgaaa tgcaaaagtc tgttccaaat aaagcttggg aattgaagaa tgaacaaaca 1800
                ttgagagcag atcagatgtt cccttcagaa tcaaaacaaa ggaasgttga agaaaattct 1860
                tgggattctg agagtctccg tgagactgtt tcacagaagg atgtgtgtgt acccaaggct 1920
                acacatcaaa agaaatggga taaaataagt ggaaaattag aagattcaac tagcctatca 1980
                aaaatcttgg atacagttca ttcttgtgaa agagcaaggg aacttcaaaa agatcactgt 2040
                gaacaacgta caggaaaaat ggaacaaatg aaaaagaaat tttgtgtact gaaaagaaa  2100
                ctgtcagaag caaaagaaat aaaatcacag ttagagaacc aaaaagttaa atgggaacaa 2160
                gagctctgca gtgtgaggtt tctcacactc atgaaaatga aaattatctc ttacatgaaa 2220
                attgcatgtt ga                                                     2232
```

<210> SEQ ID NO 492
<211> LENGTH: 1233
<212> TYPE: DNA
<213> ORGANISM: Homo sapiens

<400> SEQUENCE: 492

```
                atgaagttgc tgatggtcct catgctggcg gccctctccc agcactgcta cgcaggctct   60
                ggctgccccct tattggagaa tgtgatttcc aagacaatca atccacaagt gtcaagact  120
                gaatacaaag aacttcttca agagttcata gacgacaatg ccactacaaa tgccatagat  180
                gaattgaagg aatgtttttct taaccaaacg gatgaaactc tgagcaatgt tgaggtgttt  240
                atgcaattaa tatatgacag cagtctttgt gatttattta tgggaacaag agctctgcag  300
                tgtgaggttt ctcacactca tgaaaatgaa aattatctct acatgaaaa ttgcatgttg  360
                aaaaaggaaa ttgccatgct aaaactggaa atagccacac tgaaacacca ataccaggaa  420
                aaggaaaata aatactttga ggacattaag attttaaag aaagaatgc tgaacttcag  480
                atgaccctaa aactgaaaga ggaatcatta actaaaaggg catctcaata tagtgggcag  540
                cttaaagttc tgatagctga gaacacaatg ctcacttcta aattgaagga aaaacaagac  600
                aaagaaatac tagaggcaga aattgaatca caccatccta gactggcttt gctgtacaa  660
                gaccatgatc aaattgtgac atcaagaaaa agtcaagaac ctgctttcca cattgcagga  720
                gatgcttgtt tgcaaagaaa aatgaatgtt gatgtgagta gtacgatata taacaatgag  780
                gtgctccatc aaccactttc tgaagctcaa aggaaatcca aaagcctaaa aattaatctc  840
                aattatgccg gagatgctct aagagaaaat acattggttt cagaacatgc acaaagagac  900
                caacgtgaaa cacagtgtca aatgaaggaa gctgaacaca tgtatcaaaa cgaacaagat  960
                aatgtgaaca aacactacta acagcaggag tctctacaa atgaaattatt tcaactacaa 1020
                agcaaaaata tgtggcttca acagcaatta gttcatgcac ataagaaagc tgcaacaaa 1080
                agcaagataa caattgatat tcattttctt gagaggaaaa tgcaacatca tctcctaaaa 1140
                gagaaaaatg aggagatatt taattacaat aaccatttaa aaaaccgtat atatcaatat 1200
                gaaaaagaga aagcagaaac agaagttata taa                               1233
```

<210> SEQ ID NO 493
<211> LENGTH: 1095
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 493

```
                Met Lys Leu Leu Met Val Leu Met Leu Ala Ala Leu Ser Gln His Cys
                 1               5                  10                  15
                Tyr Ala Gly Ser Gly Cys Pro Leu Leu Glu Asn Val Ile Ser Lys Thr
                            20                  25                  30
```

-continued

```
Ile Asn Pro Gln Val Ser Lys Thr Glu Tyr Lys Glu Leu Leu Gln Glu
             35                  40                  45
Phe Ile Asp Asp Asn Ala Thr Thr Asn Ala Ile Asp Glu Leu Lys Glu
 50                  55                  60
Cys Phe Leu Asn Gln Thr Asp Glu Thr Leu Ser Asn Val Glu Val Phe
 65                  70                  75                  80
Met Gln Leu Ile Tyr Asp Ser Ser Leu Cys Asp Leu Phe Met Ser Pro
                 85                  90                  95
Ala Lys Glu Thr Ser Glu Lys Phe Thr Trp Ala Ala Lys Gly Arg Pro
                100                 105                 110
Arg Lys Ile Ala Trp Glu Lys Lys Glu Thr Pro Val Lys Thr Gly Cys
             115                 120                 125
Val Ala Arg Val Thr Ser Asn Lys Thr Lys Val Leu Glu Lys Gly Arg
         130                 135                 140
Ser Lys Met Ile Ala Cys Pro Thr Lys Glu Ser Ser Thr Lys Ala Ser
145                 150                 155                 160
Ala Asn Asp Gln Arg Phe Pro Ser Glu Ser Lys Gln Glu Glu Asp Glu
                165                 170                 175
Glu Tyr Ser Cys Asp Ser Arg Ser Leu Phe Glu Ser Ser Ala Lys Ile
                180                 185                 190
Gln Val Cys Ile Pro Glu Ser Ile Tyr Gln Lys Val Met Glu Ile Asn
             195                 200                 205
Arg Glu Val Glu Glu Pro Pro Lys Lys Pro Ser Ala Phe Lys Pro Ala
         210                 215                 220
Ile Glu Met Gln Asn Ser Val Pro Asn Lys Ala Phe Glu Leu Lys Asn
225                 230                 235                 240
Glu Gln Thr Leu Arg Ala Asp Pro Met Phe Pro Pro Glu Ser Lys Gln
                245                 250                 255
Lys Asp Tyr Glu Glu Asn Ser Trp Asp Ser Glu Ser Leu Cys Glu Thr
                260                 265                 270
Val Ser Gln Lys Asp Val Cys Leu Pro Lys Ala Thr His Gln Lys Glu
             275                 280                 285
Ile Asp Lys Ile Asn Gly Lys Leu Glu Glu Ser Pro Asn Lys Asp Gly
         290                 295                 300
Leu Leu Lys Ala Thr Cys Gly Met Lys Val Ser Ile Pro Thr Lys Ala
305                 310                 315                 320
Leu Glu Leu Lys Asp Met Gln Thr Phe Lys Ala Glu Pro Pro Gly Lys
                325                 330                 335
Pro Ser Ala Phe Glu Pro Ala Thr Glu Met Gln Lys Ser Val Pro Asn
                340                 345                 350
Lys Ala Leu Glu Leu Lys Asn Glu Gln Thr Leu Arg Ala Asp Glu Ile
             355                 360                 365
Leu Pro Ser Glu Ser Lys Gln Lys Asp Tyr Glu Glu Ser Ser Trp Asp
         370                 375                 380
Ser Glu Ser Leu Cys Glu Thr Val Ser Gln Lys Asp Val Cys Leu Pro
385                 390                 395                 400
Lys Ala Xaa His Gln Lys Glu Ile Asp Lys Ile Asn Gly Lys Leu Glu
                405                 410                 415
Gly Ser Pro Val Lys Asp Gly Leu Leu Lys Ala Asn Cys Gly Met Lys
             420                 425                 430
Val Ser Ile Pro Thr Lys Ala Leu Glu Leu Met Asp Met Gln Thr Phe
         435                 440                 445
Lys Ala Glu Pro Pro Glu Lys Pro Ser Ala Phe Glu Pro Ala Ile Glu
450                 455                 460
Met Gln Lys Ser Val Pro Asn Lys Ala Leu Glu Leu Lys Asn Glu Gln
465                 470                 475                 480
Thr Leu Arg Ala Asp Glu Ile Leu Pro Ser Glu Ser Lys Gln Lys Asp
                485                 490                 495
Tyr Glu Glu Ser Ser Trp Asp Ser Glu Ser Leu Cys Glu Thr Val Ser
                500                 505                 510
Gln Lys Asp Val Cys Leu Pro Lys Ala Xaa His Gln Lys Glu Ile Asp
             515                 520                 525
Lys Ile Asn Gly Lys Leu Glu Glu Ser Pro Asp Asn Asp Gly Phe Leu
         530                 535                 540
Lys Ala Pro Cys Arg Met Lys Val Ser Ile Pro Thr Lys Ala Leu Glu
545                 550                 555                 560
Leu Met Asp Met Gln Thr Phe Lys Ala Glu Pro Pro Glu Lys Pro Ser
                565                 570                 575
Ala Phe Glu Pro Ala Ile Glu Met Gln Lys Ser Val Pro Asn Lys Ala
                580                 585                 590
Leu Glu Leu Lys Asn Glu Gln Thr Leu Arg Ala Asp Gln Met Phe Pro
             595                 600                 605
Ser Glu Ser Lys Gln Lys Xaa Val Glu Glu Asn Ser Trp Asp Ser Glu
         610                 615                 620
Ser Leu Arg Glu Thr Val Ser Gln Lys Asp Val Cys Val Pro Lys Ala
625                 630                 635                 640
Thr His Gln Lys Glu Met Asp Lys Ile Ser Gly Lys Leu Glu Asp Ser
                645                 650                 655
Thr Ser Leu Ser Lys Ile Leu Asp Thr Val His Ser Cys Glu Arg Ala
```

```
                         660                 665                 670
      Arg Glu Leu Gln Lys Asp His Cys Glu Gln Arg Thr Gly Lys Met Glu
              675                 680                 685
      Gln Met Lys Lys Lys Phe Cys Val Leu Lys Lys Lys Leu Ser Glu Ala
          690                 695                 700
      Lys Glu Ile Lys Ser Gln Leu Glu Asn Gln Lys Val Lys Trp Glu Gln
      705                 710                 715                 720
      Glu Leu Cys Ser Val Arg Leu Thr Leu Asn Gln Glu Glu Lys Arg
                      725                 730                 735
      Arg Asn Ala Asp Ile Leu Asn Glu Lys Ile Arg Glu Glu Leu Gly Arg
                  740                 745                 750
      Ile Glu Gln His Arg Lys Gln Leu Glu Val Lys Gln Gln Leu Glu
              755                 760                 765
      Gln Ala Leu Arg Ile Gln Asp Ile Glu Leu Lys Ser Val Glu Ser Asn
          770                 775                 780
      Leu Asn Gln Val Ser His Thr His Glu Asn Asn Tyr Leu Leu His
      785                 790                 795                 800
      Glu Asn Cys Met Leu Lys Lys Glu Ile Ala Met Leu Lys Leu Glu Ile
                      805                 810                 815
      Ala Thr Leu Lys His Gln Tyr Gln Lys Glu Asn Lys Tyr Phe Glu
                  820                 825                 830
      Asp Ile Lys Ile Leu Lys Glu Lys Asn Ala Glu Leu Gln Met Thr Leu
              835                 840                 845
      Lys Leu Lys Glu Glu Ser Leu Thr Lys Arg Ala Ser Gln Tyr Ser Gly
      850                 855                 860
      Gln Leu Lys Val Leu Ile Ala Glu Asn Thr Met Leu Thr Ser Lys Leu
      865                 870                 875                 880
      Lys Glu Lys Gln Asp Lys Glu Ile Leu Glu Ala Glu Ile Glu Ser His
                      885                 890                 895
      His Pro Arg Leu Ala Ser Ala Val Gln Asp His Asp Gln Ile Val Thr
                  900                 905                 910
      Ser Arg Lys Ser Gln Glu Pro Ala Phe His Ile Ala Gly Asp Ala Cys
              915                 920                 925
      Leu Gln Arg Lys Met Asn Val Asp Val Ser Ser Thr Ile Tyr Asn Asn
          930                 935                 940
      Glu Val Leu His Gln Pro Leu Ser Glu Ala Gln Arg Lys Ser Lys Ser
      945                 950                 955                 960
      Leu Lys Ile Asn Leu Asn Tyr Ala Gly Asp Ala Leu Arg Glu Asn Thr
                      965                 970                 975
      Leu Val Ser Glu His Ala Gln Arg Asp Gln Arg Glu Thr Gln Cys Gln
                  980                 985                 990
      Met Lys Glu Ala Glu His Met Tyr Gln Asn Glu Gln Asp Asn Val Asn
              995                 1000                1005
      Lys His Thr Glu Gln Gln Glu Ser Leu Asp Gln Lys Leu Phe Gln Leu
          1010                1015                1020
      Gln Ser Lys Asn Met Trp Leu Gln Gln Gln Leu Val His Ala His Lys
      1025                1030                1035                1040
      Lys Ala Asp Asn Lys Ser Lys Ile Thr Ile Asp Ile His Phe Leu Glu
                      1045                1050                1055
      Arg Lys Met Gln His His Leu Leu Lys Leu Lys Asn Glu Gly Ile Phe
                  1060                1065                1070
      Asn Tyr Asn Asn His Leu Lys Asn Arg Ile Tyr Gln Tyr Glu Lys Glu
              1075                1080                1085
      Lys Ala Glu Thr Glu Asn Ser
          1090                1095

<210> SEQ ID NO 494
<211> LENGTH: 743
<212> TYPE: PRT
<213> ORGANISM: Homo sapiens
<220> FEATURE:
<221> NAME/KEY: VARIANT
<222> LOCATION: 403, 522, 615
<223> OTHER INFORMATION: Xaa = Any Amino Acid

<400> SEQUENCE: 494

Met Lys Leu Leu Met Val Leu Met Leu Ala Ala Leu Ser Gln His Cys
      1               5                   10                  15
      Tyr Ala Gly Ser Gly Cys Pro Leu Leu Glu Asn Val Ile Ser Lys Thr
                      20                  25                  30
      Ile Asn Pro Gln Val Ser Lys Thr Glu Tyr Lys Glu Leu Leu Gln Glu
                  35                  40                  45
      Phe Ile Asp Asp Asn Ala Thr Asn Ala Ile Asp Glu Leu Lys Glu
              50                  55                  60
      Cys Phe Leu Asn Gln Thr Asp Glu Thr Leu Ser Asn Val Glu Val Phe
      65                  70                  75                  80
      Met Gln Leu Ile Tyr Asp Ser Ser Leu Cys Asp Leu Phe Met Ser Pro
```

```
            85                    90                      95
Ala Lys Glu Thr Ser Glu Lys Phe Thr Trp Ala Ala Lys Gly Arg Pro
            100                   105                     110
Arg Lys Ile Ala Trp Glu Lys Lys Glu Thr Pro Val Lys Thr Gly Cys
            115                   120                     125
Val Ala Arg Val Thr Ser Asn Lys Thr Lys Val Leu Glu Lys Gly Arg
            130                   135                     140
Ser Lys Met Ile Ala Cys Pro Thr Lys Glu Ser Ser Thr Lys Ala Ser
145                       150                     155             160
Ala Asn Asp Gln Arg Phe Pro Ser Glu Ser Lys Gln Glu Glu Asp Glu
                165                     170                     175
Glu Tyr Ser Cys Asp Ser Arg Ser Leu Phe Glu Ser Ser Ala Lys Ile
                180                     185                     190
Gln Val Cys Ile Pro Glu Ser Ile Tyr Gln Lys Val Met Glu Ile Asn
            195                     200                     205
Arg Glu Val Glu Glu Pro Pro Lys Lys Pro Ser Ala Phe Lys Pro Ala
            210                     215                     220
Ile Glu Met Gln Asn Ser Val Pro Asn Lys Ala Phe Glu Leu Lys Asn
225                       230                     235                 240
Glu Gln Thr Leu Arg Ala Asp Pro Met Phe Pro Pro Glu Ser Lys Gln
                        245                     250                     255
Lys Asp Tyr Glu Glu Asn Ser Trp Asp Ser Glu Ser Leu Cys Glu Thr
                260                     265                     270
Val Ser Gln Lys Asp Val Cys Leu Pro Lys Ala Thr His Gln Lys Glu
            275                     280                     285
Ile Asp Lys Ile Asn Gly Lys Leu Glu Glu Ser Pro Asn Lys Asp Gly
            290                     295                     300
Leu Leu Lys Ala Thr Cys Gly Met Lys Val Ser Ile Pro Thr Lys Ala
305                       310                     315                 320
Leu Glu Leu Lys Asp Met Gln Thr Phe Lys Ala Glu Pro Pro Gly Lys
                        325                     330                     335
Pro Ser Ala Phe Glu Pro Ala Thr Glu Met Gln Lys Ser Val Pro Asn
                    340                     345                     350
Lys Ala Leu Glu Leu Lys Asn Glu Gln Thr Leu Arg Ala Asp Glu Ile
                355                     360                     365
Leu Pro Ser Glu Ser Lys Gln Lys Asp Tyr Glu Glu Ser Ser Trp Asp
            370                     375                     380
Ser Glu Ser Leu Cys Glu Thr Val Ser Gln Lys Asp Val Cys Leu Pro
385                       390                     395                 400
Lys Ala Xaa His Gln Lys Glu Ile Asp Lys Ile Asn Gly Lys Leu Glu
                        405                     410                     415
Gly Ser Pro Val Lys Asp Gly Leu Leu Lys Ala Asn Cys Gly Met Lys
                    420                     425                     430
Val Ser Ile Pro Thr Lys Ala Leu Glu Leu Met Asp Met Gln Thr Phe
                435                     440                     445
Lys Ala Glu Pro Pro Glu Lys Pro Ser Ala Phe Glu Pro Ala Ile Glu
            450                     455                     460
Met Gln Lys Ser Val Pro Asn Lys Ala Leu Glu Leu Lys Asn Glu Gln
465                       470                     475                 480
Thr Leu Arg Ala Asp Glu Ile Leu Pro Ser Glu Ser Lys Gln Lys Asp
                        485                     490                     495
Tyr Glu Glu Ser Ser Trp Asp Ser Glu Ser Leu Cys Glu Thr Val Ser
                    500                     505                     510
Gln Lys Asp Val Cys Leu Pro Lys Ala Xaa His Gln Lys Glu Ile Asp
            515                     520                     525
Lys Ile Asn Gly Lys Leu Glu Glu Ser Pro Asp Asn Asp Gly Phe Leu
            530                     535                     540
Lys Ala Pro Cys Arg Met Lys Val Ser Ile Pro Thr Lys Ala Leu Glu
545                       550                     555                 560
Leu Met Asp Met Gln Thr Phe Lys Ala Glu Pro Pro Glu Lys Pro Ser
                        565                     570                     575
Ala Phe Glu Pro Ala Ile Glu Met Gln Lys Ser Val Pro Asn Lys Ala
                    580                     585                     590
Leu Glu Leu Lys Asn Glu Gln Thr Leu Arg Ala Asp Gln Met Phe Pro
                595                     600                     605
Ser Glu Ser Lys Gln Lys Xaa Val Glu Glu Asn Ser Trp Asp Ser Glu
            610                     615                     620
Ser Leu Arg Glu Thr Val Ser Gln Lys Asp Val Cys Val Pro Lys Ala
625                       630                     635                 640
Thr His Gln Lys Glu Met Asp Lys Ile Ser Gly Lys Leu Glu Asp Ser
                        645                     650                     655
Thr Ser Leu Ser Lys Ile Leu Asp Thr Val His Ser Cys Glu Arg Ala
                    660                     665                     670
Arg Glu Leu Gln Lys Asp His Cys Glu Gln Arg Thr Gly Lys Met Glu
                675                     680                     685
Gln Met Lys Lys Lys Phe Cys Val Leu Lys Lys Leu Ser Glu Ala
            690                     695                     700
Lys Glu Ile Lys Ser Gln Leu Glu Asn Gln Lys Val Lys Trp Glu Gln
705                       710                     715                 720
```

```
        Glu Leu Cys Ser Val Arg Phe Leu Thr Leu Met Lys Met Lys Ile Ile
                        725                 730                 735
        Ser Tyr Met Lys Ile Ala Cys
                        740

<210> SEQ ID NO 495
<211> LENGTH: 410
<212> TYPE: PRT
<213> ORGANISM: Homo sapiens

<400> SEQUENCE: 495

Met Lys Leu Leu Met Val Leu Met Leu Ala Ala Leu Ser Gln His Cys
        1               5                   10                  15
        Tyr Ala Gly Ser Gly Cys Pro Leu Leu Glu Asn Val Ile Ser Lys Thr
                        20                  25                  30
        Ile Asn Pro Gln Val Ser Lys Thr Glu Tyr Lys Glu Leu Leu Gln Glu
                    35                  40                  45
        Phe Ile Asp Asp Asn Ala Thr Thr Asn Ala Ile Asp Glu Leu Lys Glu
            50                  55                  60
        Cys Phe Leu Asn Gln Thr Asp Glu Thr Leu Ser Asn Val Glu Val Phe
        65                  70                  75                  80
        Met Gln Leu Ile Tyr Asp Ser Ser Leu Cys Asp Leu Phe Met Gly Thr
                        85                  90                  95
        Arg Ala Leu Gln Cys Glu Val Ser His Thr His Glu Asn Glu Asn Tyr
                    100                 105                 110
        Leu Leu His Glu Asn Cys Met Leu Lys Lys Glu Ile Ala Met Leu Lys
                115                 120                 125
        Leu Glu Ile Ala Thr Leu Lys His Gln Tyr Gln Leu Lys Glu Asn Lys
            130                 135                 140
        Tyr Phe Glu Asp Ile Lys Ile Leu Lys Glu Lys Asn Ala Glu Leu Gln
        145                 150                 155                 160
        Met Thr Leu Lys Leu Lys Glu Glu Ser Leu Thr Lys Arg Ala Ser Gln
                        165                 170                 175
        Tyr Ser Gly Gln Leu Lys Val Leu Ile Ala Glu Asn Thr Met Leu Thr
                    180                 185                 190
        Ser Lys Leu Lys Glu Lys Gln Asp Lys Glu Ile Leu Glu Ala Glu Ile
                195                 200                 205
        Glu Ser His His Pro Arg Leu Ala Ser Ala Val Gln Asp His Asp Gln
            210                 215                 220
        Ile Val Thr Ser Arg Lys Ser Gln Glu Pro Ala Phe His Ile Ala Gly
        225                 230                 235                 240
        Asp Ala Cys Leu Gln Arg Lys Met Asn Val Asp Val Ser Ser Thr Ile
                        245                 250                 255
        Tyr Asn Asn Glu Val Leu His Gln Pro Leu Ser Glu Ala Gln Arg Lys
                    260                 265                 270
        Ser Lys Ser Leu Lys Ile Asn Leu Asn Tyr Ala Gly Asp Ala Leu Arg
                275                 280                 285
        Glu Asn Thr Leu Val Ser Glu His Ala Gln Arg Asp Gln Arg Glu Thr
            290                 295                 300
        Gln Cys Gln Met Lys Glu Ala Glu His Met Tyr Gln Asn Glu Gln Asp
        305                 310                 315                 320
        Asn Val Asn Lys His Thr Glu Gln Glu Ser Leu Asp Gln Lys Leu
                        325                 330                 335
        Phe Gln Leu Gln Ser Lys Asn Met Trp Leu Gln Gln Leu Val His
                    340                 345                 350
        Ala His Lys Lys Ala Asp Asn Lys Ser Lys Ile Thr Ile Asp Ile His
                355                 360                 365
        Phe Leu Glu Arg Lys Met Gln His His Leu Lys Glu Lys Asn Glu
            370                 375                 380
        Glu Ile Phe Asn Tyr Asn Asn His Leu Lys Asn Arg Ile Tyr Gln Tyr
        385                 390                 395                 400
        Glu Lys Glu Lys Ala Glu Thr Glu Val Ile
                        405                 410

<210> SEQ ID NO 496
<211> LENGTH: 20
<212> TYPE: PRT
<213> ORGANISM: Homo sapiens

<400> SEQUENCE: 496

Ile Asp Glu Leu Lys Glu Cys Phe Leu Asn Gln Thr Asp Glu Thr Leu
        1               5                   10                  15
        Ser Asn Val Glu
                    20
```

```
<210> SEQ ID NO 497
<211> LENGTH: 15
<212> TYPE: PRT
<213> ORGANISM: Homo sapiens

<400> SEQUENCE: 497

Thr Thr Asn Ala Ile Asp Glu Leu Lys Glu Cys Phe Leu Asn Gln
      1               5                  10                  15

<210> SEQ ID NO 498
<211> LENGTH: 21
<212> TYPE: PRT
<213> ORGANISM: Homo sapiens

<400> SEQUENCE: 498

Ser Gln His Cys Tyr Ala Gly Ser Gly Cys Pro Leu Leu Glu Asn Val
      1               5                  10                  15
      Ile Ser Lys Thr Ile
                  20

<210> SEQ ID NO 499
<211> LENGTH: 20
<212> TYPE: PRT
<213> ORGANISM: Homo sapiens

<400> SEQUENCE: 499

Glu Tyr Lys Glu Leu Leu Gln Glu Phe Ile Asp Asp Asn Ala Thr Thr
      1               5                  10                  15
      Asn Ala Ile Asp
                  20

<210> SEQ ID NO 500
<211> LENGTH: 9
<212> TYPE: PRT
<213> ORGANISM: Homo sapiens

<400> SEQUENCE: 500

Lys Leu Leu Met Val Leu Met Leu Ala
      1               5

<210> SEQ ID NO 501
<211> LENGTH: 13
<212> TYPE: PRT
<213> ORGANISM: Homo sapiens

<400> SEQUENCE: 501

Gln Glu Phe Ile Asp Asp Asn Ala Thr Thr Asn Ala Ile
      1               5                  10

<210> SEQ ID NO 502
<211> LENGTH: 13
<212> TYPE: PRT
<213> ORGANISM: Homo sapiens

<400> SEQUENCE: 502

Leu Lys Glu Cys Phe Leu Asn Gln Thr Asp Glu Thr Leu
      1               5                  10

<210> SEQ ID NO 503
<211> LENGTH: 93
<212> TYPE: PRT
<213> ORGANISM: Homo sapiens

<400> SEQUENCE: 503

Met Lys Leu Leu Met Val Leu Met Leu Ala Ala Leu Ser Gln His Cys
```

```
        1               5                  10                  15
       Tyr Ala Gly Ser Gly Cys Pro Leu Leu Glu Asn Val Ile Ser Lys Thr
                       20                  25                  30
       Ile Asn Pro Gln Val Ser Lys Thr Glu Tyr Lys Glu Leu Leu Gln Glu
                   35                  40                  45
       Phe Ile Asp Asp Asn Ala Thr Thr Asn Ala Ile Asp Glu Leu Lys Glu
               50                  55                  60
       Cys Phe Leu Asn Gln Thr Asp Glu Thr Leu Ser Asn Val Glu Val Phe
       65                  70                  75                  80
       Met Gln Leu Ile Tyr Asp Ser Ser Leu Cys Asp Leu Phe
                           85                  90
```

<210> SEQ ID NO 504
<211> LENGTH: 1964
<212> TYPE: DNA
<213> ORGANISM: Homo sapiens

<400> SEQUENCE: 504

```
gcatgctcga cgccccatgt gctgaaaggg cgaggagcct cctgcggcgg ccctgtgtc   60
cctgcctcta cctgcgcacc tgcatgtgtt caaccccgg gagaacacct ggcggcccct  120
gacccaggtg cccgaggagg ccccgcttcg gggctgcggt ctctgcacca tgcacaacta  180
cctgtttctg gcgggggca tccgtggctc cggtgccaag gccgtctgct ccaacgagt  240
cttctgctac aaccctctga ccaacatctg gagccaggtt cggcccatgc agcaggcccg  300
agcccagctc aagctggtgg ccctggacgg gctgctctat gccatcggtg gcgaatgcct  360
gtacagcatg gagtgctacg acccgcgaac agacgcctgg accccacgcg cgccactccc  420
cgcaggcacc ttccctgtgg cccacgaggc tgtggcctgc cgtgggggaca tctacgtcac  480
cggggtcac ctcttctacc gcctgctcag gtacagcccc gtgaaggatg cttgggacga  540
gtgcccatac agtgccagcc accggcgttc cagcgacatc gttgcactgg ggggcttcct  600
gtaccgcttc gacctgctgc ggggcgtggg cgccgccgtg atgcgctaca acacagtgac  660
cggctcctgg agcagggctg cctccctgcc cctgcccgcc cccgcccac tgcgctgcac  720
cacctgggc aacaccattt actgcctcaa ccccccaggt cactgccacc tcacggtctc  780
tgggggact gcccagttcc aggccaagga gctgcagccc tccccttgg ggagcaccgg  840
ggtcctcagt ccattcatcc tgactctgcc ccctgaggac cggctgcaga cctcactctg  900
agtggcaggc agagaaccaa agctgcttcg ctgctctcca gggagaccct cctgggatgg  960
gcctgagagg ccgggggctca gggaaggggc tgggatcgga acttcctgct cttgtttctg 1020
gacaactttc cccttctgct ttaaaggttg tcgattattt tgaagcccag actccctcag 1080
cctctttctg cccctcactc cacacccaga ctgttcctg actcaattcc gtacctactt 1140
acagaccctc tcagcttgct gacacccccc tgtctgtggg actccctatt ccctagagcc 1200
agggactgat gcgtctccac agacaaggac ttggctcgct ggagctctgc tgagccgaga 1260
gaggagggg tagaaaacat tcacacttcc tatgctctgt cagcaggaca gggagcaaaa 1320
acgtccccag gcaacgccct cgcctctggg actttctgcc tgtcctaagg cctcccagg  1380
taccaacccc gtagctatct gggtctgttt ggcactgtgg attctcaagg cctagaacc  1440
cttgcctctg aaactggtcc gctggtgcag ccctgctgtc tgcagctcct gcccataccc 1500
ccagcccaca ccaggccagg cccactccgg gctcaccacc ctctgcagcc ttgtgggcct 1560
ctcccagccc ctccagaagc ccacccact tctcgccaac ccccgatctc taaatgaggc 1620
ctgagcgtca ccctagttct gcccctttt agctgtgtag acttggacga gacatttgac 1680
ttcccttct ccttgtctat aaaatgtgga cagtggacgt ctgtcaccca agagagttgt 1740
gggagacaag atcacagcta tgagcaccctc gcacggtgtc caggatgcac agcacaatcc 1800
atgatgcgtt ttctcccctt acgcactttg aaacccatgc tagaaaagtg aatacatctg 1860
actgtgctcc actccaacct ccagcctgga tgtccctgtc tgggccctt ttctgttttt 1920
tattctatgt tcagcaccac tggcaccaaa tacattttaa ttca              1964
```

<210> SEQ ID NO 505
<211> LENGTH: 732
<212> TYPE: DNA
<213> ORGANISM: Homo sapiens

<400> SEQUENCE: 505

```
atgcacaact acctgtttct ggcgggggc atccgtggct ccggtgccaa ggccgtctgc   60
tccaacgagg tcttctgcta caaccctctg accaacatct ggagccaggt tcgcccatg  120
cagcaggccc gagcccagct caagctggtg gccctggacg ggctgctcta tgccatcggt  180
ggcgaatgcc tgtacagcat ggagtgctac gacccgcgaa cagacgcctg gaccccacgc  240
gcgccactcc ccgcaggcac cttccctgtg gcccacgagg ctgtggcctg ccgtggggac  300
atctacgtca ccgggggtca cctcttctac cgcctgctca ggtacagccc cgtgaaggat  360
gcttgggacg agtgcccata cagtgccagc caccggcgtt ccagcgacat cgttgcactg  420
ggggcttcc tgtaccgctt cgacctgctg cggggcgtgg gcgccgccgt gatgcgctac  480
aacacagtga ccggctcctg gagcagggct gcctccctgc cctgcccgc ccccgcccca  540
ctgcgctgca ccaccctggg caacaccatt tactgcctca ccccccaggt cactgccacc  600
ttcacggtct ctgggggac tgcccagttc caggccaagg agctgcagcc cttcccttg  660
gggagcaccg gggtcctcag tccattcatc ctgactctgc ccctgagga ccggctgcag  720
acctcactct ga                                                     732
```

<210> SEQ ID NO 506
<211> LENGTH: 729

-continued

```
<212> TYPE: DNA
<213> ORGANISM: Homo sapiens

<400> SEQUENCE: 506
atgcacaact acctgtttct ggcggggggc atccgtggct ccggtgccaa ggccgtctgc    60
     tccaacgagg tcttctgcta caaccctctg accaacatct ggagccaggt tcggcccatg   120
     cagcaggccc gagcccagct caagctggtg gccctgacg ggctgctcta tgccatcggt   180
     ggcgaatgcc tgtacagcat ggagtgctac gacccgcgaa cagacgcctg gaccccacgc   240
     gcgccactcc ccgcaggcac cttccctgtg gccacgagg ctgtggcctg ccgtggggac   300
     atctacgtca ccgggggtca cctcttctac cgcctgctca ggtacagccc cgtgaaggat   360
     gcttgggacg agtgcccata cagtgccagc caccggcgtt ccagcgacat cgttgcactg   420
     gggggcttcc tgtaccgctt cgacctgctg cggggcgtgg cgccgccgt gatgcgctac   480
     aacacagtga ccggctcctg gagcagggct gcctcccgc ccctgccgc ccccgcccca   540
     ctgcgctgca ccaccctggg caacaccatt tactgcctca ccccaggt cactgccacc   600
     ttcacggtct ctgggggac tgcccagttc caggcaaagg agctgcagcc cttcccttg   660
     gggagcaccg gggtcctcag tccattcatc ctgactctgc ccctgagga ccggctgcag   720
     acctcactc                                                         729

<210> SEQ ID NO 507
<211> LENGTH: 243
<212> TYPE: PRT
<213> ORGANISM: Homo sapiens

<400> SEQUENCE: 507

Met His Asn Tyr Leu Phe Leu Ala Gly Gly Ile Arg Gly Ser Gly Ala
  1               5                  10                  15
Lys Ala Val Cys Ser Asn Glu Val Phe Cys Tyr Asn Pro Leu Thr Asn
             20                  25                  30
Ile Trp Ser Gln Val Arg Pro Met Gln Gln Ala Arg Ala Gln Leu Lys
         35                  40                  45
Leu Val Ala Leu Asp Gly Leu Leu Tyr Ala Ile Gly Gly Glu Cys Leu
     50                  55                  60
Tyr Ser Met Glu Cys Tyr Asp Pro Arg Thr Asp Ala Trp Thr Pro Arg
 65                  70                  75                  80
Ala Pro Leu Pro Ala Gly Thr Phe Pro Val Ala His Glu Ala Val Ala
                 85                  90                  95
Cys Arg Gly Asp Ile Tyr Val Thr Gly Gly His Leu Phe Tyr Arg Leu
            100                 105                 110
Leu Arg Tyr Ser Pro Val Lys Asp Ala Trp Asp Glu Cys Pro Tyr Ser
        115                 120                 125
Ala Ser His Arg Arg Ser Ser Asp Ile Val Ala Leu Gly Gly Phe Leu
    130                 135                 140
Tyr Arg Phe Asp Leu Leu Arg Gly Val Gly Ala Ala Val Met Arg Tyr
145                 150                 155                 160
Asn Thr Val Thr Gly Ser Trp Ser Arg Ala Ala Ser Leu Pro Leu Pro
                165                 170                 175
Ala Pro Ala Pro Leu Arg Cys Thr Thr Leu Gly Asn Thr Ile Tyr Cys
            180                 185                 190
Leu Asn Pro Gln Val Thr Ala Thr Phe Thr Val Ser Gly Gly Thr Ala
        195                 200                 205
Gln Phe Gln Ala Lys Glu Leu Gln Pro Phe Pro Leu Gly Ser Thr Gly
    210                 215                 220
Val Leu Ser Pro Phe Ile Leu Thr Leu Pro Pro Glu Asp Arg Leu Gln
225                 230                 235                 240
Thr Ser Leu

<210> SEQ ID NO 508
<211> LENGTH: 158
<212> TYPE: PRT
<213> ORGANISM: Homo sapiens

<400> SEQUENCE: 508

Met His Asn Tyr Leu Phe Leu Ala Gly Gly Ile Arg Gly Ser Gly Ala
  1               5                  10                  15
Lys Ala Val Cys Ser Asn Glu Val Phe Cys Tyr Asn Pro Leu Thr Asn
             20                  25                  30
Ile Trp Ser Gln Val Arg Pro Met Gln Gln Ala Arg Ala Gln Leu Lys
         35                  40                  45
Leu Val Ala Leu Asp Gly Leu Leu Tyr Ala Ile Gly Gly Glu Cys Leu
     50                  55                  60
Tyr Ser Met Glu Cys Tyr Asp Pro Arg Thr Asp Ala Trp Thr Pro Arg
 65                  70                  75                  80
Ala Pro Leu Pro Ala Gly Thr Phe Pro Val Ala His Glu Ala Val Ala
                 85                  90                  95
```

```
        Cys Arg Gly Asp Ile Tyr Val Thr Gly Gly His Leu Phe Tyr Arg Leu
                        100                 105                 110
        Leu Arg Tyr Ser Pro Val Lys Asp Ala Trp Asp Glu Cys Pro Tyr Ser
                    115                 120                 125
        Ala Ser His Arg Arg Ser Asp Ile Val Ala Leu Gly Gly Phe Leu
                130                 135                 140
        Tyr Arg Phe Asp Leu Leu Arg Gly Val Gly Ala Ala Val Met
        145                 150                 155
```

<210> SEQ ID NO 509
<211> LENGTH: 85
<212> TYPE: PRT
<213> ORGANISM: Homo sapiens

<400> SEQUENCE: 509

```
        Arg Tyr Asn Thr Val Thr Gly Ser Trp Ser Arg Ala Ala Ser Leu Pro
        1               5                   10                  15
        Leu Pro Ala Pro Ala Pro Leu Arg Cys Thr Thr Leu Gly Asn Thr Ile
                    20                  25                  30
        Tyr Cys Leu Asn Pro Gln Val Thr Ala Thr Phe Thr Val Ser Gly Gly
                    35                  40                  45
        Thr Ala Gln Phe Gln Ala Lys Glu Leu Gln Pro Phe Pro Leu Gly Ser
            50                  55                  60
        Thr Gly Val Leu Ser Pro Phe Ile Leu Thr Leu Pro Pro Glu Asp Arg
        65                  70                  75                  80
        Leu Gln Thr Ser Leu
                        85
```

<210> SEQ ID NO 510
<211> LENGTH: 732
<212> TYPE: DNA
<213> ORGANISM: Homo sapiens

<400> SEQUENCE: 510

```
atgcgacccc agggccccgc cgcctccccg cagcggctcc gcggcctcct gctgctcctg    60
ctgctgcagc tgcccgcgcc gtcgagcgcc tctgagatcc ccaaggggaa gcaaaaggcg   120
cagctccggc agagggaggt ggtggacctg tataatggaa tgtgcttaca agggccagca   180
ggagtgcctg gtcgagacgg gagccctggg gccaatgtta ttccgggtac acctgggatc   240
ccaggtcggg atggattcaa aggagaaaag ggggaatgtc tgagggaaag ctttgaggag   300
tcctggacac ccaactacaa gcagtgttca tggagttcat tgaattatgg catagatctt   360
gggaaaattg cggagtgtac atttacaaag atgcgttcaa atagtgctct aagagttttg   420
ttcagtggct cacttcggct aaaatgcaga aatgcatgct gtcagcgttg gtatttcaca   480
ttcaatggag ctgaatgttc aggacctctt cccattgaag ctataattta tttggaccaa   540
ggaagccctg aaatgaattc aacaattaat attcatcgca cttcttctgt ggaaggactt   600
tgtgaaggaa ttggtgctgg attagtggat gttgctatct gggttggcac ttgttcagat   660
tacccaaaag gagatgcttc tactggatgg aattcagttt ctcgcatcat tattgaagaa   720
ctaccaaaat aa                                                        732
```

<210> SEQ ID NO 511
<211> LENGTH: 729
<212> TYPE: DNA
<213> ORGANISM: Homo sapiens

<400> SEQUENCE: 511

```
atgcgacccc agggccccgc cgcctccccg cagcggctcc gcggcctcct gctgctcctg    60
ctgctgcagc tgcccgcgcc gtcgagcgcc tctgagatcc ccaaggggaa gcaaaaggcg   120
cagctccggc agagggaggt ggtggacctg tataatggaa tgtgcttaca agggccagca   180
ggagtgcctg gtcgagacgg gagccctggg gccaatgtta ttccgggtac acctgggatc   240
ccaggtcggg atggattcaa aggagaaaag ggggaatgtc tgagggaaag ctttgaggag   300
tcctggacac ccaactacaa gcagtgttca tggagttcat tgaattatgg catagatctt   360
gggaaaattg cggagtgtac atttacaaag atgcgttcaa atagtgctct aagagttttg   420
ttcagtggct cacttcggct aaaatgcaga aatgcatgct gtcagcgttg gtatttcaca   480
ttcaatggag ctgaatgttc aggacctctt cccattgaag ctataattta tttggaccaa   540
ggaagccctg aaatgaattc aacaattaat attcatcgca cttcttctgt ggaaggactt   600
tgtgaaggaa ttggtgctgg attagtggat gttgctatct gggttggcac ttgttcagat   660
tacccaaaag gagatgcttc tactggatgg aattcagttt ctcgcatcat tattgaagaa   720
ctaccaaaa                                                            729
```

<210> SEQ ID NO 512
<211> LENGTH: 837
<212> TYPE: DNA
<213> ORGANISM: Homo sapiens

```
<400> SEQUENCE: 512
atgcagcctg cggcggcctc ggagcgcggc ggagcagacg ctgaccacgt tcctctcctc    60
      ggtctcctcc gcctccagct ccgcgctgcc cggcagccgg gagccatgcg accccagggc   120
      cccgccgcct ccccgcagcg gctccgcggc ctcctgctgc tcctgctgct gcagctgccc   180
      gcgccgtcga gcgcctctga gatcccaag gggaagcaaa aggcgcagct ccggcagagg    240
      gaggtggtgg acctgtataa tggaatgtgc ttacaagggc cagcaggagt gcctggtcga   300
      gacgggagcc ctggggccaa tgttattccg ggtacacctg ggatcccagg tcgggatgga   360
      ttcaaaggag aaaaggggga atgtctgagg gaaagctttg aggagtcctg gacacccaac   420
      tacaagcagt gttcatggag ttcattgaat tatggcatag atcttgggaa aattgcggag   480
      tgtacattta caaagatgcg ttcaaatagt gctctaagag ttttgttcag tggctcactt   540
      cggctaaaat gcagaaatgc atgctgtcag cgttggtatt tcacattcaa tggagctgaa   600
      tgttcaggac ctcttcccat tgaagctata atttatttgg accaaggaag ccctgaaatg   660
      aattcaacaa ttaatattca tcgcacttct tctgtggaag actttgtga aggaattggt    720
      gctggattag tggatgttgc tatctgggtt ggcacttgtt cagattaccc aaaaggagat   780
      gcttctactg gatggaattc agtttctcgc atcattattg aagaactacc aaaataa     837

<210> SEQ ID NO 513
<211> LENGTH: 837
<212> TYPE: DNA
<213> ORGANISM: Homo sapiens

<400> SEQUENCE: 513
atgcagcctg cggcggcctc ggagcgcggc ggagcagacg ctgaccacgt tcctctcctc    60
      ggtctcctcc gcctccagct ccgcgctgcc cggcagccgg gagccatgcg accccagggc   120
      cccgccgcct ccccgcagcg gctccgcggc ctcctgctgc tcctgctgct gcagctgccc   180
      gcgccgtcga gcgcctctga gatcccaag gggaagcaaa aggcgcagct ccggcagagg    240
      gaggtggtgg acctgtataa tggaatgtgc ttacaagggc cagcaggagt gcctggtcga   300
      gacgggagcc ctggggccaa tgttattccg ggtacacctg ggatcccagg tcgggatgga   360
      ttcaaaggag aaaaggggga atgtctgagg gaaagctttg aggagtcctg gacacccaac   420
      tacaagcagt gttcatggag ttcattgaat tatggcatag atcttgggaa aattgcggag   480
      tgtacattta caaagatgcg ttcaaatagt gctctaagag ttttgttcag tggctcactt   540
      cggctaaaat gcagaaatgc atgctgtcag cgttggtatt tcacattcaa tggagctgaa   600
      tgttcaggac ctcttcccat tgaagctata atttatttgg accaaggaag ccctgaaatg   660
      aattcaacaa ttaatattca tcgcacttct tctgtggaag actttgtga aggaattggt    720
      gctggattag tggatgttgc tatctgggtt ggcacttgtt cagattaccc aaaaggagat   780
      gcttctactg gatggaattc agtttctcgc atcattattg aagaactacc aaaataa     837

<210> SEQ ID NO 514
<211> LENGTH: 243
<212> TYPE: PRT
<213> ORGANISM: Homo sapiens

<400> SEQUENCE: 514

Met Arg Pro Gln Gly Pro Ala Ala Ser Pro Gln Arg Leu Arg Gly Leu
      1               5                  10                  15
      Leu Leu Leu Leu Leu Gln Leu Pro Ala Pro Ser Ser Ala Ser Glu
                 20                  25                  30
      Ile Pro Lys Gly Lys Gln Lys Ala Gln Leu Arg Gln Arg Glu Val Val
                     35                  40                  45
      Asp Leu Tyr Asn Gly Met Cys Leu Gln Gly Pro Ala Gly Val Pro Gly
         50                  55                  60
      Arg Asp Gly Ser Pro Gly Ala Asn Val Ile Pro Gly Thr Pro Gly Ile
      65                  70                  75                  80
      Pro Gly Arg Asp Gly Phe Lys Gly Glu Lys Gly Glu Cys Leu Arg Glu
                         85                  90                  95
      Ser Phe Glu Glu Ser Trp Thr Pro Asn Tyr Lys Gln Cys Ser Trp Ser
                        100                 105                 110
      Ser Leu Asn Tyr Gly Ile Asp Leu Gly Lys Ile Ala Glu Cys Thr Phe
                    115                 120                 125
      Thr Lys Met Arg Ser Asn Ser Ala Leu Arg Val Leu Phe Ser Gly Ser
                130                 135                 140
      Leu Arg Leu Lys Cys Arg Asn Ala Cys Cys Gln Arg Trp Tyr Phe Thr
      145                 150                 155                 160
      Phe Asn Gly Ala Glu Cys Ser Gly Pro Leu Pro Ile Glu Ala Ile Ile
                        165                 170                 175
      Tyr Leu Asp Gln Gly Ser Pro Glu Met Asn Ser Thr Ile Asn Ile His
                    180                 185                 190
      Arg Thr Ser Ser Val Glu Gly Leu Cys Glu Gly Ile Gly Ala Gly Leu
                195                 200                 205
      Val Asp Val Ala Ile Trp Val Gly Thr Cys Ser Asp Tyr Pro Lys Gly
         210                 215                 220
      Asp Ala Ser Thr Gly Trp Asn Ser Val Ser Arg Ile Ile Ile Glu Glu
      225                 230                 235                 240
```

Leu Pro Lys

<210> SEQ ID NO 515
<211> LENGTH: 278
<212> TYPE: PRT
<213> ORGANISM: Homo sapiens

<400> SEQUENCE: 515

Met Gln Pro Ala Ala Ala Ser Glu Arg Gly Gly Ala Asp Ala Asp His
            5                   10                  15
Val Pro Leu Leu Gly Leu Leu Arg Leu Gln Leu Arg Ala Ala Arg Gln
            20                  25                  30
Pro Gly Ala Met Arg Pro Gln Gly Pro Ala Ala Ser Pro Gln Arg Leu
            35                  40                  45
Arg Gly Leu Leu Leu Leu Leu Leu Leu Gln Leu Pro Ala Pro Ser Ser
        50                  55                  60
Ala Ser Glu Ile Pro Lys Gly Lys Gln Lys Ala Gln Leu Arg Gln Arg
65                  70                  75                  80
Glu Val Val Asp Leu Tyr Asn Gly Met Cys Leu Gln Gly Pro Ala Gly
            85                  90                  95
Val Pro Gly Arg Asp Gly Ser Pro Gly Ala Asn Val Ile Pro Gly Thr
            100                 105                 110
Pro Gly Ile Pro Gly Arg Asp Gly Phe Lys Gly Glu Lys Gly Glu Cys
            115                 120                 125
Leu Arg Glu Ser Phe Glu Glu Ser Trp Thr Pro Asn Tyr Lys Gln Cys
        130                 135                 140
Ser Trp Ser Ser Leu Asn Tyr Gly Ile Asp Leu Gly Lys Ile Ala Glu
145                 150                 155                 160
Cys Thr Phe Thr Lys Met Arg Ser Asn Ser Ala Leu Arg Val Leu Phe
            165                 170                 175
Ser Gly Ser Leu Arg Leu Lys Cys Arg Asn Ala Cys Cys Gln Arg Trp
            180                 185                 190
Tyr Phe Thr Phe Asn Gly Ala Glu Cys Ser Gly Pro Leu Pro Ile Glu
            195                 200                 205
Ala Ile Ile Tyr Leu Asp Gln Gly Ser Pro Glu Met Asn Ser Thr Ile
        210                 215                 220
Asn Ile His Arg Thr Ser Ser Val Glu Gly Leu Cys Glu Gly Ile Gly
225                 230                 235                 240
Ala Gly Leu Val Asp Val Ala Ile Trp Val Gly Thr Cys Ser Asp Tyr
            245                 250                 255
Pro Lys Gly Asp Ala Ser Thr Gly Trp Asn Ser Val Ser Arg Ile Ile
            260                 265                 270
Ile Glu Glu Leu Pro Lys
            275

<210> SEQ ID NO 516
<211> LENGTH: 197
<212> TYPE: PRT
<213> ORGANISM: Homo sapiens

<400> SEQUENCE: 516

Met Arg Pro Gln Gly Pro Ala Ala Ser Pro Gln Arg Leu Arg Gly Leu
            5                   10                  15
Leu Leu Leu Leu Leu Leu Gln Leu Pro Ala Pro Ser Ser Ala Ser Glu
            20                  25                  30
Ile Pro Lys Gly Lys Gln Lys Ala Gln Leu Arg Gln Arg Glu Val Val
            35                  40                  45
Asp Leu Tyr Asn Gly Met Cys Leu Gln Gly Pro Ala Gly Val Pro Gly
        50                  55                  60
Arg Asp Gly Ser Pro Gly Ala Asn Val Ile Pro Gly Thr Pro Gly Ile
65                  70                  75                  80
Pro Gly Arg Asp Gly Phe Lys Gly Glu Lys Gly Glu Cys Leu Arg Glu
            85                  90                  95
Ser Phe Glu Glu Ser Trp Thr Pro Asn Tyr Lys Gln Cys Ser Trp Ser
            100                 105                 110
Ser Leu Asn Tyr Gly Ile Asp Leu Gly Lys Ile Ala Glu Cys Thr Phe
            115                 120                 125
Thr Lys Met Arg Ser Asn Ser Ala Leu Arg Val Leu Phe Ser Gly Ser
        130                 135                 140
Leu Arg Leu Lys Cys Arg Asn Ala Cys Cys Gln Arg Trp Tyr Phe Thr
145                 150                 155                 160
Phe Asn Gly Ala Glu Cys Ser Gly Pro Leu Pro Ile Glu Ala Ile Ile
            165                 170                 175
Tyr Leu Asp Gln Gly Ser Pro Glu Met Asn Ser Thr Ile Asn Ile His
            180                 185                 190

```
        Arg Thr Ser Ser Val
                195

<210> SEQ ID NO 517
<211> LENGTH: 232
<212> TYPE: PRT
<213> ORGANISM: Homo sapiens

<400> SEQUENCE: 517

Met Gln Pro Ala Ala Ala Ser Glu Arg Gly Gly Ala Asp Ala Asp His
                        5                   10                  15
        Val Pro Leu Leu Gly Leu Leu Arg Leu Gln Leu Arg Ala Ala Arg Gln
                    20                  25                  30
        Pro Gly Ala Met Arg Pro Gln Gly Pro Ala Ala Ser Pro Gln Arg Leu
                35                  40                  45
        Arg Gly Leu Leu Leu Leu Leu Leu Gln Leu Pro Ala Pro Ser Ser
            50                  55                  60
        Ala Ser Glu Ile Pro Lys Gly Lys Gln Lys Ala Gln Leu Arg Gln Arg
        65                  70                  75                  80
        Glu Val Val Asp Leu Tyr Asn Gly Met Cys Leu Gln Gly Pro Ala Gly
                        85                  90                  95
        Val Pro Gly Arg Asp Gly Ser Pro Gly Ala Asn Val Ile Pro Gly Thr
                    100                 105                 110
        Pro Gly Ile Pro Gly Arg Asp Gly Phe Lys Gly Glu Lys Gly Glu Cys
                115                 120                 125
        Leu Arg Glu Ser Phe Glu Glu Ser Trp Thr Pro Asn Tyr Lys Gln Cys
            130                 135                 140
        Ser Trp Ser Ser Leu Asn Tyr Gly Ile Asp Leu Gly Lys Ile Ala Glu
        145                 150                 155                 160
        Cys Thr Phe Thr Lys Met Arg Ser Asn Ser Ala Leu Arg Val Leu Phe
                        165                 170                 175
        Ser Gly Ser Leu Arg Leu Lys Cys Arg Asn Ala Cys Cys Gln Arg Trp
                    180                 185                 190
        Tyr Phe Thr Phe Asn Gly Ala Glu Cys Ser Gly Pro Leu Pro Ile Glu
                195                 200                 205
        Ala Ile Ile Tyr Leu Asp Gln Gly Ser Pro Glu Met Asn Ser Thr Ile
            210                 215                 220
        Asn Ile His Arg Thr Ser Ser Val
        225                 230

<210> SEQ ID NO 518
<211> LENGTH: 46
<212> TYPE: PRT
<213> ORGANISM: Homo sapiens

<400> SEQUENCE: 518

Glu Gly Leu Cys Glu Gly Ile Gly Ala Gly Leu Val Asp Val Ala Ile
                        5                   10                  15
        Trp Val Gly Thr Cys Ser Asp Tyr Pro Lys Gly Asp Ala Ser Thr Gly
                    20                  25                  30
        Trp Asn Ser Val Ser Arg Ile Ile Ile Glu Glu Leu Pro Lys
                35                  40                  45

<210> SEQ ID NO 519
<211> LENGTH: 26
<212> TYPE: PRT
<213> ORGANISM: Homo sapiens

<400> SEQUENCE: 519

Cys Ser Asp Tyr Pro Lys Gly Asp Ala Ser Thr Gly Trp Asn Ser Val
                        5                   10                  15
        Ser Arg Ile Ile Ile Glu Glu Leu Pro Lys
                    20                  25

<210> SEQ ID NO 520
<211> LENGTH: 60
<212> TYPE: DNA
<213> ORGANISM: Homo sapiens

<400> SEQUENCE: 520
aaaaatgagg agatatttaa ttacaataac catttaaaaa accgtatata tcaatatgaa    60
```

```
<210> SEQ ID NO 521
<211> LENGTH: 60
<212> TYPE: DNA
<213> ORGANISM: Homo sapiens

<400> SEQUENCE: 521
atgcaacatc atctcctaaa agagaaaaat gaggagatat ttaattacaa taaccattta  60

<210> SEQ ID NO 522
<211> LENGTH: 60
<212> TYPE: DNA
<213> ORGANISM: Homo sapiens

<400> SEQUENCE: 522
gacaacaaaa gcaagataac aattgatatt cattttcttg agaggaaaat gcaacatcat  60

<210> SEQ ID NO 523
<211> LENGTH: 60
<212> TYPE: DNA
<213> ORGANISM: Homo sapiens

<400> SEQUENCE: 523
aaaaatatgt ggcttcaaca gcaattagtt catgcacata agaaagctga caacaaaagc  60

<210> SEQ ID NO 524
<211> LENGTH: 63
<212> TYPE: DNA
<213> ORGANISM: Homo sapiens

<400> SEQUENCE: 524
gatcagaaat tatttcaact acaaagcaaa atatgtggc ttcaacagca attagttcat  60
     gca                                                                63

<210> SEQ ID NO 525
<211> LENGTH: 60
<212> TYPE: DNA
<213> ORGANISM: Homo sapiens

<400> SEQUENCE: 525
actgaacagc aggagtctct agatcagaaa ttatttcaac tacaaagcaa aaatatgtgg  60

<210> SEQ ID NO 526
<211> LENGTH: 63
<212> TYPE: DNA
<213> ORGANISM: Homo sapiens

<400> SEQUENCE: 526
gctcaaagga aatccaaaag cctaaaaatt aatctcaatt atgccggaga tgctctaaga  60
     gaa                                                                63

<210> SEQ ID NO 527
<211> LENGTH: 60
<212> TYPE: DNA
<213> ORGANISM: Homo sapiens

<400> SEQUENCE: 527
agtacgatat ataacaatga ggtgctccat caaccacttt ctgaagctca aggaaatcc   60

<210> SEQ ID NO 528
<211> LENGTH: 60
<212> TYPE: DNA
<213> ORGANISM: Homo sapiens
```

```
<400> SEQUENCE: 528
agaaaaatga atgttgatgt gagtagtacg atatataaca atgaggtgct ccatcaacca    60

<210> SEQ ID NO 529
<211> LENGTH: 60
<212> TYPE: DNA
<213> ORGANISM: Homo sapiens

<400> SEQUENCE: 529
attgcaggag atgcttgttt gcaaagaaaa atgaatgttg atgtgagtag tacgatatat    60

<210> SEQ ID NO 530
<211> LENGTH: 60
<212> TYPE: DNA
<213> ORGANISM: Homo sapiens

<400> SEQUENCE: 530
aaaagtcaag aacctgcttt ccacattgca ggagatgctt gtttgcaaag aaaaatgaat    60

<210> SEQ ID NO 531
<211> LENGTH: 60
<212> TYPE: DNA
<213> ORGANISM: Homo sapiens

<400> SEQUENCE: 531 gaaataaat actttgagga cattaagatt ttaaagaaa agaatgctga acttcagatg    60

<210> SEQ ID NO 532
<211> LENGTH: 60
<212> TYPE: DNA
<213> ORGANISM: Homo sapiens

<400> SEQUENCE: 532
ctgaaacacc aataccagga aaggaaaat aaatactttg aggacattaa gattttaaaa    60

<210> SEQ ID NO 533
<211> LENGTH: 63
<212> TYPE: DNA
<213> ORGANISM: Homo sapiens

<400> SEQUENCE: 533
aattgcatgt tgaaaaagga aattgccatg ctaaaactgg aaatagccac actgaaacac    60
    caa                                                                  63

<210> SEQ ID NO 534
<211> LENGTH: 21
<212> TYPE: PRT
<213> ORGANISM: Homo sapiens

<400> SEQUENCE: 534

Asn Cys Met Leu Lys Lys Glu Ile Ala Met Leu Lys Leu Glu Ile Ala
                  5                  10                  15
    Thr Leu Lys His Gln
                 20

<210> SEQ ID NO 535
<211> LENGTH: 20
<212> TYPE: PRT
<213> ORGANISM: Homo sapiens

<400> SEQUENCE: 535

Leu Lys His Gln Tyr Gln Glu Lys Glu Asn Lys Tyr Phe Glu Asp Ile
                  5                  10                  15
    Lys Ile Leu Lys
```

```
                    20

<210> SEQ ID NO 536
<211> LENGTH: 20
<212> TYPE: PRT
<213> ORGANISM: Homo sapiens

<400> SEQUENCE: 536

Glu Asn Lys Tyr Phe Glu Asp Ile Lys Ile Leu Lys Glu Lys Asn Ala
                     5                  10                  15
    Glu Leu Gln Met
                20

<210> SEQ ID NO 537
<211> LENGTH: 20
<212> TYPE: PRT
<213> ORGANISM: Homo sapiens

<400> SEQUENCE: 537

Lys Ser Gln Glu Pro Ala Phe His Ile Ala Gly Asp Ala Cys Leu Gln
                     5                  10                  15
    Arg Lys Met Asn
                20

<210> SEQ ID NO 538
<211> LENGTH: 20
<212> TYPE: PRT
<213> ORGANISM: Homo sapiens

<400> SEQUENCE: 538

Ile Ala Gly Asp Ala Cys Leu Gln Arg Lys Met Asn Val Asp Val Ser
                     5                  10                  15
    Ser Thr Ile Tyr
                20

<210> SEQ ID NO 539
<211> LENGTH: 20
<212> TYPE: PRT
<213> ORGANISM: Homo sapiens

<400> SEQUENCE: 539

Arg Lys Met Asn Val Asp Val Ser Ser Thr Ile Tyr Asn Asn Glu Val
                     5                  10                  15
    Leu His Gln Pro
                20

<210> SEQ ID NO 540
<211> LENGTH: 20
<212> TYPE: PRT
<213> ORGANISM: Homo sapiens

<400> SEQUENCE: 540

Ser Thr Ile Tyr Asn Asn Glu Val Leu His Gln Pro Leu Ser Glu Ala
                     5                  10                  15
    Gln Arg Lys Ser
                20

<210> SEQ ID NO 541
<211> LENGTH: 21
<212> TYPE: PRT
<213> ORGANISM: Homo sapiens

<400> SEQUENCE: 541

Ala Gln Arg Lys Ser Lys Ser Leu Lys Ile Asn Leu Asn Tyr Ala Gly
                     5                  10                  15
    Asp Ala Leu Arg Glu
                20
```

<210> SEQ ID NO 542
<211> LENGTH: 20
<212> TYPE: PRT
<213> ORGANISM: Homo sapiens

<400> SEQUENCE: 542

Thr Glu Gln Gln Glu Ser Leu Asp Gln Lys Leu Phe Gln Leu Gln Ser
                 5                  10                  15
Lys Asn Met Trp
         20

<210> SEQ ID NO 543
<211> LENGTH: 21
<212> TYPE: PRT
<213> ORGANISM: Homo sapiens

<400> SEQUENCE: 543

Asp Gln Lys Leu Phe Gln Leu Gln Ser Lys Asn Met Trp Leu Gln Gln
                 5                  10                  15
Gln Leu Val His Ala
             20

<210> SEQ ID NO 544
<211> LENGTH: 20
<212> TYPE: PRT
<213> ORGANISM: Homo sapiens

<400> SEQUENCE: 544

Lys Asn Met Trp Leu Gln Gln Gln Leu Val His Ala His Lys Lys Ala
                 5                  10                  15
Asp Asn Lys Ser
         20

<210> SEQ ID NO 545
<211> LENGTH: 20
<212> TYPE: PRT
<213> ORGANISM: Homo sapiens

<400> SEQUENCE: 545

Asp Asn Lys Ser Lys Ile Thr Ile Asp Ile His Phe Leu Glu Arg Lys
                 5                  10                  15
Met Gln His His
         20

<210> SEQ ID NO 546
<211> LENGTH: 20
<212> TYPE: PRT
<213> ORGANISM: Homo sapiens

<400> SEQUENCE: 546

Met Gln His His Leu Leu Lys Glu Lys Asn Glu Glu Ile Phe Asn Tyr
                 5                  10                  15
Asn Asn His Leu
         20

<210> SEQ ID NO 547
<211> LENGTH: 20
<212> TYPE: PRT
<213> ORGANISM: Homo sapiens

<400> SEQUENCE: 547

Lys Asn Glu Glu Ile Phe Asn Tyr Asn Asn His Leu Lys Asn Arg Ile
                 5                  10                  15
Tyr Gln Tyr Glu
         20

<210> SEQ ID NO 548
<211> LENGTH: 3045
<212> TYPE: DNA
<213> ORGANISM: Homo sapiens

<400> SEQUENCE: 548

```
atgcagcatc accaccatca ccacgtcggc tccatgagtc ccgcaaaaga aacatctgag   60
aaatttacgt gggcagcaaa aggaagacct aggaagatcg catgggagaa aaaagaaaca  120
cctgtaaaga ctggatgcgt ggcaagagta acatctaata aaactaaagt tttggaaaaa  180
ggaagatcta agatgattgc atgtcctaca aaagaatcat ctacaaaagc aagtgccaat  240
gatcagaggt tcccatcaga atccaaacaa gaggaagatg aagaatattc ttgtgattct  300
cggagtctct ttgagagttc tgcaaagatt caagtgtgta tacctgagtc tatatatcaa  360
aaagtaatgg agataaatag agaagtagaa gagcctccta agaagccatc tgccttcaag  420
cctgccattg aaatgcaaaa ctctgttcca aataaagcct ttgaattgaa gaatgaacaa  480
acattgagag cagatccgat gttcccacca gaatccaaac aaaaggacta tgaagaaaat  540
tcttgggatt ctgagagtct ctgtgagact gtttcacaga aggatgtgtg tttacccaag  600
gctacacatc aaaaagaaat agataaaata aatggaaaat tagaagagtc tcctaataaa  660
gatggtcttc tgaaggctac ctgcggaaga aagtttcta ttccaactaa agccttagaa  720
ttgaaggaca tgcaaacttt caaagcagag cctccgggga agccatctgc cttcgagcct  780
gccactgaaa tgcaaaagtc tgtcccaaat aaagccttgg aattgaaaaa tgaacaaaca  840
ttgagagcag atgagatact cccatcagaa tccaaacaaa aggactatga gaaaattct   900
tgggatactg agagtctctg tgagactgtt tcacagaagg atgtgtgttt acccaaggct  960
gcgcatcaaa aagaaataga taaaataat ggaaaattag aaggtctcc tggtaaagat 1020
ggtcttctta aggctaactg cggaatgaaa gtttctattc caactaaagc cttagaattg 1080
atggacatgc aaactttcaa agcagagcct cccgagaagc catctgcctt cgagcctgcc 1140
attgaaatgc aaaagtctgt tccaaataaa gccttggaat tgaagaatga caaacattg  1200
agagcagatg agatactccc atcagaatcc aaacaaaaga ctatgagaaa aagttcttga 1260
gattctgaga gtctctgtga gactgtttca cagaaggatg tgtgtttacc caaggctgcg 1320
catcaaaaag aaatagataa aataaatgga aaattagaag agtctcctga taatgatggt 1380
tttctgaagt ctccctgcag aatgaaagtt tctattccaa ctaaagcctt agaattgatg 1440
gacatgcaaa ctttcaaagc agagcctccc gagaagccat ctgccttcga gcctgccatt 1500
gaaatgcaaa agtctgttcc aaataaagcc ttggaattga agaatgaaca aacattgaga 1560
gcagatcaga tgttcccttc agaatcaaaa caaaagaacg ttgaagaaaa ttcttgggat 1620
tctgagagtc tccgtgagac tgtttcacag aaggatgtgt gtgtacccaa ggctacacat 1680
caaaagagaa tggataaaat aagtggaaaa ttagaaagatt caactagcct atcaaaaatc 1740
ttggatacag ttcattcttg tgaaagagca agggaacttc aaaaagatca ctgtgaacaa 1800
cgtacaggaa aaatggaaca atgaaaaag aagttttgtg tactgaaaaa gaaactgtca 1860
gaagcaaaag aaataaaatc acagttagag aaccaaaaag ttaaatggga caagagctc  1920
tgcagtgtga gattgacttt aaaccaagaa gaagaagaag gaagaaatgc cgatatatta 1980
aatgaaaaaa ttagggaaga attaggaaga atcgaagagc agcataggaa agagttagaa 2040
gtgaaacaac aacttgaaca ggctctcaga atacaagata tagaattgaa gagtgtagaa 2100
agtaatttaa atcaggtttc tcacactcat gaaaatgaaa attatctctc acatgaaaat 2160
tgcatgttga aaaaggaaat tgccatgcta aaactggaaa tagccacact gaaacaccaa 2220
taccaggaaa aggaaaataa atactttgag gacattaaga ttttaaaaga aaagaatgct 2280
gaacttcaga tgaccctaaa actgaaagag gaatcattaa ctaaagggc atctcaatat 2340
agtgggcagc ttaaagttct gatagctgag aacacaatgc tcacttctaa attgaaggaa 2400
aaacaagaca agaaatact agaggcagaa attgaatcac accatcctag actggcttct 2460
gctgtacaag accatgcaa aattgtgaca tcaagaaaa gtcaagaacc tgcttccac  2520
attgcaggag atgcttgttt gcaaagaaaa atgaatgttg atgtgagtag tacgatatat 2580
aacaatgagg tgctccatca accactttct gaagctcaaa ggaaatccaa aagcctaaaa 2640
attaatctca attatgccgg agatgctcta agagaaaata cattggtttc agaacatgca 2700
caaagagacc aacgtgaaac acagtgtcaa atgaaggaag ctgaaccat gtatcaaaac 2760
gaacaagata atgtgaacaa acacactgaa cagcaggagt ctctagatca gaaattattt 2820
caactacaaa gcaaaaatat gtggcttcaa cagcaattag ttcatgcaca taagaaagct 2880
gacaacaaaa gcaagataac aattgatatt catttcttg agaggaaaat gcaacatcat 2940
ctcctaaaag agaaaaatga ggagatattt aattacaata accatttaaa aaaccgtata 3000
tatcaatatg aaaaagagaa agcagaaaca gaagttatat aatag             3045
```

<210> SEQ ID NO 549
<211> LENGTH: 1953
<212> TYPE: DNA
<213> ORGANISM: Homo sapiens
<220> FEATURE:
<221> NAME/KEY: misc_feature
<222> LOCATION: 985
<223> OTHER INFORMATION: n = A,T,C or G

<400> SEQUENCE: 549

```
atgagtcccg caaaagaaac atctgagaaa tttacgtggg cagcaaaagg aagacctagg   60
aagatcgcat gggagaaaaa agaaacacct gtaaagactg gatgcgtggc aagagtaaca  120
tctaataaaa ctaaagtttt ggaaaaagga agatctaaga tgattgcatg tcctacaaaa  180
gaatcatcta caaaagcaag tgccaatgat cagaggttcc catcagaatc caaacaagag  240
gaagatgaag aatattcttg tgattctcgg agtctctttg agagttctgc aaagattcaa  300
gtgtgtatac ctgagtctat atatcaaaaa gtaatggaga taaatagaga agtagaagag  360
cctcctaaga agccatctgc cttcaagcct gccattgaaa tgcaaaactc tgttccaaat  420
```

-continued

```
aaagcctttg aattgaagaa tgaacaaaca ttgagagcag atccgatgtt cccaccagaa 480
tccaaacaaa aggactatga agaaaattct tgggattctg agagtctctg tgagactgtt 540
tcacagaagg atgtgtgttt acccaaggct acacatcaaa agaaaataga taaaataaat 600
ggaaaattag aagagtctcc taataaagat ggtcttctga aggctacctg cggaatgaaa 660
gtttctattc caactaaagc cttagaattg aaggacatgc aaactttcaa agcagagcct 720
ccggggaagc catctgcctt cgagcctgcc actgaaatgc aaaagtctgt cccaaataaa 780
gccttggaat tgaaaaatga acaaacattg agagcagatg agatactccc atcagaatcc 840
aaacaaaagg actatgaaga aaattcttgg gatactgaag gtctctgtga gactgtttca 900
cagaaggatg tgtgtttacc caaggctgcg catcaaaaag aaatagataa aataaatgga 960
aaattagaag ggtctcctgg taaanatggt cttctgaagg ctaactgcgg aatgaaagtt 1020
tctattccaa ctaaagcctt agaattgatg acatgcaaa ctttcaaagc agagcctccc 1080
gagaagccat ctgccttcga gcctgccatt gaaatgcaaa agtctgttcc aaataaagcc 1140
ttggaattga agaatgaaca acattgaga gcagatgaga tactcccatc agaatccaaa 1200
caaaaggact atgaagaag ttcttgggat tctgagagtc tctgtgagac tgtttcacag 1260
aaggatgtgt gtttacccaa ggctgcgcat caaaaagaaa tagataaat aaatggaaaa 1320
ttagaagagt ctcctgataa tgatggtttt ctgaagtctc cctgcagaat gaaagtttct 1380
attccaacta agccttaga attgatggac atgcaaactt tcaaagcaga gcctcccgag 1440
aagccatctg ccttcgagcc tgccattgaa atgcaaaagt ctgttccaaa taaagccttg 1500
gaattgaaga tgaacaaac attgagagca gatcagatgt tcccttcaga atcaaaacaa 1560
aagaacgttg aagaaaattc ttgggattct gagagtctcc gtgagactgt ttcacagaag 1620
gatgtgtgtg tacccaaggc tacacatcaa aagaaatgg ataaaatga tggaaaatta 1680
gaagattcaa ctagcctatc aaaaatcttg gatacagttc attcttgtga agagcaagg 1740
gaacttcaaa agatcactg tgaacaacgt acaggaaaaa tggaacaat gaaaagaag 1800
ttttgtgtac tgaaaagaa actgtcagaa gcaaagaaa taaatcaca gttagagaac 1860
caaaaagtta atgggaaca agagctctgc agtgtgaggt ttctcacact catgaaaatg 1920
aaaattatct cttacatgaa aattgcatgt tga 1953
```

<210> SEQ ID NO 550
<211> LENGTH: 978
<212> TYPE: DNA
<213> ORGANISM: Homo sapiens

<400> SEQUENCE: 550

```
atgcagcatc accaccatca ccacggcaca agagctctgc agtgtgaggt ttctcacact 60
catgaaaatg aaaattatct cttacatgaa aattgcatgt tgaaaaagga aattgccatg 120
ctaaaactgg aaatagccac actgaaacac caataccagg aaaaggaaaa taaatacttt 180
gaggacatta agattttaaa agaaaagaat gctgaacttc agatgaccct aaaactgaaa 240
gaggaatcat taactaaaag ggcatctcaa tatagtgggc agcttaaagt tctgatagct 300
gagaacacaa tgctcacttc taaattgaag gaaaaacaag aaaagaaat actagaggca 360
gaaattgaat cacaccatcc tagactggct tctgctgtac aagaccatga tcaaattgtg 420
acatcaagaa aaagtcaaga acctgctttc cacattgcag gagatgcttg tttgcaaaga 480
aaaatgaatg ttgatgtgag tagtacgata tataacaatg gggtgctcca tcaaccactt 540
tctgaagctc aaaggaaatc caaaagccta aaaattaatc tcaattatgc cggagatgct 600
ctaagagaaa atacattggt ttcagaacat gcacaaagag accaacagtga aacacagtgt 660
caaatgaagg aagctgaaca catgtatcaa aacgaacaag ataatgtgaa caaacacact 720
aacagcagg agtctctaga tcagaaatta tttcaactac aaagcaaaaa tatgtggctt 780
caacagcaat tagttcatgc acataagaaa gctgacaaca aaagcaagat aacaattgat 840
attcattttc ttgagaggaa aatgcaacat catctcctaa aagagaaaaa tgaggagata 900
tttaattaca ataaccattt aaaaaaccgt atatatcaat atgaaaaaga gaaagcagaa 960
acagaagtta tataatag 978
```

<210> SEQ ID NO 551
<211> LENGTH: 324
<212> TYPE: PRT
<213> ORGANISM: Homo sapiens

<400> SEQUENCE: 551

```
Met Gln His His His His His His Gly Thr Arg Ala Leu Gln Cys Glu
                 5                  10                  15
Val Ser His Thr His Glu Asn Glu Asn Tyr Leu Leu His Glu Asn Cys
             20                  25                  30
Met Leu Lys Lys Glu Ile Ala Met Leu Lys Leu Glu Ile Ala Thr Leu
         35                  40                  45
Lys His Gln Tyr Gln Glu Lys Glu Asn Lys Tyr Phe Glu Asp Ile Lys
     50                  55                  60
Ile Leu Lys Glu Lys Asn Ala Glu Leu Gln Met Thr Leu Lys Leu Lys
 65                  70                  75                  80
Glu Glu Ser Leu Thr Lys Arg Ala Ser Gln Tyr Ser Gly Gln Leu Lys
                 85                  90                  95
Val Leu Ile Ala Glu Asn Thr Met Leu Thr Ser Lys Leu Lys Glu Lys
            100                 105                 110
Gln Asp Lys Glu Ile Leu Glu Ala Glu Ile Glu Ser His His Pro Arg
        115                 120                 125
Leu Ala Ser Ala Val Gln Asp His Asp Gln Ile Val Thr Ser Arg Lys
    130                 135                 140
```

```
        Ser Gln Glu Pro Ala Phe His Ile Ala Gly Asp Ala Cys Leu Gln Arg
        145                 150                 155                 160
        Lys Met Asn Val Asp Val Ser Ser Thr Ile Tyr Asn Asn Glu Val Leu
                        165                 170                 175
        His Gln Pro Leu Ser Glu Ala Gln Arg Lys Ser Lys Ser Leu Lys Ile
                    180                 185                 190
        Asn Leu Asn Tyr Ala Gly Asp Ala Leu Arg Glu Asn Thr Leu Val Ser
                195                 200                 205
        Glu His Ala Gln Arg Asp Gln Arg Glu Thr Gln Cys Gln Met Lys Glu
            210                 215                 220
        Ala Glu His Met Tyr Gln Asn Glu Gln Asp Asn Val Asn Lys His Thr
        225                 230                 235                 240
        Glu Gln Gln Glu Ser Leu Asp Gln Lys Leu Phe Gln Leu Gln Ser Lys
                        245                 250                 255
        Asn Met Trp Leu Gln Gln Gln Leu Val His Ala His Lys Lys Ala Asp
                    260                 265                 270
        Asn Lys Ser Lys Ile Thr Ile Asp Ile His Phe Leu Glu Arg Lys Met
                275                 280                 285
        Gln His His Leu Leu Lys Glu Lys Asn Glu Glu Ile Phe Asn Tyr Asn
            290                 295                 300
        Asn His Leu Lys Asn Arg Ile Tyr Gln Tyr Glu Lys Glu Lys Ala Glu
        305                 310                 315                 320
        Thr Glu Val Ile

<210> SEQ ID NO 552
<211> LENGTH: 661
<212> TYPE: PRT
<213> ORGANISM: Homo sapiens

<400> SEQUENCE: 552

Met Gln His His His His His Val Gly Ser Met Ser Pro Ala Lys
                        5                   10                  15
        Glu Thr Ser Glu Lys Phe Thr Trp Ala Ala Lys Gly Arg Pro Arg Lys
                        20                  25                  30
        Ile Ala Trp Glu Lys Lys Glu Thr Pro Val Lys Thr Gly Cys Val Ala
                        35                  40                  45
        Arg Val Thr Ser Asn Lys Thr Lys Val Leu Glu Lys Gly Arg Ser Lys
                    50                  55                  60
        Met Ile Ala Cys Pro Thr Lys Glu Ser Ser Thr Lys Ala Ser Ala Asn
        65                  70                  75                  80
        Asp Gln Arg Phe Pro Ser Glu Ser Lys Gln Glu Asp Glu Glu Tyr
                        85                  90                  95
        Ser Cys Asp Ser Arg Ser Leu Phe Glu Ser Ser Ala Lys Ile Gln Val
                    100                 105                 110
        Cys Ile Pro Glu Ser Ile Tyr Gln Lys Val Met Glu Ile Asn Arg Glu
                    115                 120                 125
        Val Glu Glu Pro Pro Lys Lys Pro Ser Ala Phe Lys Pro Ala Ile Glu
                130                 135                 140
        Met Gln Asn Ser Val Pro Asn Lys Ala Phe Glu Leu Lys Asn Glu Gln
        145                 150                 155                 160
        Thr Leu Arg Ala Asp Pro Met Phe Pro Pro Glu Ser Lys Gln Lys Asp
                        165                 170                 175
        Tyr Glu Glu Asn Ser Trp Asp Ser Glu Ser Leu Cys Glu Thr Val Ser
                    180                 185                 190
        Gln Lys Asp Val Cys Leu Pro Lys Ala Thr His Gln Lys Glu Ile Asp
                195                 200                 205
        Lys Ile Asn Gly Lys Leu Glu Glu Ser Pro Asn Lys Asp Gly Leu Leu
            210                 215                 220
        Lys Ala Thr Cys Gly Met Lys Val Ser Ile Pro Thr Lys Ala Leu Glu
        225                 230                 235                 240
        Leu Lys Asp Met Gln Thr Phe Lys Ala Glu Pro Pro Gly Lys Pro Ser
                        245                 250                 255
        Ala Phe Glu Pro Ala Thr Glu Met Gln Lys Ser Val Pro Asn Lys Ala
                    260                 265                 270
        Leu Glu Leu Lys Asn Glu Gln Thr Leu Arg Ala Asp Glu Ile Leu Pro
                275                 280                 285
        Ser Glu Ser Lys Gln Lys Asp Tyr Glu Glu Asn Ser Trp Asp Thr Glu
            290                 295                 300
        Ser Leu Cys Glu Thr Val Ser Gln Lys Asp Val Cys Leu Pro Lys Ala
        305                 310                 315                 320
        Ala His Gln Lys Glu Ile Asp Lys Ile Asn Gly Lys Leu Glu Gly Ser
                        325                 330                 335
        Pro Gly Lys Asp Gly Leu Leu Lys Ala Asn Cys Gly Met Lys Val Ser
                    340                 345                 350
        Ile Pro Thr Lys Ala Leu Glu Leu Met Asp Met Gln Thr Phe Lys Ala
                355                 360                 365
        Glu Pro Pro Glu Lys Pro Ser Ala Phe Glu Pro Ala Ile Glu Met Gln
```

-continued

```
            370                 375                 380
    Lys Ser Val Pro Asn Lys Ala Leu Glu Leu Lys Asn Glu Gln Thr Leu
385                 390                 395                 400
    Arg Ala Asp Glu Ile Leu Pro Ser Glu Ser Lys Gln Lys Asp Tyr Glu
                        405                 410                 415
    Glu Ser Ser Trp Asp Ser Glu Ser Leu Cys Glu Thr Val Ser Gln Lys
                420                 425                 430
    Asp Val Cys Leu Pro Lys Ala Ala His Gln Lys Glu Ile Asp Lys Ile
            435                 440                 445
    Asn Gly Lys Leu Glu Glu Ser Pro Asp Asn Asp Gly Phe Leu Lys Ser
        450                 455                 460
    Pro Cys Arg Met Lys Val Ser Ile Pro Thr Lys Ala Leu Glu Leu Met
465                 470                 475                 480
    Asp Met Gln Thr Phe Lys Ala Glu Pro Glu Lys Pro Ser Ala Phe
                        485                 490                 495
    Glu Pro Ala Ile Glu Met Gln Lys Ser Val Pro Asn Lys Ala Leu Glu
                500                 505                 510
    Leu Lys Asn Glu Gln Thr Leu Arg Ala Asp Gln Met Phe Pro Ser Glu
            515                 520                 525
    Ser Lys Gln Lys Asn Val Glu Asn Ser Trp Asp Ser Glu Ser Leu
        530                 535                 540
    Arg Glu Thr Val Ser Gln Lys Asp Val Cys Val Pro Lys Ala Thr His
545                 550                 555                 560
    Gln Lys Glu Met Asp Lys Ile Ser Gly Lys Leu Glu Asp Ser Thr Ser
                        565                 570                 575
    Leu Ser Lys Ile Leu Asp Thr Val His Ser Cys Glu Arg Ala Arg Glu
                580                 585                 590
    Leu Gln Lys Asp His Cys Glu Gln Arg Thr Gly Lys Met Glu Gln Met
            595                 600                 605
    Lys Lys Lys Phe Cys Val Leu Lys Lys Lys Leu Ser Glu Ala Lys Glu
        610                 615                 620
    Ile Lys Ser Gln Leu Glu Asn Gln Lys Val Lys Trp Glu Gln Glu Leu
625                 630                 635                 640
    Cys Ser Val Arg Phe Leu Thr Leu Met Lys Met Lys Ile Ile Ser Tyr
                        645                 650                 655
    Met Lys Ile Ala Cys
                660
```

<210> SEQ ID NO 553
<211> LENGTH: 1013
<212> TYPE: PRT
<213> ORGANISM: Homo sapiens

<400> SEQUENCE: 553

```
    Met Gln His His His His His Val Gly Ser Met Ser Pro Ala Lys
                    5                  10                  15
    Glu Thr Ser Glu Lys Phe Thr Trp Ala Ala Lys Gly Arg Pro Arg Lys
                20                  25                  30
    Ile Ala Trp Glu Lys Lys Glu Thr Pro Val Lys Thr Gly Cys Val Ala
            35                  40                  45
    Arg Val Thr Ser Asn Lys Thr Lys Val Leu Glu Lys Gly Arg Ser Lys
        50                  55                  60
    Met Ile Ala Cys Pro Thr Lys Glu Ser Ser Thr Lys Ala Ser Ala Asn
65                  70                  75                  80
    Asp Gln Arg Phe Pro Ser Glu Ser Lys Gln Glu Asp Glu Glu Tyr
                        85                  90                  95
    Ser Cys Asp Ser Arg Ser Leu Phe Glu Ser Ser Ala Lys Ile Gln Val
                100                 105                 110
    Cys Ile Pro Glu Ser Ile Tyr Gln Lys Val Met Glu Ile Asn Arg Glu
            115                 120                 125
    Val Glu Glu Pro Pro Lys Lys Pro Ser Ala Phe Lys Pro Ala Ile Glu
        130                 135                 140
    Met Gln Asn Ser Val Pro Asn Lys Ala Phe Glu Leu Lys Asn Glu Gln
145                 150                 155                 160
    Thr Leu Arg Ala Asp Pro Met Phe Pro Glu Ser Lys Gln Lys Asp
                        165                 170                 175
    Tyr Glu Glu Asn Ser Trp Asp Ser Glu Ser Leu Cys Glu Thr Val Ser
                180                 185                 190
    Gln Lys Asp Val Cys Leu Pro Lys Ala Thr His Gln Lys Glu Ile Asp
            195                 200                 205
    Lys Ile Asn Gly Lys Leu Glu Glu Ser Pro Asn Lys Asp Gly Leu Leu
        210                 215                 220
    Lys Ala Thr Cys Gly Met Lys Val Ser Ile Pro Thr Lys Ala Leu Glu
225                 230                 235                 240
    Leu Lys Asp Met Gln Thr Phe Lys Ala Glu Pro Pro Gly Lys Pro Ser
                        245                 250                 255
    Ala Phe Glu Pro Ala Thr Glu Met Gln Lys Ser Val Pro Asn Lys Ala
```

```
                    260                 265                 270
      Leu Glu Leu Lys Asn Glu Gln Thr Leu Arg Ala Asp Glu Ile Leu Pro
              275                 280                 285
      Ser Glu Ser Lys Gln Lys Asp Tyr Glu Glu Asn Ser Trp Asp Thr Glu
              290                 295                 300
      Ser Leu Cys Glu Thr Val Ser Gln Lys Asp Val Cys Leu Pro Lys Ala
      305                 310                 315                 320
      Ala His Gln Lys Glu Ile Asp Lys Ile Asn Gly Lys Leu Glu Gly Ser
                      325                 330                 335
      Pro Gly Lys Asp Gly Leu Leu Lys Ala Asn Cys Gly Met Lys Val Ser
                  340                 345                 350
      Ile Pro Thr Lys Ala Leu Glu Leu Met Asp Met Gln Thr Phe Lys Ala
              355                 360                 365
      Glu Pro Pro Glu Lys Pro Ser Ala Phe Glu Pro Ile Glu Met Gln
              370                 375                 380
      Lys Ser Val Pro Asn Lys Ala Leu Glu Leu Lys Asn Glu Gln Thr Leu
      385                 390                 395                 400
      Arg Ala Asp Glu Ile Leu Pro Ser Glu Ser Lys Gln Lys Asp Tyr Glu
                      405                 410                 415
      Glu Ser Ser Trp Asp Ser Glu Ser Leu Cys Glu Thr Val Ser Gln Lys
                  420                 425                 430
      Asp Val Cys Leu Pro Lys Ala Ala His Gln Lys Glu Ile Asp Lys Ile
              435                 440                 445
      Asn Gly Lys Leu Glu Glu Ser Pro Asp Asn Asp Gly Phe Leu Lys Ser
              450                 455                 460
      Pro Cys Arg Met Lys Val Ser Ile Pro Thr Lys Ala Leu Glu Leu Met
      465                 470                 475                 480
      Asp Met Gln Thr Phe Lys Ala Glu Pro Pro Glu Lys Pro Ser Ala Phe
                      485                 490                 495
      Glu Pro Ala Ile Glu Met Gln Lys Ser Val Pro Asn Lys Ala Leu Glu
                  500                 505                 510
      Leu Lys Asn Glu Gln Thr Leu Arg Ala Asp Gln Met Phe Pro Ser Glu
              515                 520                 525
      Ser Lys Gln Lys Asn Val Glu Glu Asn Ser Trp Asp Ser Glu Ser Leu
              530                 535                 540
      Arg Glu Thr Val Ser Gln Lys Asp Val Cys Val Pro Lys Ala Thr His
      545                 550                 555                 560
      Gln Lys Glu Met Asp Lys Ile Ser Gly Lys Leu Glu Asp Ser Thr Ser
                      565                 570                 575
      Leu Ser Lys Ile Leu Asp Thr Val His Ser Cys Glu Arg Ala Arg Glu
                  580                 585                 590
      Leu Gln Lys Asp His Cys Glu Gln Arg Thr Gly Lys Met Glu Gln Met
              595                 600                 605
      Lys Lys Lys Phe Cys Val Leu Lys Lys Leu Ser Glu Ala Lys Glu
              610                 615                 620
      Ile Lys Ser Gln Leu Glu Asn Gln Lys Val Lys Trp Glu Gln Glu Leu
      625                 630                 635                 640
      Cys Ser Val Arg Leu Thr Leu Asn Gln Glu Glu Lys Arg Arg Asn
                      645                 650                 655
      Ala Asp Ile Leu Asn Glu Lys Ile Arg Glu Glu Leu Gly Arg Ile Glu
                  660                 665                 670
      Glu Gln His Arg Lys Glu Leu Glu Val Lys Gln Gln Leu Glu Gln Ala
              675                 680                 685
      Leu Arg Ile Gln Asp Ile Glu Leu Lys Ser Val Glu Ser Asn Leu Asn
              690                 695                 700
      Gln Val Ser His Thr His Glu Asn Glu Asn Tyr Leu Leu His Glu Asn
      705                 710                 715                 720
      Cys Met Leu Lys Lys Glu Ile Ala Met Leu Lys Leu Glu Ile Ala Thr
                      725                 730                 735
      Leu Lys His Gln Tyr Gln Glu Lys Glu Asn Lys Tyr Phe Glu Asp Ile
                  740                 745                 750
      Lys Ile Leu Lys Glu Lys Asn Ala Glu Leu Gln Met Thr Leu Lys Leu
              755                 760                 765
      Lys Glu Glu Ser Leu Thr Lys Arg Ala Ser Gln Tyr Ser Gly Gln Leu
              770                 775                 780
      Lys Val Leu Ile Ala Glu Asn Thr Met Leu Thr Ser Lys Leu Lys Glu
      785                 790                 795                 800
      Lys Gln Asp Lys Glu Ile Leu Glu Ala Glu Ile Glu Ser His His Pro
                      805                 810                 815
      Arg Leu Ala Ser Ala Val Gln Asp His Asp Gln Ile Val Thr Ser Arg
                  820                 825                 830
      Lys Ser Gln Glu Pro Ala Phe His Ile Ala Gly Asp Ala Cys Leu Gln
              835                 840                 845
      Arg Lys Met Asn Val Asp Val Ser Thr Ile Tyr Asn Asn Glu Val
              850                 855                 860
      Leu His Gln Pro Leu Ser Glu Ala Gln Arg Lys Ser Lys Ser Leu Lys
      865                 870                 875                 880
      Ile Asn Leu Asn Tyr Ala Gly Asp Ala Leu Arg Glu Asn Thr Leu Val
                      885                 890                 895
```

```
        Ser Glu His Ala Gln Arg Asp Gln Arg Glu Thr Gln Cys Gln Met Lys
                    900                 905                 910
        Glu Ala Glu His Met Tyr Gln Asn Glu Gln Asp Asn Val Asn Lys His
                    915                 920                 925
        Thr Glu Gln Gln Glu Ser Leu Asp Gln Lys Leu Phe Gln Leu Gln Ser
                    930                 935                 940
        Lys Asn Met Trp Leu Gln Gln Gln Leu Val His Ala His Lys Lys Ala
        945                 950                 955                 960
        Asp Asn Lys Ser Lys Ile Thr Ile Asp Ile His Phe Leu Glu Arg Lys
                        965                 970                 975
        Met Gln His His Leu Leu Lys Glu Lys Asn Glu Gln Ile Phe Asn Tyr
                    980                 985                 990
        Asn Asn His Leu Lys Asn Arg Ile Tyr Gln Tyr Glu Lys Gln Lys Ala
                    995                 1000                1005
        Glu Thr Glu Val Ile
                    1010
```

<210> SEQ ID NO 554
<211> LENGTH: 25
<212> TYPE: DNA
<213> ORGANISM: Artificial Sequence
<220> FEATURE:
<223> OTHER INFORMATION: PCR primer

<400> SEQUENCE: 554
gtcggctcca tgagtcccgc aaaag                                    25

<210> SEQ ID NO 555
<211> LENGTH: 36
<212> TYPE: DNA
<213> ORGANISM: Artificial Sequence
<220> FEATURE:
<223> OTHER INFORMATION: PCR primer

<400> SEQUENCE: 555
cgagaattca atacttaaga agaccatctt taccag                        36

<210> SEQ ID NO 556
<211> LENGTH: 31
<212> TYPE: DNA
<213> ORGANISM: Artificial Sequence
<220> FEATURE:
<223> OTHER INFORMATION: PCR primer

<400> SEQUENCE: 556
cataagctta aggctaactg cggaatgaaa g                             31

<210> SEQ ID NO 557
<211> LENGTH: 35
<212> TYPE: DNA
<213> ORGANISM: Artificial Sequence
<220> FEATURE:
<223> OTHER INFORMATION: PCR primer

<400> SEQUENCE: 557
cccgcagaat tcaacatgca attttcatgt aagag                         35

<210> SEQ ID NO 558
<211> LENGTH: 25
<212> TYPE: DNA
<213> ORGANISM: Artificial Sequence
<220> FEATURE:
<223> OTHER INFORMATION: PCR primer

<400> SEQUENCE: 558
ctaaatgccg gcacaagagc tctgc                                    25

<210> SEQ ID NO 559

```
<211> LENGTH: 35
<212> TYPE: DNA
<213> ORGANISM: Artificial Sequence
<220> FEATURE:
<223> OTHER INFORMATION: PCR primer

<400> SEQUENCE: 559
cgcgcagaat tctattatat aacttctgtt tctgc                              35

<210> SEQ ID NO 560
<211> LENGTH: 26
<212> TYPE: DNA
<213> ORGANISM: Artificial Sequence
<220> FEATURE:
<223> OTHER INFORMATION: PCR primer

<400> SEQUENCE: 560
ggggaattgt gagcggataa caattc                                        26

<210> SEQ ID NO 561
<211> LENGTH: 36
<212> TYPE: DNA
<213> ORGANISM: Artificial Sequence
<220> FEATURE:
<223> OTHER INFORMATION: PCR primer

<400> SEQUENCE: 561
cgtagaattc aacctgattt aaattacttt ctacac                             36

<210> SEQ ID NO 562
<211> LENGTH: 31
<212> TYPE: DNA
<213> ORGANISM: Artificial Sequence
<220> FEATURE:
<223> OTHER INFORMATION: PCR primer

<400> SEQUENCE: 562
gaaagtaatt taaatcaggt ttctcacact c                                  31

<210> SEQ ID NO 563
<211> LENGTH: 23
<212> TYPE: DNA
<213> ORGANISM: Artificial Sequence
<220> FEATURE:
<223> OTHER INFORMATION: PCR primer

<400> SEQUENCE: 563
gaggccccaa ggggttatgc tag                                           23

<210> SEQ ID NO 564
<211> LENGTH: 4458
<212> TYPE: DNA
<213> ORGANISM: Homo sapiens

<400> SEQUENCE: 564
ctagtctata ccagcaacga ctcctacatc gtccactctg gggatcttag aaagatccat   60
    aaagctgcct cccggggaca agtccggaag ctggagaaga tgacaaagag gaagaagacc  120
    atcaacctta atatacaaga cgcccagaag aggactgctc tacactgggc ctgtgtcaat  180
    ggccatgagg aagtagtaac atttctggta gacagaaagt gccagcttga cgtccttgat  240
    ggcgaacaca ggacacctct gatgaaggct ctacaatgcc atcaggaggc ttgtgcaaat  300
    attctgatag attctggtgc cgatataaat ctcgtagatg tgtatggcaa catggctctc  360
    cattatgctg tttatagtga gattttgtca gtggtggcaa aactgctgtc ccatggtgca  420
    gtcatcgaag tgcacaacaa ggctagcctc acaccacttt tactatccat aacgaaaaga  480
    agtgagcaaa ttgtggaatt tttgctgata aaaaatgcaa atgcgaatgc agttaataag  540
    tataaatgca cagccctcat gcttgctgta tgtcatggat catcagagat agttggcatg  600
    cttcttcagc aaaatgttga cgtctttgct gcagatatat gtggagtaac tgcagaacat  660
    tatgctgtta cttgtggatt tcatacacat catgaacaaa ttatggaata tacgaaaaa   720
    ttatctaaaa atcatcaaaa taccaatcca gaaggaacat ctgcaggaac acctgatgag  780
```

-continued

```
gctgcaccct tggcggaaag aacacctgac acagctgaaa gcttggtgga aaaaacacct 840
gatgaggctg cacccttggt ggaaagaaca cctgacacgg ctgaaagctt ggtggaaaaa 900
acacctgatg aggctgcatc cttggtggag ggaacatctg acaaaattca atgtttggag 960
aaagcgacat ctggaaagtt cgaacagtca gcagaagaca cactagggga aattacgagt 1020
cctgcaaaag aaacatctga gaaatttacg tggccagcaa aaggaagacc taggaagatc 1080
gcatgggaga aaaagaaga cacacctagg gaaattatga gtcccgcaaa agaaacatct 1140
gagaaattta cgtgggcagc aaaaggaaga cctaggaaga tcgcatggga gaaaaaagaa 1200
acacctgtaa agactggatg cgtggcaaga gtaacatcta ataaaactaa agttttggaa 1260
aaaggaagat ctaagatgat tgcatgtcct acaaaagaat catctacaaa agcaagtgcc 1320
aatgatcaga ggttcccatc agaatccaaa caagaggaag atgaagaata ttcttgtgat 1380
tctcggagtc tctttgagag ttctgcaaag attcaagtgt gtatacctga gtctatatat 1440
caaaaagtaa tggagataaa tagagaagta gaagagcctc ctaagaagcc atctgccttc 1500
aagcctgcca ttgaaatgca aaactctgtt ccaataaaag cctttgaatt gaagaatgaa 1560
caaacattga gagcagatcc gatgttccca ccagaatcca acaaaagga ctatgaagaa 1620
aattcttggg attctgagag tctctgtgag actgtttcac agaaggatgt gtgtttaccc 1680
aaggctacac atcaaaaaga aatagataaa ataaatgaca gtctcctaat 1740
aaagatggtc ttctgaaggc tacctgcgga atgaaagttt ctattccaac taaagcctta 1800
gaattgaagg acatgcaaac tttcaaagcg gagcctccgg ggaagccatc tgccttcgag 1860
cctgccactg aaatgcaaaa gtctgtccca aataaagcct tggaattgaa aaatgaacaa 1920
acatggagag cagatgagat actcccatca gaatccaaac aaaaggacta tgaagaaaat 1980
tcttgggata ctgagagtct ctgtgagact gtttcacaga aggatgtgtg tttacccaag 2040
gctgcgcatc aaaaagaaat agataaaata aatggaaaat tagaagggtc tcctgttaaa 2100
gatggtcttc tgaaggctaa ctgcggaatg aaagtttcta ttccaactaa agccttagaa 2160
ttgatggaca tgcaaacttt caaagcagag cctcccgaga agccatctgc cttcgagcct 2220
gccattgaaa tgcaaaagtc tgttccaaat aaagccttgg aattgaagaa tgaacaaaca 2280
ttgagagcag atgagatact cccatcagaa tccaaacaaa aggactatga gaaagttct 2340
tgggattctg agagtctctg tgagactgtt tcacagaagg atgtgtgttt acccaaggct 2400
acacatcaaa aagaaataga taaataaat ggaaaattag aagagtctcc tgataatgat 2460
ggttttctga aggctccctg cagaatgaaa gtttctattc caactaaagc cttagaattg 2520
atggacatgc aaactttcaa agcagagcct cccgagaagc catctgcctt cgagcctgcc 2580
attgaaatgc aaaagtctgt tccaaataaa gccttggaat tgaagaatga acaaacattg 2640
agagcagatc agatgttccc ttcagaatca aaacaaaaga aggttgaaga aaattcttgg 2700
gattctgaga gtctccgtga gactgtttca cagaaggtg tgtgtgtacc caaggctaca 2760
catcaaaaag aaatggataa aataagtgga aaattagaag attcaactag cctatcaaaa 2820
atcttggata cagttcattc ttgtgaaaga gcaagggaac ttcaaaaaga tcactgtgaa 2880
caacgtacag gaaaatgga acaaatgaaa aagaagtttt gtgtactgaa aagaaactg 2940
tcagaagcaa aagaaataaa atcacagtta ggaacccaaa aagttaaatg ggaacaagag 3000
ctctgcagtg tgagattgac tttaaaccaa gaagaagaga agagaagaaa tgccgatata 3060
ttaaatgaaa aaattaggga agaattagga agaatcgaag agcagcatag gaaagagtta 3120
gaagtgaaac aacaacttga acaggctctc agaatacaag atatagaatt gaagagtgta 3180
gaaagtaatt tgaatcaggt ttctcacact catgaaaatg aaaattatct cttacatgaa 3240
aattgcatgt tgaaaaagga aattgccatg ctaaaactgg aaatagccac actgaaacac 3300
caataccagg aaaaggaaaa taaatacttt gaggcactta gattttaaaa gaaaagaat 3360
gctgaacttc agatgaccct aaaactgaaa gaggaatcat taactaaaag ggcatctcaa 3420
tatagtgggc agcttaaagt tctgatagct gagaacacaa tgctcacttc taaattgaag 3480
gaaaaacaag acaaagaaat actgagggca gaaattgaat cacaccatcc tagactggag 3540
tctgctgtac aagaccatga tcaaattgtg acatcaagaa aaagtcaaga acctgctttc 3600
cacattgcag gagatgcttg tttgcaaaga aaaatgaatg ttgatgtgag tagtacgata 3660
tataacaatg aggtgctcca tcaaccactt tctgaagctc aaaggaaatc caaaagccta 3720
aaaattaatt tcaattatgc aggagatgct ctaagagaaa tacattggt ttcagaacat 3780
gcacaaagag accaacgtga aacacagtgt caaatgaagg aagctgaaca catgtatcaa 3840
aacgaacaag ataatgtgaa caaacacact gaacagcagg agtctctaga tcagaaatta 3900
tttcaactac aaagcaaaaa tatgtggctt caacagcaat tagttcatgc acataagaaa 3960
gctgacaaca aaagcaagat aacaattgat attcattttc ttgagaggaa aatgcaacat 4020
catctcctaa aagagaaaaa tgaggagata tttaattaca ataaccatt aaaaaaccgt 4080
atatatcaat atgaaaaaga gaaagcagaa acagaaaact catgagagac aagcagtaag 4140
aaacttcttt tggagaaaca acagaccaga tctttactca caactcatgc taggaggcca 4200
gtcctagcat caccttatgt tgaaaatctt accaatagtc tgtgtcaaca gaatacttat 4260
tttagaagaa aaattcatga tttcttcctg aagcctacag acataaaata acagtgtgaa 4320
gaattacttg ttcacgaatt gcataaagct gcacaggatt cccatctacc ctgatgatgc 4380
agcagacatc attcaatcca accagaatct cgctctgcac tccagcctag gtgacagagt 4440
gagactccac ctcggaaa                                                4458
```

<210> SEQ ID NO 565
<211> LENGTH: 1341
<212> TYPE: PRT
<213> ORGANISM: Homo sapiens

<400> SEQUENCE: 565

```
Met Thr Lys Arg Lys Lys Thr Ile Asn Leu Asn Ile Gln Asp Ala Gln
              5                  10                  15
Lys Arg Thr Ala Leu His Trp Ala Cys Val Asn Gly His Glu Glu Val
         20                  25                  30
Val Thr Phe Leu Val Asp Arg Lys Cys Gln Leu Asp Val Leu Asp Gly
     35                  40                  45
Glu His Arg Thr Pro Leu Met Lys Ala Leu Gln Cys His Gln Glu Ala
 50                  55                  60
```

```
Cys Ala Asn Ile Leu Ile Asp Ser Gly Ala Asp Ile Asn Leu Val Asp
 65                  70                  75                  80
Val Tyr Gly Asn Met Ala Leu His Tyr Ala Val Tyr Ser Glu Ile Leu
                 85                  90                  95
Ser Val Val Ala Lys Leu Leu Ser His Gly Ala Val Ile Glu Val His
            100                 105                 110
Asn Lys Ala Ser Leu Thr Pro Leu Leu Ser Ile Thr Lys Arg Ser
        115                 120                 125
Glu Gln Ile Val Glu Phe Leu Leu Ile Lys Asn Ala Asn Ala Asn Ala
    130                 135                 140
Val Asn Lys Tyr Lys Cys Thr Ala Leu Met Leu Ala Val Cys His Gly
145                 150                 155                 160
Ser Ser Glu Ile Val Gly Met Leu Leu Gln Gln Asn Val Asp Val Phe
                165                 170                 175
Ala Ala Asp Ile Cys Gly Val Thr Ala Glu His Tyr Ala Val Thr Cys
            180                 185                 190
Gly Phe His His Ile His Glu Gln Ile Met Glu Tyr Ile Arg Lys Leu
        195                 200                 205
Ser Lys Asn His Gln Asn Thr Asn Pro Glu Gly Thr Ser Ala Gly Thr
    210                 215                 220
Pro Asp Glu Ala Ala Pro Leu Ala Glu Arg Thr Pro Asp Thr Ala Glu
225                 230                 235                 240
Ser Leu Val Glu Lys Thr Pro Asp Glu Ala Ala Pro Leu Val Glu Arg
                245                 250                 255
Thr Pro Asp Thr Ala Glu Ser Leu Val Glu Lys Thr Pro Asp Glu Ala
            260                 265                 270
Ala Ser Leu Val Glu Gly Thr Ser Asp Lys Ile Gln Cys Leu Glu Lys
        275                 280                 285
Ala Thr Ser Gly Lys Phe Glu Gln Ser Ala Glu Glu Thr Pro Arg Glu
    290                 295                 300
Ile Thr Ser Pro Ala Lys Glu Thr Ser Glu Lys Phe Thr Trp Pro Ala
305                 310                 315                 320
Lys Gly Arg Pro Arg Lys Ile Ala Trp Glu Lys Lys Glu Asp Thr Pro
                325                 330                 335
Arg Glu Ile Met Ser Pro Ala Lys Glu Thr Ser Glu Lys Phe Thr Trp
            340                 345                 350
Ala Ala Lys Gly Arg Pro Arg Lys Ile Ala Trp Glu Lys Lys Glu Thr
        355                 360                 365
Pro Val Lys Thr Gly Cys Val Ala Arg Val Thr Ser Asn Lys Thr Lys
    370                 375                 380
Val Leu Glu Lys Gly Arg Ser Lys Met Ile Ala Cys Pro Thr Lys Glu
385                 390                 395                 400
Ser Ser Thr Lys Ala Ser Ala Asn Asp Gln Arg Phe Pro Ser Glu Ser
                405                 410                 415
Lys Gln Glu Glu Asp Glu Glu Tyr Ser Cys Asp Ser Arg Ser Leu Phe
            420                 425                 430
Glu Ser Ser Ala Lys Ile Gln Val Cys Ile Pro Glu Ser Ile Tyr Gln
        435                 440                 445
Lys Val Met Glu Ile Asn Arg Glu Val Glu Glu Pro Pro Lys Lys Pro
    450                 455                 460
Ser Ala Phe Lys Pro Ala Ile Glu Met Gln Asn Ser Val Pro Asn Lys
465                 470                 475                 480
Ala Phe Glu Leu Lys Asn Glu Gln Thr Leu Arg Ala Asp Pro Met Phe
                485                 490                 495
Pro Pro Glu Ser Lys Gln Lys Asp Tyr Glu Glu Asn Ser Trp Asp Ser
            500                 505                 510
Glu Ser Leu Cys Glu Thr Val Ser Gln Lys Asp Val Cys Leu Pro Lys
        515                 520                 525
Ala Thr His Gln Lys Glu Ile Asp Lys Ile Asn Gly Lys Leu Glu Glu
    530                 535                 540
Ser Pro Asn Lys Asp Gly Leu Leu Lys Ala Thr Cys Gly Met Lys Val
545                 550                 555                 560
Ser Ile Pro Thr Lys Ala Leu Glu Leu Lys Asp Met Gln Thr Phe Lys
                565                 570                 575
Ala Glu Pro Pro Gly Lys Pro Ser Ala Phe Glu Pro Ala Thr Glu Met
            580                 585                 590
Gln Lys Ser Val Pro Asn Lys Ala Leu Glu Leu Lys Asn Glu Gln Thr
        595                 600                 605
Trp Arg Ala Asp Glu Ile Leu Pro Ser Glu Ser Lys Gln Lys Asp Tyr
    610                 615                 620
Glu Glu Asn Ser Trp Asp Thr Glu Ser Leu Cys Glu Thr Val Ser Gln
625                 630                 635                 640
Lys Asp Val Cys Leu Pro Lys Ala His Gln Lys Glu Ile Asp Lys
                645                 650                 655
Ile Asn Gly Lys Leu Glu Gly Ser Pro Val Lys Asp Gly Leu Leu Lys
            660                 665                 670
Ala Asn Cys Gly Met Lys Val Ser Ile Pro Thr Lys Ala Leu Glu Leu
        675                 680                 685
Met Asp Met Gln Thr Phe Lys Ala Glu Pro Pro Glu Lys Pro Ser Ala
```

-continued

```
            690                 695                 700
    Phe Glu Pro Ala Ile Glu Met Gln Lys Ser Val Pro Asn Lys Ala Leu
705                 710                 715                 720
    Glu Leu Lys Asn Glu Gln Thr Leu Arg Ala Asp Glu Ile Leu Pro Ser
                        725                 730                 735
    Glu Ser Lys Gln Lys Asp Tyr Glu Glu Ser Ser Trp Asp Ser Glu Ser
                        740                 745                 750
    Leu Cys Glu Thr Val Ser Gln Lys Asp Val Cys Leu Pro Lys Ala Thr
                        755                 760                 765
    His Gln Lys Glu Ile Asp Lys Ile Asn Gly Lys Leu Glu Glu Ser Pro
                        770                 775                 780
    Asp Asn Asp Gly Phe Leu Lys Ala Pro Cys Arg Met Lys Val Ser Ile
785                 790                 795                 800
    Pro Thr Lys Ala Leu Glu Leu Met Asp Met Gln Thr Phe Lys Ala Glu
                        805                 810                 815
    Pro Pro Glu Lys Pro Ser Ala Phe Glu Pro Ala Ile Glu Met Gln Lys
                        820                 825                 830
    Ser Val Pro Asn Lys Ala Leu Glu Leu Lys Asn Glu Gln Thr Leu Arg
                        835                 840                 845
    Ala Asp Gln Met Phe Pro Ser Glu Ser Lys Gln Lys Lys Val Glu Glu
                        850                 855                 860
    Asn Ser Trp Asp Ser Glu Ser Leu Arg Glu Thr Val Ser Gln Lys Asp
865                 870                 875                 880
    Val Cys Val Pro Lys Ala Thr His Gln Lys Glu Met Asp Lys Ile Ser
                        885                 890                 895
    Gly Lys Leu Glu Asp Ser Thr Ser Leu Ser Lys Ile Leu Asp Thr Val
                        900                 905                 910
    His Ser Cys Glu Arg Ala Arg Glu Leu Gln Lys Asp His Cys Glu Gln
                        915                 920                 925
    Arg Thr Gly Lys Met Glu Gln Met Lys Lys Phe Cys Val Leu Lys
                        930                 935                 940
    Lys Lys Leu Ser Glu Ala Lys Glu Ile Lys Ser Gln Leu Glu Asn Gln
945                 950                 955                 960
    Lys Val Lys Trp Glu Gln Glu Leu Cys Ser Val Arg Leu Thr Leu Asn
                        965                 970                 975
    Gln Glu Glu Glu Lys Arg Arg Asn Ala Asp Ile Leu Asn Glu Lys Ile
                        980                 985                 990
    Arg Glu Glu Leu Gly Arg Ile Glu Glu Gln His Arg Lys Glu Leu Glu
                        995                 1000                1005
    Val Lys Gln Gln Leu Glu Gln Ala Leu Arg Ile Gln Asp Ile Glu Leu
                        1010                1015                1020
    Lys Ser Val Glu Ser Asn Leu Asn Gln Val Ser His Thr His Glu Asn
1025                1030                1035                1040
    Glu Asn Tyr Leu Leu His Glu Asn Cys Met Leu Lys Lys Glu Ile Ala
                        1045                1050                1055
    Met Leu Lys Leu Glu Ile Ala Thr Leu Lys His Gln Tyr Gln Glu Lys
                        1060                1065                1070
    Glu Asn Lys Tyr Phe Glu Asp Ile Lys Ile Leu Lys Glu Lys Asn Ala
                        1075                1080                1085
    Glu Leu Gln Met Thr Leu Lys Leu Lys Glu Glu Ser Leu Thr Lys Arg
                        1090                1095                1100
    Ala Ser Gln Tyr Ser Gly Gln Leu Lys Val Leu Ile Ala Glu Asn Thr
1105                1110                1115                1120
    Met Leu Thr Ser Lys Leu Lys Glu Lys Gln Asp Lys Glu Ile Leu Glu
                        1125                1130                1135
    Ala Glu Ile Glu Ser His His Pro Arg Leu Ala Ser Ala Val Gln Asp
                        1140                1145                1150
    His Asp Gln Ile Val Thr Ser Arg Lys Ser Gln Glu Pro Ala Phe His
                        1155                1160                1165
    Ile Ala Gly Asp Ala Cys Leu Gln Arg Lys Met Asn Val Asp Val Ser
                        1170                1175                1180
    Ser Thr Ile Tyr Asn Asn Glu Val Leu His Gln Pro Leu Ser Glu Ala
1185                1190                1195                1200
    Gln Arg Lys Ser Lys Ser Leu Lys Ile Asn Leu Asn Tyr Ala Gly Asp
                        1205                1210                1215
    Ala Leu Arg Glu Asn Thr Leu Val Ser Glu His Ala Gln Arg Asp Gln
                        1220                1225                1230
    Arg Glu Thr Gln Cys Gln Met Lys Glu Ala Glu His Met Tyr Gln Asn
                        1235                1240                1245
    Glu Gln Asp Asn Val Asn Lys His Thr Glu Gln Gln Glu Ser Leu Asp
                        1250                1255                1260
    Gln Lys Leu Phe Gln Leu Gln Ser Lys Asn Met Trp Leu Gln Gln Gln
1265                1270                1275                1280
    Leu Val His Ala His Lys Lys Ala Asp Asn Lys Ser Lys Ile Thr Ile
                        1285                1290                1295
    Asp Ile His Phe Leu Glu Arg Lys Met Gln His His Leu Leu Lys Glu
                        1300                1305                1310
    Lys Asn Glu Glu Ile Phe Asn Tyr Asn Asn His Leu Lys Asn Arg Ile
                        1315                1320                1325
```

```
Tyr Gln Tyr Glu Lys Glu Lys Ala Glu Thr Glu Asn Ser
    1330            1335                1340
```

<210> SEQ ID NO 566
<211> LENGTH: 4047
<212> TYPE: DNA
<213> ORGANISM: Homo sapiens

<400> SEQUENCE: 566

```
atgcagcatc accaccatca ccaccacaca aagaggaaga agaccatcaa ccttaatata   60
caagacgccc agaagaggac tgctctacac tgggcctgtg tcaatggcca tgaggaagta  120
gtaacatttc tggtagacag aaagtgccag cctgacgtcc ttgatggcga acacaggaca  180
cctctgatga aggctctaca atgccatcag gaggcttgtg caaatattct gatagattct  240
ggtgccgata taaatctcgt agatgtgtat ggcaacatgg ctctccatta tgctgtttat  300
agtgagattt tgtcagtggt ggcaaaactg ctgtcccatg gtgcagtcat cgaagtgcac  360
aacaaggcta gcctcacacc acttttacta tccataacga aaagaagtga gcaaattgtg  420
gaattttttgc tgataaaaaa tgcaaatgcg aatgcagtta ataagtataa atgcacagcc  480
ctcatgcttg ctgtatgtca tggattatca gatagagttg gcatgcttct tcagcaaaat  540
gttgacgtct ttgctgcaga tatatgtgga gtaactgcag aacattatgc tgttacttgt  600
ggatttcatc acattcatga acaattatg gaatatatac gaaaattatc taaaaatcat  660
caaaatacca atccagaagg aacatctgca ggaacacctg atgaggctgc acccttggcg  720
gaaagaacac tgacacagc tgaaagcttg gtggaaaaaa cacctgatga ggctgcaccc  780
ttggtggaaa gaacacctga cacggctgaa agcttggtgg aaaaaacacc tgatgaggct  840
gcatccttgg tggagggaac atctgacaaa attcaatgtt tggagaaagc gacatctgga  900
aagttcgaac agtcagcaga agaaacacct agggaaatta cgagtcctgc aaaagaaaca  960
tctgagaaat ttacgtggcc agcaaaagga agacctagga agatcgcatg ggagaaaaaa 1020
gaagcacac ctagggaaat tatgagtccc gcaaaagaaa catctgagaa attttacgtgg 1080
gcagcaaaag gaagacctag gaagatcgca tgggagaaaa agaaacacc tgtaaagact 1140
ggatgcgtgg caagagtaac atctaataaa actaaagttt tggaaaaagg aagatctaag 1200
atgattgcat gtcctacaaa agaatcatct acaaaagcaa gtgccaatga tcagaggttc 1260
ccatcagaat ccaaacaaga ggaagatgaa gaatattctt gtgattctga gagtctcttc 1320
gagagttctg caaagattca agtgtgtata cctgagtcta tatatcaaaa agtaatggag 1380
ataaatagag aagtagaaga gcctcctaag aagccatctg ccttcaagcc tgccattgaa 1440
atgcaaaact ctgttccaaa taaagccttt gaattgaaga atgaacaaac attgagagca 1500
gatccgatgt tcccaccaga atccaaacaa aaggactatg aagaaattc ttgggattct 1560
gagagtctct gtgagactgt ttcacagaag gatgtgtgtt tacccaaggc tacacatcaa 1620
aaagaaatag ataaaataaa tggaaaatta gaagagtctc taataaaga tggtcttctg 1680
aaggctacct gcggaatgaa agtttctatt ccaactaaag ccttagaatt gaaggacatg 1740
caaactttca aagcggagcc tccggggaac ccatctgcct tcgagcctgc cactgaaatg 1800
caaaagtctg tcccaaataa agccttggaa ttgaaaaatg aacaaacatg gagagcagat 1860
gagatactcc catcagaatc caaacaaaag gactatgaag aaattcttg gatactgag 1920
agtctctgtg agactgtttc acagaaggat gtgtgtttac caaggctgc gcatcaaaaa 1980
gaaatagata aaataaatgg aaaattagaa gggtctcctg ttaaagatgg tcttctgaag 2040
gctaactgcg gaatgaaagt ttctattcca actaaagcct tagaattgat ggacatgcaa 2100
actttcaaag cagagcctcc cgagaagcca tctgccttcg agcctgccat tgaaatgcaa 2160
aagtctgttc aaataaagc cttggaattg aagaatgaac aaacattgag agcagatgag 2220
atactcccat cagaatccaa acaaaaggac tatgaagaaa gttcttggga ttctgagagt 2280
ctctgtgaga ctgtttcaca gaaggatgtg tgtttaccca agctacacac tcaaaaagaa 2340
atagataaaa taaatggaaa attagaagag tctcctgata atgatggttt tctgaaggct 2400
ccctgcagaa tgaaagtttc tattccaact aaagcttag aattgatgga catgcaaact 2460
ttcaaagcag agcctcccga agaagccatct gccttcgagc tgccattga aatgcaaaag 2520
tctgttccaa ataaagcctt ggaattgaag aatgaacaaa cattgagagc agatcagtg 2580
ttcccttcag aatcaaaaca aaagaaggtt gaagaaaatt cttgggattc tgagagtctc 2640
cgtgagactg tttcacagaa ggatgtgtgt gtacccaagg ctacacatca aaaagaaatg 2700
gataaaataa gtggaaaatt agaagattca actagccat caaaaatctt ggatacagtt 2760
cattcttgtg aaagagcaag ggaacttcaa aaagatcatc gtgaacacg tacaggaaaa 2820
atggaacaaa tgaaaaagaa gttttgtgta ctgaaaaaga aactgtcaga agcaaaagaa 2880
ataaaatcac agttagaaa ccaaaaagtt aaatgggaac aagagctctg cagtgtgaga 2940
ttgacttaa accaagaaga agagaagaga agaaatgccg atatattaaa tgaaaaaatt 3000
agggaagaat taggaagaat cgaagagcag catagggaag agttagaagt gaaacaacaa 3060
cttgaacagg ctctcagaat acaagatata gaattgaaga gtgtagaaag taatttgaat 3120
caggttttctc acactcatga aaatgaaaat tatctcttac atgaaaattg catgttgaaa 3180
aaggaaattg ccatgctaaa actggaaata gccacactga acaccaata ccaggaaaag 3240
gaaaataaat actttgagga cattaagatt ttaaaagaaa agaatgctga acttcagatg 3300
accctaaaac tgaaagagga atcattaact aaaagggcat ctcaatatag tgggcagctt 3360
aaagttctga tagctgaaa cacaatgctc acttctaaat tgaaggaaaa acaagacaaa 3420
gaaatactag aggcagaaat tgaatcacac catcctagac tggcttctgc tgtacaagac 3480
catgatcaaa ttgtgacatc aagaaaaagt caagaacctg cttttccacat tgcaggagat 3540
gcttgttttgc aaagaaaaat gaatgttgat gtgagtagta cgatatataa caatgaggtg 3600
ctccatcaac cacttttctga agctcaaagg aaatccaaaa gcctaaaaat taatctcaat 3660
tatgcaggag atgctctaag agaaaataca ttggtttcag aacatgcaca aagagaccaa 3720
cgtgaaacac agtgtcaaat gaaggaagct gaacacatgt atcaaaacga acaagataat 3780
gtgaacaaac acactgaaca gcaggagtct ctagatcaga attattttca actacaaagc 3840
aaaaatatgt ggcttcaaca gcaattagtt catgcacata gaaaagctga caacaaaagc 3900
aagataacaa ttgatattca ttttcttgag aggaaaatgc aacatcatct cctaaaagag 3960
aaaaatgagg agatatttaa ttacaataac catttaaaaa accgtatata tcaatgaag 4020
aaagagaaag cagaaacaga agttata                                      4047
```

<210> SEQ ID NO 567
<211> LENGTH: 1199
<212> TYPE: DNA
<213> ORGANISM: Homo sapiens

<400> SEQUENCE: 567

```
acaaagagga agaagaccat caaccttaat atacaagacg cccagaagag gactgctcta   60
cactgggcct gtgtcaatgg ccatgaggaa gtagtaacat ttctggtaga cagaaagtgc  120
cagcctgacg tccttgatgg cgaacacagg acacctctga tgaaggctct acaatgccat  180
caggaggctt gtgcaaatat tctgatagat tctggtgccg atataaatct cgtagatgtg  240
tatggcaaca tggctctcca ttatgctgtt tatagtgaga ttttgtcagt ggtggcaaaa  300
ctgctgtccc atggtgcagt catcgaagtg cacaacaagg ctagcctcac accactttta  360
ctatccataa cgaaaagaag tgagcaaatt gtggaatttt tgctgataaa aaatgcaaat  420
gcgaatgcag ttaataagta taaatgcaca gccctcatgc ttgctgtatg tcatggatta  480
tcagagatag ttggcatgct tcttcagcaa aatgttgacg tctttgctgc agatatatgt  540
ggagtaactg cagaacatta tgctgttact tgtggatttc atcacattca tgaacaaatt  600
atggaatata tacgaaaatt atctaaaaat catcaaaata ccaatccaga ggaacatcat  660
gcaggaacac ctgatgaggc tgcacccttg gcggaaagaa cacctgacac agctgaaagc  720
ttggtggaaa aaacacctga tgaggctgca cccttggtgg aagaacacc tgcacggct  780
gaaagcttgg tgaaaaaac acctgatgag gctgcatcct tggtggaggg aacatctgac  840
aaaattcaat gtttggagaa agcgacatct ggaaagttcg aacagtcagc agaagaaaca  900
cctagggaaa ttacgagtcc tgcaaaagaa acatctggaa aatttacgtg gccagcaaaa  960
ggaagaccta ggaagatcgc atgggagaaa aaagaagaca cactctaggga aattatgagt 1020
cccgcaaaag aaacatctga gaaatttacg tgggcagcaa aaggaagacc taggaagatc 1080
gcatgggaga aaaaagaaac acctgtaaag actggatgcg tggcaagagt aacatctaat 1140
aaaactaaag tttttggaaaa aggaagatct aagatgattg catgtcctac aaaagaatc  1199
```

<210> SEQ ID NO 568
<211> LENGTH: 1199
<212> TYPE: DNA
<213> ORGANISM: Homo sapiens

<400> SEQUENCE: 568

```
acaaagagga agaagaccat caaccttaat atacaagacg cccagaagag gactgctcta   60
cactgggcct gtgtcaatgg ccatgaggaa gtagtaacat ttctggtaga cagaaagtgc  120
cagcttgacg tccttgatgg cgaacacagg acacctctga tgaaggctct acaatgccat  180
caggaggctt gtgcaaatat tctgatagat tctggtgccg atataaatct cgtagatgtg  240
tatgacaaca cggctctcca ttatgctgtt tatagtgaga ttttgtcagt ggtggcaaaa  300
ctgctgtccc atggtgcagt catctaagcg cacaacaagg ctagcctcac accactttta  360
ctatccataa cgaaaagaag tgagcaaatt gtggaatttt tgctgataaa aaatgcaaat  420
gcgaatgcag ttaataagta taaatgcaca gccctcatgc ttgctgtatg tcatggatca  480
tcagagatag ttggcatgct tcttcagcaa aatgttgacg tctttgctgc agatatatgt  540
ggagtaactg cagaacatta tgctgttact tgtggatttc atcacattca tgaacaaatt  600
atggaatata tacgaaaatt atctaaaaat catcaaaata ccaatccaga ggaacatcat  660
gcaggaacac ctgatgaggc tgcacccttg gcggaaagaa cacctgacac agctgaaagc  720
ttggtggaaa aaacacctga tgaggctgca cccttggtgg aagaacacc tgcacggct  780
gaaagcttgg tgaaaaaac acctgatgag gctgcatcct tggtggaggg aacatctgac  840
aaaattcaat gtttggagaa agcgacatct ggaaagttcg aacagtcagc agaagaaaca  900
cctagggaaa ttacgagtcc tgcaaaagaa acatctggaa aatttacgtg gccagcaaaa  960
ggaagaccta ggaagatcgc atgggagaaa aaagaagaca cactctaggga aattatgagt 1020
cccgcaaaag aaacatctga gaaatttacg tgggcagcaa aaggaagacc taggaagatc 1080
gcatgggaga aaaaagaaac acctgtaaag actggatgcg tggcaagagt aacatctaat 1140
aaaactaaag tttttggaaaa aggaagatct aagatgattg catgtcctac aaaagaatc  1199
```

<210> SEQ ID NO 569
<211> LENGTH: 1199
<212> TYPE: DNA
<213> ORGANISM: Homo sapiens

<400> SEQUENCE: 569

```
acaaagagga agaagaccat caaccttaat atacaagacg cccagaagag gactgctcta   60
cactgggcct gtgtcaatgg ccatgaggaa gtagtaacat ttctggtaga cagaaagtgc  120
cagcttgacg tccttgatgg cgaacacagg acacctctga tgaaggctct acaatgccat  180
caggaggctt gtgcaaatat tctgatagat tctggtgccg atataaatct cgtagatgtg  240
tatggcaaca tggctctcca ttatgctgtt tatagtgaga ttttgtcagt ggtggcaaaa  300
ctgctgtccc atggtgcagt catcgaagtg cacaacaagg ctagcctcac accactttta  360
ctatccataa cgaaaagaag tgagcaaatt gtggaatttt tgctgataaa aaatgcaaat  420
gcgaatgcag ttaataagta taaatgcaca gccctcatgc ttgctgtatg tcatggatca  480
tcagagatag ttggcatgct tcttcagcaa aatgttgacg tctttgctgc agatatatgt  540
ggagtaactg cagaacatta tgctgttact tgtggatttc atcacattca tgaacaaatt  600
atggaatata tacgaaaatt atctaaaaat catcaaaata ccaatccaga ggaacatcat  660
gcaggaacac ctgatgaggc tgcacccttg gcggaaagaa cacctgacac agctgaaagc  720
```

```
                  ttggtggaaa aaacacctga tgaggctgca cccttggtgg aaagaacacc tgacacggct   780
                  gaaagcttgg tggaaaaaac acctgatgag gctgcatcct tggtggaggg aacatctgac   840
                  aaaattcaat gtttggagaa agcgacatct ggaaagttcg aacagtcagc agaagaaaca   900
                  cctagggaaa ttacgagtcc tgcaaaagaa acatctgaga aatttacgtg gccagcaaaa   960
                  ggaagaccta ggaagatcgc atgggagaaa aaagaagaca cacctaggga aattatgagt  1020
                  cccgcaaaag aaacatctga gaaatttacg tgggcagcaa aaggaagacc taggaagatc  1080
                  gcatgggaga aaaagaaac acctgtaaag actggatgcg tggcaagagt aacatctaat  1140
                  aaaactaaag ttttggaaaa aggaagatct aagatgattg catgtcctac aaaagaatc   1199
```

<210> SEQ ID NO 570
<211> LENGTH: 399
<212> TYPE: PRT
<213> ORGANISM: Homo sapiens

<400> SEQUENCE: 570

```
Thr Lys Arg Lys Lys Thr Ile Asn Leu Asn Ile Gln Asp Ala Gln Lys
                 5                  10                  15
Arg Thr Ala Leu His Trp Ala Cys Val Asn Gly His Glu Glu Val Val
             20                  25                  30
Thr Phe Leu Val Asp Arg Lys Cys Gln Leu Asp Val Leu Asp Gly Glu
         35                  40                  45
His Arg Thr Pro Leu Met Lys Ala Leu Gln Cys His Gln Glu Ala Cys
     50                  55                  60
Ala Asn Ile Leu Ile Asp Ser Gly Ala Asp Ile Asn Leu Val Asp Val
 65                  70                  75                  80
Tyr Gly Asn Met Ala Leu His Tyr Ala Val Tyr Ser Glu Ile Leu Ser
                 85                  90                  95
Val Val Ala Lys Leu Leu Ser His Gly Ala Val Ile Glu Val His Asn
            100                 105                 110
Lys Ala Ser Leu Thr Pro Leu Leu Leu Ser Ile Thr Lys Arg Ser Glu
        115                 120                 125
Gln Ile Val Glu Phe Leu Leu Ile Lys Asn Ala Asn Ala Asn Ala Val
    130                 135                 140
Asn Lys Tyr Lys Cys Thr Ala Leu Met Leu Ala Val Cys His Gly Ser
145                 150                 155                 160
Ser Glu Ile Val Gly Met Leu Leu Gln Gln Asn Val Asp Val Phe Ala
                165                 170                 175
Ala Asp Ile Cys Gly Val Thr Ala Glu His Tyr Ala Val Thr Cys Gly
            180                 185                 190
Phe His His Ile His Glu Gln Ile Met Glu Tyr Ile Arg Lys Leu Ser
        195                 200                 205
Lys Asn His Gln Asn Thr Asn Pro Glu Gly Thr Ser Ala Gly Thr Pro
    210                 215                 220
Asp Glu Ala Ala Pro Leu Ala Glu Arg Thr Pro Asp Thr Ala Glu Ser
225                 230                 235                 240
Leu Val Glu Lys Thr Pro Asp Glu Ala Ala Pro Leu Val Glu Arg Thr
                245                 250                 255
Pro Asp Thr Ala Glu Ser Leu Val Glu Lys Thr Pro Asp Glu Ala Ala
            260                 265                 270
Ser Leu Val Glu Gly Thr Ser Asp Lys Ile Gln Cys Leu Glu Lys Ala
        275                 280                 285
Thr Ser Gly Lys Phe Glu Gln Ser Ala Glu Thr Pro Arg Glu Ile
    290                 295                 300
Thr Ser Pro Ala Lys Glu Thr Ser Glu Lys Phe Thr Trp Pro Ala Lys
305                 310                 315                 320
Gly Arg Pro Arg Lys Ile Ala Trp Glu Lys Lys Glu Asp Thr Pro Arg
                325                 330                 335
Glu Ile Met Ser Pro Ala Lys Glu Thr Ser Glu Lys Phe Thr Trp Ala
            340                 345                 350
Ala Lys Gly Arg Pro Arg Lys Ile Ala Trp Glu Lys Lys Glu Thr Pro
        355                 360                 365
Val Lys Thr Gly Cys Val Ala Arg Val Thr Ser Asn Lys Thr Lys Val
    370                 375                 380
Leu Glu Lys Gly Arg Ser Lys Met Ile Ala Cys Pro Thr Lys Glu
385                 390                 395
```

<210> SEQ ID NO 571
<211> LENGTH: 247
<212> TYPE: PRT
<213> ORGANISM: Homo sapiens

<400> SEQUENCE: 571

```
Met Leu Ala Val Cys His Gly Ser Ser Glu Ile Val Gly Met Leu Leu
                 5                  10                  15
Gln Gln Asn Val Asp Val Phe Ala Ala Asp Ile Cys Gly Val Thr Ala
```

```
            20                  25                  30
Glu His Tyr Ala Val Thr Cys Gly Phe His His Ile His Glu Gln Ile
        35                  40                  45
Met Glu Tyr Ile Arg Lys Leu Ser Lys Asn His Gln Asn Thr Asn Pro
    50                  55                  60
Glu Gly Thr Ser Ala Gly Thr Pro Asp Ala Ala Pro Leu Ala Glu
65                  70                  75                  80
Arg Thr Pro Asp Thr Ala Glu Ser Leu Val Glu Lys Thr Pro Asp Glu
                85                  90                  95
Ala Ala Pro Leu Val Glu Arg Thr Pro Asp Thr Ala Glu Ser Leu Val
            100                 105                 110
Glu Lys Thr Pro Asp Glu Ala Ala Ser Leu Val Glu Gly Thr Ser Asp
        115                 120                 125
Lys Ile Gln Cys Leu Glu Lys Ala Thr Ser Gly Lys Phe Glu Gln Ser
    130                 135                 140
Ala Glu Glu Thr Pro Arg Glu Ile Thr Ser Pro Ala Lys Glu Thr Ser
145                 150                 155                 160
Glu Lys Phe Thr Trp Pro Ala Lys Gly Arg Pro Arg Lys Ile Ala Trp
                165                 170                 175
Glu Lys Lys Glu Asp Thr Pro Arg Glu Ile Met Ser Pro Ala Lys Glu
            180                 185                 190
Thr Ser Glu Lys Phe Thr Trp Ala Ala Lys Gly Arg Pro Arg Lys Ile
        195                 200                 205
Ala Trp Glu Lys Lys Glu Thr Pro Val Lys Thr Gly Cys Val Ala Arg
    210                 215                 220
Val Thr Ser Asn Lys Thr Lys Val Leu Glu Lys Gly Arg Ser Lys Met
225                 230                 235                 240
Ile Ala Cys Pro Thr Lys Glu
                245
```

<210> SEQ ID NO 572
<211> LENGTH: 399
<212> TYPE: PRT
<213> ORGANISM: Homo sapiens

<400> SEQUENCE: 572

```
Thr Lys Arg Lys Lys Thr Ile Asn Leu Asn Ile Gln Asp Ala Gln Lys
                5                   10                  15
Arg Thr Ala Leu His Trp Ala Cys Val Asn Gly His Glu Glu Val Val
            20                  25                  30
Thr Phe Leu Val Asp Arg Lys Cys Gln Pro Asp Val Leu Asp Gly Glu
        35                  40                  45
His Arg Thr Pro Leu Met Lys Ala Leu Gln Cys His Gln Glu Ala Cys
    50                  55                  60
Ala Asn Ile Leu Ile Asp Ser Gly Ala Asp Ile Asn Leu Val Asp Val
65                  70                  75                  80
Tyr Gly Asn Met Ala Leu His Tyr Ala Val Tyr Ser Glu Ile Leu Ser
                85                  90                  95
Val Val Ala Lys Leu Leu Ser His Gly Ala Val Ile Glu Val His Asn
            100                 105                 110
Lys Ala Ser Leu Thr Pro Leu Leu Leu Ser Ile Thr Lys Arg Ser Glu
        115                 120                 125
Gln Ile Val Glu Phe Leu Leu Ile Lys Asn Ala Asn Ala Asn Ala Val
    130                 135                 140
Asn Lys Tyr Lys Cys Thr Ala Leu Met Leu Ala Val Cys His Gly Leu
145                 150                 155                 160
Ser Glu Ile Val Gly Met Leu Leu Gln Gln Asn Val Asp Val Phe Ala
                165                 170                 175
Ala Asp Ile Cys Gly Val Thr Ala Glu His Tyr Ala Val Thr Cys Gly
            180                 185                 190
Phe His His Ile His Glu Gln Ile Met Glu Tyr Ile Arg Lys Leu Ser
        195                 200                 205
Lys Asn His Gln Asn Thr Asn Pro Glu Gly Thr Ser Ala Gly Thr Pro
    210                 215                 220
Asp Glu Ala Ala Pro Leu Ala Glu Arg Thr Pro Asp Thr Ala Glu Ser
225                 230                 235                 240
Leu Val Glu Lys Thr Pro Asp Glu Ala Ala Pro Leu Val Glu Arg Thr
                245                 250                 255
Pro Asp Thr Ala Glu Ser Leu Val Glu Lys Thr Pro Asp Glu Ala Ala
            260                 265                 270
Ser Leu Val Glu Gly Thr Ser Asp Lys Ile Gln Cys Leu Glu Lys Ala
        275                 280                 285
Thr Ser Gly Lys Phe Glu Gln Ser Ala Glu Glu Thr Pro Arg Glu Ile
    290                 295                 300
Thr Ser Pro Ala Lys Glu Thr Ser Glu Lys Phe Thr Trp Pro Ala Lys
305                 310                 315                 320
Gly Arg Pro Arg Lys Ile Ala Trp Glu Lys Lys Glu Asp Thr Pro Arg
```

-continued

```
                       325                     330                     335
    Glu Ile Met Ser Pro Ala Lys Glu Thr Ser Glu Lys Phe Thr Trp Ala
                340                     345                     350
    Ala Lys Gly Arg Pro Arg Lys Ile Ala Trp Glu Lys Lys Glu Thr Pro
            355                     360                     365
    Val Lys Thr Gly Cys Val Ala Arg Val Thr Ser Asn Lys Thr Lys Val
        370                     375                     380
    Leu Glu Lys Gly Arg Ser Lys Met Ile Ala Cys Pro Thr Lys Glu
    385                     390                     395

<210> SEQ ID NO 573
<211> LENGTH: 1349
<212> TYPE: PRT
<213> ORGANISM: Homo sapiens

<400> SEQUENCE: 573

Met Gln His His His His His His Thr Lys Arg Lys Lys Thr Ile
                        5                      10                      15
    Asn Leu Asn Ile Gln Asp Ala Gln Lys Arg Thr Ala Leu His Trp Ala
                 20                      25                      30
    Cys Val Asn Gly His Glu Glu Val Val Thr Phe Leu Val Asp Arg Lys
             35                      40                      45
    Cys Gln Pro Asp Val Leu Asp Gly Glu His Arg Thr Pro Leu Met Lys
         50                      55                      60
    Ala Leu Gln Cys His Gln Glu Ala Cys Ala Asn Ile Leu Ile Asp Ser
    65                      70                      75                      80
    Gly Ala Asp Ile Asn Leu Val Asp Val Tyr Gly Asn Met Ala Leu His
                     85                      90                      95
    Tyr Ala Val Tyr Ser Glu Ile Leu Ser Val Val Ala Lys Leu Leu Ser
                100                     105                     110
    His Gly Ala Val Ile Glu Val His Asn Lys Ala Ser Leu Thr Pro Leu
             115                     120                     125
    Leu Leu Ser Ile Thr Lys Arg Ser Glu Gln Ile Val Glu Phe Leu Leu
         130                     135                     140
    Ile Lys Asn Ala Asn Ala Asn Ala Val Asn Lys Tyr Lys Cys Thr Ala
    145                     150                     155                     160
    Leu Met Leu Ala Val Cys His Gly Leu Ser Glu Ile Val Gly Met Leu
                     165                     170                     175
    Leu Gln Gln Asn Val Asp Val Phe Ala Ala Asp Ile Cys Gly Val Thr
                 180                     185                     190
    Ala Glu His Tyr Ala Val Thr Cys Gly Phe His His Ile His Glu Gln
             195                     200                     205
    Ile Met Glu Tyr Ile Arg Lys Leu Ser Lys Asn His Gln Asn Thr Asn
         210                     215                     220
    Pro Glu Gly Thr Ser Ala Gly Thr Pro Asp Glu Ala Ala Pro Leu Ala
    225                     230                     235                     240
    Glu Arg Thr Pro Asp Thr Ala Glu Ser Leu Val Glu Lys Thr Pro Asp
                     245                     250                     255
    Glu Ala Ala Pro Leu Val Glu Arg Thr Pro Asp Thr Ala Glu Ser Leu
                 260                     265                     270
    Val Glu Lys Thr Pro Asp Glu Ala Ala Ser Leu Val Glu Gly Thr Ser
             275                     280                     285
    Asp Lys Ile Gln Cys Leu Glu Lys Ala Thr Ser Gly Lys Phe Glu Gln
         290                     295                     300
    Ser Ala Glu Glu Thr Pro Arg Glu Ile Thr Ser Pro Ala Lys Glu Thr
    305                     310                     315                     320
    Ser Glu Lys Phe Thr Trp Pro Ala Lys Gly Arg Pro Arg Lys Ile Ala
                     325                     330                     335
    Trp Glu Lys Lys Glu Asp Thr Pro Arg Glu Ile Met Ser Pro Ala Lys
                 340                     345                     350
    Glu Thr Ser Glu Lys Phe Thr Trp Ala Ala Lys Gly Arg Pro Arg Lys
             355                     360                     365
    Ile Ala Trp Glu Lys Lys Glu Thr Pro Val Lys Thr Gly Cys Val Ala
         370                     375                     380
    Arg Val Thr Ser Asn Lys Thr Lys Val Leu Glu Lys Gly Arg Ser Lys
    385                     390                     395                     400
    Met Ile Ala Cys Pro Thr Lys Glu Ser Ser Thr Lys Ala Ser Ala Asn
                     405                     410                     415
    Asp Gln Arg Phe Pro Ser Glu Ser Lys Gln Glu Glu Asp Glu Glu Tyr
                 420                     425                     430
    Ser Cys Asp Ser Arg Ser Leu Phe Glu Ser Ala Lys Ile Gln Val
             435                     440                     445
    Cys Ile Pro Glu Ser Ile Tyr Gln Lys Val Met Glu Ile Asn Arg Glu
         450                     455                     460
    Val Glu Glu Pro Pro Lys Lys Pro Ser Ala Phe Lys Pro Ala Ile Glu
    465                     470                     475                     480
    Met Gln Asn Ser Val Pro Asn Lys Ala Phe Glu Leu Lys Asn Glu Gln
```

-continued

```
                        485                 490                 495
    Thr Leu Arg Ala Asp Pro Met Phe Pro Glu Ser Lys Gln Lys Asp
                    500                 505                 510
    Tyr Glu Glu Asn Ser Trp Asp Ser Glu Ser Leu Cys Glu Thr Val Ser
                515                 520                 525
    Gln Lys Asp Val Cys Leu Pro Lys Ala Thr His Gln Lys Glu Ile Asp
            530                 535                 540
    Lys Ile Asn Gly Lys Leu Glu Glu Ser Pro Asn Lys Asp Gly Leu Leu
    545                 550                 555                 560
    Lys Ala Thr Cys Gly Met Lys Val Ser Ile Pro Thr Lys Ala Leu Glu
                    565                 570                 575
    Leu Lys Asp Met Gln Thr Phe Lys Ala Glu Pro Pro Gly Lys Pro Ser
                580                 585                 590
    Ala Phe Glu Pro Ala Thr Glu Met Gln Lys Ser Val Pro Asn Lys Ala
                595                 600                 605
    Leu Glu Leu Lys Asn Glu Gln Thr Trp Arg Ala Asp Glu Ile Leu Pro
            610                 615                 620
    Ser Glu Ser Lys Gln Lys Asp Tyr Glu Glu Asn Ser Trp Asp Thr Glu
    625                 630                 635                 640
    Ser Leu Cys Glu Thr Val Ser Gln Lys Asp Val Cys Leu Pro Lys Ala
                    645                 650                 655
    Ala His Gln Lys Glu Ile Asp Lys Ile Asn Gly Lys Leu Glu Gly Ser
                    660                 665                 670
    Pro Val Lys Asp Gly Leu Leu Lys Ala Asn Cys Gly Met Lys Val Ser
                675                 680                 685
    Ile Pro Thr Lys Ala Leu Glu Leu Met Asp Met Gln Thr Phe Lys Ala
            690                 695                 700
    Glu Pro Pro Glu Lys Pro Ser Ala Phe Glu Pro Ala Ile Glu Met Gln
    705                 710                 715                 720
    Lys Ser Val Pro Asn Lys Ala Leu Glu Leu Lys Asn Glu Gln Thr Leu
                    725                 730                 735
    Arg Ala Asp Glu Ile Leu Pro Ser Glu Ser Lys Gln Lys Asp Tyr Glu
                740                 745                 750
    Glu Ser Ser Trp Asp Ser Glu Ser Leu Cys Glu Thr Val Ser Gln Lys
                755                 760                 765
    Asp Val Cys Leu Pro Lys Ala Thr His Gln Lys Glu Ile Asp Lys Ile
            770                 775                 780
    Asn Gly Lys Leu Glu Glu Ser Pro Asp Asn Asp Gly Phe Leu Lys Ala
    785                 790                 795                 800
    Pro Cys Arg Met Lys Val Ser Ile Pro Thr Lys Ala Leu Glu Leu Met
                    805                 810                 815
    Asp Met Gln Thr Phe Lys Ala Glu Pro Pro Glu Lys Pro Ser Ala Phe
                820                 825                 830
    Glu Pro Ala Ile Glu Met Gln Lys Ser Val Pro Asn Lys Ala Leu Glu
                835                 840                 845
    Leu Lys Asn Glu Gln Thr Leu Arg Ala Asp Gln Met Phe Pro Ser Glu
            850                 855                 860
    Ser Lys Gln Lys Lys Val Glu Glu Asn Ser Trp Asp Ser Glu Ser Leu
    865                 870                 875                 880
    Arg Glu Thr Val Ser Gln Lys Asp Val Cys Val Pro Lys Ala Thr His
                    885                 890                 895
    Gln Lys Glu Met Asp Lys Ile Ser Gly Lys Leu Glu Asp Ser Thr Ser
                900                 905                 910
    Leu Ser Lys Ile Leu Asp Thr Val His Ser Cys Glu Arg Ala Arg Glu
                915                 920                 925
    Leu Gln Lys Asp His Cys Glu Gln Arg Thr Gly Lys Met Glu Gln Met
            930                 935                 940
    Lys Lys Lys Phe Cys Val Leu Lys Lys Lys Leu Ser Glu Ala Lys Glu
    945                 950                 955                 960
    Ile Lys Ser Gln Leu Glu Asn Gln Lys Val Lys Trp Glu Gln Glu Leu
                    965                 970                 975
    Cys Ser Val Arg Leu Thr Leu Asn Gln Glu Glu Lys Arg Arg Asn
                980                 985                 990
    Ala Asp Ile Leu Asn Glu Lys Ile Arg Glu Glu Leu Gly Arg Ile Glu
                995                 1000                1005
    Glu Gln His Arg Lys Glu Leu Glu Val Lys Gln Gln Leu Glu Gln Ala
            1010                1015                1020
    Leu Arg Ile Gln Asp Ile Glu Leu Lys Ser Val Glu Ser Asn Leu Asn
    1025                1030                1035                1040
    Gln Val Ser His Thr His Glu Asn Glu Asn Tyr Leu Leu His Glu Asn
                        1045                1050                1055
    Cys Met Leu Lys Lys Glu Ile Ala Met Leu Lys Leu Glu Ile Ala Thr
                    1060                1065                1070
    Leu Lys His Gln Tyr Gln Glu Lys Glu Asn Lys Tyr Phe Glu Asp Ile
                    1075                1080                1085
    Lys Ile Leu Lys Glu Lys Asn Ala Glu Leu Gln Met Thr Leu Lys Leu
            1090                1095                1100
    Lys Glu Glu Ser Leu Thr Lys Arg Ala Ser Gln Tyr Ser Gly Gln Leu
    1105                1110                1115                1120
```

```
        Lys Val Leu Ile Ala Glu Asn Thr Met Leu Thr Ser Lys Leu Lys Glu
                        1125                1130                1135
        Lys Gln Asp Lys Glu Ile Leu Glu Ala Glu Ile Ser His His Pro
                    1140                1145                1150
        Arg Leu Ala Ser Ala Val Gln Asp His Asp Gln Ile Val Thr Ser Arg
                        1155                1160                1165
        Lys Ser Gln Glu Pro Ala Phe His Ile Ala Gly Asp Ala Cys Leu Gln
                    1170                1175                1180
        Arg Lys Met Asn Val Asp Val Ser Ser Thr Ile Tyr Asn Asn Glu Val
        1185                1190                1195                1200
        Leu His Gln Pro Leu Ser Glu Ala Gln Arg Lys Ser Lys Ser Leu Lys
                        1205                1210                1215
        Ile Asn Leu Asn Tyr Ala Gly Asp Ala Leu Arg Glu Asn Thr Leu Val
                    1220                1225                1230
        Ser Glu His Ala Gln Arg Asp Gln Arg Glu Thr Gln Cys Gln Met Lys
                    1235                1240                1245
        Glu Ala Glu His Met Tyr Gln Asn Glu Gln Asp Asn Val Asn Lys His
                1250                1255                1260
        Thr Glu Gln Gln Glu Ser Leu Asp Gln Lys Leu Phe Gln Leu Gln Ser
        1265                1270                1275                1280
        Lys Asn Met Trp Leu Gln Gln Gln Leu Val His Ala His Lys Lys Ala
                        1285                1290                1295
        Asp Asn Lys Ser Lys Ile Thr Ile Asp Ile His Phe Leu Glu Arg Lys
                    1300                1305                1310
        Met Gln His His Leu Leu Lys Glu Lys Asn Glu Glu Ile Phe Asn Tyr
                    1315                1320                1325
        Asn Asn His Leu Lys Asn Arg Ile Tyr Gln Tyr Glu Lys Glu Lys Ala
            1330                1335                1340
        Glu Thr Glu Val Ile
        1345

<210> SEQ ID NO 574
<211> LENGTH: 24
<212> TYPE: DNA
<213> ORGANISM: Artificial Sequence
<220> FEATURE:
<223> OTHER INFORMATION: PCR primer

<400> SEQUENCE: 574
cacacaaaga ggaagaagac catc                                        24

<210> SEQ ID NO 575
<211> LENGTH: 27
<212> TYPE: DNA
<213> ORGANISM: Artificial Sequence
<220> FEATURE:
<223> OTHER INFORMATION: PCR primer

<400> SEQUENCE: 575
gattcttttg taggacatgc aatcatc                                     27

<210> SEQ ID NO 576
<211> LENGTH: 3720
<212> TYPE: DNA
<213> ORGANISM: Homo sapiens
<220> FEATURE:
<221> NAME/KEY: misc_feature
<222> LOCATION: 1149
<223> OTHER INFORMATION: n = A,T,C or G

<400> SEQUENCE: 576
atggtggcaa cactgctgtc ctatggtgca gtcatcgagg tgcaaaacaa ggctagcctc    60
    acacccttt  tactggccat acagaaaaga agcaagcaaa ctgtggaatt tttactaaca   120
    aaaaatgcaa atgcaaacgc atttaatgag tctaaatgca cagccctcat gcttgccata   180
    tgtgaaggct catcagagat agtcggcatg cttcttcagc aaaatgttga cgtctttgct   240
    gaagacatac atggaataac tgcagaacgt tatgctgctg ctcgtggagt taattacatt   300
    catcaacaac ttttggaaca tatacgaaaa ttacctaaaa atcctcaaaa taccaatcca   360
    gaaggaacat ctacaggaac acctgatgag gctgcaccct tggcggaaag aacacctgac   420
    acggctgaaa gcttgctgga aaaacacct gacgaggctg cacgcttggt ggagggaacg   480
    tctgccaaaa ttcaatgtct ggggaaagca acatctggaa agtttgaaca gtcaacagaa   540
    gaaacaccta ggaaaatttt gaggcctaca aagaaacat  ctgagaaatt tcatggcca   600
    gcaaaagaaa gatctaggaa gatcacatgg gaggaaaaag aaacatctgt aaagactgaa   660
    tgcgtggcag gagtaacacc taataaaact gaagttttgg aaaaaggaac atctaatatg   720
```

-continued

```
attgcatgtc ctacaaaaga aacatctaca aaagcaagta caaatgtgga tgtgagttct 780
gtagagccta tattcagtct ttttggcaca cggactattg aaaattcaca gtgtacaaaa 840
gttgaggaag actttaatct tgctaccaag attatctcta agagtgctgc acagaattat 900
acgtgtttac ctgatgctac atatcaaaaa gatatcaaaa caataaatca caaaatgaag 960
gatcagatgt tcccatcaga atccaaacga gaggaagatg aagaatattc ttgggattct 1020
gggagtctct ttgagagttc tgcaaagact caagtgtgta tacctgagtc tatgtatcag 1080
aaagtaatgg agataaatag agaagtagaa gagcttcctg agaagccatc tgccttcaag 1140
cctgccgtng aaatgcaaaa gactgttcca aataaagcct ttgaattgaa gaatgaacaa 1200
acattgagag cagctcagat gttcccatca gaatccaaac aaaaggacga tgaagaaaat 1260
tcttgggatt ctgagagtcc ctgtgagacg gtttcacaga aggatgtgta tttacccaaa 1320
gctacacatc aaaaagaatt cgataccttaa gtggaaaat tagaagagtc tcctgttaaa 1380
gatggtcttc tgaagcctac ctgtggaagg aaagtttctc ttccaaataa agccttagaa 1440
ttaaaggaca gagaaacatt caaagcagag tctcctgata agatggtctc tctgaagcct 1500
acctgtggaa ggaaagtttc tcttccaaat aaagcttag aattaaagga cagagaaaca 1560
ctcaaagcag agtctcctga taatgatggt cttctgaagc ctacctgtgg aaggaaagtt 1620
tctcttccaa ataaagcttt agaattgaag gacagagaaa cattcaaagc agctcagatg 1680
ttcccatcag aatccaaaca aaaggatgat gaagaaaatt cttgggattt tgagagtttc 1740
cttgagactc tcttacagaa tgatgtgtgt ttacccaagg ctacacatca aaaagaattc 1800
gataccttaa gtggaaaatt agaagagtct cctgataaag atggtcttct gaagcctacc 1860
tgtggaatga aaatttctct tccaaataaa gccttagaat tgaaggacag agaaacattc 1920
aaagcagagg atgtgagttc tgtagagtcc acattcagtc ttttggcaa accgactact 1980
gaaaattcac agtctacaaa agttgaggaa gactttaatc ttactaccaa ggagggagca 2040
acaaagacag taactggaca acaggaacgt gatattggca ttattgaacg agctccacaa 2100
gatcaaacaa ataagatgcc cacatcagaa ttaggaagaa aagaagatac aaaatcaact 2160
tcagattctg agattatctc tgtgagtgat acacagaatt atgagtgttt acctgaggct 2220
acatatcaaa aagaaataaa gacaacaaat ggcaaaatag aagagtctcc tgaaaagcct 2280
tctcactttg agcctgccac tgaaatgcaa aactctgttc aaataaaggg cttagaatgg 2340
aagaataaac aaacattgag agcagattca actaccctat caaaaatctt ggatgcactt 2400
ccttcttgtg aaagaggaag ggaacttaaa aaagataact gtgaacaaat tacagcaaaa 2460
atggaacaaa tgaaaaataa gttttgtgta ctacaaaagg aactgtcaga agcgaaagaa 2520
ataaaatcac agttagaaaa ccaaaaagct aaatgggaac aagagctctg cagtgtgaga 2580
ttgcctttaa atcaagaaga agagaagaga agaaatgtcg atatattaaa agaaaaaatt 2640
agacccgaag agcaacttag gaaaaagtta gaagtgaaac accaacttga acagactctc 2700
agaatacaag atatagaatt gaaaagtgta acagtaatt tgaatcaggt ttctcacact 2760
catgaaagtg aaaatgatct ctttcatgaa aattgcatgt tgaaaaagga aattgccatg 2820
ctaaaactgg aagtagccac actgaaacat caaccaccagg tgaaggaaaa taaatacttt 2880
gaggacatta agattttaca agaaaagaat gctgaacttc aaatgaccct aaaactgaaa 2940
cagaaaacag taacaaaag ggcatctcag tatagagagc agcttaaagt tctgacggca 3000
gagaacacga tgctgacttc taaattgaag gaaaacaag acaaagaaat actgagaca 3060
gaaattgaat cacaccatcc tagactggct tctgctttac aagaccatga tcaaagtgtc 3120
acatcaagaa aaaaaccaaga acttgctttc cacagtgcag gagatgctcc tttgcaagga 3180
ataatgaatg ttgatgtgag taatacaata tataacaatg aggtgctcca tcaaccactt 3240
tatgaagctc aaaggaaatc caaaagccca aaaattaatc tcaattatgc aggagatgat 3300
ctaagagaaa atgcattggt ttcagaacat gcacaaagag accgatgtga aacacagtgt 3360
caaatgaaga aagctgaaca catgtatcaa aatgaacaag ataaagtgga caaacacact 3420
gaacagcagg agtctctgga gcagaaatta tttcaactag aaagcaaaaa taggtggctt 3480
cgacagcaat tagttttatgc acataagaaa gttaacaaaa gcaaggtaac aattaatatt 3540
cagtttcctg agatgaaaat gcaacgtcat ctaaaagaga aaatgagga ggtattcaat 3600
tatggtaacc attttaaaaga acgtatagat caatatgaaa aagagaaagc agaaagagaa 3660
gtaagtatca aaaaatataa atacttttca aacttcctga agaaagtgg ccttggctaa 3720
```

<210> SEQ ID NO 577
<211> LENGTH: 1239
<212> TYPE: PRT
<213> ORGANISM: Homo sapiens

<400> SEQUENCE: 577

```
Met Val Ala Thr Leu Leu Ser Tyr Gly Ala Val Ile Glu Val Gln Asn
             5                   10                  15
Lys Ala Ser Leu Thr Pro Leu Leu Leu Ala Ile Gln Lys Arg Ser Lys
         20                  25                  30
Gln Thr Val Glu Phe Leu Leu Thr Lys Asn Ala Asn Ala Asn Ala Phe
     35                  40                  45
Asn Glu Ser Lys Cys Thr Ala Leu Met Leu Ala Ile Cys Glu Gly Ser
 50                  55                  60
Ser Glu Ile Val Gly Met Leu Leu Gln Gln Asn Val Asp Val Phe Ala
65                  70                  75                  80
Glu Asp Ile His Gly Ile Thr Ala Glu Arg Tyr Ala Ala Ala Gly
                 85                  90                  95
Val Asn Tyr Ile His Gln Gln Leu Glu His Ile Arg Lys Leu Pro
            100                 105                 110
Lys Asn Pro Gln Asn Thr Asn Pro Glu Gly Thr Ser Thr Gly Thr Pro
        115                 120                 125
Asp Glu Ala Ala Pro Leu Ala Glu Arg Thr Pro Asp Thr Ala Glu Ser
    130                 135                 140
Leu Leu Glu Lys Thr Pro Asp Glu Ala Ala Arg Leu Val Glu Gly Thr
145                 150                 155                 160
```

-continued

```
Ser Ala Lys Ile Gln Cys Leu Gly Lys Ala Thr Ser Gly Lys Phe Glu
                165                 170                 175
Gln Ser Thr Glu Glu Thr Pro Arg Lys Ile Leu Arg Pro Thr Lys Glu
            180                 185                 190
Thr Ser Glu Lys Phe Ser Trp Pro Ala Lys Glu Arg Ser Arg Lys Ile
        195                 200                 205
Thr Trp Glu Glu Lys Glu Thr Ser Val Lys Thr Glu Cys Val Ala Gly
    210                 215                 220
Val Thr Pro Asn Lys Thr Glu Val Leu Glu Lys Gly Thr Ser Asn Met
225                 230                 235                 240
Ile Ala Cys Pro Thr Lys Glu Thr Ser Thr Lys Ala Ser Thr Asn Val
                245                 250                 255
Asp Val Ser Ser Val Glu Pro Ile Phe Ser Leu Phe Gly Thr Arg Thr
            260                 265                 270
Ile Glu Asn Ser Gln Cys Thr Lys Val Glu Asp Phe Asn Leu Ala
        275                 280                 285
Thr Lys Ile Ile Ser Lys Ser Ala Ala Gln Asn Tyr Thr Cys Leu Pro
    290                 295                 300
Asp Ala Thr Tyr Gln Lys Asp Ile Lys Thr Ile Asn His Lys Ile Glu
305                 310                 315                 320
Asp Gln Met Phe Pro Ser Glu Ser Lys Arg Glu Glu Asp Glu Glu Tyr
                325                 330                 335
Ser Trp Asp Ser Gly Ser Leu Phe Glu Ser Ala Lys Thr Gln Val
            340                 345                 350
Cys Ile Pro Glu Ser Met Tyr Gln Lys Val Met Glu Ile Asn Arg Glu
        355                 360                 365
Val Glu Glu Leu Pro Glu Lys Pro Ser Ala Phe Lys Pro Ala Val Glu
    370                 375                 380
Met Gln Lys Thr Val Pro Asn Lys Ala Phe Glu Leu Lys Asn Glu Gln
385                 390                 395                 400
Thr Leu Arg Ala Ala Gln Met Phe Pro Ser Glu Ser Lys Gln Lys Asp
                405                 410                 415
Asp Glu Asn Ser Trp Asp Ser Glu Ser Pro Cys Glu Thr Val Ser
            420                 425                 430
Gln Lys Asp Val Tyr Leu Pro Lys Ala Thr His Gln Lys Glu Phe Asp
        435                 440                 445
Thr Leu Ser Gly Lys Leu Glu Glu Ser Pro Val Lys Asp Gly Leu Leu
    450                 455                 460
Lys Pro Thr Cys Gly Arg Lys Val Ser Leu Pro Asn Lys Ala Leu Glu
465                 470                 475                 480
Leu Lys Asp Arg Glu Thr Phe Lys Ala Glu Ser Pro Asp Lys Asp Gly
                485                 490                 495
Leu Leu Lys Pro Thr Cys Gly Arg Lys Val Ser Leu Pro Asn Lys Ala
            500                 505                 510
Leu Glu Leu Lys Asp Arg Glu Thr Leu Lys Ala Glu Ser Pro Asp Asn
        515                 520                 525
Asp Gly Leu Leu Lys Pro Thr Cys Gly Arg Lys Val Ser Leu Pro Asn
    530                 535                 540
Lys Ala Leu Glu Leu Lys Asp Arg Glu Thr Phe Lys Ala Ala Gln Met
545                 550                 555                 560
Phe Pro Ser Glu Ser Lys Gln Lys Asp Asp Glu Glu Asn Ser Trp Asp
                565                 570                 575
Phe Glu Ser Phe Leu Glu Thr Leu Leu Gln Asn Asp Val Cys Leu Pro
            580                 585                 590
Lys Ala Thr His Gln Lys Glu Phe Asp Thr Leu Ser Gly Lys Leu Glu
        595                 600                 605
Glu Ser Pro Asp Lys Asp Gly Leu Leu Lys Pro Thr Cys Gly Met Lys
    610                 615                 620
Ile Ser Leu Pro Asn Lys Ala Leu Glu Leu Lys Asp Arg Glu Thr Phe
625                 630                 635                 640
Lys Ala Glu Asp Val Ser Ser Val Glu Ser Thr Phe Ser Leu Phe Gly
                645                 650                 655
Lys Pro Thr Thr Glu Asn Ser Gln Ser Thr Lys Val Glu Glu Asp Phe
            660                 665                 670
Asn Leu Thr Thr Lys Glu Gly Ala Thr Lys Thr Val Thr Gly Gln Gln
        675                 680                 685
Glu Arg Asp Ile Gly Ile Ile Glu Arg Ala Pro Gln Asp Gln Thr Asn
    690                 695                 700
Lys Met Pro Thr Ser Glu Leu Gly Arg Lys Glu Asp Thr Lys Ser Thr
705                 710                 715                 720
Ser Asp Ser Glu Ile Ile Ser Val Ser Asp Thr Gln Asn Tyr Glu Cys
                725                 730                 735
Leu Pro Glu Ala Thr Tyr Gln Lys Glu Ile Lys Thr Thr Asn Gly Lys
            740                 745                 750
Ile Glu Glu Ser Pro Glu Lys Pro Ser His Phe Glu Pro Ala Thr Glu
        755                 760                 765
Met Gln Asn Ser Val Pro Asn Lys Gly Leu Glu Trp Lys Asn Lys Gln
    770                 775                 780
Thr Leu Arg Ala Asp Ser Thr Thr Leu Ser Lys Ile Leu Asp Ala Leu
```

```
            785                 790                 795                 800
        Pro Ser Cys Glu Arg Gly Arg Glu Leu Lys Lys Asp Asn Cys Glu Gln
                            805                 810                 815
        Ile Thr Ala Lys Met Glu Gln Met Lys Asn Lys Phe Cys Val Leu Gln
                        820                 825                 830
        Lys Glu Leu Ser Glu Ala Lys Glu Ile Lys Ser Gln Leu Glu Asn Gln
                    835                 840                 845
        Lys Ala Lys Trp Glu Gln Glu Leu Cys Ser Val Arg Leu Pro Leu Asn
                850                 855                 860
        Gln Glu Glu Glu Lys Arg Arg Asn Val Asp Ile Leu Lys Glu Lys Ile
        865                 870                 875                 880
        Arg Pro Glu Glu Gln Leu Arg Lys Lys Leu Glu Val Lys His Gln Leu
                            885                 890                 895
        Glu Gln Thr Leu Arg Ile Gln Asp Ile Glu Leu Lys Ser Val Thr Ser
                        900                 905                 910
        Asn Leu Asn Gln Val Ser His Thr His Glu Ser Glu Lys Asn Asp Leu Phe
                    915                 920                 925
        His Glu Asn Cys Met Leu Lys Lys Glu Ile Ala Met Leu Lys Leu Glu
                930                 935                 940
        Val Ala Thr Leu Lys His Gln His Gln Val Lys Val Glu Asn Lys Tyr Phe
        945                 950                 955                 960
        Glu Asp Ile Lys Ile Leu Gln Glu Lys Asn Ala Glu Leu Gln Met Thr
                            965                 970                 975
        Leu Lys Leu Lys Gln Lys Thr Val Thr Lys Arg Ala Ser Gln Tyr Arg
                        980                 985                 990
        Glu Gln Leu Lys Val Leu Thr Ala Glu Asn Thr Met Leu Thr Ser Lys
                    995                 1000                1005
        Leu Lys Glu Lys Gln Asp Lys Glu Ile Leu Glu Thr Glu Ile Glu Ser
                1010                1015                1020
        His His Pro Arg Leu Ala Ser Ala Leu Gln Asp His Asp Gln Ser Val
        1025                1030                1035                1040
        Thr Ser Arg Lys Asn Gln Glu Leu Ala Phe His Ser Ala Gly Asp Ala
                            1045                1050                1055
        Pro Leu Gln Gly Ile Met Asn Val Asp Val Ser Asn Thr Ile Tyr Asn
                        1060                1065                1070
        Asn Glu Val Leu His Gln Pro Leu Tyr Glu Ala Gln Arg Lys Ser Lys
                    1075                1080                1085
        Ser Pro Lys Ile Asn Leu Asn Tyr Ala Gly Asp Asp Leu Arg Glu Asn
                1090                1095                1100
        Ala Leu Val Ser Glu His Ala Gln Arg Asp Arg Cys Glu Thr Gln Cys
        1105                1110                1115                1120
        Gln Met Lys Lys Ala Glu His Met Tyr Gln Asn Glu Gln Asp Asn Val
                            1125                1130                1135
        Asp Lys His Thr Glu Gln Gln Glu Ser Leu Glu Gln Lys Leu Phe Gln
                        1140                1145                1150
        Leu Glu Ser Lys Asn Arg Trp Leu Arg Gln Gln Leu Val Tyr Ala His
                    1155                1160                1165
        Lys Lys Val Asn Lys Ser Lys Val Thr Ile Asn Ile Gln Phe Pro Glu
                1170                1175                1180
        Met Lys Met Gln Arg His Leu Lys Glu Lys Asn Glu Lys Val Phe Asn
        1185                1190                1195                1200
        Tyr Gly Asn His Leu Lys Glu Arg Ile Asp Gln Tyr Glu Lys Glu Lys
                            1205                1210                1215
        Ala Glu Arg Glu Val Ser Ile Lys Lys Tyr Lys Tyr Phe Ser Asn Phe
                        1220                1225                1230
        Leu Lys Glu Ser Gly Leu Gly
                    1235

<210> SEQ ID NO 578
<211> LENGTH: 20
<212> TYPE: PRT
<213> ORGANISM: Homo sapiens

<400> SEQUENCE: 578

Lys Asn Glu Glu Ile Phe Asn Tyr Asn Asn His Leu Lys Asn Arg Ile
                        5                   10                  15
        Tyr Gln Tyr Glu
                    20

<210> SEQ ID NO 579
<211> LENGTH: 20
<212> TYPE: PRT
<213> ORGANISM: Homo sapiens

<400> SEQUENCE: 579
```

-continued

```
      Glu Gln Asp Asn Val Asn Lys His Thr Glu Gln Gln Glu Ser Leu Asp
                       5                  10                  15
      Gln Lys Leu Phe
                  20

<210> SEQ ID NO 580
<211> LENGTH: 20
<212> TYPE: PRT
<213> ORGANISM: Homo sapiens

<400> SEQUENCE: 580

Thr Glu Gln Gln Glu Ser Leu Asp Gln Lys Leu Phe Gln Leu Gln Ser
                       5                  10                  15
      Lys Asn Met Trp
                  20

<210> SEQ ID NO 581
<211> LENGTH: 20
<212> TYPE: PRT
<213> ORGANISM: Homo sapiens

<400> SEQUENCE: 581

Lys Glu Glu Ser Leu Thr Lys Arg Ala Ser Gln Tyr Ser Gly Gln Leu
                       5                  10                  15
      Lys Val Leu Ile
                  20

<210> SEQ ID NO 582
<211> LENGTH: 20
<212> TYPE: PRT
<213> ORGANISM: Homo sapiens

<400> SEQUENCE: 582

Ile Ala Gly Asp Ala Cys Leu Gln Arg Lys Met Asn Val Asp Val Ser
                       5                  10                  15
      Ser Thr Ile Tyr
                  20

<210> SEQ ID NO 583
<211> LENGTH: 20
<212> TYPE: PRT
<213> ORGANISM: Homo sapiens

<400> SEQUENCE: 583

Arg Lys Met Asn Val Asp Val Ser Ser Thr Ile Tyr Asn Asn Glu Val
                       5                  10                  15
      Leu His Gln Pro
                  20

<210> SEQ ID NO 584
<211> LENGTH: 20
<212> TYPE: PRT
<213> ORGANISM: Homo sapiens

<400> SEQUENCE: 584

Met Gly Thr Arg Ala Leu Gln Cys Glu Val Ser His Thr His Glu Asn
                       5                  10                  15
      Glu Asn Tyr Leu
                  20

<210> SEQ ID NO 585
<211> LENGTH: 20
<212> TYPE: PRT
<213> ORGANISM: Homo sapiens

<400> SEQUENCE: 585

Glu Val Ser His Thr His Glu Asn Glu Asn Tyr Leu Leu His Glu Asn
```

```
                        5                  10                  15
         Cys Met Leu Lys
                  20

<210> SEQ ID NO 586
<211> LENGTH: 20
<212> TYPE: PRT
<213> ORGANISM: Homo sapiens

<400> SEQUENCE: 586

Glu Asn Tyr Leu Leu His Glu Asn Leu Met Leu Lys Lys Glu Ile Ala
                        5                  10                  15
         Met Leu Lys Leu
                  20

<210> SEQ ID NO 587
<211> LENGTH: 21
<212> TYPE: PRT
<213> ORGANISM: Homo sapiens

<400> SEQUENCE: 587

Asn Cys Met Leu Lys Lys Glu Ile Ala Met Leu Lys Leu Glu Ile Ala
                        5                  10                  15
         Thr Leu Lys His Gln
                  20

<210> SEQ ID NO 588
<211> LENGTH: 20
<212> TYPE: PRT
<213> ORGANISM: Homo sapiens

<400> SEQUENCE: 588

Met Leu Thr Ser Lys Leu Lys Glu Lys Gln Asp Lys Glu Ile Leu Glu
                        5                  10                  15
         Ala Glu Ile Glu
                  20

<210> SEQ ID NO 589
<211> LENGTH: 20
<212> TYPE: PRT
<213> ORGANISM: Homo sapiens

<400> SEQUENCE: 589

Lys Gln Asp Lys Glu Ile Leu Glu Ala Glu Ile Glu Ser His His Pro
                        5                  10                  15
         Arg Leu Ala Ser
                  20

<210> SEQ ID NO 590
<211> LENGTH: 20
<212> TYPE: PRT
<213> ORGANISM: Homo sapiens

<400> SEQUENCE: 590

Ala Glu Ile Glu Ser His His Pro Arg Leu Ala Ser Ala Val Gln Asp
                        5                  10                  15
         His Asp Gln Ile
                  20

<210> SEQ ID NO 591
<211> LENGTH: 20
<212> TYPE: PRT
<213> ORGANISM: Homo sapiens

<400> SEQUENCE: 591

Arg Leu Ala Ser Ala Val Gln Asp His Asp Gln Ile Val Thr Ser Arg
                        5                  10                  15
```

```
        Lys Ser Gln Glu
                    20

<210> SEQ ID NO 592
<211> LENGTH: 20
<212> TYPE: PRT
<213> ORGANISM: Homo sapiens

<400> SEQUENCE: 592

His Asp Gln Ile Val Thr Ser Arg Lys Ser Gln Glu Pro Ala Phe His
                      5                  10                  15
     Ile Ala Gly Asp
                 20

<210> SEQ ID NO 593
<211> LENGTH: 20
<212> TYPE: PRT
<213> ORGANISM: Homo sapiens

<400> SEQUENCE: 593

Lys Ser Gln Glu Pro Ala Phe His Ile Ala Gly Asp Ala Cys Leu Gln
                      5                  10                  15
     Arg Lys Met Asn
                 20

<210> SEQ ID NO 594
<211> LENGTH: 20
<212> TYPE: PRT
<213> ORGANISM: Homo sapiens

<400> SEQUENCE: 594

Met Gly Thr Arg Ala Leu Gln Cys Glu Val Ser His Thr His Glu Asn
     1                5                  10                  15
     Glu Asn Tyr Leu
                 20

<210> SEQ ID NO 595
<211> LENGTH: 20
<212> TYPE: PRT
<213> ORGANISM: Homo sapiens

<400> SEQUENCE: 595

Ser His Thr His Glu Asn Glu Asn Tyr Leu Leu His Glu Asn Cys Met
     1                5                  10                  15
     Leu Lys Lys Glu
                 20

<210> SEQ ID NO 596
<211> LENGTH: 20
<212> TYPE: PRT
<213> ORGANISM: Homo sapiens

<400> SEQUENCE: 596

Leu His Glu Asn Cys Met Leu Lys Lys Glu Ile Ala Met Leu Lys Leu
     1                5                  10                  15
     Glu Ile Ala Thr
                 20

<210> SEQ ID NO 597
<211> LENGTH: 20
<212> TYPE: PRT
<213> ORGANISM: Homo sapiens

<400> SEQUENCE: 597

Ile Ala Met Leu Lys Leu Glu Ile Ala Thr Leu Lys His Gln Tyr Gln
     1                5                  10                  15
     Glu Lys Glu Asn
```

20

<210> SEQ ID NO 598
<211> LENGTH: 20
<212> TYPE: PRT
<213> ORGANISM: Homo sapiens

<400> SEQUENCE: 598

Leu Lys His Gln Tyr Gln Glu Lys Glu Asn Lys Tyr Phe Glu Asp Ile
1               5                   10                  15
Lys Ile Leu Lys
            20

<210> SEQ ID NO 599
<211> LENGTH: 20
<212> TYPE: PRT
<213> ORGANISM: Homo sapiens

<400> SEQUENCE: 599

Lys Tyr Phe Glu Asp Ile Lys Ile Leu Lys Glu Lys Asn Ala Glu Leu
1               5                   10                  15
Gln Met Thr Leu
            20

<210> SEQ ID NO 600
<211> LENGTH: 20
<212> TYPE: PRT
<213> ORGANISM: Homo sapiens

<400> SEQUENCE: 600

Glu Lys Asn Ala Glu Leu Gln Met Thr Leu Lys Leu Lys Glu Glu Ser
1               5                   10                  15
Leu Thr Lys Arg
            20

<210> SEQ ID NO 601
<211> LENGTH: 20
<212> TYPE: PRT
<213> ORGANISM: Homo sapiens

<400> SEQUENCE: 601

Lys Leu Lys Glu Glu Ser Leu Thr Lys Arg Ala Ser Gln Tyr Ser Gly
1               5                   10                  15
Gln Leu Lys Val
            20

<210> SEQ ID NO 602
<211> LENGTH: 20
<212> TYPE: PRT
<213> ORGANISM: Homo sapiens

<400> SEQUENCE: 602

Ala Ser Gln Tyr Ser Gly Gln Leu Lys Val Leu Ile Ala Glu Asn Thr
1               5                   10                  15
Met Leu Thr Ser
            20

<210> SEQ ID NO 603
<211> LENGTH: 20
<212> TYPE: PRT
<213> ORGANISM: Homo sapiens

<400> SEQUENCE: 603

Leu Ile Ala Glu Asn Thr Met Leu Thr Ser Lys Leu Lys Glu Lys Gln
1               5                   10                  15
Asp Lys Glu Ile
            20

```
<210> SEQ ID NO 604
<211> LENGTH: 20
<212> TYPE: PRT
<213> ORGANISM: Homo sapiens

<400> SEQUENCE: 604

Lys Leu Lys Glu Lys Gln Asp Lys Glu Ile Leu Glu Ala Glu Ile Glu
    1               5                   10                  15
    Ser His His Pro
                20

<210> SEQ ID NO 605
<211> LENGTH: 20
<212> TYPE: PRT
<213> ORGANISM: Homo sapiens

<400> SEQUENCE: 605

Leu Glu Ala Glu Ile Glu Ser His His Pro Arg Leu Ala Ser Ala Val
    1               5                   10                  15
    Gln Asp His Asp
                20

<210> SEQ ID NO 606
<211> LENGTH: 20
<212> TYPE: PRT
<213> ORGANISM: Homo sapiens

<400> SEQUENCE: 606

Arg Leu Ala Ser Ala Val Gln Asp His Asp Gln Ile Val Thr Ser Arg
    1               5                   10                  15
    Lys Ser Gln Glu
                20

<210> SEQ ID NO 607
<211> LENGTH: 22
<212> TYPE: PRT
<213> ORGANISM: Homo sapiens

<400> SEQUENCE: 607

Asp Gln Ile Val Thr Ser Arg Lys Ser Gln Glu Pro Ala Phe His Ile
    1               5                   10                  15
    Ala Gly Asp Ala Cys Leu
                20

<210> SEQ ID NO 608
<211> LENGTH: 20
<212> TYPE: PRT
<213> ORGANISM: Homo sapiens

<400> SEQUENCE: 608

Pro Ala Phe His Ile Ala Gly Asp Ala Cys Leu Gln Arg Lys Met Asn
    1               5                   10                  15
    Val Asp Val Ser
                20

<210> SEQ ID NO 609
<211> LENGTH: 20
<212> TYPE: PRT
<213> ORGANISM: Homo sapiens

<400> SEQUENCE: 609

Leu Gln Arg Lys Met Asn Val Asp Val Ser Ser Thr Ile Tyr Asn Asn
    1               5                   10                  15
    Glu Val Leu His
                20
```

```
<210> SEQ ID NO 610
<211> LENGTH: 20
<212> TYPE: PRT
<213> ORGANISM: Homo sapiens

<400> SEQUENCE: 610

Ser Thr Ile Tyr Asn Asn Glu Val Leu His Gln Pro Leu Ser Glu Ala
    1               5                   10                  15
    Gln Arg Lys Ser
                20

<210> SEQ ID NO 611
<211> LENGTH: 21
<212> TYPE: PRT
<213> ORGANISM: Homo sapiens

<400> SEQUENCE: 611

His Gln Pro Leu Ser Glu Ala Gln Arg Lys Ser Lys Ser Leu Lys Ile
    1               5                   10                  15
    Asn Leu Asn Tyr Ala
                20

<210> SEQ ID NO 612
<211> LENGTH: 20
<212> TYPE: PRT
<213> ORGANISM: Homo sapiens

<400> SEQUENCE: 612

Lys Ser Leu Lys Ile Asn Leu Asn Tyr Ala Gly Asp Ala Leu Arg Glu
    1               5                   10                  15
    Asn Thr Leu Val
                20

<210> SEQ ID NO 613
<211> LENGTH: 20
<212> TYPE: PRT
<213> ORGANISM: Homo sapiens

<400> SEQUENCE: 613

Gly Asp Ala Leu Arg Glu Asn Thr Leu Val Ser Glu His Ala Gln Arg
    1               5                   10                  15
    Asp Gln Arg Glu
                20

<210> SEQ ID NO 614
<211> LENGTH: 20
<212> TYPE: PRT
<213> ORGANISM: Homo sapiens

<400> SEQUENCE: 614

Ser Glu His Ala Gln Arg Asp Gln Arg Glu Thr Gln Cys Gln Met Lys
    1               5                   10                  15
    Glu Ala Glu His
                20

<210> SEQ ID NO 615
<211> LENGTH: 20
<212> TYPE: PRT
<213> ORGANISM: Homo sapiens

<400> SEQUENCE: 615

Thr Gln Cys Gln Met Lys Glu Ala Glu His Met Tyr Gln Asn Glu Gln
    1               5                   10                  15
    Asp Asn Val Asn
                20
```

<210> SEQ ID NO 616
<211> LENGTH: 20
<212> TYPE: PRT
<213> ORGANISM: Homo sapiens

<400> SEQUENCE: 616

Met Tyr Gln Asn Glu Gln Asp Asn Val Asn Lys His Thr Glu Gln Gln
1               5                   10                  15
Glu Ser Leu Asp
            20

<210> SEQ ID NO 617
<211> LENGTH: 20
<212> TYPE: PRT
<213> ORGANISM: Homo sapiens

<400> SEQUENCE: 617

Lys His Thr Glu Gln Gln Glu Ser Leu Asp Gln Lys Leu Phe Gln Leu
1               5                   10                  15
Gln Ser Lys Asn
            20

<210> SEQ ID NO 618
<211> LENGTH: 21
<212> TYPE: PRT
<213> ORGANISM: Homo sapiens

<400> SEQUENCE: 618

Asp Gln Lys Leu Phe Gln Leu Gln Ser Lys Asn Met Trp Leu Gln Gln
1               5                   10                  15
Gln Leu Val His Ala
            20

<210> SEQ ID NO 619
<211> LENGTH: 20
<212> TYPE: PRT
<213> ORGANISM: Homo sapiens

<400> SEQUENCE: 619

Met Trp Leu Gln Gln Gln Leu Val His Ala His Lys Lys Ala Asp Asn
1               5                   10                  15
Lys Ser Lys Ile
            20

<210> SEQ ID NO 620
<211> LENGTH: 20
<212> TYPE: PRT
<213> ORGANISM: Homo sapiens

<400> SEQUENCE: 620

His Lys Lys Ala Asp Asn Lys Ser Lys Ile Thr Ile Asp Ile His Phe
1               5                   10                  15
Leu Glu Arg Lys
            20

<210> SEQ ID NO 621
<211> LENGTH: 20
<212> TYPE: PRT
<213> ORGANISM: Homo sapiens

<400> SEQUENCE: 621

Thr Ile Asp Ile His Phe Leu Glu Arg Lys Met Gln His His Leu Leu
1               5                   10                  15
Lys Glu Lys Asn
            20

<210> SEQ ID NO 622

```
<211> LENGTH: 20
<212> TYPE: PRT
<213> ORGANISM: Homo sapiens

<400> SEQUENCE: 622

Met Gln His His Leu Leu Lys Glu Lys Asn Glu Glu Ile Phe Asn Tyr
    1               5                   10                  15
    Asn Asn His Leu
                20

<210> SEQ ID NO 623
<211> LENGTH: 20
<212> TYPE: PRT
<213> ORGANISM: Homo sapiens

<400> SEQUENCE: 623

Glu Glu Ile Phe Asn Tyr Asn Asn His Leu Lys Asn Arg Ile Tyr Gln
    1               5                   10                  15
    Tyr Glu Lys Glu
                20

<210> SEQ ID NO 624
<211> LENGTH: 20
<212> TYPE: PRT
<213> ORGANISM: Homo sapiens

<400> SEQUENCE: 624

Asn His Leu Lys Asn Arg Ile Tyr Gln Tyr Glu Lys Glu Lys Ala Glu
    1               5                   10                  15
    Thr Glu Val Ile
                20

<210> SEQ ID NO 625
<211> LENGTH: 27
<212> TYPE: PRT
<213> ORGANISM: Homo sapiens

<400> SEQUENCE: 625

Leu Thr Leu Asn Gln Glu Glu Glu Lys Arg Arg Asn Ala Asp Ile Leu
    1               5                   10                  15
    Asn Glu Lys Ile Arg Glu Glu Leu Gly Cys Gly
                20                  25

<210> SEQ ID NO 626
<211> LENGTH: 29
<212> TYPE: PRT
<213> ORGANISM: Homo sapiens

<400> SEQUENCE: 626

Ile Arg Glu Glu Leu Gly Arg Ile Glu Glu Gln His Arg Lys Glu Leu
    1               5                   10                  15
    Glu Val Lys Gln Gln Leu Glu Gln Ala Leu Gly Cys Gly
                20                  25

<210> SEQ ID NO 627
<211> LENGTH: 24
<212> TYPE: PRT
<213> ORGANISM: Homo sapiens

<400> SEQUENCE: 627

Leu Glu Gln Ala Leu Arg Ile Gln Asp Ile Glu Leu Lys Ser Val Glu
    1               5                   10                  15
    Ser Asn Leu Asn Gln Gly Cys Gly
                20
```

COMPOSITIONS AND METHODS FOR THE THERAPY AND DIAGNOSIS OF BREAST CANCER

TECHNICAL FIELD OF THE INVENTION

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

BACKGROUND OF THE INVENTION

1. Field of the Invention

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

2. Description of the Related Art

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO:1–61, 63–175, 178, 180, 182–468, 474, 476, 477, 479, 482, 484, 486, 489–492, 504–506, 510–513, 520–533, 548–550, 564, 566–569, and 576;

(b) complements of the sequences provided in SEQ ID NO:1–61, 63–175, 178, 180, 182–468, 474, 476, 477, 479, 482, 484, 486, 489–492, 504–506, 510–513, 520–533, 548–550, 564, 566–569, and 576;

(c) sequences consisting of at least 20 contiguous residues of a sequence provided in SEQ ID NO:1–61, 63–175, 178, 180, 182–468, 474, 476, 477, 479, 482, 484, 486, 489–492, 504–506, 510–513, 520–533, 548–550, 564, 566–569, and 576;

(d) sequences that hybridize to a sequence provided in SEQ ID NO:1–61, 63–175, 178, 180, 182–468, 474, 476, 477, 479, 482, 484, 486, 489–492, 504–506, 510–513, 520–533, 548–550, 564, 566–569, and 576, under moderately stringent conditions;

(e) sequences having at least 75% identity to a sequence of SEQ ID NO:1–61, 63–175, 178, 180, 182–468, 474, 476, 477, 479, 482, 484, 486, 489–492, 504–506, 510–513, 520–533, 548–550, 564, 566–569, and 576;

(f) sequences having at least 90% identity to a sequence of SEQ ID NO:1–61, 63–175, 178, 180, 182–468, 474, 476, 477, 479, 482, 484, 486, 489–492, 504–506, 510–513, 520–533, 548–550, 564, 566–569, and 576; and (g) degenerate variants of a sequence provided in SEQ ID NO:1–61, 63–175, 178, 180, 182–468, 474, 476, 477, 479, 482, 484, 486, 489–492, 504–506, 510–513, 520–533, 548–550, 564, 566–569, and 576.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO:62, 176, 179, 181, 469–473, 475, 478, 483, 485, 487, 488, 493–503, 507–509, 514–519, 534–547, 551–553, 565, 570–573, and 577–627.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NO: 62, 176, 179, 181, 469–473, 475, 478, 483, 485, 487, 488, 493–503, 507–509, 514–519, 534–547, 551–553, 565, 570–573, and 577–627 or a polypeptide sequence encoded by a polynucleotide sequence set forth in SEQ ID NO: 1–61, 63–175, 178, 180, 182–468, 474, 476, 477, 479, 482, 484, 486, 489–492, 504–506, 510–513, 520–533, 548–550, 564, 566–569, and 576.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

The present invention further provides, in other aspects, fusion proteins that comprise at least one polypeptide as described above, as well as polynucleotides encoding such fusion proteins. Exemplary fusion proteins according to the present invention comprise a first amino acid portion and a second amino acid portion wherein the first amino acid portion includes 9 or more contiguous amino acids from mammaglobin as depicted by amino acids 1–93 of SEQ ID NO:493 (SEQ ID NO:503); wherein the second amino acid portion includes 9 or more contiguous amino acids from B726P as depicted by SEQ ID NO:475, SEQ ID NO:469, or SEQ ID NO:176; and wherein the first amino acid portion is connected to either the amino terminal or carboxy-terminal end of the second amino acid portion.

Still further embodiments of the present invention provide fusion proteins wherein said first amino acid portion is selected from the group consisting of: IDELKECFLNQT-DETLSNVE (SEQ ID NO:496; amino acids 59–78 of SEQ ID NO:493); TTNAIDELKECFLNQ (SEQ ID NO:497; amino acids 55–69 of SEQ ID NO:493); SQHCYAGSGC-PLLENVISKTI (SEQ ID NO:498; amino acids 13–33 of SEQ ID NO:493); EYKELLQEFIDDNATTNAID (SEQ ID NO:499; amino acids 41–60 of SEQ ID NO:493); KLLM-VLMLA (SEQ ID NO:500; amino acids 2–10 of SEQ ID NO:493); QEFIDD<u>N</u>ATTNAI (SEQ ID NO:501; amino acids 47–59 of SEQ ID NO:493); LKECFL<u>N</u>QTDETL (SEQ ID NO:502; amino acids 62–74 of SEQ ID NO:493), and any one of the amino acid sequences set forth in SEQ ID NO:578–593.

Alternative embodiments provide fusion proteins wherein the second amino acid portion includes 9 or more contiguous amino acids encoded by (1) the combined upstream and downstream open reading frame (ORF) of B726P as depicted in SEQ ID NO:475; (2) the upstream ORF of B726P as depicted in SEQ ID NO:469; and (3) the downstream ORF of B726P as depicted in SEQ ID NO:176. Fusion proteins according to the present invention may also comprise a second amino acid portion that includes 9 or more contiguous amino acids from the amino acid sequence depicted by amino acids 1–129 of SEQ ID NO:475. Still additional exemplary fusion proteins are depicted herein by SEQ ID NO:493, SEQ ID NO:494, and SEQ ID NO:495.

Fusion proteins are provided wherein the mammaglobin amino acid portion is connected to the amino-terminus of the B726P amino acid portion while other fusion proteins are provided wherein the mammaglobin amino acid portion is connected to the carboxy-terminus of the B726P amino acid portion. The connection between the mammaglobin amino acid portion and the B726P portion may be a covalent bond. Additionally, a stretch of amino acids either unrelated or related to either mammaglobin and/or B726P may be incorporated between or either amino- or carboxy-terminal to either the mammaglobin and/or B726P amino acid portion.

The present invention also provides isolated polynucleotides that encode any of the fusion proteins that are specifically disclosed herein as well as those fusion proteins that may be accomplished with routine experimentation by the ordinarily skilled artisan.

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating CD4$^+$ and/or CD8$^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

Figure 1:
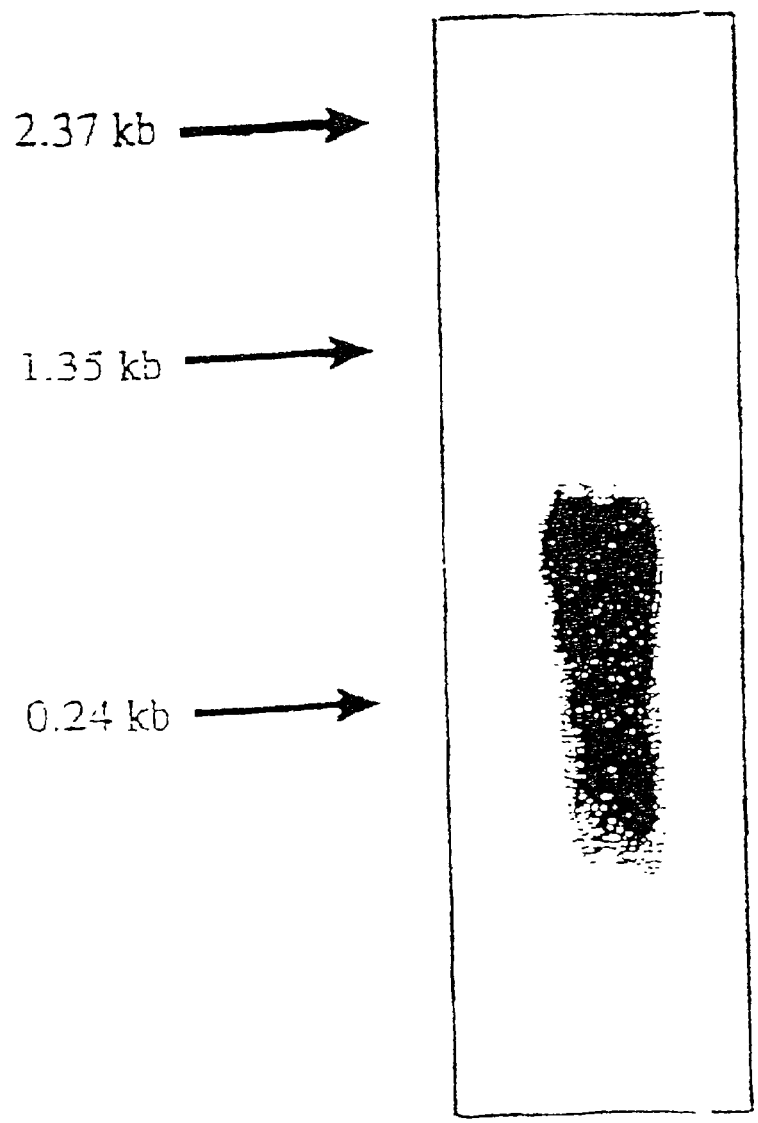
FIG. 1 shows the results of a Northern blot of the clone SYN18C6 (SEQ ID NO:40).

SEQ ID NO:1 is the determined cDNA sequence of JBT2.

SEQ ID NO:2 is the determined cDNA sequence of JBT6.

SEQ ID NO:3 is the determined cDNA sequence of JBT7.

SEQ ID NO:4 is the determined cDNA sequence of JBT10.

SEQ ID NO:5 is the determined cDNA sequence of JBT13.

SEQ ID NO:6 is the determined cDNA sequence of JBT14.

SEQ ID NO:7 is the determined cDNA sequence of JBT15.

SEQ ID NO:8 is the determined cDNA sequence of JBT16.

SEQ ID NO:9 is the determined cDNA sequence of JBT17.

SEQ ID NO:10 is the determined cDNA sequence of JBT22.

SEQ ID NO:11 is the determined cDNA sequence of JBT25.

SEQ ID NO:12 is the determined cDNA sequence of JBT28.

SEQ ID NO:13 is the determined cDNA sequence of JBT32.

SEQ ID NO:14 is the determined cDNA sequence of JBT33.

SEQ ID NO:15 is the determined cDNA sequence of JBT34.

SEQ ID NO:16 is the determined cDNA sequence of JBT36.

SEQ ID NO:17 is the determined cDNA sequence of JBT37.

SEQ ID NO:18 is the determined cDNA sequence of JBT51.

SEQ ID NO:19 is the determined cDNA sequence of JBTT1.

SEQ ID NO:20 is the determined cDNA sequence of JBTT7.

SEQ ID NO:21 is the determined cDNA sequence of JBTT11.

SEQ ID NO:22 is the determined cDNA sequence of JBTT14.

SEQ ID NO:23 is the determined cDNA sequence of JBTT18.

SEQ ID NO:24 is the determined cDNA sequence of JBTT19.

SEQ ID NO:25 is the determined cDNA sequence of JBTT20.

SEQ ID NO:26 is the determined cDNA sequence of JBTT21.

SEQ ID NO:27 is the determined cDNA sequence of JBTT22.

SEQ ID NO:28 is the determined cDNA sequence of JBTT28.

SEQ ID NO:29 is the determined cDNA sequence of JBTT29.

SEQ ID NO:30 is the determined cDNA sequence of JBTT33.

SEQ ID NO:31 is the determined cDNA sequence of JBTT37.

SEQ ID NO:32 is the determined cDNA sequence of JBTT38.

SEQ ID NO:33 is the determined cDNA sequence of JBTT47.

SEQ ID NO:34 is the determined cDNA sequence of JBTT48.

SEQ ID NO:35 is the determined cDNA sequence of JBTT50.

SEQ ID NO:36 is the determined cDNA sequence of JBTT51.

SEQ ID NO:37 is the determined cDNA sequence of JBTT52.

SEQ ID NO:38 is the determined cDNA sequence of JBTT54.

SEQ ID NO:39 is the determined cDNA sequence of SYN17F4.

SEQ ID NO:40 is the determined cDNA sequence of SYN18C6 (also known as B709P).

SEQ ID NO:41 is the determined cDNA sequence of SYN19A2.

SEQ ID NO:42 is the determined cDNA sequence of SYN19C8.

SEQ ID NO:43 is the determined cDNA sequence of SYN20A12.

SEQ ID NO:44 is the determined cDNA sequence of SYN20G6.

SEQ ID NO:45 is the determined cDNA sequence of SYN20G6-2.

SEQ ID NO:46 is the determined cDNA sequence of SYN21B9.

SEQ ID NO:47 is the determined cDNA sequence of SYN21B9-2.

SEQ ID NO:48 is the determined cDNA sequence of SYN21C10.

SEQ ID NO:49 is the determined cDNA sequence of SYN21G10.

SEQ ID NO:50 is the determined cDNA sequence of SYN21G10-2.

SEQ ID NO:51 is the determined cDNA sequence of SYN21G11.

SEQ ID NO:52 is the determined cDNA sequence of SYN21G11-2.

SEQ ID NO:53 is the determined cDNA sequence of SYN21H8.

SEQ ID NO:54 is the determined cDNA sequence of SYN22A10.

SEQ ID NO:55 is the determined cDNA sequence of SYN22A10-2.

SEQ ID NO:56 is the determined cDNA sequence of SYN22A12.

SEQ ID NO:57 is the determined cDNA sequence of SYN22A2 (also referred to as B718P).

SEQ ID NO:58 is the determined cDNA sequence of SYN22B4.

SEQ ID NO:59 is the determined cDNA sequence of SYN22C2.

SEQ ID NO:60 is the determined cDNA sequence of SYN22E10.

SEQ ID NO:61 is the determined cDNA sequence of SYN22F2.

SEQ ID NO:62 is a predicted amino acid sequence for SYN18C6 (also known as B709P).

SEQ ID NO:63 is the determined cDNA sequence of B723P.

SEQ ID NO:64 is the determined cDNA sequence for B724P.

SEQ ID NO:65 is the determined cDNA sequence of B770P.

SEQ ID NO:66 is the determined cDNA sequence of B716P.

SEQ ID NO:67 is the determined cDNA sequence of B725P.

SEQ ID NO:68 is the determined cDNA sequence of B717P.

SEQ ID NO:69 is the determined cDNA sequence of B771P.

SEQ ID NO:70 is the determined cDNA sequence of B722P.

SEQ ID NO:71 is the determined cDNA sequence of B726P.

SEQ ID NO:72 is the determined cDNA sequence of B727P.

SEQ ID NO:73 is the determined cDNA sequence of B728P.

SEQ ID NO:74–87 are the determined cDNA sequences of isolated clones which show homology to known sequences.

SEQ ID NO:88 is the determined cDNA sequence of 13053.

SEQ ID NO:89 is the determined cDNA sequence of 13057.

SEQ ID NO:90 is the determined cDNA sequence of 13059.

SEQ ID NO:91 is the determined cDNA sequence of 13065.

SEQ ID NO:92 is the determined cDNA sequence of 13067.

SEQ ID NO:93 is the determined cDNA sequence of 13068.

SEQ ID NO:94 is the determined cDNA sequence of 13071.

SEQ ID NO:95 is the determined cDNA sequence of 13072.

SEQ ID NO:96 is the determined cDNA sequence of 13073.

SEQ ID NO:97 is the determined cDNA sequence of 13075.

SEQ ID NO:98 is the determined cDNA sequence of 13078.

SEQ ID NO:99 is the determined cDNA sequence of 13079.

SEQ ID NO:100 is the determined cDNA sequence of 13081.

SEQ ID NO:101 is the determined cDNA sequence of 13082.
SEQ ID NO:102 is the determined cDNA sequence of 13092.
SEQ ID NO:103 is the determined cDNA sequence of 13097.
SEQ ID NO:104 is the determined cDNA sequence of 13101.
SEQ ID NO:105 is the determined cDNA sequence of 13102.
SEQ ID NO:106 is the determined cDNA sequence of 13119.
SEQ ID NO:107 is the determined cDNA sequence of 13131.
SEQ ID NO:108 is the determined cDNA sequence of 13133.
SEQ ID NO:109 is the determined cDNA sequence of 13135.
SEQ ID NO:110 is the determined cDNA sequence of 13139.
SEQ ID NO:111 is the determined cDNA sequence of 13140.
SEQ ID NO:112 is the determined cDNA sequence of 13146.
SEQ ID NO:113 is the determined cDNA sequence of 13147.
SEQ ID NO:114 is the determined cDNA sequence of 13148.
SEQ ID NO:115 is the determined cDNA sequence of 13149.
SEQ ID NO:116 is the determined cDNA sequence of 13151.
SEQ ID NO:117 is the determined cDNA sequence of 13051
SEQ ID NO:118 is the determined cDNA sequence of 13052
SEQ ID NO:119 is the determined cDNA sequence of 13055
SEQ ID NO:120 is the determined cDNA sequence of 13058
SEQ ID NO:121 is the determined cDNA sequence of 13062
SEQ ID NO:122 is the determined cDNA sequence of 13064
SEQ ID NO:123 is the determined cDNA sequence of 13080
SEQ ID NO:124 is the determined cDNA sequence of 13093
SEQ ID NO:125 is the determined cDNA sequence of 13094
SEQ ID NO:126 is the determined cDNA sequence of 13095
SEQ ID NO:127 is the determined cDNA sequence of 13096
SEQ ID NO:128 is the determined cDNA sequence of 13099
SEQ ID NO:129 is the determined cDNA sequence of 13100
SEQ ID NO:130 is the determined cDNA sequence of 13103
SEQ ID NO:131 is the determined cDNA sequence of 13106
SEQ ID NO:132 is the determined cDNA sequence of 13107
SEQ ID NO:133 is the determined cDNA sequence of 13108
SEQ ID NO:134 is the determined cDNA sequence of 13121
SEQ ID NO:135 is the determined cDNA sequence of 13126
SEQ ID NO:136 is the determined cDNA sequence of 13129
SEQ ID NO:137 is the determined cDNA sequence of 13130
SEQ ID NO:138 is the determined cDNA sequence of 13134
SEQ ID NO:139 is the determined cDNA sequence of 13141
SEQ ID NO:140 is the determined cDNA sequence of 13142
SEQ ID NO:141 is the determined cDNA sequence of 14376
SEQ ID NO:142 is the determined cDNA sequence of 14377
SEQ ID NO:143 is the determined cDNA sequence of 14383
SEQ ID NO:144 is the determined cDNA sequence of 14384
SEQ ID NO:145 is the determined cDNA sequence of 14387
SEQ ID NO:146 is the determined cDNA sequence of 14392
SEQ ID NO:147 is the determined cDNA sequence of 14394
SEQ ID NO:148 is the determined cDNA sequence of 14398
SEQ ID NO:149 is the determined cDNA sequence of 14401
SEQ ID NO:150 is the determined cDNA sequence of 14402
SEQ ID NO:151 is the determined cDNA sequence of 14405
SEQ ID NO:152 is the determined cDNA sequence of 14409
SEQ ID NO:153 is the determined cDNA sequence of 14412
SEQ ID NO:154 is the determined cDNA sequence of 14414
SEQ ID NO:155 is the determined cDNA sequence of 14415
SEQ ID NO:156 is the determined cDNA sequence of 14416
SEQ ID NO:157 is the determined cDNA sequence of 14419
SEQ ID NO:158 is the determined cDNA sequence of 14426
SEQ ID NO:159 is the determined cDNA sequence of 14427
SEQ ID NO:160 is the determined cDNA sequence of 14375
SEQ ID NO:161 is the determined cDNA sequence of 14378
SEQ ID NO:162 is the determined cDNA sequence of 14379

SEQ ID NO:163 is the determined cDNA sequence of 14380

SEQ ID NO:164 is the determined cDNA sequence of 14381

SEQ ID NO:165 is the determined cDNA sequence of 14382

SEQ ID NO:166 is the determined cDNA sequence of 14388

SEQ ID NO:167 is the determined cDNA sequence of 14399

SEQ ID NO:168 is the determined cDNA sequence of 14406

SEQ ID NO:169 is the determined cDNA sequence of 14407

SEQ ID NO:170 is the determined cDNA sequence of 14408

SEQ ID NO:171 is the determined cDNA sequence of 14417

SEQ ID NO:172 is the determined cDNA sequence of 14418

SEQ ID NO:173 is the determined cDNA sequence of 14423

SEQ ID NO:174 is the determined cDNA sequence of 14424

SEQ ID NO:175 is the determined cDNA sequence of B726P-20

SEQ ID NO:176 is the predicted amino acid sequence of B726P-20 (also referred to as B726P downstream ORF)

SEQ ID NO:177 is a PCR primer

SEQ ID NO:178 is the determined cDNA sequence of B726P-74

SEQ ID NO:179 is the predicted amino acid sequence of B726P-74

SEQ ID NO:180 is the determined cDNA sequence of B726P-79

SEQ ID NO:181 is the predicted amino acid sequence of B726P-79

SEQ ID NO:182 is the determined cDNA sequence of 19439.1, showing homology to the mammaglobin gene SEQ ID NO:183 is the determined cDNA sequence of 19407.1, showing homology to the human keratin gene SEQ ID NO:184 is the determined cDNA sequence of 19428.1, showing homology to human chromosome 17 clone SEQ ID NO:185 is the determined cDNA sequence of B808P (19408), showing no significant homology to any known gene SEQ ID NO:186 is the determined cDNA sequence of 19460.1, showing no significant homology to any known gene SEQ ID NO:187 is the determined cDNA sequence of 19419.1, showing homology to Ig kappa light chain SEQ ID NO:188 is the determined cDNA sequence of 19411.1, showing homology to human alpha-1 collagen SEQ ID NO:189 is the determined cDNA sequence of 19420.1, showing homology to mus musculus proteinase-3

SEQ ID NO:190 is the determined cDNA sequence of 19432.1, showing homology to human high motility group box SEQ ID NO:191 is the determined cDNA sequence of 19412.1, showing homology to the human plasminogen activator gene SEQ ID NO:192 is the determined cDNA sequence of 19415.1, showing homology to mitogen activated protein kinase SEQ ID NO:193 is the determined cDNA sequence of 19409.1, showing homology to the chondroitin sulfate proteoglycan protein SEQ ID NO:194 is the determined cDNA sequence of 19406.1, showing no significant homology to any known gene SEQ ID NO:195 is the determined cDNA sequence of 19421.1, showing homology to human fibronectin SEQ ID NO:196 is the determined cDNA sequence of 19426.1, showing homology to the retinoic acid receptor responder 3

SEQ ID NO:197 is the determined cDNA sequence of 19425.1, showing homology to MyD88 mRNA SEQ ID NO:198 is the determined cDNA sequence of 19424.1, showing homology to peptide transporter (TAP-1) mRNA SEQ ID NO:199 is the determined cDNA sequence of 19429.1, showing no significant homology to any known gene SEQ ID NO:200 is the determined cDNA sequence of 19435.1, showing homology to human polymorphic epithelial mucin SEQ ID NO:201 is the determined cDNA sequence of B813P (19434.1), showing homology to human GATA-3 transcription factor SEQ ID NO:202 is the determined cDNA sequence of 19461.1, showing homology to the human AP-2 gene SEQ ID NO:203 is the determined cDNA sequence of 19450.1, showing homology to DNA binding regulatory factor SEQ ID NO:204 is the determined cDNA sequence of 19451.1, showing homology to Na/H exchange regulatory co-factor SEQ ID NO:205 is the determined cDNA sequence of 19462.1, showing no significant homology to any known gene SEQ ID NO:206 is the determined cDNA sequence of 19455.1, showing homology to human mRNA for histone HAS.Z SEQ ID NO:207 is the determined cDNA sequence of 19459.1, showing homology to PAC clone 179N16

SEQ ID NO:208 is the determined cDNA sequence of 19464.1, showing no significant homology to any known gene SEQ ID NO:209 is the determined cDNA sequence of 19414.1, showing homology to lipophilin B SEQ ID NO:210 is the determined cDNA sequence of 19413.1, showing homology to chromosome 17 clone hRPK.209_J_20

SEQ ID NO:211 is the determined cDNA sequence of 19416.1, showing no significant homology to any known gene SEQ ID NO:212 is the determined cDNA sequence of 19437.1, showing homology to human clone 24976 mRNA SEQ ID NO:213 is the determined cDNA sequence of 19449.1, showing homology to mouse DNA for PG-M core protein SEQ ID NO:214 is the determined cDNA sequence of 19446.1, showing no significant homology to any known gene SEQ ID NO:215 is the determined cDNA sequence of 19452.1, showing no significant homology to any known gene SEQ ID NO:216 is the determined cDNA sequence of 19483.1, showing no significant homology to any known gene SEQ ID NO:217 is the determined cDNA sequence of 19526.1, showing homology to human lipophilin C SEQ ID NO:218 is the determined cDNA sequence of 19484.1, showing homology to the secreted cement gland protein XAG-2

SEQ ID NO:219 is the determined cDNA sequence of 19470.1, showing no significant homology to any known gene SEQ ID NO:220 is the determined cDNA sequence of 19469.1, showing homology to the human HLA-DM gene SEQ ID NO:221 is the determined cDNA sequence of 19482.1, showing homology to the human pS2 protein gene SEQ ID NO:222 is the determined cDNA sequence of B805P (19468.1), showing no significant homology to any known gene SEQ ID NO:223 is the determined cDNA sequence of 19467.1, showing homology to human thrombospondin mRNA SEQ ID NO:224 is the determined cDNA sequence of 19498.1, showing homology to the CDC2 gene involved in cell cycle control SEQ ID NO:225 is the determined cDNA sequence of 19506.1, showing homology to human cDNA for TREB protein SEQ ID NO:226 is the determined cDNA sequence of B806P (19505.1), showing no significant homology to any known gene SEQ ID NO:227 is the determined cDNA sequence of 19486.1, showing homology to type I epidermal keratin SEQ ID NO:228 is the determined cDNA sequence of 19510.1, showing homology to glucose transporter for glycoprotein SEQ ID NO:229 is the determined cDNA sequence of 19512.1, showing homology to the human lysyl hydroxylase gene SEQ ID NO:230 is the determined cDNA sequence of 19511.1, showing homology to human palimotoyl-protein thioesterase SEQ ID NO:231 is the determined cDNA sequence of 19508.1, showing homology to human alpha enolase SEQ ID NO:232 is the determined cDNA sequence of B807P (19509.1), showing no significant homology to any known gene SEQ ID NO:233 is the determined cDNA sequence of B809P (19520.1), showing homology to clone 102D24 on chromosome 11q13.31

SEQ ID NO:234 is the determined cDNA sequence of 19507.1, showing homology toprosome beta-subunit SEQ ID NO:235 is the determined cDNA sequence of 19525.1, showing homology to human pro-urokinase precursor SEQ ID NO:236 is the determined cDNA sequence of 19513.1, showing no significant homology to any known gene SEQ ID NO:237 is the determined cDNA sequence of 19517.1, showing homology to human PAC 128M19 clone SEQ ID NO:238 is the determined cDNA sequence of 19564.1, showing homology to human cytochrome P450-IIB SEQ ID NO:239 is the determined cDNA sequence of 19553.1, showing homology to human GABA-A receptor pi subunit SEQ ID NO:240 is the determined cDNA sequence of B811P (19575.1), showing no significant homology to any known gene SEQ ID NO:241 is the determined cDNA sequence of B810P (19560.1), showing no significant homology to any known gene SEQ ID NO:242 is the determined cDNA sequence of 19588.1, showing homology to aortic carboxypetidase-like protein SEQ ID NO:243 is the determined cDNA sequence of 19551.1, showing homology to human BCL-1 gene SEQ ID NO:244 is the determined cDNA sequence of 19567.1, showing homology to human proteasome-related mRNA SEQ ID NO:245 is the determined cDNA sequence of B803P (19583.1), showing no significant homology to any known gene SEQ ID NO:246 is the determined cDNA sequence of B812P (19587.1), showing no significant homology to any known gene SEQ ID NO:247 is the determined cDNA sequence of B802P (19392.2), showing homology to human chromosome 17

SEQ ID NO:248 is the determined cDNA sequence of 19393.2, showing homology to human nicein B2 chain SEQ ID NO:249 is the determined cDNA sequence of 19398.2, human MHC class II DQ alpha mRNA SEQ ID NO:250 is the determined cDNA sequence of B804P (19399.2), showing homology to human Xp22 BAC GSHB-184P14

SEQ ID NO:251 is the determined cDNA sequence of 19401.2, showing homology to human ikB kinase-b gene SEQ ID NO:252 is the determined cDNA sequence of 20266, showing no significant homology to any known gene SEQ ID NO:253 is the determined cDNA sequence of B826P (20270), showing no significant homology to any known gene SEQ ID NO:254 is the determined cDNA sequence of 20274, showing no significant homology to any known gene SEQ ID NO:255 is the determined cDNA sequence of 20276, showing no significant homology to any known gene SEQ ID NO:256 is the determined cDNA sequence of 20277, showing no significant homology to any known gene SEQ ID NO:257 is the determined cDNA sequence of B823P (20280), showing no significant homology to any known gene SEQ ID NO:258 is the determined cDNA sequence of B821P (20281), showing no significant homology to any known gene SEQ ID NO:259 is the determined cDNA sequence of B824P (20294), showing no significant homology to any known gene SEQ ID NO:260 is the determined cDNA sequence of 20303, showing no significant homology to any known gene SEQ ID NO:261 is the determined cDNA sequence of B820P (20310), showing no significant homology to any known gene SEQ ID NO:262 is the determined cDNA sequence of B825P (20336), showing no significant homology to any known gene SEQ ID NO:263 is the determined cDNA sequence of B827P (20341), showing no significant homology to any known gene SEQ ID NO:264 is the determined cDNA sequence of 20941, showing no significant homology to any known gene SEQ ID NO:265 is the determined cDNA sequence of 20954, showing no significant homology to any known gene SEQ ID NO:266 is the determined cDNA sequence of 20961, showing no significant homology to any known gene SEQ ID NO:267 is the determined cDNA sequence of 20965, showing no significant homology to any known gene SEQ ID NO:268 is the determined cDNA sequence of 20975, showing no significant homology to any known gene SEQ ID NO:269 is the determined cDNA sequence of 20261, showing homology to Human p120 catenin SEQ ID NO:270 is the determined cDNA sequence of B822P (20262), showing homology to Human membrane glycoprotein 4F2

SEQ ID NO:271 is the determined cDNA sequence of 20265, showing homology to Human Na, K-ATPase Alpha 1

SEQ ID NO:272 is the determined cDNA sequence of 20267, showing homology to Human heart HS 90, partial cds SEQ ID NO:273 is the determined cDNA sequence of 20268, showing homology to Human mRNA GPI-anchored protein p137

SEQ ID NO:274 is the determined cDNA sequence of 20271, showing homology to Human cleavage stimulation factor 77 kDa subunit SEQ ID NO:275 is the determined cDNA sequence of 20272, showing homology to Human p190-B SEQ ID NO:276 is the determined cDNA sequence of 20273, showing homology to Human ribophorin SEQ ID NO:277 is the determined cDNA sequence of 20278, showing homology to Human ornithine amino transferase SEQ ID NO:278 is the determined cDNA sequence of 20279, showing homology to Human S-adenosylmethionine synthetase SEQ ID NO:279 is the determined cDNA sequence of 20293, showing homology to Human x inactivation transcript SEQ ID NO:280 is the determined cDNA sequence of 20300, showing homology to Human cytochrome p450

SEQ ID NO:281 is the determined cDNA sequence of 20305, showing homology to Human elongation factor-1 alpha SEQ ID NO:282 is the determined cDNA sequence of 20306, showing homology to Human epithelial ets protein SEQ ID NO:283 is the determined cDNA sequence of 20307, showing homology to Human signal transducer mRNA SEQ ID NO:284 is the determined cDNA sequence of 20313, showing homology to Human GABA-A receptor pi subunit mRNA SEQ ID NO:285 is the determined cDNA sequence of 20317, showing homology to Human tyrosine phosphatase SEQ ID NO:286 is the determined cDNA sequence of 20318, showing homology to Human cathepsine B proteinase SEQ ID NO:287 is the determined cDNA sequence of 20320, showing homology to Human 2-phosphopyruvate-hydratase-alpha-enolase SEQ ID NO:288 is the determined cDNA sequence of 20321, showing homology to Human E-cadherin SEQ ID NO:289 is the determined cDNA sequence of 20322, showing homology to Human hsp86

SEQ ID NO:290 is the determined cDNA sequence of B828P (20326), showing homology to Human x inactivation transcript SEQ ID NO:291 is the determined cDNA sequence of 20333, showing homology to Human chromatin regulator, SMARCA5

SEQ ID NO:292 is the determined cDNA sequence of 20335, showing homology to Human sphingolipid activator protein 1

SEQ ID NO:293 is the determined cDNA sequence of 20337, showing homology to Human hepatocyte growth factor activator inhibitor type 2

SEQ ID NO:294 is the determined cDNA sequence of 20338, showing homology to Human cell adhesion molecule CD44

SEQ ID NO:295 is the determined cDNA sequence of 20340, showing homology to Human nuclear factor (erythroid-derived)-like 1

SEQ ID NO:296 is the determined cDNA sequence of 20938, showing homology to Human vinculin mRNA SEQ ID NO:297 is the determined cDNA sequence of 20939, showing homology to Human elongation factor EF-1-alpha SEQ ID NO:298 is the determined cDNA sequence of 20940, showing homology to Human nestin gene SEQ ID NO:299 is the determined cDNA sequence of 20942, showing homology to Human pancreatic ribonuclease SEQ ID NO:300 is the determined cDNA sequence of 20943, showing homology to Human transcobalamin I SEQ ID NO:301 is the determined cDNA sequence of 20944, showing homology to Human beta-tubulin SEQ ID NO:302 is the determined cDNA sequence of 20946, showing homology to Human HS1 protein SEQ ID NO:303 is the determined cDNA sequence of 20947, showing homology to Human cathepsin B SEQ ID NO:304 is the determined cDNA sequence of 20948, showing homology to Human testis enhanced gene transcript SEQ ID NO:305 is the determined cDNA sequence of 20949, showing homology to Human elongation factor EF-1-alpha SEQ ID NO:306 is the determined cDNA sequence of 20950, showing homology to Human ADP-ribosylation factor 3

SEQ ID NO:307 is the determined cDNA sequence of 20951, showing homology to Human IFP53 or WRS for tryptophanyl-tRNA synthetase SEQ ID NO:308 is the determined cDNA sequence of 20952, showing homology to Human cyclin-dependent protein kinase SEQ ID NO:309 is the determined cDNA sequence of 20957, showing homology to Human alpha-tubulin isoform 1

SEQ ID NO:310 is the determined cDNA sequence of 20959, showing homology to Human tyrosine phosphatase-61bp deletion SEQ ID NO:311 is the determined cDNA sequence of 20966, showing homology to Human tyrosine phosphatase SEQ ID NO:312 is the determined cDNA sequence of B830P (20976), showing homology to Human nuclear factor NF 45

SEQ ID NO:313 is the determined cDNA sequence of B829P (20977), showing homology to Human delta-6 fatty acid desaturase SEQ ID NO:314 is the determined cDNA sequence of 20978, showing homology to Human nuclear aconitase SEQ ID NO:315 is the determined cDNA sequence of clone 23176.

SEQ ID NO:316 is the determined cDNA sequence of clone 23140.

SEQ ID NO:317 is the determined cDNA sequence of clone 23166.

SEQ ID NO:318 is the determined cDNA sequence of clone 23167.

SEQ ID NO:319 is the determined cDNA sequence of clone 23177.

SEQ ID NO:320 is the determined cDNA sequence of clone 23217.

SEQ ID NO:321 is the determined cDNA sequence of clone 23169.

SEQ ID NO:322 is the determined cDNA sequence of clone 23160.

SEQ ID NO:323 is the determined cDNA sequence of clone 23182.

SEQ ID NO:324 is the determined cDNA sequence of clone 23232.

SEQ ID NO:325 is the determined cDNA sequence of clone 23203.

SEQ ID NO:326 is the determined cDNA sequence of clone 23198.

SEQ ID NO:327 is the determined cDNA sequence of clone 23224.

SEQ ID NO:328 is the determined cDNA sequence of clone 23142.

SEQ ID NO:329 is the determined cDNA sequence of clone 23138.

SEQ ID NO:330 is the determined cDNA sequence of clone 23147.

SEQ ID NO:331 is the determined cDNA sequence of clone 23148.

SEQ ID NO:332 is the determined cDNA sequence of clone 23149.

SEQ ID NO:333 is the determined cDNA sequence of clone 23172.

SEQ ID NO:334 is the determined cDNA sequence of clone 23158.

SEQ ID NO:335 is the determined cDNA sequence of clone 23156.

SEQ ID NO:336 is the determined cDNA sequence of clone 23221.

SEQ ID NO:337 is the determined cDNA sequence of clone 23223.

SEQ ID NO:338 is the determined cDNA sequence of clone 23155.

SEQ ID NO:339 is the determined cDNA sequence of clone 23225.

SEQ ID NO:340 is the determined cDNA sequence of clone 23226.

SEQ ID NO:341 is the determined cDNA sequence of clone 23228.

SEQ ID NO:342 is the determined cDNA sequence of clone 23229.

SEQ ID NO:343 is the determined cDNA sequence of clone 23231.

SEQ ID NO:344 is the determined cDNA sequence of clone 23154.

SEQ ID NO:345 is the determined cDNA sequence of clone 23157.

SEQ ID NO:346 is the determined cDNA sequence of clone 23153.

SEQ ID NO:347 is the determined cDNA sequence of clone 23159.

SEQ ID NO:348 is the determined cDNA sequence of clone 23152.

SEQ ID NO:349 is the determined cDNA sequence of clone 23161.

SEQ ID NO:350 is the determined cDNA sequence of clone 23162.

SEQ ID NO:351 is the determined cDNA sequence of clone 23163.

SEQ ID NO:352 is the determined cDNA sequence of clone 23164.

SEQ ID NO:353 is the determined cDNA sequence of clone 23165.

SEQ ID NO:354 is the determined cDNA sequence of clone 23151.

SEQ ID NO:355 is the determined cDNA sequence of clone 23150.

SEQ ID NO:356 is the determined cDNA sequence of clone 23168.

SEQ ID NO:357 is the determined cDNA sequence of clone 23146.

SEQ ID NO:358 is the determined cDNA sequence of clone 23170.

SEQ ID NO:359 is the determined cDNA sequence of clone 23171.

SEQ ID NO:360 is the determined cDNA sequence of clone 23145.

SEQ ID NO:361 is the determined cDNA sequence of clone 23174.

SEQ ID NO:362 is the determined cDNA sequence of clone 23175.

SEQ ID NO:363 is the determined cDNA sequence of clone 23144.

SEQ ID NO:364 is the determined cDNA sequence of clone 23178.

SEQ ID NO:365 is the determined cDNA sequence of clone 23179.

SEQ ID NO:366 is the determined cDNA sequence of clone 23180.

SEQ ID NO:367 is the determined cDNA sequence of clone 23181.

SEQ ID NO:368 is the determined cDNA sequence of clone 23143

SEQ ID NO:369 is the determined cDNA sequence of clone 23183.

SEQ ID NO:370 is the determined cDNA sequence of clone 23184.

SEQ ID NO:371 is the determined cDNA sequence of clone 23185.

SEQ ID NO:372 is the determined cDNA sequence of clone 23186.

SEQ ID NO:373 is the determined cDNA sequence of clone 23187.
SEQ ID NO:374 is the determined cDNA sequence of clone 23190.
SEQ ID NO:375 is the determined cDNA sequence of clone 23189.
SEQ ID NO:376 is the determined cDNA sequence of clone 23202.
SEQ ID NO:378 is the determined cDNA sequence of clone 23191.
SEQ ID NO:379 is the determined cDNA sequence of clone 23188.
SEQ ID NO:380 is the determined cDNA sequence of clone 23194.
SEQ ID NO:381 is the determined cDNA sequence of clone 23196.
SEQ ID NO:382 is the determined cDNA sequence of clone 23195.
SEQ ID NO:383 is the determined cDNA sequence of clone 23193.
SEQ ID NO:384 is the determined cDNA sequence of clone 23199.
SEQ ID NO:385 is the determined cDNA sequence of clone 23200.
SEQ ID NO:386 is the determined cDNA sequence of clone 23192.
SEQ ID NO:387 is the determined cDNA sequence of clone 23201.
SEQ ID NO:388 is the determined cDNA sequence of clone 23141.
SEQ ID NO:389 is the determined cDNA sequence of clone 23139.
SEQ ID NO:390 is the determined cDNA sequence of clone 23204.
SEQ ID NO:391 is the determined cDNA sequence of clone 23205.
SEQ ID NO:392 is the determined cDNA sequence of clone 23206.
SEQ ID NO:393 is the determined cDNA sequence of clone 23207.
SEQ ID NO:394 is the determined cDNA sequence of clone 23208.
SEQ ID NO:395 is the determined cDNA sequence of clone 23209.
SEQ ID NO:396 is the determined cDNA sequence of clone 23210.
SEQ ID NO:397 is the determined cDNA sequence of clone 23211.
SEQ ID NO:398 is the determined cDNA sequence of clone 23212.
SEQ ID NO:399 is the determined cDNA sequence of clone 23214.
SEQ ID NO:400 is the determined cDNA sequence of clone 23215.
SEQ ID NO:401 is the determined cDNA sequence of clone 23216.
SEQ ID NO:402 is the determined cDNA sequence of clone 23137.
SEQ ID NO:403 is the determined cDNA sequence of clone 23218.
SEQ ID NO:404 is the determined cDNA sequence of clone 23220.
SEQ ID NO:405 is the determined cDNA sequence of clone 19462.
SEQ ID NO:406 is the determined cDNA sequence of clone 19430.
SEQ ID NO:407 is the determined cDNA sequence of clone 19407.
SEQ ID NO:408 is the determined cDNA sequence of clone 19448.
SEQ ID NO:409 is the determined cDNA sequence of clone 19447.
SEQ ID NO:410 is the determined cDNA sequence of clone 19426.
SEQ ID NO:411 is the determined cDNA sequence of clone 19441.
SEQ ID NO:412 is the determined cDNA sequence of clone 19454.
SEQ ID NO:413 is the determined cDNA sequence of clone 19463.
SEQ ID NO:414 is the determined cDNA sequence of clone 19419.
SEQ ID NO:415 is the determined cDNA sequence of clone 19434.
SEQ ID NO:416 is the determined extended cDNA sequence of B820P.
SEQ ID NO:417 is the determined extended cDNA sequence of B821P.
SEQ ID NO:418 is the determined extended cDNA sequence of B822P.
SEQ ID NO:419 is the determined extended cDNA sequence of B823P.
SEQ ID NO:420 is the determined extended cDNA sequence of B824P.
SEQ ID NO:421 is the determined extended cDNA sequence of B825P.
SEQ ID NO:422 is the determined extended cDNA sequence of B826P.
SEQ ID NO:423 is the determined extended cDNA sequence of B827P.
SEQ ID NO:424 is the determined extended cDNA sequence of B828P.
SEQ ID NO:425 is the determined extended cDNA sequence of B829P.
SEQ ID NO:426 is the determined extended cDNA sequence of B830P.
SEQ ID NO:427 is the determined cDNA sequence of clone 266B4.
SEQ ID NO:428 is the determined cDNA sequence of clone 22892.
SEQ ID NO:429 is the determined cDNA sequence of clone 266G3.
SEQ ID NO:430 is the determined cDNA sequence of clone 22890.
SEQ ID NO:431 is the determined cDNA sequence of clone 264B4.
SEQ ID NO:432 is the determined cDNA sequence of clone 22883.
SEQ ID NO:433 is the determined cDNA sequence of clone 22882.
SEQ ID NO:434 is the determined cDNA sequence of clone 22880.
SEQ ID NO:435 is the determined cDNA sequence of clone 263G1.

SEQ ID NO:436 is the determined cDNA sequence of clone 263G6.

SEQ ID NO:437 is the determined cDNA sequence of clone 262B2.

SEQ ID NO:438 is the determined cDNA sequence of clone 262B6.

SEQ ID NO:439 is the determined cDNA sequence of clone 22869.

SEQ ID NO:440 is the determined cDNA sequence of clone 21374.

SEQ ID NO:441 is the determined cDNA sequence of clone 21362.

SEQ ID NO:442 is the determined cDNA sequence of clone 21349.

SEQ ID NO:443 is the determined cDNA sequence of clone 21309.

SEQ ID NO:444 is the determined cDNA sequence of clone 21097.

SEQ ID NO:445 is the determined cDNA sequence of clone 21096.

SEQ ID NO:446 is the determined cDNA sequence of clone 21094.

SEQ ID NO:447 is the determined cDNA sequence of clone 21093.

SEQ ID NO:448 is the determined cDNA sequence of clone 21091.

SEQ ID NO:449 is the determined cDNA sequence of clone 21089.

SEQ ID NO:450 is the determined cDNA sequence of clone 21087.

SEQ ID NO:451 is the determined cDNA sequence of clone 21085.

SEQ ID NO:452 is the determined cDNA sequence of clone 21084.

SEQ ID NO:453 is a first partial cDNA sequence of clone 2BT1-40.

SEQ ID NO:454 is a second partial cDNA sequence of clone 2BT1-40.

SEQ ID NO:455 is the determined cDNA sequence of clone 21063.

SEQ ID NO:456 is the determined cDNA sequence of clone 21062.

SEQ ID NO:457 is the determined cDNA sequence of clone 21060.

SEQ ID NO:458 is the determined cDNA sequence of clone 21053.

SEQ ID NO:459 is the determined cDNA sequence of clone 21050.

SEQ ID NO:460 is the determined cDNA sequence of clone 21036.

SEQ ID NO:461 is the determined cDNA sequence of clone 21037.

SEQ ID NO:462 is the determined cDNA sequence of clone 21048.

SEQ ID NO:463 is a consensus DNA sequence of B726P (referred to as B726P-spliced_seq_B726P).

SEQ ID NO:464 is the determined cDNA sequence of a second splice form of B726P (referred to as 27490.seq_B726P).

SEQ ID NO:465 is the determined cDNA sequence of a third splice form of B726P (referred to as 27068.seq_B726P).

SEQ ID NO:466 is the determined cDNA sequence of a second splice form of B726P (referred to as 23113.seq_B726P).

SEQ ID NO:467 is the determined cDNA sequence of a second splice form of B726P (referred to as 23103.seq_B726P).

SEQ ID NO:468 is the determined cDNA sequence of a second splice form of B726P (referred to as 19310.seq_B726P).

SEQ ID NO:469 is the predicted amino acid sequence encoded by the upstream ORF of SEQ ID NO:463.

SEQ ID NO:470 is the predicted amino acid sequence encoded by SEQ ID NO:464.

SEQ ID NO:471 is the predicted amino acid sequence encoded by SEQ ID NO:465.

SEQ ID NO:472 is the predicted amino acid sequence encoded by SEQ ID NO:466.

SEQ ID NO:473 is the predicted amino acid sequence encoded by SEQ ID NO:467.

SEQ ID NO:474 is the determined cDNA sequence for an alternative splice form of B726P.

SEQ ID NO:475 is the amino acid sequence encoded by SEQ ID NO:474.

SEQ ID NO:476 is the isolated cDNA sequence of B720P.

SEQ ID NO:477 is the cDNA sequence of a known keratin gene.

SEQ ID NO:478 is the amino acid sequence encoded by SEQ ID NO:477.

SEQ ID NO:479 is the determined cDNA sequence for clone 19465.

SEQ ID NO:480 and 481 are PCR primers.

SEQ ID NO:482 is the cDNA sequence for the expressed downstream ORF of B726P.

SEQ ID NO:483 is the amino acid sequence for the expressed recombinant downstream ORF of B726P.

SEQ ID NO:484 is the determined full-length cDNA sequence for B720P.

SEQ ID NO:485 is the amino acid sequence encoded by SEQ ID NO:484.

SEQ ID NO:486 is the determined cDNA sequence of a truncated form of B720P, referred to as B720P-tr.

SEQ ID NO:487 is the amino acid sequence of B720P-tr.

SEQ ID NO:488 is the amino acid sequence of a naturally processed epitope of B726P recognized by B726P-specific CTL.

SEQ ID NO:489 is a DNA sequence encoding the B726P epitope set forth in SEQ ID NO:488.

SEQ ID NO:490 is a DNA sequence encoding a fusion protein wherein mammaglobin is fused to the B726P combined upstream and downstream open reading frame (ORF) (the amino acid sequence of the B726P combined ORF is disclosed herein as SEQ ID NO:475 which is encoded by the DNA sequence of SEQ ID NO:474).

SEQ ID NO:491 is a DNA sequence encoding a fusion protein wherein mammaglobin is fused to the B726P upstream ORF (the amino acid sequence of the B726P upstream ORF is disclosed herein as SEQ ID NO:469 which is encoded by the DNA sequence of SEQ ID NO:463).

SEQ ID NO:492 is a DNA sequence encoding a fusion protein wherein mammaglobin is fused to the B726P downstream ORF (the amino acid sequence of the B726P downstream ORF is disclosed herein as SEQ ID NO:176 which is encoded by the DNA sequence of SEQ ID NO:175).

SEQ ID NO:493 is the amino acid sequence encoded by the DNA sequence of SEQ ID NO:490.

SEQ ID NO:494 is the amino acid sequence encoded by the DNA sequence of SEQ ID NO:491.

SEQ ID NO:495 is the amino acid sequence encoded by the DNA sequence of SEQ ID NO:492.

SEQ ID NO:496 is amino acids 59–78 of SEQ ID NO:493.

SEQ ID NO:497 is amino acids 55–69 of SEQ ID NO:493.

SEQ ID NO:498 is amino acids 13–33 of SEQ ID NO:493.

SEQ ID NO:499 is amino acids 41–60 of SEQ ID NO:493.

SEQ ID NO:500 is amino acids 2–10 of SEQ ID NO:493.

SEQ ID NO:501 is amino acids 47–59 of SEQ ID NO:493.

SEQ ID NO:502 is amino acids 62–74 of SEQ ID NO:493.

SEQ ID NO:503 is amino acids 1–93 of SEQ ID NO:493.

SEQ ID NO:504 is the full-length cDNA sequence for B718P.

SEQ ID NO:505 is the cDNA sequence of the open reading frame of B718P including stop codon.

SEQ ID NO:506 is the cDNA sequence of the open reading frame of B718P without stop codon.

SEQ ID NO:507 is the full-length amino acid sequence of B718P.

SEQ ID NO:508 represents amino acids 1–158 of SEQ ID NO:507.

SEQ ID NO:509 represents amino acids 159–243 of SEQ ID NO:509.

SEQ ID NO:510 is the entire cDNA sequence of the open reading frame, including stop codon, of a first variant of B723P, referred to as B723P-short.

SEQ ID NO:511 is the entire cDNA sequence of the open reading frame, without stop codon, of a first variant of B723P, referred to as B723P-short.

SEQ ID NO:512 is the entire cDNA sequence of the open reading frame, including stop codon, of a second variant of B723P, referred to as B723P-long.

SEQ ID NO:513 is the entire cDNA sequence of the open reading frame, without stop codon, of a second variant of B723P, referred to as B723P-long.

SEQ ID NO:514 is the amino acid sequence of B723P-short.

SEQ ID NO:515 is the amino acid sequence of B723P-long.

SEQ ID NO:516 is amino acids 1–197 of B723P-short.

SEQ ID NO:517 is amino acids 1–232 of B723P-long.

SEQ ID NO:518 is amino acids 198–243 of B723P-short.

SEQ ID NO:519 is amino acids 218–243 of B723P-short.

SEQ ID NO:520–533 are the DNA sequences of epitopes of B726P.

SEQ ID NO:534–547 are the amino acid sequences of epitopes of B726P.

SEQ ID NO:548 is the cDNA sequence of B726P Combined ORF coding_region for expression in E. coli.

SEQ ID NO:549 is the cDNA sequence of B726P Upstream ORF coding_region for expression in E. coli.

SEQ ID NO:550 is the cDNA sequence of B726P Downstream ORF coding_region for expression in E. coli.

SEQ ID NO:551 is the amino acid sequence of B726P Downstream ORF encoded by the cDNA set forth in SEQ ID NO:550.

SEQ ID NO:552 is the amino acid sequence of B726P Upstream ORF with HIS, encoded by the cDNA set forth in SEQ ID NO:549.

SEQ ID NO:553 is the amino acid sequence of B726P Combined ORF correct, encoded by the cDNA set forth in SEQ ID NO:548.

SEQ ID NO:554–563 are PCR primers as described in Example 8.

SEQ ID NO:564 is the cDNA sequence for NY-BR-1, an extended sequence of B726P.

SEQ ID NO:565 is the amino acid sequence for NY-BR-1, an extended sequence of B726P, and encoded by the nucleotide sequence set forth in SEQ ID NO:564.

SEQ ID NO:566 is the cDNA sequence for B726P XC coding region with changes.

SEQ ID NO:567 is the cDNA sequence for B726P XB clone 83686 with 2 changes from the published NY-BR-1 sequence in SEQ ID NO:564.

SEQ ID NO:568 is the cDNA sequence for B726P XB clone 84330 with 4 changes from the published NY-BR-1 sequence in SEQ ID NO:564.

SEQ ID NO:569 is the cDNA sequence for B726P XB clone 84328 with 3 changes from the published NY-BR-1 sequence in SEQ ID NO:564.

SEQ ID NO:570 is the amino acid sequence for B726P XB clone 84328, encoded by the sequence set forth in SEQ ID NO:569.

SEQ ID NO:571 is the amino acid sequence for B726P XB clone 84330, encoded by the sequence set forth in SEQ ID NO:568.

SEQ ID NO:572 is the amino acid sequence for B726P XB clone 83686, encoded by the sequence set forth in SEQ ID NO:567.

SEQ ID NO:573 is the amino acid sequence for B726P XC, encoded by the sequence set forth in SEQ ID NO:566.

SEQ ID NO:574–575 are PCR primers as described in Example 12.

SEQ ID NO:576 is the full-length cDNA sequence for NY-BR-1.1.

SEQ ID NO:577 is the full-length amino acid sequence for NY-BR -1.1, encoded by the nucleotide sequence set forth in SEQ ID NO:576.

SEQ ID NO:578 is amino acids 289–308 of the B726P downstream ORF and corresponds to the peptide recognized by the 220A2.1 antibody.

SEQ ID NO:579 is amino acids 225–244 of the B726P downstream ORF and corresponds to the peptide recognized by the 220A19.1 antibody.

SEQ ID NO:580 is amino acids 232–252 of the B726P downstream ORF and corresponds to the peptide recognized by the 220A19.1 and the 220A43 antibodies.

SEQ ID NO:581 is amino acids 73–92 of the B726P downstream ORF and corresponds to the peptide recognized by the 220A94.1 antibody.

SEQ ID NO:582 is amino acids 145–164 of the B726P downstream ORF and corresponds to the peptide recognized by the 220A151.1 and 220A86 antibodies.

SEQ ID NO:583 is amino acids 153–172 of the B726P downstream ORF and corresponds to the peptide recognized by the 220A151.1 and 220A86 antibodies.

SEQ ID NO:584 is amino acids 1–20 of the B726P downstream ORF and corresponds to the peptide recognized by purified B726 polyclonal antibodies.

SEQ ID NO:585 is amino acids 9–28 of the B726P downstream ORF and corresponds to the peptide recognized by purified B726 polyclonal antibodies.

SEQ ID NO:586 is amino acids 17–36 of the B726P downstream ORF and corresponds to the peptide recognized by purified B726 polyclonal antibodies.

SEQ ID NO:587 is amino acids 24–44 of the B726P downstream ORF and corresponds to the peptide recognized by purified B726 polyclonal antibodies.

SEQ ID NO:588 is amino acids 97–116 of the B726P downstream ORF and corresponds to the peptide recognized by purified B726 polyclonal antibodies.

SEQ ID NO:589 is amino acids 105–124 of the B726P downstream ORF and corresponds to the peptide recognized by purified B726 polyclonal antibodies.

SEQ ID NO:590 is amino acids 113–132 of the B726P downstream ORF and corresponds to the peptide recognized by purified B726 polyclonal antibodies.

SEQ ID NO:591 is amino acids 121–140 of the B726P downstream ORF and corresponds to the peptide recognized by purified B726 polyclonal antibodies.

SEQ ID NO:592 is amino acids 129–148 of the B726P downstream ORF and corresponds to the peptide recognized by purified B726 polyclonal antibodies.

SEQ ID NO:593 is amino acids 137–156 of the B726P downstream ORF and corresponds to the peptide recognized by purified B726 polyclonal antibodies.

SEQ ID NO:594 is the amino acid sequence of peptide #2732 and corresponds to amino acids 1–20 of the B726P downstream ORF.

SEQ ID NO:595 is the amino acid sequence of peptide #2733 and corresponds to amino acids 11–30 of the B726P downstream ORF.

SEQ ID NO:596 is the amino acid sequence of peptide #2734 and corresponds to amino acids 21–40 of the B726P downstream ORF.

SEQ ID NO:597 is the amino acid sequence of peptide #2735 and corresponds to amino acids 31–50 of the B726P downstream ORF.

SEQ ID NO:598 is the amino acid sequence of peptide #2736 and corresponds to amino acids 41–60 of the B726P downstream ORF.

SEQ ID NO:599 is the amino acid sequence of peptide #2737 and corresponds to amino acids 51–70 of the B726P downstream ORF.

SEQ ID NO:600 is the amino acid sequence of peptide #2738 and corresponds to amino acids 61–80 of the B726P downstream ORF.

SEQ ID NO:601 is the amino acid sequence of peptide #2739 and corresponds to amino acids 71–90 of the B726P downstream ORF.

SEQ ID NO:602 is the amino acid sequence of peptide #2740 and corresponds to amino acids 81–100 of the B726P downstream ORF.

SEQ ID NO:603 is the amino acid sequence of peptide #2741 and corresponds to amino acids 91–110 of the B726P downstream ORF.

SEQ ID NO:604 is the amino acid sequence of peptide #2742 and corresponds to amino acids 101–120 of the B726P downstream ORF.

SEQ ID NO:605 is the amino acid sequence of peptide #2743 and corresponds to amino acids 111–130 of the B726P downstream ORF.

SEQ ID NO:606 is the amino acid sequence of peptide #2744 and corresponds to amino acids 121–140 of the B726P downstream ORF.

SEQ ID NO:607 is the amino acid sequence of peptide #2745 and corresponds to amino acids 130–151 of the B726P downstream ORF.

SEQ ID NO:608 is the amino acid sequence of peptide #2746 and corresponds to amino acids 141–160 of the B726P downstream ORF.

SEQ ID NO:609 is the amino acid sequence of peptide #2747 and corresponds to amino acids 151–170 of the B726P downstream ORF.

SEQ ID NO:610 is the amino acid sequence of peptide #2748 and corresponds to amino acids 161–180 of the B726P downstream ORF.

SEQ ID NO:611 is the amino acid sequence of peptide #2749 and corresponds to amino acids 170–190 of the B726P downstream ORF.

SEQ ID NO:612 is the amino acid sequence of peptide #2750 and corresponds to amino acids 181–200 of the B726P downstream ORF.

SEQ ID NO:613 is the amino acid sequence of peptide #2751 and corresponds to amino acids 191–210 of the B726P downstream ORF.

SEQ ID NO:614 is the amino acid sequence of peptide #2752 and corresponds to amino acids 201–220 of the B726P downstream ORF.

SEQ ID NO:615 is the amino acid sequence of peptide #2753 and corresponds to amino acids 211–230 of the B726P downstream ORF.

SEQ ID NO:616 is the amino acid sequence of peptide #2765 and corresponds to amino acids 221–240 of the B726P downstream ORF.

SEQ ID NO:617 is the amino acid sequence of peptide #2766 and corresponds to amino acids 231–250 of the B726P downstream ORF.

SEQ ID NO:618 is the amino acid sequence of peptide #2767 and corresponds to amino acids 240–260 of the B726P downstream ORF.

SEQ ID NO:619 is the amino acid sequence of peptide #2768 and corresponds to amino acids 251–270 of the B726P downstream ORF.

SEQ ID NO:620 is the amino acid sequence of peptide #2769 and corresponds to amino acids 261–280 of the B726P downstream ORF.

SEQ ID NO:621 is the amino acid sequence of peptide #2770 and corresponds to amino acids 271–290 of the B726P downstream ORF.

SEQ ID NO:622 is the amino acid sequence of peptide #2771 and corresponds to amino acids 281–300 of the B726P downstream ORF.

SEQ ID NO:623 is the amino acid sequence of peptide #2772 and corresponds to amino acids 291–310 of the B726P downstream ORF.

SEQ ID NO:624 is the amino acid sequence of peptide #2773 and corresponds to amino acids 298–317 of the B726P downstream ORF.

SEQ ID NO:625 is the amino acid sequence of peptide #3535 of B726P.

SEQ ID NO:626 is the amino acid sequence of peptide #3536 of B726P.

SEQ ID NO:627 is the amino acid sequence of peptide #3534 of B726P.

DETAILED DESCRIPTION OF THE INVENTION

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NO: 1–61, 63–175, 178, 180, 182–468, 474, 476, 477, 479, 482, 484, 486, 489–492, 504–506, 510–513, 520–533, 548–550, 564, 566–569, and 576, or a sequence that hybridizes under moderately stringent conditions, or, alternatively, under highly stringent conditions, to a polynucleotide sequence set forth in any one of SEQ ID NO: 1–61, 63–175, 178, 180, 182–468, 474, 476, 477, 479, 482, 484, 486, 489–492, 504–506, 510–513, 520–533, 548–550, 564, 566–569, and 576. Certain other illustrative polypeptides of the invention comprise amino acid sequences as set forth in any one of SEQ ID NO: 62, 176, 179, 181, 469–473, 475, 478, 483, 485, 487, 488, 493–503, 507–509, 514–519, 534–547, 551–553, 565, 570–573, and 577–627.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NO: 62, 176, 179, 181, 469–473, 475, 478, 483, 485, 487, 488, 493–503, 507–509, 514–519, 534–547, 551–553, 565, 570–573, and 577–627, or those encoded by a polynucleotide sequence set forth in a sequence of SEQ ID NO: 1–61, 63–175, 178, 180, 182–468, 474, 476, 477, 479, 482, 484, 486, 489–492, 504–506, 510–513, 520–533, 548–550, 564, 566–569, and 576.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86–91, 1997).

In one preferred embodiment, the immunological fusion partner is derived from a Mycobacterium sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application Ser. No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application Ser. No. 60/158,585; see also, Skeiky et al., *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NO: 1–61, 63–175, 178, 180, 182–468, 474, 476, 477, 479, 482, 484, 486, 489–492, 504–506, 510–513, 520–533, 548–550, 564, 566–569, and 576, complements of a polynucleotide sequence set forth in any one of SEQ ID NO: 1–61, 63–175, 178, 180, 182–468, 474, 476, 477, 479, 482, 484, 486, 489–492, 504–506, 510–513, 520–533, 548–550, 564, 566–569, and 576, and degenerate variants of a polynucleotide sequence set forth in any one of SEQ ID NO: 1–61, 63–175, 178, 180, 182–468, 474, 476, 477, 479, 482, 484, 486, 489–492, 504–506, 510–513, 520–533, 548–550, 564, 566–569, and 576. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NO: 1–61, 63–175, 178, 180, 182–468, 474, 476, 477, 479, 482, 484, 486, 489–492, 504–506, 510–513, 520–533, 548–550, 564, 566–569, and 576, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nuc. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal GABA$_A$ receptor and human EGF (Jaskulski et al., Science. Jun. 10, 1988;240(4858):1544–6; Vasanthakumar and Ahmed, Cancer Commun. 1989;1(4):225–32; Peris et al., Brain Res Mol Brain Res. Jun. 15, 1998;57(2):310–20; U.S. Pat. No. 5,801, 154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise R NA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. 1997 Jul. 15;25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. 1987 December;84(24):8788–92; Forster and Symons, Cell. 1987 Apr. 24;49(2):211–20). For example, a large number of ribozymes accelerate phosphoester transfer reactions with a high degree of specificity, often cleaving only one of several phosphoesters in an oligonucleotide substrate (Cech et al., Cell. 1981 Dec.;27(3 Pt 2):487–96; Michel and Westhof, J Mol Biol. 1990 Dec. 5;216(3):585–610; Reinhold-Hurek and Shub, Nature. 1992 May 14;357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. 1992 Aug. 15;89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. 1992 Sep. 11;20(17):4559–65. Examples of hairpin motifs are described by Hampel et al. (Eur. Pat. Appl. Publ. No. EP 0360257), Hampel and Tritz, Biochemistry 1989 Jun. 13;28 (12):4929–33; Hampel et al., Nucleic Acids Res. 1990 Jan. 25;18(2):299–304 and U.S. Pat. No. 5,631,359. An example of the hepatitis δ virus motif is described by Perrotta and Been, Biochemistry. 1992 Dec. 1;31(47): 11843–52; an example of the RNaseP motif is described by Guerrier-Takada et al., Cell. 1983 December..;35(3 Pt 2):849–57; Neurospora VS RNA ribozyme motif is described by Collins (Saville and Collins, Cell. 1990 May 18;61(4):685–96; Saville and Collins, Proc Natl Acad Sci USA. 1991 Oct. 1;88(19):8826–30; Collins and Olive, Biochemistry. 1993 Mar. 23;32(11):2795–9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 1997 Jun.;15(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 1991 Dec. 6;254(5037):1497–500; Hanvey et al., Science. 1992 Nov. 27;258(5087):1481–5; Hyrup and Nielsen, Bioorg Med Chem. 1996 Jan.;4(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. 1995 Apr.;3(4):437–45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. 1995 Apr.;3(4):437–45; Petersen et al., J Pept Sci. 1995 May–Jun.;1(3):175–83; Orum et al., Biotechniques. 1995 Sep.;19(3):472–80; Footer et al., Biochemistry. 1996 Aug. 20;35(33):10673–9; Griffith et al., Nucleic Acids Res. 1995 Aug. 11;23(15):3003–8;

Pardridge et al, Proc Natl Acad Sci US A. 1995 Jun. 6;92(12):5592–6; Boffa et al., Proc Natl Acad Sci USA. 1995 Mar. 14;92(6):1901–5; Gambacorti-Passerini et al., Blood. 1996 Aug. 15;88(4):1411–7; Armitage et al., Proc Natl Acad Sci USA. 1997 Nov. 11;94(23):12320–5; Seeger et al., Biotechniques. 1997 Sep.;23(3):512–7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. 1993 Dec. 15;65(24):3545–9) and Jensen et al. (Biochemistry. 1997 Apr. 22;36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g. NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 43 1A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g, cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae.* The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad Sci.* 91 :3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the *Rous sarcoma* virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980)

Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif 3:263–281) while the enterokinase cleavage site provides a means for purifying the desired polypeptide from the fusion protein. A discussion of vectors which contain fusion proteins is provided in Kroll, D. J. et al. (1993; DNA Cell Biol. 12:441–453).

In addition to recombinant production methods, polypeptides of the invention, and fragments thereof, may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) Proc. Nat. Acad. Sci.

USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_{H^-}$ and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures— regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J. Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 μg/ml, preferably 200 ng/ml–25 μg/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be CD4+ and/or CD8+. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, CD4+ or CD8+ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus*-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8 3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., Proc. Natl. Acad. Sci. USA 86:317–321, 1989; Flexner et al., Ann. N.Y. Acad. Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616–627, 1988; Rosenfeld et al., Science 252:431–434, 1991; Kolls et al., Proc. Natl. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, −7, −12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n\text{—}A\text{—}R, \qquad (I)$$

wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$-$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4–1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27;386(6623):410–4; Hwang et al., Crit Rev Ther Drug Carrier Syst 1998;15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifingal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2;52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 Jul.;16(7):307–21; Takakura, Nippon Rinsho 1998 Mar.;56(3):691–5; Chandran et al., Indian J Exp Biol. 1997 August;35(8):801–9; Margalit, Crit Rev Ther Drug Carrier Syst. 1995;12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25;265(27):16337–42; Muller et al., DNA Cell Biol. 1990 Apr.;9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 Dec.;24(12):1113–28). To avoid side effects due to intracellular polymeric overloading, such ultrafine particles (sized around 0.1 $\mu$m) may be designed using polymers able to be degraded in vivo. Such particles can be made as described, for example, by Couvreur et al., Crit Rev Ther Drug Carrier Syst. 1988;5(1):1–20; zur Muhlen et al., Eur J. Pharm Biopharm. 1998 Mar.;45(2):149–55; Zambaux et al. J Controlled Release. 1998 Jan. 2;50(1–3):31–40; and U.S. Pat. No. 5,145,684.

Cancer Therapeutic Methods

In further aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 µg/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO:1–61, 72 and 73, respectively. Comparison of these cDNA sequences with known sequences in the gene bank using the EMBL and GenBank databases (Release 97) revealed no significant homologies to the sequences provided in SEQ ID NO:14, 21, 22, 27, 29, 30, 32, 38, 44, 45, 53, 57, 72 and 73. The sequences of SEQ ID NO: 1, 3, 16, 17, 34, 48, 60 and 61 were found to represent known human genes. The sequences of SEQ ID NO:2, 4, 23, 39 and 50 were found to show some similarity to previously identified non-human genes. The remaining clones (SEQ ID NO:5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

Further studies resulted in the isolation of the full-length cDNA sequence for the clone of SEQ ID NO:57 (referred to as B718P). By computer analysis, the full-length sequence was found to contain a putative transmembrane domain at amino acids 137–158. The full-length cDNA sequence of B718P is provided in SEQ ID NO:504, with the cDNA sequence of the open reading frame including stop codon being provided in SEQ ID NO:505 and the cDNA sequence of the open reading frame without stop codon being provided in SEQ ID NO:506. The full-length amino acid sequence of B718P is provided is SEQ ID NO:507. SEQ ID NO:508 represents amino acids 1–158 of B718P, and SEQ ID NO:509 represents amino acids 159–243 of B718P.

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO:40, 46, 59 and 73 were found to be overexpressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO:41 and 48 were found to be over-expressed in breast tumor and expressed at low levels in all other tissues tested, with the exception of bone marrow. The clone of SEQ ID NO:42 was found to be over-expressed in breast tumor and expressed at low levels in all other tissues tested except bone marrow and spinal cord. The clone of SEQ ID NO:43 was found to be over-expressed in breast tumor and expressed at low levels in all other tissues tested with the exception of spinal cord, heart and small intestine. The clone of SEQ ID NO:51 was found to be over-expressed in breast tumor and expressed at low levels in all other tissues tested with the exception of large intestine. The clone of SEQ ID NO:54 was found to be over-expressed in breast tumor and expressed at low levels in all other tissues tested with the exception of PBMC, stomach and small intestine. The clone of SEQ ID NO:56 was found to be over-expressed in breast tumor and expressed at low levels in all other tissues tested with the exception of large and small intestine, human mammary epithelia cells and SCID mouse-passaged breast tumor. The clone of SEQ ID NO:60 was found to be over-expressed in breast tumor and expressed at low levels in all other tissues tested with the exception of spinal cord and heart. The clone of SEQ ID NO:61 was found to be over-expressed in breast tumor and expressed at low levels in all other tissues tested with the exception of small intestine. The clone of SEQ ID NO:72 was found to be over-expressed in breast tumor and expressed at low levels in all other tissues tested with the exception of colon and salivary gland.

The results of a Northern blot analysis of the clone SYN18C6 (SEQ ID NO:40) are shown in FIG. 1. A predicted protein sequence encoded by SYN18C6 is provided in SEQ ID NO:62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above.

Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO:63–87. Comparison of the sequences of SEQ ID NO:74–87 with those in the gene bank as described above, revealed homology to previously identified human genes. No significant homologies were found to the sequences of SEQ ID NO:63–73.

Three DNA isoforms for the clone B726P (partial sequence provided in SEQ ID NO:71) were isolated as follows. A radioactive probe was synthesized from B726P by excising B726P DNA from a pT7Blue vector (Novagen) by a BamHI/Xbal restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO:175, with the corresponding predicted amino acid sequence being provided in SEQ ID NO:176. The determined cDNA sequence of the isoform B726P-74 is provided in SEQ ID NO:178, with the corresponding predicted amino acid sequence being provided in SEQ ID NO:179. The determined cDNA sequence of the isoform B726P-79 is provided in SEQ ID NO:180, with the corresponding predicted amino acid sequence being provided in SEQ ID NO:181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO:464–468, with the predicted amino acid sequences encoded by SEQ ID NO: 464–467 being provided in SEQ ID NO:470–473, respectively. Using standard computer techniques, a 3,681 bp consensus DNA sequence (SEQ ID NO:463) was created that contains two large open reading frames. The downstream ORF encodes the amino acid sequence of SEQ ID NO:176. The predicted amino acid sequence encoded by the upstream ORF is provided in SEQ ID NO:469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO:474, with the corresponding amino acid sequence being provided in SEQ ID NO:475.

Comparison of the cDNA sequence of SEQ ID NO:63 (referred to as B723P) with the sequences in the GeneSeq™ DNA database showed matches to 5 DNA sequences (Accession nos. A26456, A37144, A26424, V84525 and T22133), 4 of which appear to represent the full-length sequence of the gene. Three of these sequences encode a 243 amino acid open reading frame (ORF), while one of the DNA sequences (Accession no. A37144) contains an extra C at position 35, resulting in a 278 amino acid ORF. The open reading frame, including stop codon, of the first variant of B723P (referred to as B723P-short) is provided in SEQ ID NO:510, with the open reading frame without stop codon being provided in SEQ ID NO:511. The open reading frame, including stop codon, of the second variant of B723P (referred to as B723P-long) is provided in SEQ ID NO:512, with the open reading frame without stop codon being provided in SEQ ID NO:513. The amino acid sequences of B723P-short and B723P-long are provided in SEQ ID NO:514 and 515, respectively. Computer analysis of these sequences demonstrated the presence of putative transmembrane domains at amino acids 233–252 of the B723P-long ORF and amino acids 198–217 of the B723P-short ORF. SEQ ID NO:516, 518 and 519 represent amino acids 1–197, 198–243 and 218–243, respectively of B723P-short. SEQ ID NO:517 represents amino acids 1–232 of B723P-long.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO:182–251 and 479 were 2 or more fold over-expressed in human breast tumor tissues over normal human tissues. No significant homologies were found for nineteen of these clones, including, SEQ ID NO:185, 186, 194, 199, 205, 208, 211, 214–216, 219, 222, 226, 232, 236, 240, 241, 245, 246 and 479, with the exception of some previously identified expressed sequence tags (ESTs). The remaining clones share some homology to previously identified genes, specifically SEQ ID NO:181–184, 187–193, 195–198, 200–204, 206, 207, 209, 210, 212, 213, 217, 218, 220, 221, 223–225, 227–231, 233–235, 237–239, 242–244 and 247–251.

One of the cDNA clones isolated by PCR subtraction as described above (SEQ ID NO:476; referred to as B720P) which was shown by microarray to be over-expressed in breast tumor tissues, was found to be identical to a known keratin gene. The full-length cDNA sequence of the known keratin gene is provided in SEQ ID NO:477, with the corresponding amino acid sequence being provided in SEQ ID NO:478. Primers were generated based on the sequence of SEQ ID NO:477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO:484, with the corresponding amino acid sequence being provided in SEQ ID NO:485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO:486. B720P-tr has an ORF of 708 base pairs which encodes a 236 amino acid protein (SEQ ID NO:487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO:216) was over-expressed in a few breast tumors, with no overexpression in any normal tissues tested. Clone 19470.1 (SEQ ID NO:219) was found to be slightly over-expressed in some breast tumors. Clone 19468.1 (SEQ ID NO:222) was found to be slightly over-expressed in the majority of breast tumors tested. Clone 19505.1 (SEQ ID NO:226) was found to be slightly over-expressed in 50% of breast tumors, as well as in SCID tumor tissues, with some degree of over-expression in found in normal breast. Clone 1509.1 (SEQ ID NO:232) was found to be over-expressed in very few breast tumors, but with a certain degree of over-expression in metastatic breast tumor tissues, as well as no significant over-expression found in normal tissues. Clone 19513.1 (SEQ ID NO:236) was shown to be slightly over-expressed in few breast tumors, with no significant over-expression levels found in normal tissues. Clone 19575.1 (SEQ ID NO:240) showed low level over-expression in some breast tumors and also in normal breast. Clone 19560.1 (SEQ ID NO:241) was over-expressed in 50% of breast tumors tested, as well as in some normal breast tissues. Clone 19583.1 (SEQ ID NO:245) was slightly over-expressed in some breast tumors, with very low levels of over-expression found in normal tissues. Clone 19587.1 (SEQ ID NO:246) showed low level over-expression in some breast tumors and no significant over-expression in normal tissues.

Clone 19520.1 (SEQ ID NO:233), showing homology to clone 102D24 on chromosome 11q13.31, was found to be over-expressed in breast tumors and in SCID tumors. Clone 19517.1 (SEQ ID NO:237), showing homology to human PAC 128M19 clone, was found to be slightly over-expressed in the majority of breast tumors tested. Clone 19392.2 (SEQ ID NO:247), showing homology to human chromosome 17, was shown to be over-expressed in 50% of breast tumors tested. Clone 19399.2 (SEQ ID NO:250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO:405–415. Comparison of these sequences to those in the public database, as outlined above, revealed homologies between the sequences of SEQ ID NO:408, 411, 413 and 414 and previously isolated ESTs. The sequences of SEQ ID NO:405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO:316–404. Comparison of these sequences with those in the public database, as described above, revealed no significant homologies to the sequence of SEQ ID NO:366. The sequences of SEQ ID NO:321–325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO:427–439. The determined cDNA sequences of 22 clones identified using the modified Gemtools analysis are provided in SEQ ID NO:440–462, wherein SEQ ID NO:453 and 454 represent two partial, non-overlapping, sequences of the same clone.

Comparison of the clone sequences of SEQ ID NO:436 and 437 (referred to as 263G6 and 262B2) with those in the public databases, as described above, revealed no significant homologies to previously identified sequences. The sequences of SEQ ID NO:427, 429, 431, 435, 438, 441, 443, 444, 445, 446, 450, 453 and 454 (referred to as 266B4, 266G3, 264B4, 263G1, 262B6, 2BT2–34, 2BT1–77, 2BT1–62, 2BT1-60, 61, 2BT1-59, 2BT1–52 and 2BT1–40, respectively) showed some homology to previously isolated expressed sequences tags (ESTs). The sequences of SEQ ID NO:428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained by PCR-based Subtraction Using SCID-passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed Nov. 13, 1995, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO:88–116, respectively. The isolated cDNA sequences of SEQ ID NO:117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO:141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO:252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO:269–314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO:416–426, respectively.

EXAMPLE 3

Synthesis of Polypeptides

Polypeptides may be synthesized on an Perkin Elmer/ Applied Biosystems Division 430A peptide synthesizer using FMOC chemistry with HPTU (O-Benzotriazole-N,N, N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:176) at an M.O.I. of 2.5 and matured for 8 hours by the addition of 2 micrograms/ml CD40 ligand. CD8 positive cells were enriched for by the depletion of CD4 and CD14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., J. Exp. Med 186:859–865, 1997) using IFN-gamma treated autologous fibroblasts transduced to express either B726P or an irrelevant, control, antigen as antigen presenting cells (APC). Of approximately 96 lines, one line (referred to as 6–2B) was identified that appeared to specifically recognize B726P-transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

In order to define more accurately the location of the epitope recognized by the B726P-specific CTL clones, a deletion construct comprising only the N-terminal half (a.a. 1–129) of B726P (referred to as B726Pdelta3') was constructed in the pBIB retroviral expression plasmid. This plasmid, as well as other plasmids containing B726P, were transfected into COS-7 cells either alone or in combination with a plasmid expressing HLA-B*1501. Aproximately 48 hours after transfection, a B726P-specific CTL clone (1-9B) was added at approximately $10^4$ cells per well. The cells were harvested the next day and the amount of IFN-gamma released was measured by ELISA. The CTL responded above background (EGFP) to COS-7 cells that had been transfected with both B726P and HLA-B*1501. There was no response above background to COS-7 cells that had been transfected with either B726P or HLA-B*1501 alone. Importantly, a higher response was seen with COS-7 cells that had been transfected with both HLA-B*1501 and B726Pdelta3'. This result indicated that the epitope was likely to be located in the N-terminal region (a.a. 1–129) of B726P. This region was examined and amino acid sequences that corresponded to the HLA-B*1501 peptide binding motif (*J. Immunol.*1999, 162:7277–84) were identified and synthesized. These peptides were pulsed at 10 ug/ml onto autologous B-LCL overnight. The next day, the cells were washed and the ability of the cells to stimulate the B726P-specific CTL clone 1-9B was assayed in a IFN-gamma ELISPOT assay. Of the eleven peptides tested, only one peptide, having the amino acid sequence SLTKRASQY (a.a. 76–84 of B726P; SEQ ID NO: 488) was recognized by the CTL clone. This result identifies this peptide as being a naturally-processed epitope recognized by this B726P-specific CTL clone.

Figure 2:
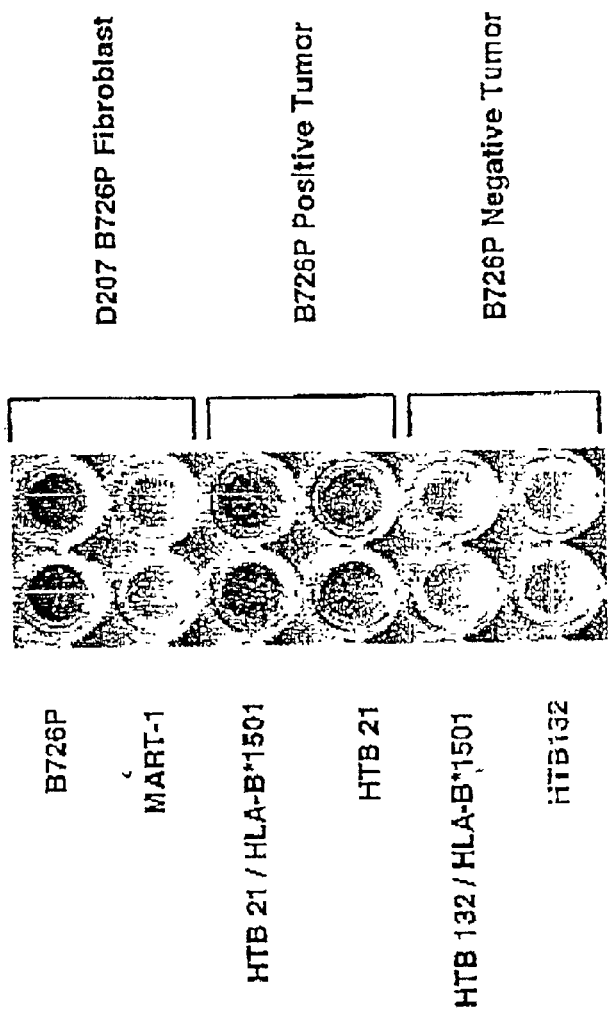
FIG. 2 shows the results of an IFN-gamma ELISPOT assay demonstrating that the B726P-specific CTL clone recognizes and lyses breast tumor cell lines expressing B726P.

In further studies, a panel of breast tumor cell lines obtained from the American Type Culture Collection (Manassas, Va.), was analyzed using real time PCR to determine their B726P message level. The cell line that expressed the highest level of B726P (referred to as HTB21) and a line that expressed no B726P (referred to as HTB132) were transduced with HLA-B*1501. These cell lines were grown up and analyzed using FACS to determine their B1501 expression. The line HTB 21 was found to endogenously express B1501. To determine if clone 1-9A would recognize the tumor cell line HTB21, an IFN-gamma ELISPOT assay was performed using 20,000 T cells, low dose IL-2 (5 ug/ml), and 20,000 of the following targets: autologous B726P or Mart-1 fibroblasts, untransduced or B1501-transduced HTB21; or untransduced or B1501-transduced HTB132. These were incubated overnight and the assay was developed the next day. The results of this assay are shown in FIG. 2. These studies demonstrate that B726P-specific CTL can recognize and lyse breast tumor cells expressing B726P.

EXAMPLE 5

Identification of Immunogenic CD4 T Cell Epitopes in Breast Antigens

Immunogenic CD4 T cell epitopes derived from the breast antigen B726P were identified as follows.

A total of thirty-five 20-mer peptides overlapping by 12 amino acids and derived from the downstream ORF of B726P (corresponding to amino acids 1–317 of SEQ ID NO:176) were generated by standard procedure. Dendritic cells (DC) were derived from PBMC of a normal male donor using GMCSF and IL-4 by standard protocol. Purified CD4 T cells were generated from the same donor as the DC using MACS beads and negative selection of PBMCs. DC were pulsed overnight with pools of the 20-mer peptides, with each peptide at an individual concentration of 0.5 micrograms/mL. Pulsed DC were washed and plated at 10,000 cells/well of 96-well U bottom plates, and purified CD4 T cells were added at 100,000 cells/well. Cultures were supplemented with 10 ng/mL IL-6 and 5 ng/mL IL-12 and incubated at 37° C. Cultures were restimulated as above on a weekly basis using DC made and pulsed as above as the antigen presenting cell, supplemented with 10 u/mL IL-2 and 5 ng/mL IL-7. Following three in vitro stimulation cycles (the initial priming+two restimulations), cell lines (each corresponding to one well) were tested for specific proliferation and cytokine production in response to the stimulating pool versus an irrelevant pool of peptides derived from unrelated antigens. A number of individual CD4 T cell lines (36/672 by IFN-gamma and 64/672 by proliferation) demonstrated significant cytokine release (IFN-gamma) and proliferation in response to the B726P peptide pools but not to the control peptide pool. Twenty-five of these T cell lines were restimulated on the appropriate pool of B726P peptides and reassayed on autologous DC pulsed with either the individual peptides or recombinant B726P protein made in *E. coli*. Approximately 14 immunogenic peptides were recognized by the T cells from the entire set of peptide antigens tested. The amino acid sequences of these 14 peptides are provided in SEQ ID NO:534–547, with the corresponding DNA sequences being provided in SEQ ID NO:520–533, respectively. In some cases the peptide reactivity of the T cell line could be mapped to a single peptide but some could be mapped to more than one peptide in each pool. Thirteen of the fifteen T cell lines recognized the recombinant B726P protein. These results demonstrate that 13 of the 14 peptide sequences (SEQ ID NO:534–542 and 544–547) may be naturally processed CD4 epitopes of the B726P protein.

EXAMPLE 6

Preparation and Characterization of Antibodies Against Breast Tumor Antigen B726P Polyclonal antibodies against both the downstream (SEQ ID NO:176) and upstream (SEQ ID NO:469) ORF of the breast tumor antigen B726P were prepared as follows.

The downstream or upstream ORF of B726P expressed in an *E. coli* recombinant expression system was grown overnight in LB broth with the appropriate antibiotics at 37° C. in a shaking incubator. The next morning, 10 ml of the overnight culture was added to 500 ml to 2×YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of the B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the colorimetric reaction was stopped with 100 microliters of iN $H_2SO_4$ and read immediately at 450 nm. All the polyclonal antibodies showed immunoreactivity to the appropriate B726P antigen.

B) Preparation of Polyclonal Antibodies Against B709P and B720P

The breast antigens B709P (SEQ ID NO: 62) and B720P (SEQ ID NO: 485) expressed in an *E. coli* recombinant expression system were grown overnight in LB Broth with the appropriate antibiotics at 37° C. in a shaking incubator. Ten ml of the overnight culture was added to 500 ml of 2×YT plus appropriate antibiotics in a 2L-baffled Erlenmeyer flask. When the optical density (at 560 nanometers) of the culture reached 0.4–0.6, the cells were induced with IPTG (1 mM). Four hours after induction with IPTG, the cells were harvested by centrifugation. The cells were washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, the mixture was run through a French Press at a pressure of 16,000 psi. The cells were centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature (RT) with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. The proteins were then vialed after filtration through a 0.22-micron filter and frozen until needed for immunization.

Four hundred micrograms of antigen was combined with 100 micrograms of muramyldipeptide (MDP). An equal volume of Incomplete Freund's Adjuvant (IFA) was added and mixed, and the mixture was injected into a rabbit. The rabbit was boosted with 100 micrograms of antigen mixed with an equal volume of IFA every four weeks. The animal was bled seven days following each boost. Sera was generated by incubating the blood at 4° C. for 12–24 hours followed by centrifugation.

The reactivity of the polyclonal antibodies to recombinant antigen (B709P or B720P) was determined by ELISA as follows. Ninety-six well plates were coated with antigen by incubating with 50 microliters (typically 1 microgram) at 4° C. for 20 hrs. 250 microliters of BSA blocking buffer was added to the wells and incubated at RT for 2 hrs. Plates were washed 6 times with PBS/0.01% Tween. Rabbit sera were diluted in PBS. Fifty microliters of diluted sera was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB Microwell Peroxidase Substrate was added to each well. Following a 15-minute incubation in the dark at RT, the colorimetric reaction was stopped with 100 microliters of 1N $H_2SO_4$ and read immediately at 450 nm. The polyclonal antibodies showed immunoreactivity to the appropriate antigen.

EXAMPLE 7

Protein Expression of Breast Tumor Antigens

The downstream ORF of B726P (SEQ ID NO:176), together with a C-terminal 6× His Tag, was expressed in insect cells using the baculovirus expression system as follows.

The cDNA for the full-length downstream ORF of B726P was PCR amplified using the primers of SEQ ID NO:480 and 481. The PCR product with the expected size was recovered from agarose gel, restriction digested with EcoRI and Hind II, and ligated into the transfer plasmid pFastBac1, which was digested with the same restriction enzymes. The sequence of the insert was confirmed by DNA sequencing. The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO:482 and 483, respectively.

EXAMPLE 8

Generation of Constructs for Protein Expression of B726P in *E. coli*

Three different open reading frames (ORFs) of B726P were subcloned into pPDM, a modified pET28 vector for exression in *E. coli*.

Construct for the expression of B726P Upstream ORF in *E. coli* (cDNA: SEQ ID NO:549; amino acid: SEQ ID NO:552):

The partial B726P upstream ORF (A) from clone 23113 was PCR amplified with the following primers:

PMD-416 (SEQ ID NO:554)    5' gtcggctccatgagtcccgcaaaag 3'                        Tm 63° C.

PMD-431 (SEQ ID NO:555)    5' cgagaattcaatacttaagaagaccatctttaccag 3'    Tm 61° C.

The amplification conditions were as follows 10 µl 10×Pfu buffer, 1 µl 10 µM dNTPs, 2 µl 10 µM each oligo, 83 µl sterile water, 1.5 µl Pfu DNA polymerase (Stratagene, La Jolla, Calif.), 1 µl PCR 23113. The reaction was first denatured for 2 minutes at 96° C., followed by 40 cylces of 96° C. for 20 seconds, 62° C. for 15 seconds, and extension at 72° C. for 2 minutes. This was followed by a final extension of 72° C. for 4 minutes.

The second partial B726P upstream ORF (B) from clone 19310 was PCR amplified with the following primers:

```
PDM-432 (SEQ ID NO:556)   5' cataagccttaaggctaactgcggaatgaaag 3'       Tm 63° C.

PDM-427 (SEQ ID NO:557)   5' cccgcagaattcaacatgcaattttcatgtaagag 3'    Tm 62° C.
```

The amplification and cycling conditions were as described above. The first PCR product was digested with EcoRI and cloned into pPDM His (a modified pET28 vector) that had been digested with EcoRi and Eco72I. The second PCR product was digested with BfrI and EcoRI and cloned into the resulting construct: pPDM B726P UP-A-5 at the EcoRI and BfrI sites. The construct (pPDM B726P Up-4) was confirmed to be correct through sequence analysis and transformed into BL21 (DE3) pLys S and BL21 CodonPlus RIL (DE3) cells. Protein expression was confirmed by Coomassie stained SDS-PAGE and N-terminal protein sequence analysis.

Construct for B726P D-ORF expression in *E. coli* (cDNA: SEQ ID NO:550; amino acid: SEQ ID NO:551):

The B726P D-ORF was PCR amplified with the following primers:

```
PDM-290 (SEQ ID NO:558)   5' ctaaatgccggcacaagagctctgc 3'              Tm 61° C.

PDM-291 (SEQ ID NO:559)   5' cgcgcagaattctattatataacttctgtttctgc 3'    Tm 61° C.
```

The reaction conditions were as described. The cycling conditions were altered slightly in that the annealing temperature was lowered to 61° C. from 62° C. and was held for 15 seconds. The extension time was also increased to 2 minutes and 15 seconds. The PCR product was digested with Nael and EcoRI and cloned into pPDM His which has been digested with Eco72I and EcoRI. Construct was confirmed by sequencing and then transformed into BL21 (DE3) pLys S cells (Novagen, Madison, Wis.). Protein expression was confirmed by Coomassie stained SDS-PAGE and N-terminal protein sequence analysis.

Construct for B726P Combined ORF expression in *E. coli* (cDNA: SEQ ID NO:548; amino acid: SEQ ID NO:553):

The B726P C-1 coding region was PCR amplified including the 183bp insert, with the following primers:

The reaction conditions for these PCR reactions were the same as described above. The cycling conditions were as follows: 1$^{st}$ PCR: The reaction was first denatured for 2 minutes at 96° C., followed by 40 cylces of 96° C for 20 seconds, 58° C. for 15 seconds, and extension at 72° C. for 4 minutes. This was followed by a final extension of 72° C. for 4 minutes; 2$^{nd}$ PCR. The reaction was first denatured for 2 minutes at 96° C., followed by 40 cylces of 96° C. for 20 seconds, 59° C. for 15 seconds, and extension at 72° C. for 2 minutes. This was followed by a final extension of 72° C. for 4 minutes. The first PCR product was digested with EcoRI and cloned into pPDM His (a modified pET28 vector) at the Eco 72I and EcoRI sites. The construct was confirmed to be correct through sequence analysis. The second PCR product was digested with EcoRI and cloned into pPDM His at the same sites. The resulting constructs pPDM B726P UA-8 and pPDM B726P DA-7 respectively were digested with SwaI and EcoRI. The pPDM B726P UA-8 construct was used as vector and the insert from the pPDM B726P DA-7 was cloned into this construct successfully. The construct was confirmed to be correct through sequence analysis and then transformed into BLR (DE3) pLys S and HMS 174 (DE3) pLys S cells (Novagen, Madison, Wis.). Protein expression was confirmed by Coomassie stained SDS-PAGE and N-terminal protein sequence analysis.

EXAMPLE 9

Additional Sequence Identified for Breast Tumor Antigen B726P by Bioinformatic Analysis The combined ORF of the breast tumor antigen, B726P (amino acid sequence set forth in SEQ ID NO:475), was used to search public databases. A sequence essentially identical to the combined ORF with additional N-terminal sequence was identified in the GenBank nonredundant protein database and the cDNA and predicted amino acid sequences are set forth in SEQ ID NO:564 and 565, respectively. The gene is also referred to as NY-BR-1 and was described in described in Cancer Research 61(5):2055–2061, Mar. 1, 2001.

```
PDM-750 (SEQ ID NO:560)   5' ggggaattgtgagcggataacaattc 3'             Tm 58° C.

PDM-752 (SEQ ID NO:561)   5' cgtagaattcaacctgatttaaattactttctacac 3'   Tm 59° C.
```

The B726P Downstream ORF was PCR amplified with the following primers:

```
PDM-753 (SEQ ID NO:562)   5' gaaagtaatttaaatcaggtttctcacactc 3'   Tm 59°0 C.

PDM-751 (SEQ ID NO:563)   5' gaggccccaaggggttatgctag 3'             Tm 61° C.
```

EXAMPLE 10

Analysis of B726P Expression Using Immunohistochemistry

Affinity purified polyclonal antibodies anti-B726Pup (generated against the B726P upstream ORF protein) and anti-B726Pdown (generated against the B726P downstream ORF) were used to assess B726P protein expression in breast cancer and in a variety of normal tissue sections.

In order to determine which tissues express the breast cancer antigen protein B726P immunohistochemistry (IHC) analysis was performed on a diverse range of tissue sections. Tissue samples were fixed in formalin solution for 12–24 hrs and embedded in paraffin before being sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (either rabbit affinity purified anti-B726Pdown or anti-B726Pup) was added to each section for 25 minutes followed by 25 minute incubation with anti-rabbit biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize antigen expression. Slides were counterstainied with hematoxylin to visualize cell nuclei. Anti-B726Pup and anti-B726Pdown immunoreactivity was observed in about 30–40% of breast cancer samples analyzed but not observed in a majority of various normal tissues. Anti-B726Pdown and anti-b726Pup also stained roughly the same breast cancer samples. Thus, these data confirm earlier microarray analysis (see Example 1) showing that B726P is overexpressed in breast tumor tissue as compared to normal tissue. Therefore, this antigen may be used in diagnostic and immunotherapeutic applications for breast cancer.

EXAMPLE 11

Generation of Monoclonal Antiodies to B726P Downstream and Upstream ORFs

Production and purification of protein used for antibody generation. B726 upstream ORF and B726 downstream ORF proteins were expressed in an *E. coli* recombinant expression system (see Example 8). Cells were grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the optical density (at 560 nanometers) of the culture reached 0.4–0.6 the cells were induced with IPTG (1 mM). Four hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole.

The solubilized protein was added to 5 ml of nickel-chelate resin (Qiagen, Valencia, Calif.) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then submitted to Quality Control for final release. The release criteria were purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22-micron filter and the antigens were frozen until needed for immunization.

To generate anti-B726P mouse monoclonal antibodies, mice were immunized IP with 50 micrograms of recombinant B726P upstream ORF and B726P downstream ORF proteins that had been mixed to form an emulsion with an equal volume of Complete Freund's Adjuvant (CFA). Every three weeks animals were injected IP with 50 micrograms of recombinant B726P upstream ORF and B726P downstream ORF that had been mixed with an equal volume of IFA to form an emulsion. After the fourth injection, spleens were isolated and standard hybridoma fusion procedures were used to generate anti-B726P mouse monoclonal antibody hybridomas. Anti-B726P monoclonal antibodies were screened using the ELISA analysis using the bacterially expressed recombinant B726P upstream ORF and B726P downstream ORF proteins.

A list of the mouse anti-B726P monoclonal antibodies that were generated, as well as their anti-B726P reactivity in an ELISA assay and Western blot are shown in Table 2. The hybridomas were then subcloned and the subclones further tested for reactivity with B726P upstream ORF and B726P downstream ORF proteins. Several monoclonal antibodies showed particularly favorable reactivity: 220A2–21, 220A19–25, 220A94–29, 220A151–33.

For Western blot analysis, recombinant B726P upstream ORF and B726P downstream ORF protein was diluted with SDS-PAGE loading buffer containing beta-mercaptoethanol, then boiled for 10 minutes prior to loading the SDS-PAGE gel. Protein was transferred to nitrocellulose and probed with each of the anti-B726P hybridoma supernatants. Protein A-HRP was used to visualize the anti-B726P reactive bands by incubation in ECL substrate.

TABLE 2

B726PUP AND B726PDOWN MONOCLONAL ANTIBODY REACTIVITY

| Anti-B726P mAbs | ELISA | | | Western Blots | |
|---|---|---|---|---|---|
| | B726PDown | B726PUp | L523S | B726Pdown | B726Pup |
| 220A2 | +++ | + | – | +++ | ++ |
| 220A10 | – | – | – | N/A | N/A |
| 220A14 | +++ | +++ | +++ | +++ | ++ |
| 220A19 | ++ | – | – | ++ | + |
| 220A43 | +++ | + | – | +++ | ++ |
| 220A86 | +++ | + | – | +++ | ++ |
| 220A94 | +++ | – | – | ++ | +/– |
| 220A123 | ++ | – | – | + | – |
| 220A139 | +/– | – | – | + | – |
| 220A140 | – | – | – | N/A | N/A |
| 220A141 | – | – | – | N/A | N/A |
| 220A143 | – | – | – | N/A | N/A |
| 220A151 | ++ | – | – | ++ | – |
| 220A176 | +/– | – | – | + | – |

EXAMPLE 12

Identification of Additional Sequences for B726P

Additional 5' sequence was obtained for B726P—this sequence was obtained by PCR from 1st strand cDNA prepared from three separate mRNA sources (metastatic breast tumor, breast tumor, normal testis). Disclosed herein are clones that were isolated, each with differences from the expected published sequence of NY-BR-1.

A 1300 bp fragment of B726P otherwise known as NY-BR-1 was PCR amplified from 1st strand cDNA and cloned into pPDM, a modified pET28 vector as follows:

The B726P XB coding region (NY-BR-1) was PCR amplified with the following primers

```
PDM-784  5' cacacaaagaggaagaagaccatc 3'   Tm 56° C.

PDM-814  5' gattcttttgtaggacatgcaatcatc 3' Tm 55° C.
```

The following PCR conditions were used: 10 µl 10×Herculase buffer, 1 µl 10 mM dNTPs, 2 µl 10. µM each oligo, 83 µl sterile water, 1.5 µl Herculase DNA polymerase (Stratagene, La Jolla, Calif.), 50 ng DNA. The thermalcycling conditions were as follows:

- 98° C. 3 minutes
- 98° C. 40 seconds, 51° C. 15 seconds, 72° C. 4 minutes, ×10 cycles
- 98° C. 40 seconds, 51° C. 15 seconds, 72° C. 5 minutes, ×10 cycles
- 98° C. 40 seconds, 51° C. 15 seconds, 72° C. 6 minutes, ×10 cycles
- 98° C. 40 seconds, 51° C. 15 seconds, 72° C. 7 minutes, ×10 cycles
- 72° C. 10 minutes The PCR product was ligated into the pPDM vector (a modified pET28) that had been digested with Eco72I and de-phosphorylated. PCR amplification of this gene proved very difficult and required the use of a polymerase lacking proofreading capabilities. However, use of such an enzyme, in this case, Herculase from Stratagene (La Jolla, Calif.), led to what is likely PCR errors in the resulting clones. The cDNA sequence of three of the isolated clones containing mutations are disclosed in SEQ ID NO:567–569 with the corresponding amino acid sequences disclosed in SEQ ID NO:572, 571, and 570, respectively.

The resulting construct, pPDM B726P XB (clone 83686), was then digested with BglII and the insert which dropped out from the 5' vector BglII site and the internal BglII site at amino acids 390–391 was cloned into the pPDM B726P C-ORF (SEQ ID NO:548) that had been digested with BglII and was de-phosphorylated. This construct, pPDM B726P XC, was then DNA sequenced and showed two nucleotide changes, which result in two amino acid changes. The cDNA of the full-length clone containing these 2 mutations is disclosed in SEQ ID NO:566 with the corresponding amino acid sequence in SEQ ID NO:573. The full-length expected, published NY-BR-1 is disclosed in SEQ ID NO:564 (cDNA); amino acid SEQ ID NO:565.

EXAMPLE 13

Isolation of Additional 3' Sequence and Real-time PCR Analysis of B726P Homolog NY-BRL1.1

A sequence homolog to the breast candidate B726P, called NY-BR-1.1, was identified and published in Cancer Research 61(5):2055–2061; Mar. 1, 2001. The NY-BR-1.1 gene, thought to be located on chomosome 9 based on 100% sequence identity to genomic sequence from chromosome 9, was shown to be expressed as mRNA in breast tumors as well as in normal brain. However, the published sequence was lacking 3' sequence. Published incomplete sequence for NY-BR-1.1 is represented by GenBank accession number AF269088. A recent BlastN search of the GenBank High Throughput Genomic Sequence database using Ny-Br-1.1 as a query sequence showed a 100% match to the working draft sequence of chromosome 9 (GenBank accession number AL359312), yielding further 3' DNA sequence for Ny-Br-1.1. The compilation of the Ny-Br-1.1 sequence with the additional 3' sequence from chromosome 9 yielded a 3720 bp ORF sequence (SEQ ID NO:576) which encodes a 1240 amino acid protein sequence (SEQ ID NO:577).

Real time PCR primers were designed to a unique region of NY-BR-1.1 to distinguish its mRNA expression profile from B726P. This experiment represents relative values, as it was done without template. The first-strand cDNA used in the quantitative real-time PCR was synthesized from 20 µg of total RNA that was treated with DNase I (Amplification Grade, Gibco BRL Life Technology, Gaithersburg, Md.), using Superscript Reverse Transcriptase (RT) (Gibco BRL Life Technology, Gaithersburg, Md.). Real-time PCR was performed with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence was monitored during the whole amplification process. The optimal concentration of primers was determined using a checkerboard approach and a pool of cDNAs from tumors was used in this process. The PCR reaction was performed in 25 µl volumes that included 2.5 µl of SYBR green buffer, 2 µl of cDNA template and 2.5 µl each of the forward and reverse primers for the gene of interest. The cDNAs used for quantitative real time PCR reactions were diluted 1:10 for each gene of interest and 1:100 for the β-actin control. Levels of mRNA were expressed relative to ureter where NY-BR-1.1 expression was not observed when compared to the β-actin control.

The real time PCR results show that mRNA expression for NY-BR-1.1 is present in breast tumors as well as in normal adrenal gland, brain, retina and testis.

EXAMPLE 14

Characterization of B726P Monoclonal and Purified Polyclonal Antibody Epitopes

Mouse monoclonal antibodies and rabbit polyclonal sera were raised against *E. coli* derived B726P recombinant protein and tested by ELISA as described in further detail below, for antibody epitope recognition against overlapping 20 mer peptides that correspond to the amino acid sequence of the downstream ORF of B726P (B726P dORF, set forth in SEQ ID NO:176, encoded by SEQ ID NO:175). Numerous peptides were recognized by the monoclonal and polyclonal antibodies. The corresponding amino acid sequences of these peptide antibody epitopes are summarized in Table 3 and are set forth in SEQ ID NO:578–593.

ELISA ANALYSIS: B726P recombinant protein and peptides were coated onto 96 well ELISA plate: 50ul/well at 2 ug/ml for 20 hrs at 4C. Plates were then washed 5 times with PBS+0.1% Tween 20 and blocked with PBS+1% BSA for 2 hr. Affinity purified B726P polyclonal antibodies were then added to the wells at 1 ug/ml and B726P monoclonal supernatants were added neat (220A43 and 220A86 were diluted 1/60 and 1/20 respectively). Plates were incubated at room temperature for 30 minutes and then washed again as above, followed by the addition of 50 ul/well donkey anti-mouse-Ig-HRP antibody for 30 minutes at room temperature. Plates were washed, then developed by the addition of 100 ul/well of TMB substrate. The reaction was incubated 15 minutes in the dark at room temperature and then stopped by the addition of 100 ul/well of 1N H2SO4. Plates were read at OD450 in an automated plate reader. Peptides with OD450 readings three times background or above were considered to be positively recognized by the corresponding antibody.

ning the entire B726P protein. These 33 peptides were tested in ELISAs to evaluate which epitopes reacted with breast cancer sera. Reactive epitopes were identified throughout the molecule and a total of 16/74 sera samples from breast cancer patients had reactivity with one or more peptides.

Thirty-one overlapping synthetic peptides spanning the entire B726P downstream ORF sequence (amino acid sequence set forth in SEQ ID NO:176) were synthesized and 30 of these were tested in ELISA with sera from breast cancer patients as well as control sera. The amino acid sequences of the 31 overlapping peptides of the B726P downstream ORF are set forth in SEQ ID NO:594–624. Three additional peptides of B726P, set forth in SEQ ID NO:625–627 were also tested. Several peptides thoughout the molecule showed reactivity, in particular peptide #2735 (amino acids 31–50; SEQ ID NO:597), peptide #2747 (amino acids 151–170; SEQ ID NO:609), peptide #2750 (amino acids 181–200; SEQ ID NO:612), peptide #2753 (amino acids 211–230; SEQ ID NO:615), and peptide #2766 (amino acids 231–250; SEQ ID NO:617). A total of 16/74 breast cancer sera were reactive with at least one peptide.

B726P antibody epitopes were also mapped using rabbit antisera generated against the B726P downstream ORF (SEQ ID NO:176). The epitopes identified using the rabbit antisera were as follows: peptide #2732 (amino acids 1–20; SEQ ID NO:594), peptide #2733 (amino acids 11–30; SEQ ID NO:595), peptide #2742 (amino acids 101–120; SEQ ID NO:604), peptide #2743 (amino acids 111–130; SEQ ID NO:605), peptide #2744 (amino acids 121–140; SEQ ID NO:606), peptide #2745 (amino acids 130–151; SEQ ID NO:607), peptide #2751 (amino acids 191–210; SEQ ID NO:613), and peptide #2753 (amino acid 211–230; SEQ ID NO:615). Some low level reactivity was observed for peptide #2772 (amino acids 291–310; SEQ ID NO:623) and peptide #2773 (amino acids 298–317; SEQ ID NO:624).

The above results confirm that B726P can be used alone or in combination with other breast tumor antigens as avaccine target. Additionally, these results show that detection of antibodies to B726P can be used as a diagnostic indicator of breast cancer either alone or in combination with detection of antibodies to other antigens (e.g. Her-2/Neu or other antigens known to be expressed in breast cancer tissue).

TABLE 3

Peptides recognized by B726P Antibodies

| | B726P Monoclonal Supernatant | | | | | | B726P Purified Polyclonal |
|---|---|---|---|---|---|---|---|
| | 220A2.1 | 220A19.1 | 220A94.1 | 220A151.1 | 220A43 | 220A86 | (1 μg/ml) |
| B726P peptides (amino acids) | 289-308 | 225-244, 232-252 | 73-252 | 145-164 153-172 | 232-252 | 145-164, 153-172 | 1-20, 9-28, 17-36, 24-44 97-116, 105-124, 113-132, 121-140, 129-148, 137-156 |

EXAMPLE 15

Analysis of Autoantibodies to B726P in Breast Cancer Sera and Epitope Mapping of the Antigenic Sites Specific B726P peptide epitopes were identified that react with autoantibodies in the serum of breast cancer patients. Thirty-three overlapping peptides were synthesized span- From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for stimulating an immune response in a patient, comprising administering to the patient a composition comprising a first component selected from the group consisting of physiologically acceptable carriers and immunostimulants, and a second component comprising a polypeptide comprising the sequence set forth in SEQ ID NO:475.

2. The method of claim 1 wherein said immunostimulant is selected from the group consisting of monophosphoryl lipid A, 3-de-O-acylated monophosphoryl lipid A, and a saponin, alone or in combination.

* * * * *

UNITED STATES PATENT AND TRADEMARK OFFICE
CERTIFICATE OF CORRECTION

PATENT NO. : 6,958,361 B2
DATED : October 25, 2005
INVENTOR(S) : Raymond L. Houghton et al.

It is certified that error appears in the above-identified patent and that said Letters Patent is hereby corrected as shown below:

Title page,
Item [56], References Cited, FOREIGN PATENT DOCUMENTS, insert the following:
-- WO  98/33915      8/1998
   WO  98/21331      5/1998 --.
OTHER PUBLICATIONS,
"Geneseq (Derwent) Database, Accession No. AAV90291, Feb. 15, 1999" should read
-- Geneseq (Derwent) Database, Accession No. AAV90219, Feb. 15, 1999 --.

Signed and Sealed this

Third Day of January, 2006

JON W. DUDAS
*Director of the United States Patent and Trademark Office*